United States Patent
Whelan et al.

(10) Patent No.: US 11,123,423 B2
(45) Date of Patent: Sep. 21, 2021

(54) ZIKA VIRUS VACCINE

(71) Applicant: President and Fellows of Harvard College, Cambridge, MA (US)

(72) Inventors: Sean P. J. Whelan, Cambridge, MA (US); Sayantan Bose, Brookline, MA (US); Joseph Timpona, Roxbury Crossing, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/343,113

(22) PCT Filed: Oct. 19, 2017

(86) PCT No.: PCT/US2017/057361
§ 371 (c)(1),
(2) Date: Apr. 18, 2019

(87) PCT Pub. No.: WO2018/075751
PCT Pub. Date: Apr. 26, 2018

(65) Prior Publication Data
US 2019/0255170 A1 Aug. 22, 2019

Related U.S. Application Data

(60) Provisional application No. 62/410,165, filed on Oct. 19, 2016.

(51) Int. Cl.
*A61K 39/205* (2006.01)
*C12N 7/00* (2006.01)
*A61K 39/12* (2006.01)
*A61K 39/00* (2006.01)

(52) U.S. Cl.
CPC ............ *A61K 39/205* (2013.01); *A61K 39/12* (2013.01); *C12N 7/00* (2013.01); *A61K 2039/5256* (2013.01); *A61K 2039/5258* (2013.01); *C12N 2760/20021* (2013.01); *C12N 2760/20223* (2013.01); *C12N 2760/20234* (2013.01); *C12N 2760/20241* (2013.01); *C12N 2760/20243* (2013.01); *C12N 2770/24121* (2013.01); *C12N 2770/24134* (2013.01); *C12N 2770/24171* (2013.01); *Y02A 50/30* (2018.01)

(58) Field of Classification Search
None
See application file for complete search history.

(56) References Cited

U.S. PATENT DOCUMENTS

2017/0298119 A1* 10/2017 Wollacott ................. C12N 7/00

FOREIGN PATENT DOCUMENTS

WO WO/15/066715 * 5/2015
WO WO-2017/192856 A1 11/2017

OTHER PUBLICATIONS

Gen Bank Accession AND01116, polyprotein [Zika virus], Sep. 2016.*
Abbink et al., Protective Efficacy of Multiple Vaccine Platforms Against Zika Virus Challenge in Rhesus Monkeys, 2016, Science, vol. 353, No. 6304, pp. 1129-1132.*
Iyer et al., Recombinant vesicular stomatitis virus-based west Nile vaccine elicits strong humoral and cellular immune responses and protects mice against lethal challenge with the virulent west Nile virus strain LSU-AR01, 2009, Vaccine, vol. 27, pp. 893-903.*
Abbink et al., "Protective efficacy of multiple vaccine platforms against Zika virus challenge in rhesus monkeys," Science, 353(6304):1129-1132 (2016).
Anonymous: "Zika Virus: The Hunt for a Vaccine," Immunity Tales, pp. 1-2 (2016) [http://immunitytales.com/zika-virus-the-hunt-for-a-vaccine/].
Awasthi, "Zika virus: prospects for the development of vaccine and antiviral agents," J Antivir Antiretrovir, 8(1):LXI-LXIII (2016).
Betancourt et al., "Cutting Edge: Innate Immune Augmenting Vesicular Stomatitis Virus Expressing Zika Virus Proteins Confers Protective Immunity," J Immunol, 198(8):3023-3028 (2017).
Dai et al., "Structures of the Zika virus envelope protein and its complex with a flavivirus broadly protective antibody," Cell Host Microbe, 19(5):696-704 (2016).
Dowd et al., Rapid development of a DNA vaccine for Zika virus, Science, 354(6309): 237-240 (2016).
International Search Report and Written Opinion for International Application No. PCT/US2017/057361 dated Feb. 19, 2018.
Kim et al., "Preventative vaccines for Zika virus outbreak: preliminary evaluation," EBioMedicine, 13:315-320 (2016).
Larocca et al., "Vaccine protection against Zika virus from Brazil," Nature, 536(7617):474-478 (2016).
Lauretti et al., "Recombinant vesicular stomatitis virus-based dengue-2 vaccine candidate induces humoral response and protects mice against lethal infection," Hum Vaccin Immunother, 12(9):2327-2333 (2016).

* cited by examiner

*Primary Examiner* — Benjamin P Blumel
(74) *Attorney, Agent, or Firm* — Foley Hoag LLP

(57) ABSTRACT

Compositions and methods useful for treating and/or preventing a Zika virus infection are provided.

6 Claims, 16 Drawing Sheets

Specification includes a Sequence Listing.

Fig. 1A rVSVΔG-Zika-prME

| Le | GFP | N | P | M | prME | L | Tr | rVSVΔG-Zika-CprME

| Le | GFP | N | P | M | CprME | L | Tr | rVSV-Zika-prME

| Le | prME | N | P | M | G | L | Tr | rVSV-Zika-CprME

| Le | CprME | N | P | M | G | L | Tr |

Fig. 1B

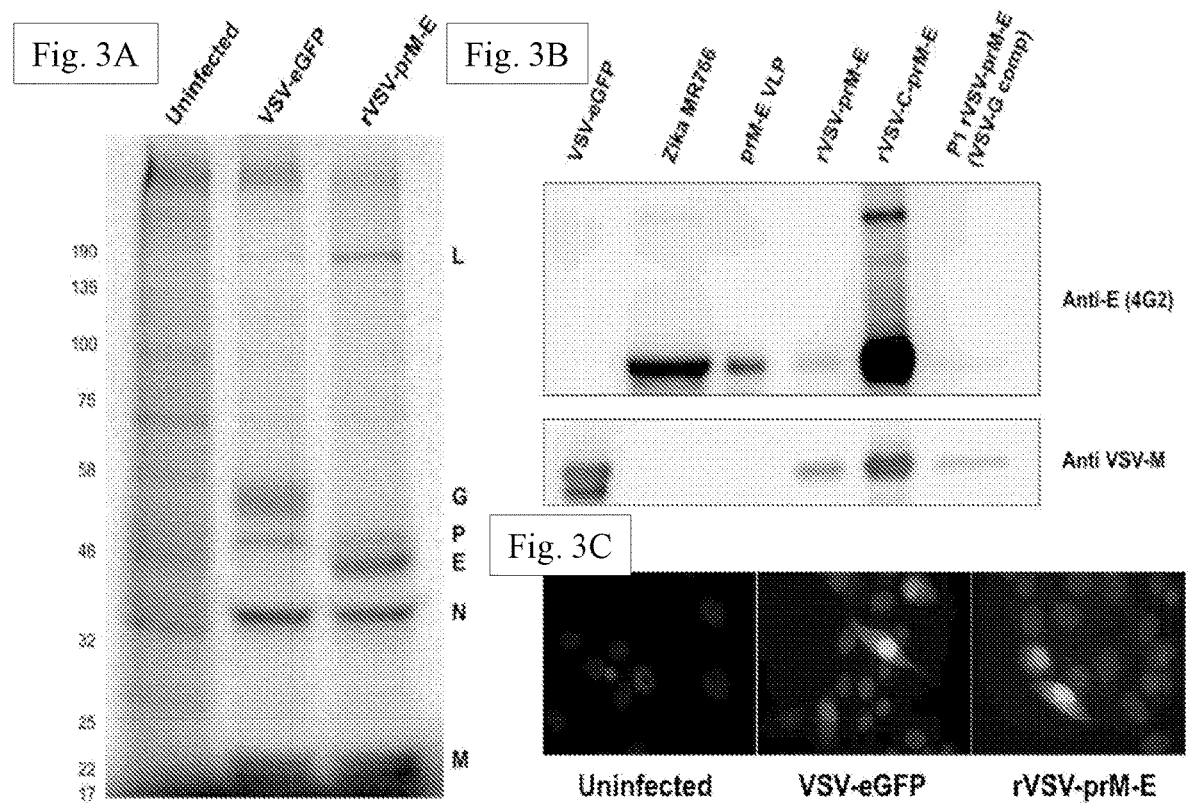

Fig. 6

Fig. 7A rVSVΔG-Zika-CprME

Fig. 7C  rVSV-Zika-CprME

Fig. 7D

VSVΔG-Zika-prME

Zika-E

VSV-M

VSV-Zika-prME

Zika-E

VSV-M

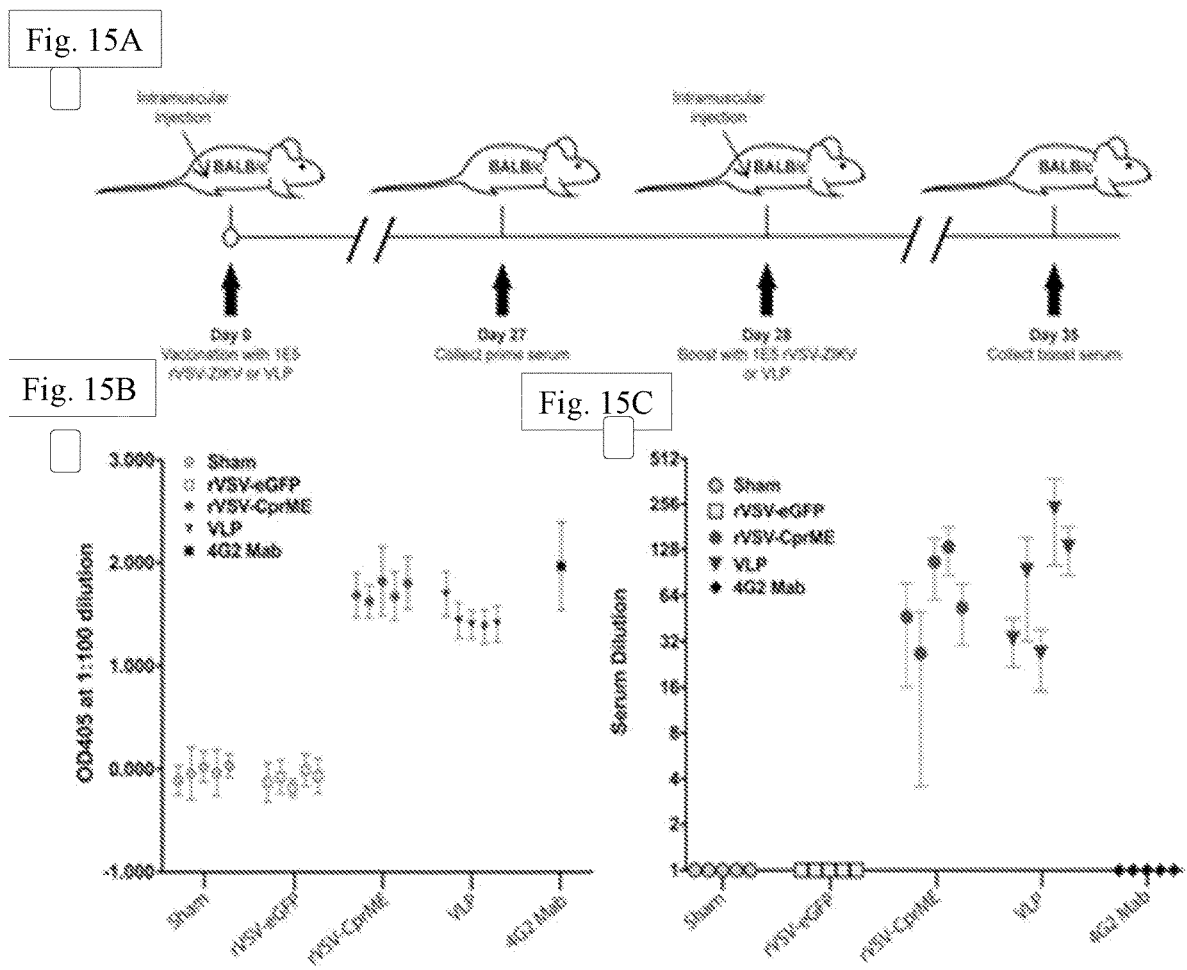

SEQUENCE LISTING

<160> NUMBER OF SEQ ID NOS: 12

<210> SEQ ID NO 1
<211> LENGTH: 14232
<212> TYPE: DNA
<213> ORGANISM: Vesiculovirus sp.

<400> SEQUENCE: 1

```
acgaagacaa acaaaccatt attatcatta aaaggctcag gagaaacttt aacagtaatc     60
aaaatgtctg ttacagtcaa gagaatcatt gacaacacag tcatagttcc aaaacttcct    120
gcaaatgagg atccagtgga atacccggca gattacttca gaaaatcaaa ggagattcct    180
ctttacatca atactacaaa aagtttgtca gatctaagag gatatgtcta ccaaggcctc    240
aaatccggaa atgtatcaat catacatgtc aacagctact tgtatggagc attaaaggac    300
atccggggta agttggataa agattggtca agtttcggaa taaacatcgg gaaagcaggg    360
gatacaatcg gaatatttga ccttgtatcc ttgaaagccc tggacggcgt acttccagat    420
ggagtatcgg atgcttccag aaccagcgca gatgacaaat ggttgccttt gtatctactt    480
ggcttataca gagtgggcag aacacaaatg cctgaataca gaaaaaagct catggatggg    540
ctgacaaatc aatgcaaaat gatcaatgaa cagtttgaac ctcttgtgcc agaaggtcgt    600
gacatttttg atgtgtgggg aaatgacagt aattacacaa aaattgtcgc tgcagtggac    660
atgttcttcc acatgttcaa aaaacatgaa tgtgcctcgt tcagatacgg aactattgtt    720
tccagattca aagattgtgc tgcattggca acatttggac acctctgcaa aataaccgga    780
atgtctacag aagatgtaac gacctggatc ttgaaccgag aagttgcaga tgaaatggtc    840
caaatgatgc ttccaggcca agaaattgac aaggccgatt catacatgcc ttatttgatc    900
gactttggat tgtcttctaa gtctccatat tcttccgtca aaaaccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgccg acttggcaca acagttttgt gttggagata acaaatacac tccagatgat   1140
agtaccggag gattgacgac taatgcaccg ccacaaggca gagatgtggt cgaatggctc   1200
ggatggtttg aagatcaaaa cagaaaaccg actcctgata tgatgcagta tgcgaaaaga   1260
gcagtcatgt cactgcaagg cctaagagag aagacaattg gcaagtatgc taagtcagaa   1320
tttgacaaat gaccctataa ttctcagatc acctattata tattatgcta catatgaaaa   1380
aaactaacag atatcatgga taatctcaca aaagttcgtg agtatctcaa gtcctattct   1440
cgtctggatc aggcggtagg agagatagat gagatcgaag cacaacgagc tgaaaagtcc   1500
aattatgagt tgttccaaga ggatggagtg gaagagcata ctaagccctc ttattttcag   1560
gcagcagatg attctgacac agaatctgaa ccagaaattg aagacaatca aggtttgtat   1620
gcacaggatc cagaagctga gcaagttgaa ggctttatac aggggccttt agatgactat   1680
gcagatgagg aagtggatgt tgtatttact tcggactgga aaccacctga gcttgaatct   1740
gacgagcatg gaaagacctt acggttgaca tcgccagagg gtttaagtgg agagcagaaa   1800
tcccagtggc tttcgacgat taaagcagtc gtgcaaagtg ccaaatactg gaatctggca   1860
gagtgcacat ttgaagcatc gggagaaggg gtcattatga aggagcgcca gataactccg   1920
gatgtatata aggtcactcc agtgatgaac acacatccgt cccaatcaga agcagtatca   1980
gatgtttggt ctctctcaaa gacatccatg actttccaac ccaagaaagc aagtcttcag   2040
cctctcacca tatccttgga tgaattgttc tcatctagag gagagttcat ctctgtcgga   2100
```

```
ggtgacggac gaatgtctca taaagaggcc atcctgctcg gcctgagata caaaaagttg   2160
tacaatcagg cgagagtcaa atattctctg tagactatga aaaaaagtaa cagatatcac   2220
gatctaagtg ttatcccaat ccattcatca tgagttcctt aaagaagatt ctcggtctga   2280
aggggaaagg taagaaatct aagaaattag ggatcgcacc accccttat gaagaggaca    2340 ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga aacgtcccht ctacaaaatc ttggcttttt   2580
tgggttcttc taatctaaag gccactccag cggtattggc agatcaaggt caaccagagt   2640
atcacactca ctgcgaaggc agggcttatt tgccacatag gatggggaag accccctccca  2700 tgctcaatgt accagagcac ttcagaagac cattcaatat aggtctttac aagggaacga   2760
ttgagctcac aatgaccatc tacgatgatg agtcactgga agcagctcct atgatctggg   2820
atcatttcaa ttcttccaaa ttttctgatt tcagagagaa ggccttaatg tttggcctga   2880
ttgtcgagaa aaaggcatct ggagcgtggg tcctggattc tatcagccac ttcaaatgag   2940
ctagtctaac ttctagcttc tgaacaatcc ccggtttact cagtctctcc taattccagc   3000
ctctcgaaca actaatatcc tgtcttttct atccctatga aaaaaactaa cagagatcga   3060
tctgttctcc tgacactatg aagtgccttt tgtacttagc cttttfattc attggggtga   3120 attgcaagtt caccatagtt tttccacaca accaaaaagg aaactggaaa atgttccttt   3180
ctaattacca ttattgcccg tcaagctcag atttaaattg gcataatgac ttaataggca   3240
cagccataca agtcaaaatg cccaagagtc acaaggctat tcaagcagac ggttggatgt   3300
gtcatgcttc caaatgggtc actacttgtg atttccgctg gtatggaccg aagtatataa   3360
cacagtccat ccgatccttc actccatctg tagaacaatg caaggaaagc attgaacaaa   3420
cgaaacaagg aacttggctg aatccaggct tccctcctca aagttgtgga tatgcaactg   3480
tgacggatgc cgaagcagtg attgtccagg tgactcctca ccatgtgctg gttgatgaat   3540
acacaggaga atgggttgat tcacagttca tcaacgaaaa atgcagcaat tacatatgcc   3600
ccactgtcca taactctaca acctggcatt ctgactataa ggtcaaaggg ctatgtgatt   3660
ctaacctcat ttccatggac atcaccttct tctcagagga cggagagcta tcatccctgg   3720
gaaaggaggg cacagggttc agaagtaact actttgctta tgaaactgga ggcaaggcct   3780
gcaaaatgca atactgcaag cattgggag tcagactccc atcaggtgtc tggttcgaga   3840
tggctgataa ggatctcttt gctgcagcca gattccctga atgcccagaa gggtcaagta   3900
tctctgctcc atctcagacc tcagtggatg taagtctaat tcaggacgtt gagaggatct   3960
tggattattc cctctgccaa gaaacctgga gcaaaatcag agcgggtctt ccaatctctc   4020
cagtggatct cagctatctt gctcctaaaa acccaggaac cggtcctgct ttcaccataa   4080
tcaatggtac cctaaaatac tttgagacca gatacatcag agtcgatatt gctgctccaa   4140
tcctctcaag aatggtcgga atgatcagtg gaactaccac agaaagggaa ctgtgggatg   4200
actgggcacc atatgaagac gtggaaattg acccaatgg agttctgagg accagttcag   4260
gatataagtt tcctttatac atgattggac atggtatgtt ggactccgat cttcatctta   4320
gctcaaaggc tcaggtgttc gaacatcctc acattcaaga cgctgcttcg caacttcctg   4380
atgatgagag tttattttt ggtgatactg ggctatccaa aaatccaatc gagcttgtag   4440
```

```
aaggttggtt cagtagttgg aaaagctcta ttgcctctct tttctttatc atagggttaa    4500
tcattggact attcttggtt ctccgagttg gtatccatct ttgcattaaa ttaaagcaca    4560
ccaagaaaag acagatttat acagacatag agatgaaccg acttggaaag taactcaaat    4620
cctgcacaac agattcttca tgtttggacc aaatcaactt gtgataccat gctcaaagag    4680
gcctcaatta tatttgagtt tttaattttt atgaaaaaaa ctaacagcaa tcatggaagt    4740
ccacgatttt gagaccgacg agttcaatga tttcaatgaa gatgactatg ccacaagaga    4800
attcctgaat cccgatgagc gcatgacgta cttgaatcat gctgattaca atttgaattc    4860
tcctctaatt agtgatgata ttgacaattt gatcaggaaa ttcaattctc ttccgattcc    4920
ctcgatgtgg gatagtaaga actgggatgg agttcttgag atgttaacat catgtcaagc    4980
caatcccatc tcaacatctc agatgcataa atggatggga agttggttaa tgtctgataa    5040
tcatgatgcc agtcaagggt atagtttttt acatgaagtg gacaaagagg cagaaataac    5100
atttgacgtg gtggagacct tcatccgcgg ctggggcaac aaaccaattg aatacatcaa    5160
aaaggaagaa tggactgact cattcaaaat tctcgcttat ttgtgtcaaa agtttttgga    5220
cttacacaag ttgacattaa tcttaaatgc tgtctctgag gtggaattgc tcaacttggc    5280
gaggactttc aaaggcaaag tcagaagaag ttctcatgga acgaacatat gcaggattag    5340
ggttcccagc ttgggtccta ctttatttc agaaggatgg gcttacttca agaaacttga    5400
tattctaatg gaccgaaaact ttctgttaat ggtcaaagat gtgattatag ggaggatgca    5460
aacggtgcta tccatggtat gtagaataga caacctgttc tcagagcaag acatcttctc    5520
ccttctaaat atctacagaa ttggagataa aattgtggag aggcagggaa attttttctta    5580 tgacttgatt aaaatggtgg aaccgatatg caacttgaag ctgatgaaat tagcaagaga    5640
atcaaggcct ttagtcccac aattccctca ttttgaaaat catatcaaga cttctgttga    5700
tgaaggggca aaaattgacc gaggtataag attcctccat gatcagataa tgagtgtgaa    5760
aacagtggat ctcacactgg tgattatggg atcgttcaga cattgggggtc atcctttat     5820 agattattac actggactag aaaaattaca ttcccaagta accatgaaga aagatattga    5880
tgtgtcatat gcaaaagcac ttgcaagtga tttagctcgg attgttctat ttcaacagtt    5940
caatgatcat aaaaagtggt tcgtgaatgg agacttgctc cctcatgatc atcccttaa    6000 aagtcatgtt aaagaaaata catggcccac agctgctcaa gttcaagatt ttggagataa    6060
atggcatgaa cttccgctga ttaaatgttt tgaaataccc gacttactag acccatcgat    6120
aatatactct gacaaaagtc attcaatgaa taggtcagag gtgttgaaac atgtccgaat    6180
gaatccgaac actcctatcc ctagtaaaaa ggtgttgcag actatgttgg acacaaaggc    6240
taccaattgg aaagaatttc ttaaagagat tgatgagaag ggcttagatg atgatgatct    6300
aattattggt cttaaaggaa aggagaggga actgaagttg gcaggtagat ttttctccct    6360
aatgtcttgg aaattgcgag aatactttgt aattaccgaa tatttgataa agactcatt    6420 cgtccctatg tttaaaggcc tgacaatggc ggacgatcta actgcagtca ttaaaaagat    6480
gttagattcc tcatccggcc aaggattgaa gtcatatgag gcaatttgca tagccaatca    6540
cattgattac gaaaatgga ataaccacca aggaagtta tcaaacggcc cagtgttccg    6600
agttatgggc cagttcttag gttatccatc cttaatcgag agaactcatg aatttttga    6660 gaaaagtctt atatactaca atggaagacc agacttgatg cgtgttcaca acaacacact    6720
gatcaattca acctcccaac gagtttgttg gcaaggacaa gagggtggac tggaaggtct    6780
acggcaaaaa ggatggacta tcctcaatct actggttatt caaagagagg ctaaaatcag    6840
```

```
aaacactgct gtcaaagtct tggcacaagg tgataatcaa gttatttgca cacagtataa    6900
aacgaagaaa tcgagaaacg ttgtagaatt acagggtgct ctcaatcaaa tggtttctaa    6960
taatgagaaa attatgactg caatcaaaat agggacaggg aagttaggac ttttgataaa    7020
tgacgatgag actatgcaat ctgcagatta cttgaattat ggaaaaatac cgattttccg    7080
tggagtgatt agagggttag agaccaagag atggtcacga gtgacttgtg tcaccaatga    7140
ccaaataccc acttgtgcta atataatgag ctcagtttcc acaaatgctc tcaccgtagc    7200
tcattttgct gagaacccaa tcaatgccat gatacagtac aattattttg gacatttgc     7260
tagactcttg ttgatgatgc atgatcctgc tcttcgtcaa tcattgtatg aagttcaaga    7320
taagataccg ggcttgcaca gttctacttt caaatacgcc atgttgtatt tggacccttc    7380
cattggagga gtgtcgggca tgtctttgtc aggttttttg attagagcct tcccagatcc    7440
cgtaacagaa agtctctcat tctggagatt catccatgta catgctcgaa gtgagcatct    7500
gaaggagatg agtgcagtat ttggaaaccc cgagatagcc aagtttcgaa taactcacat    7560
agacaagcta gtagaagatc caacctctct gaacatcgct atgggaatga gtccagcgaa    7620
cttgttaaag actgaggtta aaaaatgctt aatcgaatca agacaaacca tcaggaacca    7680
ggtgattaag gatgcaacca tatatttgta tcatgaagag gatcggctca gaagtttctt    7740
atggtcaata aatcctctgt tccctagatt tttaagtgaa ttcaaatcag gcactttttt    7800
gggagtcgca gacgggctca tcagtctatt tcaaaattct cgtactattc ggaactcctt    7860
taagaaaaag tatcataggg aattggatga tttgattgtg aggagtgagg tatcctcttt    7920
gacacattta gggaaacttc atttgagaag gggatcatgt aaaatgtgga catgttcagc    7980
tactcatgct gacacattaa gatacaaatc ctggggccgt acagttattg gacaactgt     8040
accccatcca ttagaaatgt tgggtccaca acatcgaaaa gagactcctt gtgcaccatg    8100
taacacatca gggttcaatt atgtttctgt gcattgtcca gacgggatcc atgacgtctt    8160
tagttcacgg ggaccattgc ctgcttatct agggtctaaa acatctgaat ctacatctat    8220
tttgcagcct tgggaaaggg aaagcaaagt cccactgatt aaaagagcta cacgtcttag    8280
agatgctatc tcttggtttg ttgaacccga ctctaaacta gcaatgacta cttttctaa     8340
catccactct ttaacaggcg aagaatggac caaaaggcag catgggttca aaagaacagg    8400
gtctgccctt cataggtttt cgacatctcg gatgagccat ggtgggttcg catctcagag    8460
cactgcagca ttgaccaggt tgatggcaac tacagacacc atgagggatc tgggagatca    8520
gaatttcgac tttttattcc aagcaacgtt gctctatgct caaattacca ccactgttgc    8580
aagagacgga tggatcacca gttgtacaga tcattatcat attgcctgta agtcctgttt    8640
gagacccata gaagagatca ccctggactc aagtatggac tacacgcccc cagatgtatc    8700
ccatgtgctg aagacatgga ggaatgggga aggttcgtgg ggacaagaga taaaacagat    8760
ctatcccttta gaagggaatt ggaagaattt agcacctgct gagcaatcct atcaagtcgg    8820
cagatgtata ggttttctat atggagactt ggcgtataga aaatctactc atgccgagga    8880
cagttctcta tttcctctat ctatacaagg tcgtattaga ggtcgaggtt tcttaaaagg    8940
gttgctagac ggattaatga gagcaagttg ctgccaagta atacaccgga gaagtctggc    9000
tcatttgaag aggccggcca acgcagtgta cggaggtttg atttacttga ttgataaatt    9060
gagtgtatca cctccattcc tttctcttac tagatcagga cctattagag acgaattaga    9120
aacgattccc cacaagatcc caacctccta tccgacaagc aaccgtgata tgggggtgat    9180
```

```
tgtcagaaat tacttcaaat accaatgccg tctaattgaa aagggaaaat acagatcaca    9240
ttattcacaa ttatggttat tctcagatgt cttatccata gacttcattg gaccattctc    9300
tatttccacc accctcttgc aaatcctata caagccattt ttatctggga aagataagaa    9360
tgagttgaga gagctggcaa atctttcttc attgctaaga tcaggagagg ggtgggaaga    9420
catacatgtg aaattcttca ccaaggacat attattgtgt ccagaggaaa tcagacatgc    9480
ttgcaagttc gggattgcta aggataataa taaagacatg agctatcccc cttggggaag    9540
ggaatccaga gggacaatta caacaatccc tgtttattat acgaccaccc cttacccaaa    9600
gatgctagag atgcctccaa gaatccaaaa tccctgctg tccggaatca ggttgggcca     9660
attaccaact ggcgctcatt ataaaattcg gagtatatta catggaatgg gaatccatta    9720
cagggacttc ttgagttgtg gagacggctc cggaggatg actgctgcat tactacgaga     9780
aaatgtgcat agcagaggaa tattcaatag tctgttagaa ttatcagggt cagtcatgcg    9840
aggcgcctct cctgagcccc ccagtgccct agaaacttta ggaggagata atcgagatg     9900 tgtaaatggt gaaacatgtt gggaatatcc atctgactta tgtgacccaa ggacttggga    9960
ctatttcctc cgactcaaag caggcttggg gcttcaaatt gatttaattg taatggatat    10020
ggaagttcgg gattcttcta ctagcctgaa aattgagacg aatgttagaa attatgtgca    10080 ccggatttg gatgagcaag gagttttaat ctacaagact tatggaacat atatttgtga     10140
gagcgaaaag aatgcagtaa caatccttgg tcccatgttc aagacggtcg acttagttca    10200
aacagaattt agtagttctc aaacgtctga agtatatatg gtatgtaaag gtttgaagaa    10260
attaatcgat gaacccaatc ccgattggtc ttccatcaat gaatcctgga aaaacctgta    10320
cgcattccag tcatcagaac aggaatttgc cagagcaaag aaggttagta catactttac    10380
cttgacaggt attccctccc aattcattcc tgatcctttt gtaaacattg agactatgct    10440
acaaatattc ggagtaccca cgggtgtgtc tcatgcggct gccttaaaat catctgatag    10500
acctgcagat ttattgacca ttagcccttt ttatatggcg attatatcgt attataacat    10560
caatcatatc agagtaggac cgatacctcc gaaccccca tcagatggaa ttgcacaaaa     10620
tgtggggatc gctataactg gtataagctt ttggctgagt ttgatggaga aagacattcc    10680
actatatcaa cagtgtttag cagttatcca gcaatcattc ccgattaggt gggaggctgt    10740
ttcagtaaaa ggaggataca agcagaagtg gagtactaga ggtgatgggc tcccaaaaga    10800
tacccgaact tcagactcct ggccccaat cgggaactgg atcagatctc tggaattggt     10860
ccgaaaccaa gttcgtctaa atccattcaa tgagatcttg ttcaatcagc tatgtcgtac    10920
agtggataat catttgaaat ggtcaaattt gcgaagaaac acaggaatga ttgaatggat    10980
caatagacga atttcaaaag aagaccggtc tatactgatg ttgaagagtg acctacacga    11040
ggaaaactct tggagagatt aaaaaatcat gaggagactc caaactttaa gtatgaaaaa    11100
aactttgatc cttaagaccc tcttgtggtt tttattttt atctggtttt gtggtcttcg     11160
tgggtcggca tggcatctcc acctcctcgc ggtccgacct gggcatccga aggaggacgt    11220
cgtccactcg gatggctaag ggagagctcg gatccggctg ctaacaaagc ccgaaaggaa    11280
gctgagttgg ctgctgccac cgctgagcaa taactagcat aacccccttgg ggcctctaaa   11340 cgggtcttga ggggtttttt gctgaaagga ggaactatat ccggatcgag atcctctaga    11400
gtcgacctgc aggcatgcaa gcttgtattc tatagtgtca cctaaatcgt atgtgtatga    11460
tacataaggt tatgtattaa ttgtagccgc gttctaacga caatatgtac aagcctaatt    11520
gtgtagcatc tggcttactg aagcagaccc tatcatctct ctcgtaaact gccgtcagag    11580
```

```
tcggtttggt tggacgaacc ttctgagttt ctggtaacgc cgtcccgcac ccggaaatgg    11640
tcagcgaacc aatcagcagg gtcatcgcta gccagatcct ctacgccgga cgcatcgtgt    11700
ccggcatcac cggcgccaca ggtgcggttg ctggcgccta tatcgccgac atcaccgatg    11760
gggaagatcg ggctcgccac ttcgggctca tgagcgcttg tttcggcgtg ggtatggtgt    11820
caggccccgt ggccggggga ctgttgggcg ccatctcctt gcaccattcc ttgcggcggc    11880
ggtgctcaac ggcctcaacc tactactggg ctgcttccta atgcaggagt cgcataaggg    11940
agagcgtcga atggtgcact ctcagtacaa tctgctctga tgccgcatag ttaagccagc    12000
cccgacaccc gccaacaccc gctgacgcgc cctgacgggc ttgtctgctc ccggcatccg    12060
cttacagaca agctgtgacc gtctccggga gctgcatgtg tcagaggttt tcaccgtcat    12120
caccgaaacg cgcgagacga aagggcctcg tgatacgcct atttttatag gttaatgtca    12180
tgataataat ggtttcttag acgtcaggtg gcacttttcg gggaaatgtg cgcggaaccc    12240
ctatttgttt attttctaa atacattcaa atatgtatcc gctcatgaga caataaccct    12300
gataaatgct tcaataatat tgaaaaagga agagtatgag tattcaacat ttccgtgtcg    12360
cccttattcc cttttttgcg gcattttgcc ttcctgtttt tgctcaccca gaaacgctgg    12420
tgaaagtaaa agatgctgaa gatcagttgg gtgcacgagt gggttacatc gaactggatc    12480
tcaacagcgg taagatcctt gagagttttc gccccgaaga acgttttcca atgatgagca    12540
cttttaaagt tctgctatgt ggcgcggtat tatcccgtat tgacgccggg caagagcaac    12600
tcggtcgccg catacactat tctcagaatg acttggttga gtactcacca gtcacagaaa    12660
agcatcttac ggatggcatg acagtaagag aattatgcag tgctgccata accatgagtg    12720
ataacactgc ggccaactta cttctgacaa cgatcggagg accgaaggag ctaaccgctt    12780
ttttgcacaa catgggggat catgtaactc gccttgatcg ttgggaaccg gagctgaatg    12840
aagccatacc aaacgacgag cgtgacacca cgatgcctgt agcaatggca acaacgttgc    12900
gcaaactatt aactggcgaa ctacttactc tagcttcccg gcaacaatta atagactgga    12960
tggaggcgga taaagttgca ggaccacttc tgcgctcggc ccttccggct ggctggttta    13020
ttgctgataa atctggagcc ggtgagcgtg ggtctcgcgg tatcattgca gcactggggc    13080
cagatggtaa gccctcccgt atcgtagtta tctacacgac ggggagtcag gcaactatgg    13140
atgaacgaaa tagacagatc gctgagatag gtgcctcact gattaagcat tggtaactgt    13200
cagaccaagt ttactcatat atactttaga ttgatttaaa acttcatttt taatttaaaa    13260
ggatctaggt gaagatcctt tttgataatc tcatgaccaa aatcccttaa cgtgagtttt    13320
cgttccactg agcgtcagac cccgtagaaa agatcaaagg atcttcttga gatccttttt    13380
ttctgcgcgt aatctgctgc ttgcaaacaa aaaaaccacc gctaccagcg gtggtttgtt    13440
tgccggatca agagctacca actctttttc cgaaggtaac tggcttcagc agagcgcaga    13500
taccaaatac tgtccttcta gtgtagccgt agttaggcca ccacttcaag aactctgtag    13560
caccgcctac atacctcgct ctgctaatcc tgttaccagt ggctgctgcc agtggcgata    13620
agtcgtgtct taccgggttg gactcaagac gatagttacc ggataaggcg cagcggtcgg    13680
gctgaacggg gggttcgtgc acacagccca gcttggagcg aacgacctac accgaactga    13740
gatacctaca gcgtgagcta tgagaaagcg ccacgcttcc cgaagggaga aaggcggaca    13800
ggtatccggt aagcggcagg gtcggaacag gagagcgcac gagggagctt ccaggggaa    13860 acgcctggta tctttatagt cctgtcgggt ttcgccacct ctgacttgag cgtcgatttt    13920
```

-continued

```
tgtgatgctc gtcagggggg cggagcctat ggaaaaacgc cagcaacgcg gcctttttac  13980
ggttcctggc cttttgctgg ccttttgctc acatgttctt tcctgcgtta tcccctgatt  14040
ctgtggataa ccgtattacc gcctttgagt gagctgatac cgctcgccgc agccgaacga  14100
ccgagcgcag cgagtcagtg agcgaggaag cggaagagcg cccaatacgc aaaccgcctc  14160
tccccgcgcg ttggccgatt cattaatgca gggggatctc gatcccgcga aattaatacg  14220
actcactata gg                                                      14232
```

<210> SEQ ID NO 2
<211> LENGTH: 1512
<212> TYPE: DNA
<213> ORGANISM: Zika virus

<400> SEQUENCE: 2

```
atccggtgta tcggcgtgtc caaccgggac ttcgtggaag gcatgagcgg cggcacatgg     60
gtggacgtgg tgctggaaca tggcggctgc gtgacagtga tggctcagga caagcccacc    120
gtggacatcg agctcgtgac caccaccgtg tccaatatgg ccgaagtgcg gagctactgc    180
tacgaggcca gcatcagcga catggcaagc gacagcagat gccctacaca gggcgaggcc    240
tacctggaca agcagtccga cacccagtac gtgtgcaagc ggaccctggt ggatagaggc    300
tggggcaatg gctgcggcct gtttggcaag ggcagcctcg tgacctgcgc caagttcgcc    360
tgcagcaaga agatgaccgg caagagcatc cagcccgaga acctggaata ccggatcatg    420
ctgagcgtgc acggcagcca gcactccggc atgatcgtga acgacaccgg ccacgagaca    480
gacgagaacc gggccaaggt ggaaatcacc cccaacagcc ctagagccga ggccacactg    540
ggcggctttg gatctctggg cctggactgc gagcctagaa ccggcctgga tttcagcgac    600
ctgtactacc tgaccatgaa caacaagcac tggctggtgc acaaagagtg gttccacgac    660 atcccccctgc cctggcatgc cggcgctgat acaggcacac cccactggaa caacaaagag    720
gctctggtgg aattcaagga cgcccacgcc aagcggcaga ccgtggtggt gctgggatct    780
caggaaggcg ccgtgcatac agctctggct ggcgccctgg aagccgaaat ggatggcgcc    840
aaaggcagac tgtccagcgg ccacctgaag tgccggctga agatggacaa gctgcggctg    900
aagggcgtgt cctacagcct gtgtaccgcc gccttcacct tcaccaagat ccccgccgag    960
acactgcacg gcaccgtgac tgtggaagtg cagtacgccg gcaccgacgg cccttgtaaa   1020
gtgcctgctc agatggccgt ggatatgcag accctgaccc ccgtgggcag actgatcacc   1080
gccaaccctg tgatcaccga gagcaccgag aacagcaaga tgatgctgga actggacccc   1140
cccttcggcg actcctacat cgtgatcggc gtgggagaga agaagatcac ccaccactgg   1200
cacagaagcg gcagcaccat cggcaaggcc tttgaggcta cagtgcgggg agccaagaga   1260
atggccgtgc tgggagatac cgcctgggac tttggctctg tgggcggagc cctgaactct   1320
ctgggcaagg gaatccacca gatcttcgga gccgccttta agagcctgtt cggcggcatg   1380
agctggttca gccagatcct gatcggcacc ctgctgatgt ggctgggcct gaacgccaag   1440
aacggcagca tctccctgat gtgcctggct ctgggaggcg tgctgatctt cctgagcaca   1500
gccgtgtctg cc                                                       1512
```

<210> SEQ ID NO 3
<211> LENGTH: 492
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 3

```
agaagaggca gcgcctacta catgtacctg gaccggaacg atgccggcga ggccatcagc      60
tttccaacca ccctgggcat gaacaagtgc tacatccaga tcatggacct gggccacacc     120
tgtgacgcca ccatgagcta cgagtgcccc atgctggacg agggcgtgga acccgacgat     180
gtggactgct ggtgcaacac caccagcacc tgggtggtgt acggcacctg tcaccacaag     240
aagggcgaag ccagacggtc cagacgggcc gtgacactgc ctagccacag caccagaaag     300
ctgcagaccc ggtcccagac ctggctggaa agcagagagt acaccaagca cctgatccgg     360
gtggaaaact ggatcttccg gaaccccggc tttgccctgg ccgctgctgc tattgcttgg     420
ctgctgggca gcagcacctc ccagaaagtg atctacctcg tgatgatcct gctgatcgcc     480
cctgcctaca gc                                                         492
```

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
accagcgtgg gcatcgtggg cctgctgctg accaccgcca tggccgccga ggtgacc         57
```

<210> SEQ ID NO 5
<211> LENGTH: 15483
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
acgaagacaa acaaaccatt attatcatta aaaggctcag gagaaacttt aacagtaatc      60
agaattctcg agaaagccac catggtgagc aagggcgagg agctgttcac cggggtggtg     120
cccatcctgg tcgagctgga cggcgacgta aacggccaca gttcagcgt gtccggcgag      180
ggcgagggcg atgccaccta cggcaagctg accctgaagt tcatctgcac caccggcaag     240
ctgcccgtgc cctggcccac cctcgtgacc accctgacct acggcgtgca gtgcttcagc     300
cgctaccccg accacatgaa gcagcacgac ttcttcaagt ccgccatgcc cgaaggctac     360
gtccaggagc gcaccatctt cttcaaggac gacggcaact acaagacccg cgccgaggtg     420
aagttcgagg gcgacaccct ggtgaaccgc atcgagctga agggcatcga cttcaaggag     480
gacggcaaca tcctggggca caagctggag tacaactaca acagccacaa cgtctatatc     540
atggccgaca agcagaagaa cggcatcaag gtgaacttca gatccgcca caacatcgag      600
gacggcagcg tgcagctcgc cgaccactac cagcagaaca cccccatcgg cgacggcccc     660
gtgctgctgc ccgacaacca ctacctgagc acccagtccg ccctgagcaa agaccccaac     720
gagaagcgcg atcacatggt cctgctggag ttcgtgaccg ccgcgggat cactctcggc      780
atggacgagc tgtacaagta atggccatat gaaaaaaact aacagtaatc aaaatgtctg     840
ttacagtcaa gagaatcatt gacaacacag tcatagttcc aaaacttcct gcaaatgagg     900
atccagtgga atacccggca gattacttca gaaaatcaaa ggagattcct ctttacatca     960
atactacaaa aagtttgtca gatctaagag gatatgtcta ccaaggcctc aaatccggaa    1020
```

```
atgtatcaat catacatgtc aacagctact tgtatggagc attaaaggac atccggggta      1080
agttggataa agattggtca agtttcggaa taaacatcgg gaaagcaggg gatacaatcg      1140
gaatatttga ccttgtatcc ttgaaagccc tggacggcgt acttccagat ggagtatcgg      1200
atgcttccag aaccagcgca gatgacaaat ggttgccttt gtatctactt ggcttataca      1260
gagtgggcag aacacaaatg cctgaataca gaaaaaagct catggatggg ctgacaaatc      1320
aatgcaaaat gatcaatgaa cagtttgaac ctcttgtgcc agaaggtcgt gacattttg       1380 atgtgtgggg aaatgacagt aattacacaa aaattgtcgc tgcagtggac atgttcttcc      1440
acatgttcaa aaaacatgaa tgtgcctcgt tcagatacgg aactattgtt ccagattca       1500 aagattgtgc tgcattggca acatttggac acctctgcaa aataaccgga atgtctacag      1560
aagatgtaac gacctggatc ttgaaccgag aagttgcaga tgaaatggtc caaatgatgc      1620
ttccaggcca agaaattgac aaggccgatt catacatgcc ttatttgatc gactttggat      1680
tgtcttctaa gtctccatat tcttccgtca aaaaccctgc cttccacttc tgggggcaat      1740
tgacagctct tctgctcaga tccaccagag caaggaatgc cgacagcct gatgacattg       1800 agtatacatc tcttactaca gcaggtttgt tgtacgctta tgcagtagga tcctctgccg      1860
acttggcaca acagttttgt gttggagata caaatacac tccagatgat agtaccggag       1920
gattgacgac taatgcaccg ccacaaggca gagatgtggt cgaatggctc ggatggtttg      1980
aagatcaaaa cagaaaaccg actcctgata tgatgcagta tgcgaaaaga gcagtcatgt      2040
cactgcaagg cctaagagag aagacaattg gcaagtatgc taagtcagaa tttgacaaat      2100
gaccctataa ttctcagatc acctattata tattatgcta catatgaaaa aaactaacag      2160
atatcatgga taatctcaca aaagttcgtg agtatctcaa gtcctattct cgtctggatc      2220
aggcggtagg agagatagat gagatcgaag cacaacgagc tgaaaagtcc aattatgagt      2280
tgttccaaga ggatggagtg gaagagcata ctaagccctc ttattttcag gcagcagatg      2340
attctgacac agaatctgaa ccagaaattg aagacaatca aggtttgtat gcacaggatc      2400
cagaagctga gcaagttgaa ggctttatac agggccttt agatgactat gcagatgagg       2460
aagtggatgt tgtatttact tcggactgga aaccacctga gcttgaatct gacgagcatg      2520
gaaagacctt acggttgaca tcgccagagg gtttaagtgg agagcagaaa tcccagtggc      2580
tttcgacgat taaagcagtc gtgcaaagtg ccaaatactg gaatctggca gagtgcacat      2640
ttgaagcatc gggagaaggg gtcattatga aggagcgcca gataactccg gatgtatata      2700
aggtcactcc agtgatgaac acacatccgt cccaatcaga agcagtatca gatgtttggt      2760
ctctctcaaa gacatccatg actttccaac caagaaagc aagtcttcag cctctcacca       2820
tatccttgga tgaattgttc tcatctagag gagagttcat ctctgtcgga ggtgacggac      2880
gaatgtctca taaagaggcc atcctgctcg gcctgagata caaaaagttg tacaatcagg      2940
cgagagtcaa atattctctg tagactatga aaaaagtaa cagatatcac gatctaagtg       3000
ttatcccaat ccattcatca tgagttcctt aaagaagatt ctcggtctga aggggaaagg      3060
taagaaatct aagaaattag ggatcgcacc accccttat gaagaggaca ctagcatgga       3120
gtatgctccg agcgctccaa ttgacaaatc ctattttgga gttgacgaga tggacaccta      3180
tgatccgaat caattaagat atgagaaatt cttctttaca gtgaaaatga cggttagatc      3240
taatcgtccg ttcagaacat actcagatgt ggcagccgct gtatcccatt gggatcacat      3300
gtacatcgga atggcaggga aacgtccctt ctacaaaatc ttggcttttt tgggttcttc      3360
```

```
taatctaaag gccactccag cggtattggc agatcaaggt caaccagagt atcacactca    3420
ctgcgaaggc agggcttatt tgccacatag gatggggaag acccctccca tgctcaatgt    3480
accagagcac ttcagaagac cattcaatat aggtctttac aagggaacga ttgagctcac    3540
aatgaccatc tacgatgatg agtcactgga agcagctcct atgatctggg atcatttcaa    3600
ttcttccaaa ttttctgatt tcagagagaa ggccttaatg tttggcctga ttgtcgagaa    3660
aaaggcatct ggagcgtggg tcctggattc tatcagccac ttcaaatgag ctagtctaac    3720
ttctagcttc tgaacaatcc ccggtttact cagtctctcc taattccagc ctctcgaaca    3780
actaatatcc tgtcttttct atccctatga aaaaaactaa cagagatcga tctgtttcct    3840
tgacacgcgt accatgagaa gaggcagcgc ctactacatg tacctggacc ggaacgatgc    3900
cggcgaggcc atcagctttc aaccacccct gggcatgaac aagtgctaca tccagatcat    3960
ggacctgggc cacacctgtg acgccaccat gagctacgag tgccccatgc tggacgaggg    4020
cgtggaaccc gacgatgtgg actgctggtg caacaccacc agcacctggg tggtgtacgg    4080
cacctgtcac cacaagaagg gcgaagccag acggtccaga cgggccgtga cactgcctag    4140
ccacagcacc agaaagctgc agacccggtc ccagacctgg ctggaaagca gagagtacac    4200
caagcacctg atccgggtgg aaaactggat cttccggaac cccggctttg ccctggccgc    4260
tgctgctatt gcttggctgc tgggcagcag cacctcccag aaagtgatct acctcgtgat    4320
gatcctgctg atcgcccctg cctacagcat ccggtgtatc ggcgtgtcca accgggactt    4380
cgtggaaggc atgagcggcg gcacatgggt ggacgtggtg ctgaacatgc gcggctgcgt    4440
gacagtgatg gctcaggaca gcccaccgt ggacatcgag ctcgtgacca ccaccgtgtc    4500
caatatggcc gaagtgcgga gctactgcta cgaggccagc atcagcgaca tggccagcga    4560
cagcagatgc cctacacagg gcgaggccta cctggacaag cagtccgaca cccagtacgt    4620
gtgcaagcgg accctggtgg atagaggctg gggcaatggc tgcggcctgt ttggcaaggg    4680
cagcctcgtg acctgcgcca agttcgcctg cagcaagaag atgaccggca agagcatcca    4740
gcccgagaac ctggaatacc ggatcatgct gagcgtgcac ggcagccagc actccggcat    4800
gatcgtgaac gacaccggcc acgagacaga cgagaaccgg gccaaggtgg aaatcacccc    4860
caacagccct agagccgagg ccacactggg cggctttgga tctctgggcc tggactgcga    4920
gcctagaacc ggcctggatt tcagcgacct gtactacctg accatgaaca acaagcactg    4980
gctggtgcac aaagagtggt tccacgacat cccctgccc tggcatgccg cgctgatac    5040
aggcacaccc cactggaaca caaagaggc tctggtggaa ttcaaggacg cccacgccaa    5100
gcggcagacc gtggtggtgc tgggatctca ggaaggcgcc gtgcatacag ctctggctgg    5160
cgccctggaa gccgaaatgg atggcgccaa aggcagactg tccagcggcc acctgaagtg    5220
ccggctgaag atggacaagc tgcggctgaa gggcgtgtcc tacagcctgt gtaccgccgc    5280
cttcaccttc accaagatcc ccgccgagac actgcacggc accgtgactg tggaagtgca    5340
gtacgccggc accgacggcc cttgtaaagt gcctgctcag atggccgtgg atatgcagac    5400
cctgaccccc gtgggcagac tgatcaccgc caaccctgtg atcaccgaga caccgagaa    5460
cagcaagatg atgctggaac tggacccccc cttcggcgac tcctacatcg tgatcggcgt    5520
gggagagaag aagatcaccc accactggca cagaagcggc agcaccatcg gcaaggcctt    5580
tgaggctaca gtgcggggag ccaagagaat ggccgtgctg ggagataccg cctgggactt    5640
tggctctgtg gcggagcccc tgaactctct gggcaaggga atccaccaga tcttcggagc    5700
cgcctttaag agcctgttcg gcggcatgag ctggttcagc cagatcctga tcggcaccct    5760
```

```
gctgatgtgg ctgggcctga acgccaagaa cggcagcatc tccctgatgt gcctggctct    5820
gggaggcgtg ctgatcttcc tgagcacagc cgtgtctgcc taagcggccg ccctgcacaa    5880
cagattcttc atgtttggac caaatcaact tgtgatacca tgctcaaaga ggcctcaatt    5940
atatttgagt ttttaatttt tatgaaaaaa actaacagca atcatggaag tccacgattt    6000
tgagaccgac gagttcaatg atttcaatga agatgactat gccacaagag aattcctgaa    6060
tcccgatgag cgcatgacgt acttgaatca tgctgattac aatttgaatt ctcctctaat    6120
tagtgatgat attgacaatt tgatcaggaa attcaattct cttccgattc cctcgatgtg    6180
ggatagtaag aactgggatg gagttcttga gatgttaaca tcatgtcaag ccaatcccat    6240
ctcaacatct cagatgcata aatggatggg aagttggtta atgtctgata atcatgatgc    6300
cagtcaaggg tatagttttt tacatgaagt ggacaaagag gcagaaataa catttgacgt    6360
ggtggagacc ttcatccgcg gctggggcaa caaaccaatt gaatacatca aaaaggaaag    6420
atggactgac tcattcaaaa ttctcgctta tttgtgtcaa aagttttgg acttacacaa     6480 gttgacatta atcttaaatg ctgtctctga ggtggaattg ctcaacttgg cgaggacttt    6540
caaaggcaaa gtcagaagaa gttctcatgg aacgaacata tgcaggatta gggttcccag    6600
cttgggtcct acttttatt cagaaggatg ggcttacttc aagaaacttg atattctaat    6660
ggaccgaaac tttctgttaa tggtcaaaga tgtgattata gggaggatgc aaacggtgct    6720
atccatggta tgtagaatag acaacctgtt ctcagagcaa gacatcttct cccttctaaa    6780
tatctacaga attggagata aaattgtgga gaggcaggga aattttttctt atgacttgat    6840 taaaatggtg gaaccgatat gcaacttgaa gctgatgaaa ttagcaagag aatcaaggcc    6900
tttagtccca caattccctc attttgaaaa tcatatcaag acttctgttg atgaaggggc    6960
aaaaattgac cgaggtataa gattcctcca tgatcagata atgagtgtga aaacagtgga    7020
tctcacactg gtgatttatg gatcgttcag acattgggt catccttta tagattatta     7080 cactggacta gaaaaattac attcccaagt aaccatgaag aaagatattg atgtgtcata    7140
tgcaaaagca cttgcaagtg atttagctcg gattgttcta tttcaacagt tcaatgatca    7200
taaaaagtgg ttcgtgaatg gagacttgct ccctcatgat catcccttta aaagtcatgt    7260
taaagaaaat acatggccca cagctgctca agttcaagat tttggagata atggcatga    7320 acttccgctg attaaatgtt ttgaaatacc cgacttacta gacccatcga taatactc      7380 tgacaaaagt cattcaatga ataggtcaga ggtgttgaaa catgtccgaa tgaatccgaa    7440
cactcctatc cctagtaaaa aggtgttgca gactatgttg gacacaaagg ctaccaattg    7500
gaaagaattt cttaaagaga ttgatgagaa gggcttagat gatgatgatc taattattgg    7560
tcttaaagga aaggagaggg aactgaagtt ggcaggtaga ttttctccc taatgtcttg     7620 gaaattgcga gaatactttg taattaccga atatttgata aagactcatt tcgtccctat    7680
gtttaaaggc ctgacaatgg cggacgatct aactgcagtc attaaaaaga tgttagattc    7740
ctcatccggc caaggattga agtcatatga ggcaatttgc atagccaatc acattgatta    7800
cgaaaaatgg aataaccacc aaaggaagtt atcaaacggc ccagtgttcc gagttatggg    7860
ccagttctta ggttatccat ccttaatcga gagaactcat gaattttttg agaaaagtct    7920
tatatactac aatggaagac cagacttgat gcgtgttcac aacaacacac tgatcaattc    7980
aacctcccaa cgagtttgtt ggcaaggaca agagggtgga ctggaaggtc tacggcaaaa    8040
aggatggact atcctcaatc tactggttat tcaaagagag gctaaaatca gaaacactgc    8100
```

```
tgtcaaagtc ttggcacaag gtgataatca agttatttgc acacagtata aaacgaagaa   8160
atcgagaaac gttgtagaat tacagggtgc tctcaatcaa atggtttcta ataatgagaa   8220
aattatgact gcaatcaaaa tagggacagg gaagttagga cttttgataa atgacgatga   8280
gactatgcaa tctgcagatt acttgaatta tggaaaaata ccgattttcc gtggagtgat   8340
tagagggtta gagaccaaga gatggtcacg agtgacttgt gtcaccaatg accaaatacc   8400
cacttgtgct aatataatga gctcagtttc cacaaatgct ctcaccgtag ctcattttgc   8460
tgagaaccca atcaatgcca tgatacagta caattatttt gggacatttg ctagactctt   8520
gttgatgatg catgatcctg ctcttcgtca atcattgtat gaagttcaag ataagatacc   8580
gggcttgcac agttctactt tcaaatacgc catgttgtat ttggacccct tccattggagg   8640 agtgtcgggc atgtctttgt ccaggttttt gattagagcc ttcccagatc ccgtaacaga   8700
aagtctctca ttctggagat tcatccatgt acatgctcga agtgagcatc tgaaggagat   8760
gagtgcagta tttggaaacc ccgagatagc caagtttcga ataactcaca tagacaagct   8820
agtagaagat ccaacctctc tgaacatcgc tatgggaatg agtccagcga acttgttaaa   8880
gactgaggtt aaaaaatgct taatcgaatc aagacaaacc atcaggaacc aggtgattaa   8940
ggatgcaacc atatatttgt atcatgaaga ggatcggctc agaagtttct tatggtcaat   9000
aaatcctctg ttccctagat ttttaagtga attcaaatca ggcacttttt tgggagtcgc   9060
agacgggctc atcagtctat ttcaaaattc tcgtactatt cggaactcct ttaagaaaaa   9120
gtatcatagg gaattggatg atttgattgt gaggagtgag gtatcctctt tgacacattt   9180
agggaaactt catttgagaa ggggatcatg taaaatgtgg acatgttcag ctactcatgc   9240
tgacacatta agatacaaat cctggggccg tacagttatt gggacaactg taccccatcc   9300
attagaaatg ttgggtccac aacatcgaaa agagactcct tgtgcaccat gtaacacatc   9360
agggttcaat tatgtttctg tgcattgtcc agacgggatc catgacgtct ttagttcacg   9420
gggaccattg cctgcttatc tagggtctaa aacatctgaa tctacatcta ttttgcagcc   9480
ttgggaaagg gaaagcaaag tcccactgat taaaagagct acacgtctta gagatgctat   9540
ctcttggttt gttgaacccg actctaaact agcaatgact atactttcta acatccactc   9600
tttaacaggc gaagaatgga ccaaaaggca gcatgggttc aaaagaacag ggtctgccct   9660
tcataggttt tcgacatctc ggatgagcca tggtgggttc gcatctcaga gcactgcagc   9720
attgaccagg ttgatggcaa ctacagacac catgagggat ctgggagatc agaatttcga   9780 cttttttattc caagcaacgt tgctctatgc tcaaattacc accactgttg caagagacgg   9840
atggatcacc agttgtacag atcattatca tattgcctgt aagtcctgtt tgagacccat   9900
agaagagatc accctggact caagtatgga ctacacgccc ccagatgtat cccatgtgct   9960
gaagacatgg aggaatgggg aaggttcgtg gggacaagag ataaaacaga tctatccttt  10020
agaagggaat tggaagaatt tagcacctgc tgagcaatcc tatcaagtcg gcagatgtat  10080
aggttttcta tatggagact ggcgtatag aaaatctact catgccgagg acagttctct  10140
atttcctcta tctatacaag gtcgtattag aggtcgaggt ttcttaaaag ggttgctaga  10200
cggattaatg agagcaagtt gctgccaagt aatacaccgg agaagtctgg ctcatttgaa  10260
gaggccggcc aacgcagtgt acggaggttt gatttacttg attgataaat tgagtgtatc  10320
acctccattc ctttctctta ctagatcagg acctattaga gacgaattag aaacgattcc  10380
ccacaagatc ccaacctcct atccgacaag caaccgtgat atgggggtga ttgtcagaaa  10440
ttacttcaaa taccaatgcc gtctaattga aaagggaaaa tacagatcac attattcaca  10500
```

```
attatggtta ttctcagatg tcttatccat agacttcatt ggaccattct ctatttccac    10560
caccctcttg caaatcctat acaagccatt tttatctggg aaagataaga atgagttgag    10620
agagctggca aatctttctt cattgctaag atcaggagag gggtgggaag acatacatgt    10680
gaaattcttc accaaggaca tattattgtg tccagaggaa atcagacatg cttgcaagtt    10740
cgggattgct aaggataata ataaagacat gagctatccc ccttggggaa gggaatccag    10800
agggacaatt acaacaatcc ctgttttatta tacgaccacc ccttacccaa agatgctaga    10860
gatgcctcca agaatccaaa atccctgct gtccggaatc aggttgggcc aattaccaac    10920
tggcgctcat tataaaattc ggagtatatt acatggaatg ggaatccatt acagggactt    10980
cttgagttgt ggagacggct ccggagggat gactgctgca ttactacgag aaaatgtgca    11040
tagcagagga atattcaata gtctgttaga attatcaggg tcagtcatgc gaggcgcctc    11100
tcctgagccc cccagtgccc tagaaacttt aggaggagat aaatcgagat gtgtaaatgg    11160
tgaaacatgt tgggaatatc catctgactt atgtgaccca aggacttggg actatttcct    11220
ccgactcaaa gcaggcttgg ggcttcaaat tgatttaatt gtaatggata tggaagttcg    11280
ggattcttct actagcctga aaattgagac gaatgttaga aattatgtgc accggatttt    11340
ggatgagcaa ggagttttaa tctacaagac ttatggaaca tatatttgtg agagcgaaaa    11400
gaatgcagta acaatccttg gtcccatgtt caagacggtc gacttagttc aaacagaatt    11460
tagtagttct caaacgtctg aagtatatat ggtatgtaaa ggtttgaaga aattaatcga    11520
tgaacccaat cccgattggt cttccatcaa tgaatcctgg aaaaacctgt acgcattcca    11580
gtcatcagaa caggaatttg ccagagcaaa gaaggttagt acatacttta ccttgacagg    11640
tattccctcc caattcattc ctgatccttt tgtaaacatt gagactatgc tacaaatatt    11700
cggagtaccc acgggtgtgt ctcatgcggc tgccttaaaa tcatctgata gacctgcaga    11760
tttattgacc attagccttt tttatatggc gattatatcg tattataaca tcaatcatat    11820
cagagtagga ccgatacctc cgaaccccc atcagatgga attgcacaaa atgtggggat    11880
cgctataact ggtataagct tttggctgag tttgatggag aaagacattc cactatatca    11940
acagtgttta gcagttatcc agcaatcatt cccgattagg tgggaggctg tttcagtaaa    12000
aggaggatac aagcagaagt ggagtactag aggtgatggg ctcccaaaag atacccgaac    12060
ttcagactcc ttggccccaa tcgggaactg gatcagatct ctggaattgg tccgaaacca    12120
agttcgtcta aatccattca atgagatctt gttcaatcag ctatgtcgta cagtggataa    12180
tcatttgaaa tggtcaaatt tgcgaagaaa cacaggaatg attgaatgga tcaatagacg    12240
aatttcaaaa gaagaccggt ctatactgat gttgaagagt gacctacacg aggaaaactc    12300
ttggagagat taaaaaatca tgaggagact ccaaacttta agtatgaaaa aaactttgat    12360
ccttaagacc ctcttgtggt ttttattttt tatctggttt tgtggtcttc gtgggtcggc    12420
atggcatctc cacctcctcg cggtccgacc tgggcatccg aaggaggacg tcgtccactc    12480
ggatggctaa gggagagctc ggatccggct gctaacaaag cccgaaagga agctgagttg    12540
gctgctgcca ccgctgagca ataactagca taacccttg gggcctctaa acgggtcttg    12600
agggttttt tgctgaaagg aggaactata tccggatcga gatcctctag agtcgacctg    12660
caggcatgca agcttgtatt ctatagtgtc acctaaatcg tatgtgtatg atacataagg    12720
ttatgtatta attgtagccg cgttctaacg acaatatgta caagcctaat tgtgtagcat    12780
ctggcttact gaagcagacc ctatcatctc tctcgtaaac tgccgtcaga gtcggtttgg    12840
```

```
ttggacgaac cttctgagtt tctggtaacg ccgtcccgca cccggaaatg gtcagcgaac   12900
caatcagcag ggtcatcgct agccagatcc tctacgccgg acgcatcgtg gccggcatca   12960
ccggcgccac aggtgcggtt gctggcgcct atatcgccga catcaccgat ggggaagatc   13020
gggctcgcca cttcgggctc atgagcgctt gtttcggcgt gggtatggtg gcaggccccg   13080
tggccggggg actgttgggc gccatctcct tgcaccattc cttgcggcgg cggtgctcaa   13140
cggcctcaac ctactactgg gctgcttcct aatgcaggag tcgcataagg gagagcgtcg   13200
aatggtgcac tctcagtaca atctgctctg atgccgcata gttaagccag ccccgacacc   13260
cgccaacacc cgctgacgcg ccctgacggg cttgtctgct cccggcatcc gcttacagac   13320
aagctgtgac cgtctccggg agctgcatgt gtcagaggtt ttcaccgtca tcaccgaaac   13380
gcgcgagacg aaagggcctc gtgatacgcc tatttttata ggttaatgtc atgataataa   13440
tggtttctta gacgtcaggt ggcacttttc ggggaaatgt gcgcggaacc cctatttgtt   13500
tatttttcta aatacattca aatatgtatc cgctcatgag acaataaccc tgataaatgc   13560
ttcaataata ttgaaaaagg aagagtatga gtattcaaca tttccgtgtc gcccttattc   13620
ccttttttgc ggcattttgc cttcctgttt ttgctcaccc agaaacgctg gtgaaagtaa   13680
aagatgctga agatcagttg ggtgcacgag tgggttacat cgaactggat ctcaacagcg   13740
gtaagatcct tgagagtttt cgccccgaag aacgttttcc aatgatgagc acttttaaag   13800
ttctgctatg tggcgcggta ttatcccgta ttgacgccgg gcaagagcaa ctcggtcgcc   13860
gcatacacta ttctcagaat gacttggttg agtactcacc agtcacagaa aagcatctta   13920
cggatggcat gacagtaaga gaattatgca gtgctgccat aaccatgagt gataacactg   13980
cggccaactt acttctgaca acgatcggag gaccgaagga gctaaccgct tttttgcaca   14040
acatggggga tcatgtaact cgccttgatc gttgggaacc ggagctgaat gaagccatac   14100
caaacgacga gcgtgacacc acgatgcctg tagcaatggc aacaacgttg cgcaaactat   14160
taactggcga actacttact ctagcttccc ggcaacaatt aatagactgg atggaggcgg   14220
ataaagttgc aggaccactt ctgcgctcgg cccttccggc tggctggttt attgctgata   14280
aatctggagc cggtgagcgt gggtctcgcg gtatcattgc agcactgggg ccagatggta   14340
agccctcccg tatcgtagtt atctacacga cggggagtca ggcaactatg gatgaacgaa   14400
atagacagat cgctgagata ggtgcctcac tgattaagca ttggtaactg tcagaccaag   14460
tttactcata tatactttag attgatttaa aacttcattt ttaatttaaa aggatctagg   14520
tgaagatcct ttttgataat ctcatgacca aaatccctta acgtgagttt tcgttccact   14580
gagcgtcaga ccccgtagaa aagatcaaag gatcttcttg agatcctttt tttctgcgcg   14640
taatctgctg cttgcaaaca aaaaaaccac cgctaccagc ggtggtttgt ttgccggatc   14700
aagagctacc aactctttt ccgaaggtaa ctggcttcag cagagcgcag ataccaaata   14760
ctgtccttct agtgtagccg tagttaggcc accacttcaa gaactctgta gcaccgccta   14820
catacctcgc tctgctaatc ctgttaccag tggctgctgc cagtggcgat aagtcgtgtc   14880
ttaccgggtt ggactcaaga cgatagttac cggataaggc gcagcggtcg ggctgaacgg   14940
ggggttcgtg cacacagccc agcttggagc gaacgaccta caccgaactg agatacctac   15000
agcgtgagct atgagaaagc gccacgcttc ccgaagggag aaaggcggac aggtatccgg   15060
taagcggcag ggtcggaaca ggagagcgca cgagggagct tccaggggga aacgcctggt   15120
atctttatag tcctgtcggg tttcgccacc tctgacttga gcgtcgattt ttgtgatgct   15180
cgtcaggggg gcggagccta tggaaaaacg ccagcaacgc ggcctttta cggttcctgg   15240
```

```
ccttttgctg gccttttgct cacatgttct ttcctgcgtt atccctgat  tctgtggata    15300 accgtattac cgcctttgag tgagctgata ccgctcgccg cagccgaacg accgagcgca    15360
gcgagtcagt gagcgaggaa gcggaagagc gcccaatacg caaaccgcct ctccccgcgc    15420
gttggccgat tcattaatgc aggggatct  cgatcccgcg aaattaatac gactcactat    15480
agg                                                                  15483
```

<210> SEQ ID NO 6
<211> LENGTH: 15543
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
acgaagacaa acaaaccatt attatcatta aaaggctcag gagaaacttt aacagtaatc      60
agaattctcg agaaagccac catggtgagc aagggcgagg agctgttcac cggggtggtg     120
cccatcctgg tcgagctgga cggcgacgta acggccaca  agttcagcgt gtccggcgag     180
ggcgagggcg atgccaccta cggcaagctg accctgaagt tcatctgcac caccggcaag     240
ctgcccgtgc cctggcccac cctcgtgacc accctgacct acggcgtgca gtgcttcagc     300
cgctaccccg accacatgaa gcagcacgac ttcttcaagt ccgccatgcc cgaaggctac     360
gtccaggagc gcaccatctt cttcaaggac gacggcaact acaagacccg cgccgaggtg     420
aagttcgagg gcgacaccct ggtgaaccgc atcgagctga agggcatcga cttcaaggag     480
gacggcaaca tcctggggca agctggag tacaactaca  acagccacaa cgtctatatc     540
atggccgaca agcagaagaa cggcatcaag gtgaacttca gatccgcca  caacatcgag     600 gacggcagcg tgcagctcgc cgaccactac cagcagaaca ccccatcgg  cgacggcccc     660 gtgctgctgc ccgacaacca ctacctgagc acccagtccg ccctgagcaa agaccccaac     720
gagaagcgcg atcacatggt cctgctggag ttcgtgaccg ccgccgggat cactctcggc     780
atggacgagc tgtacaagta atggccatat gaaaaaaact aacagtaatc aaaatgtctg     840
ttacagtcaa gagaatcatt gacaacacag tcatagttcc aaaacttcct gcaaatgagg     900
atccagtgga atacccggca gattacttca gaaaatcaaa ggagattcct ctttacatca     960
atactacaaa aagtttgtca gatctaagag gatatgtcta ccaaggcctc aaatccggaa    1020
atgtatcaat catacatgtc aacagctact gtatggagc  attaaaggac atccggggta    1080
agttggataa agattggtca agtttcggaa taaacatcgg gaaagcaggg gatacaatcg    1140
gaatatttga ccttgtatcc ttgaaagccc tggacgcgt  acttccagat ggagtatcgg    1200
atgcttccag aaccagcgca gatgacaaat ggttgccttt gtatctactt ggcttataca    1260
gagtgggcag aacacaaatg cctgaataca gaaaaaagct catggatggg ctgacaaatc    1320
aatgcaaaat gatcaatgaa cagtttgaac ctcttgtgcc agaaggtcgt gacatttttg    1380
atgtgtgggg aaatgacagt aattacacaa aaattgtcgc tgcagtggac atgttcttcc    1440
acatgttcaa aaaacatgaa tgtgcctcgt tcagatacgg aactattgtt tccagattca    1500
aagattgtgc tgcattggca acatttggac acctctgcaa ataaccgga  atgtctacag    1560 aagatgtaac gacctggatc ttgaaccgag aagttgcaga tgaaatggtc caaatgatgc    1620
ttccaggcca agaaattgac aaggccgatt catacatgcc ttatttgatc gactttggat    1680
tgtcttctaa gtctccatat tcttccgtca aaaaccctgc cttccacttc tgggggcaat    1740
```

```
tgacagctct tctgctcaga tccaccagag caaggaatgc ccgacagcct gatgacattg    1800
agtatacatc tcttactaca gcaggtttgt tgtacgctta tgcagtagga tcctctgccg    1860
acttggcaca acagttttgt gttggagata acaaatacac tccagatgat agtaccggag    1920
gattgacgac taatgcaccg ccacaaggca gagatgtggt cgaatggctc ggatggtttg    1980
aagatcaaaa cagaaaaccg actcctgata tgatgcagta tgcgaaaaga gcagtcatgt    2040
cactgcaagg cctaagagag aagacaattg caagtatgc taagtcagaa tttgacaaat     2100
gaccctataa ttctcagatc acctattata tattatgcta catatgaaaa aaactaacag    2160
atatcatgga taatctcaca aaagttcgtg agtatctcaa gtcctattct cgtctggatc    2220
aggcggtagg agagatagat gagatcgaag cacaacgagc tgaaaagtcc aattatgagt    2280
tgttccaaga ggatggagtg gaagagcata ctaagccctc ttattttcag gcagcagatg    2340
attctgacac agaatctgaa ccagaaattg aagacaatca aggtttgtat gcacaggatc    2400
cagaagctga gcaagttgaa ggctttatac aggggccttt agatgactat gcagatgagg    2460
aagtggatgt tgtatttact tcggactgga aaccacctga gcttgaatct gacgagcatg    2520
gaaagacctt acggttgaca tcgccagagg gtttaagtgg agagcagaaa tcccagtggc    2580
tttcgacgat taaagcagtc gtgcaaagtg ccaaatactg gaatctggca gagtgcacat    2640
ttgaagcatc gggagaaggg gtcattatga aggagcgcca gataactccg gatgtatata    2700
aggtcactcc agtgatgaac acacatccgt cccaatcaga agcagtatca gatgtttggt    2760
ctctctcaaa gacatccatg actttccaac ccaagaaagc aagtcttcag cctctcacca    2820
tatccttgga tgaattgttc tcatctagag gagagttcat ctctgtcgga ggtgacggac    2880
gaatgtctca taaagaggcc atcctgctcg gcctgagata caaaaagttg tacaatcagg    2940
cgagagtcaa atattctctg tagactatga aaaaaagtaa cagatatcac gatctaagtg    3000
ttatcccaat ccattcatca tgagttcctt aaagaagatt ctcggtctga aggggaaagg    3060
taagaaatct aagaaattag ggatcgcacc acccccttat gaagaggaca ctagcatgga    3120
gtatgctccg agcgctccaa ttgacaaatc ctattttgga gttgacgaga tggacaccta    3180
tgatccgaat caattaagat atgagaaatt cttctttaca gtgaaaatga cggttagatc    3240
taatcgtccg ttcagaacat actcagatgt ggcagccgct gtatcccatt gggatcacat    3300
gtacatcgga atggcaggga aacgtccctt ctacaaaatc ttggcttttt tgggttcttc    3360
taatctaaag gccactccag cggtattggc agatcaaggt caaccagagt atcacactca    3420
ctgcgaaggc agggcttatt tgccacatag gatggggaag acccctccca tgctcaatgt    3480
accagagcac ttcagaagac cattcaatat aggtctttac aagggaacga ttgagctcac    3540
aatgaccatc tacgatgatg agtcactgga agcagctcct atgatctggg atcatttcaa    3600
ttcttccaaa ttttctgatt tcagagagaa ggccttaatg tttggcctga ttgtcgagaa    3660
aaaggcatct ggagcgtggg tcctggattc tatcagccac ttcaaatgag ctagtctaac    3720
ttctagcttc tgaacaatcc ccggtttact cagtctctcc taattccagc ctctcgaaca    3780
actaatatcc tgtctttcct atccctatga aaaaaactaa cagagatcga tctgtttcct    3840
tgacacgcgt gccaccatga ccagcgtggg catcgtgggc ctgctgctga ccaccgccat    3900
ggccgccgag gtgaccagaa gaggcagcgc ctactacatg tacctggacc ggaacgatgc    3960
cggcgaggcc atcagctttc aaccaccct gggcatgaac aagtgctaca tccagatcat    4020
ggacctgggc cacacctgtg acgccaccat gagctacgag tgccccatgc tggacgaggg    4080
```

```
cgtggaaccc gacgatgtgg actgctggtg caacaccacc agcacctggg tggtgtacgg    4140
cacctgtcac cacaagaagg gcgaagccag acggtccaga cgggccgtga cactgcctag    4200
ccacagcacc agaaagctgc agacccggtc ccagacctgg ctggaaagca gagagtacac    4260
caagcacctg atccgggtgg aaaactggat cttccggaac cccggctttg ccctggccgc    4320
tgctgctatt gcttggctgc tgggcagcag cacctcccag aaagtgatct acctcgtgat    4380
gatcctgctg atcgccctg cctacagcat ccggtgtatc ggcgtgtcca accgggactt    4440
cgtggaaggc atgagcggcg gcacatgggt ggacgtggtg ctggaacatg gcggctgcgt    4500
gacagtgatg gctcaggaca agcccaccgt ggacatcgag ctcgtgacca ccaccgtgtc    4560
caatatggcc gaagtgcgga gctactgcta cgaggccagc atcagcgaca tggccagcga    4620
cagcagatgc cctacacagg gcgaggccta cctggacaag cagtccgaca cccagtacgt    4680
gtgcaagcgg accctggtgg atagaggctg ggcaatggc tgcggcctgt ttggcaaggg    4740
cagcctcgtg acctgcgcca gttcgcctg cagcaagaag atgaccggca agagcatcca    4800
gcccgagaac ctggaatacc ggatcatgct gagcgtgcac ggcagccagc actccggcat    4860
gatcgtgaac gacaccggcc acgagacaga cgagaaccgg gccaaggtgg aaatcacccc    4920
caacagccct agagccgagg ccacactggg cggctttgga tctctgggcc tggactgcga    4980
gcctagaacc ggcctggatt tcagcgacct gtactacctg accatgaaca acaagcactg    5040
gctggtgcac aaagagtggt ccacgacat ccccctgccc tggcatgccg cgctgatac    5100 aggcacaccc cactggaaca caaagaggc tctggtggaa ttcaaggacg cccacgccaa    5160
gcggcagacc gtggtggtgc tgggatctca ggaaggcgcc gtgcatacag ctctggctgg    5220
cgccctggaa gccgaaatgg atggcgccaa aggcagactg tccagcggcc acctgaagtg    5280
ccggctgaag atggacaagc tgcggctgaa gggcgtgtcc tacagcctgt gtaccgccgc    5340
cttcaccttc accaagatcc ccgccgagac actgcacggc accgtgactg tggaagtgca    5400
gtacgccggc accgacggcc cttgtaaagt gcctgctcag atggccgtgg atatgcagac    5460 cctgacccc gtgggcagac tgatcaccgc caaccctgtg atcaccgaga gcaccgagaa    5520
cagcaagatg atgctggaac tggaccccccc cttcggcgac tcctacatcg tgatcggcgt    5580
gggagagaag aagatcaccc caccactggca cagaagcggc agcaccatcg gcaaggcctt    5640
tgaggctaca gtgcggggag ccaagagaat ggccgtgctg ggagataccg cctgggactt    5700
tggctctgtg ggcggagccc tgaactctct gggcaaggga atccaccaga tcttcggagc    5760
cgcctttaag agcctgttcg gcggcatgag ctggttcagc cagatcctga tcggcaccct    5820
gctgatgtgg ctgggcctga cgccaagaa cggcagcatc tccctgatgt gcctggctct    5880
gggaggcgtg ctgatcttcc tgagcacagc cgtgtctgcc tgagcggccg ccctgcacaa    5940
cagattcttc atgtttggac caaatcaact tgtgatacca tgctcaaaga ggcctcaatt    6000
atatttgagt tttaatttt tatgaaaaaa actaacagca atcatggaag tccacgattt    6060
tgagaccgac gagttcaatg atttcaatga agatgactat gccacaagag aattcctgaa    6120
tcccgatgag cgcatgacgt acttgaatca tgctgattac aatttgaatt ctcctctaat    6180
tagtgatgat attgacaatt tgatcaggaa attcaattct cttccgattc cctcgatgtg    6240
ggatagtaag aactgggatg gagttcttga gatgttaaca tcatgtcaag ccaatcccat    6300
ctcaacatct cagatgcata aatggatggg aagttggtta atgtctgata atcatgatgc    6360
cagtcaaggg tatagttttt tacatgaagt ggacaaagag gcagaaataa catttgacgt    6420
ggtggagacc ttcatccgcg gctggggcaa caaaccaatt gaatacatca aaaaggaaag    6480
```

```
atggactgac tcattcaaaa ttctcgctta tttgtgtcaa aagttttgg acttacacaa      6540
gttgacatta atcttaaatg ctgtctctga ggtggaattg ctcaacttgg cgaggacttt      6600
caaaggcaaa gtcagaagaa gttctcatgg aacgaacata tgcaggatta gggttcccag      6660
cttgggtcct actttattt cagaaggatg ggcttacttc aagaaacttg atattctaat      6720
ggaccgaaac tttctgttaa tggtcaaaga tgtgattata gggaggatgc aaacggtgct      6780
atccatggta tgtagaatag acaacctgtt ctcagagcaa gacatcttct cccttctaaa      6840
tatctacaga attggagata aaattgtgga gaggcaggga aattttttctt atgacttgat      6900
taaaatggtg gaaccgatat gcaacttgaa gctgatgaaa ttagcaagag aatcaaggcc      6960
tttagtccca caattccctc attttgaaaa tcatatcaag acttctgttg atgaagggc      7020
aaaaattgac cgaggtataa gattcctcca tgatcagata atgagtgtga aaacagtgga      7080
tctcacactg gtgatttatg gatcgttcag acattgggt catccttta tagattatta      7140
cactggacta gaaaaattac attcccaagt aaccatgaag aaagatattg atgtgtcata      7200
tgcaaaagca cttgcaagtg atttagctcg gattgttcta tttcaacagt tcaatgatca      7260
taaaaagtgg ttcgtgaatg gagacttgct ccctcatgat catccttta aaagtcatgt      7320
taaagaaaat acatggccca cagctgctca agttcaagat tttggagata aatggcatga      7380
acttccgctg attaaatgtt ttgaaatacc cgacttacta gacccatcga taatatactc      7440
tgacaaagt cattcaatga ataggtcaga ggtgttgaaa catgtccgaa tgaatccgaa      7500
cactcctatc cctagtaaaa aggtgttgca gactatgttg gacacaaagg ctaccaattg      7560
gaaagaattt cttaaagaga ttgatgagaa gggcttagat gatgatgatc taattattgg      7620
tcttaaagga aaggagaggg aactgaagtt ggcaggtaga ttttttctccc taatgtcttg      7680
gaaattgcga gaatactttg taattaccga atatttgata aagactcatt tcgtccctat      7740
gtttaaaggc ctgacaatgg cggacgatct aactgcagtc attaaaaaga tgttagattc      7800
ctcatccggc caaggattga agtcatatga ggcaatttgc atagccaatc acattgatta      7860
cgaaaaatgg aataaccacc aaaggaagtt atcaaacggc ccagtgttcc gagttatggg      7920
ccagttctta ggttatccat ccttaatcga gagaactcat gaattttttg agaaaagtct      7980
tatatactac aatggaagac cagacttgat gcgtgttcac aacaacacac tgatcaattc      8040
aacctcccaa cgagtttgtt ggcaaggaca agaggtgga ctggaaggtc tacggcaaaa      8100
aggatggact atcctcaatc tactggttat tcaaagagag gctaaaatca gaaacactgc      8160
tgtcaaagtc ttggcacaag gtgataatca agttatttgc acacagtata aaacgaagaa      8220
atcgagaaac gttgtagaat tacagggtgc tctcaatcaa atggtttcta ataatgagaa      8280
aattatgact gcaatcaaaa tagggacagg gaagttagga cttttgataa atgacgatga      8340
gactatgcaa tctgcagatt acttgaatta tggaaaaata ccgattttcc gtggagtgat      8400
tagagggtta gagaccaaga gatggtcacg agtgacttgt gtcaccaatg accaaatacc      8460
cacttgtgct aatataatga gctcagtttc cacaaatgct ctcaccgtag ctcattttgc      8520
tgagaaccca atcaatgcca tgatacagta caattattt gggacatttg ctagactctt      8580
gttgatgatg catgatcctg ctcttcgtca atcattgtat gaagttcaag ataagatacc      8640
gggcttgcac agttctactt tcaaatacgc catgttgtat ttggacccctt ccattggagg      8700
agtgtcgggc atgtctttgt ccaggttttt gattagagcc ttcccagatc ccgtaacaga      8760
aagtctctca ttctggagat tcatccatgt acatgctcga agtgagcatc tgaaggagat      8820
```

```
gagtgcagta tttggaaacc ccgagatagc caagtttcga ataactcaca tagacaagct   8880
agtagaagat ccaacctctc tgaacatcgc tatgggaatg agtccagcga acttgttaaa   8940
gactgaggtt aaaaaatgct taatcgaatc aagacaaacc atcaggaacc aggtgattaa   9000
ggatgcaacc atatatttgt atcatgaaga ggatcggctc agaagtttct tatggtcaat   9060
aaatcctctg ttccctagat ttttaagtga attcaaatca ggcactttt  tgggagtcgc   9120 agacgggctc atcagtctat ttcaaaattc tcgtactatt cggaactcct ttaagaaaaa   9180
gtatcatagg gaattggatg atttgattgt gaggagtgag gtatcctctt tgacacattt   9240
agggaaactt catttgagaa ggggatcatg taaaatgtgg acatgttcag ctactcatgc   9300
tgacacatta agatacaaat cctggggccg tacagttatt gggacaactg taccccatcc   9360
attagaaatg ttgggtccac aacatcgaaa agagactcct tgtgcaccat gtaacacatc   9420
agggttcaat tatgtttctg tgcattgtcc agacgggatc catgacgtct ttagttcacg   9480
gggaccattg cctgcttatc tagggtctaa aacatctgaa tctacatcta ttttgcagcc   9540
ttgggaaagg gaaagcaaag tcccactgat taaaagagct acacgtctta gagatgctat   9600
ctcttggttt gttgaacccg actctaaact agcaatgact atactttcta acatccactc   9660
tttaacaggc gaagaatgga ccaaaaggca gcatgggttc aaaagaacag ggtctgccct   9720
tcataggttt tcgacatctc ggatgagcca tggtgggttc gcatctcaga gcactgcagc   9780
attgaccagg ttgatggcaa ctacagacac catgagggat ctgggagatc agaatttcga   9840
ctttttattc caagcaacgt tgctctatgc tcaaattacc accactgttg caagagacgg   9900
atggatcacc agttgtacag atcattatca tattgcctgt aagtcctgtt tgagacccat   9960
agaagagatc accctggact caagtatgga ctacacgccc ccagatgtat cccatgtgct  10020
gaagacatgg aggaatgggg aaggttcgtg gggacaagag ataaaacaga tctatccttt  10080
agaagggaat tggaagaatt tagcacctgc tgagcaatcc tatcaagtcg gcagatgtat  10140
aggttttcta tatggagact tggcgtatag aaaatctact catgccgagg acagttctct  10200
atttcctcta tctatacaag gtcgtattag aggtcgaggt ttcttaaaag ggttgctaga  10260
cggattaatg agagcaagtt gctgccaagt aatacaccgg agaagtctgg ctcatttgaa  10320
gaggccggcc aacgcagtgt acggaggttt gatttacttg attgataaat tgagtgtatc  10380
acctccattc ctttctctta ctagatcagg acctattaga gacgaattag aaacgattcc  10440
ccacaagatc ccaacctcct atccgacaag caaccgtgat atgggggtga ttgtcagaaa  10500
ttacttcaaa taccaatgcc gtctaattga aaagggaaaa tacagatcac attattcaca  10560
attatggtta ttctcagatg tcttatccat agacttcatt ggaccattct ctatttccac  10620
caccctcttg caaatcctat acaagccatt tttatctggg aaagataaga atgagttgag  10680
agagctggca aatctttctt cattgctaag atcaggagag gggtgggaag acatacatgt  10740
gaaattcttc accaaggaca tattattgtg tccagaggaa atcagacatg cttgcaagtt  10800
cgggattgct aaggataata ataaagacat gagctatccc ccttggggaa gggaatccag  10860
agggacaatt acaacaatcc ctgtttatta tacgaccacc ccttacccaa agatgctaga  10920
gatgcctcca agaatccaaa atccctgct  gtccggaatc aggttgggcc aattaccaac  10980
tggcgctcat tataaaattc ggagtatatt acatggaatg gaatccatt  acagggactt  11040 cttgagttgt ggagacggct ccggagggat gactgctgca ttactacgag aaaatgtgca  11100
tagcagagga atattcaata gtctgttaga attatcaggg tcagtcatgc gaggcgcctc  11160
tcctgagccc cccagtgccc tagaaacttt aggaggagat aaatcgagat gtgtaaatgg  11220
```

```
tgaaacatgt tgggaatatc catctgactt atgtgaccca aggacttggg actatttcct    11280
ccgactcaaa gcaggcttgg ggcttcaaat tgatttaatt gtaatggata tggaagttcg    11340
ggattcttct actagcctga aaattgagac gaatgttaga aattatgtgc accggatttt    11400
ggatgagcaa ggagttttaa tctacaagac ttatggaaca tatatttgtg agagcgaaaa    11460
gaatgcagta acaatccttg gtcccatgtt caagacggtc gacttagttc aaacagaatt    11520
tagtagttct caaacgtctg aagtatatat ggtatgtaaa ggtttgaaga aattaatcga    11580
tgaacccaat cccgattggt cttccatcaa tgaatcctgg aaaaacctgt acgcattcca    11640
gtcatcagaa caggaatttg ccagagcaaa gaaggttagt acatacttta ccttgacagg    11700
tattccctcc caattcattc ctgatccttt tgtaaacatt gagactatgc tacaaatatt    11760
cggagtaccc acgggtgtgt ctcatgcggc tgccttaaaa tcatctgata gacctgcaga    11820
tttattgacc attagccttt tttatatggc gattatatcg tattataaca tcaatcatat    11880
cagagtagga ccgatacctc cgaaccccc atcagatgga attgcacaaa atgtggggat     11940
cgctataact ggtataagct tttggctgag tttgatggag aaagacattc cactatatca    12000
acagtgttta gcagttatcc agcaatcatt cccgattagg tgggaggctg tttcagtaaa    12060
aggaggatac aagcagaagt ggagtactag aggtgatggg ctcccaaaag atacccgaac    12120
ttcagactcc ttggcccccaa tcgggaactg gatcagatct ctggaattgg tccgaaacca    12180
agttcgtcta aatccattca atgagatctt gttcaatcag ctatgtcgta cagtggataa    12240
tcatttgaaa tggtcaaatt tgcgaagaaa cacaggaatg attgaatgga tcaatagacg    12300
aatttcaaaa gaagaccggt ctatactgat gttgaagagt gacctacacg aggaaaactc    12360
ttggagagat taaaaaatca tgaggagact ccaaacttta agtatgaaaa aaactttgat    12420
ccttaagacc ctcttgtggt ttttatttt tatctggttt tgtggtcttc gtgggtcggc      12480
atggcatctc cacctcctcg cggtccgacc tgggcatccg aaggaggacg tcgtccactc    12540
ggatggctaa gggagagctc ggatccggct gctaacaaag cccgaaagga agctgagttg    12600
gctgctgcca ccgctgagca ataactagca taacccttg gggcctctaa acgggtcttg     12660
aggggttttt tgctgaaagg aggaactata tccggatcga gatcctctag agtcgacctg    12720
caggcatgca agcttgtatt ctatagtgtc acctaaatcg tatgtgtatg atacataagg    12780
ttatgtatta attgtagccg cgttctaacg acaatatgta caagcctaat tgtgtagcat    12840
ctggcttact gaagcagacc ctatcatctc tctcgtaaac tgccgtcaga gtcggtttgg    12900
ttggacgaac cttctgagtt tctggtaacg ccgtcccgca cccggaaatg gtcagcgaac    12960
caatcagcag ggtcatcgct agccagatcc tctacgccgg acgcatcgtg gccggcatca    13020
ccggcgccac aggtgcggtt gctggcgcct atatcgccga catcaccgat ggggaagatc    13080
gggctcgcca cttcgggctc atgagcgctt gtttcggcgt gggtatggtg gcaggccccg    13140
tggccggggg actgttgggc gccatctcct tgcaccattc cttgcggcgg cggtgctcaa    13200
cggcctcaac ctactactgg gctgcttcct aatgcaggag tcgcataagg gagagcgtcg    13260
aatggtgcac tctcagtaca atctgctctg atgccgcata gttaagccag ccccgacacc    13320
cgccaacacc cgctgacgcg ccctgacggg cttgtctgct cccggcatcc gcttacagac    13380
aagctgtgac cgtctccggg agctgcatgt gtcagaggtt ttcaccgtca tcaccgaaac    13440
gcgcgagacg aaagggcctc gtgatacgcc tatttttata ggttaatgtc atgataataa    13500
tggtttctta gacgtcaggt ggcacttttc ggggaaatgt gcgcggaacc cctatttgtt    13560
```

-continued

```
tatttttcta aatacattca aatatgtatc cgctcatgag acaataaccc tgataaatgc    13620
ttcaataata ttgaaaaagg aagagtatga gtattcaaca tttccgtgtc gcccttattc    13680
cctttttgc  ggcattttgc cttcctgttt ttgctcaccc agaaacgctg gtgaaagtaa    13740
aagatgctga agatcagttg ggtgcacgag tgggttacat cgaactggat ctcaacagcg    13800
gtaagatcct tgagagtttt cgccccgaag aacgttttcc aatgatgagc acttttaaag    13860
ttctgctatg tggcgcggta ttatcccgta ttgacgccgg gcaagagcaa ctcggtcgcc    13920
gcatacacta ttctcagaat gacttggttg agtactcacc agtcacagaa aagcatctta    13980
cggatggcat gacagtaaga gaattatgca gtgctgccat aaccatgagt gataacactg    14040
cggccaactt acttctgaca acgatcggag gaccgaagga gctaaccgct ttttgcaca    14100
acatggggga tcatgtaact cgccttgatc gttgggaacc ggagctgaat gaagccatac    14160
caaacgacga gcgtgacacc acgatgcctg tagcaatggc aacaacgttg cgcaaactat    14220
taactggcga actacttact ctagcttccc ggcaacaatt aatagactgg atggaggcgg    14280
ataaagttgc aggaccactt ctgcgctcgg cccttccggc tggctggttt attgctgata    14340
aatctggagc cggtgagcgt gggtctcgcg gtatcattgc agcactgggg ccagatggta    14400
agccctcccg tatcgtagtt atctacacga cggggagtca ggcaactatg gatgaacgaa    14460
atagacagat cgctgagata ggtgcctcac tgattaagca ttggtaactg tcagaccaag    14520
tttactcata tatactttag attgatttaa aacttcattt ttaatttaaa aggatctagg    14580
tgaagatcct ttttgataat ctcatgacca aaatccctta acgtgagttt cgttccact    14640
gagcgtcaga ccccgtagaa aagatcaaag gatcttcttg agatcctttt tttctgcgcg    14700
taatctgctg cttgcaaaca aaaaaaccac cgctaccagc ggtggtttgt ttgccggatc    14760
aagagctacc aactctttt ccgaaggtaa ctggcttcag cagagcgcag ataccaaata    14820
ctgtccttct agtgtagccg tagttaggcc accacttcaa gaactctgta gcaccgccta    14880
catacctcgc tctgctaatc ctgttaccag tggctgctgc cagtggcgat aagtcgtgtc    14940
ttaccgggtt ggactcaaga cgatagttac cggataaggc gcagcggtcg ggctgaacgg    15000
ggggttcgtg cacacagccc agcttggagc gaacgaccta caccgaactg agatacctac    15060
agcgtgagct atgagaaagc gccacgcttc ccgaagggag aaaggcggac aggtatccgg    15120
taagcggcag ggtcggaaca ggagagcgca cgagggagct tccaggggga aacgcctggt    15180
atctttatag tcctgtcggg tttcgccacc tctgacttga gcgtcgattt tgtgatgct    15240
cgtcaggggg gcggagccta tggaaaaacg ccagcaacgc ggcctttta cggttcctgg    15300
ccttttgctg gccttttgct cacatgttct ttcctgcgtt atcccctgat tctgtggata    15360
accgtattac cgcctttgag tgagctgata ccgctcgccg cagccgaacg accgagcgca    15420
gcgagtcagt gagcgaggaa gcggaagagc gcccaatacg caaaccgcct ctccccgcgc    15480
gttggccgat tcattaatgc agggggatct cgatcccgcg aaattaatac gactcactat    15540
agg                                                                 15543
```

<210> SEQ ID NO 7
<211> LENGTH: 16299
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

-continued

```
acgaagacaa acaaaccatt attatcatta aaaggctcag gagaaacttt aacagtaatc      60
agaattctcg agaaagccac catgagaaga ggcagcgcct actacatgta cctggaccgg     120
aacgatgccg gcgaggccat cagctttcca accaccctgg gcatgaacaa gtgctacatc     180
cagatcatgg acctgggcca cacctgtgac gccaccatga gctacgagtg ccccatgctg     240
gacgagggcg tggaacccga cgatgtggac tgctggtgca acaccaccag cacctgggtg     300
gtgtacggca cctgtcacca caagaagggc gaagccagac ggtccagacg ggccgtgaca     360
ctgcctagcc acagcaccag aaagctgcag acccggtccc agacctggct ggaaagcaga     420
gagtacacca gcacctgat ccgggtggaa aactggatct tccggaaccc cggctttgcc      480
ctggccgctg ctgctattgc ttggctgctg ggcagcagca cctcccagaa agtgatctac     540
ctcgtgatga tcctgctgat cgcccctgcc tacagcatcc ggtgtatcgg cgtgtccaac     600
cgggacttcg tggaaggcat gagcggcggc acatgggtgg acgtggtgct ggaacatggc     660
ggctgcgtga cagtgatggc tcaggacaag cccaccgtgg acatcgagct cgtgaccacc     720
accgtgtcca atatggccga agtgcggagc tactgctacg aggccagcat cagcgacatg     780
gccagcgaca gcagatgccc tacacagggc gaggcctacc tggacaagca gtccgacacc     840
cagtacgtgt gcaagcggac cctggtggat agaggctggg gcaatggctg cggcctgttt     900
ggcaagggca gcctcgtgac ctgcgccaag ttcgcctgca gcaagaagat gaccggcaag     960
agcatccagc ccgagaacct ggaataccgg atcatgctga gcgtgcacgg cagccagcac    1020
tccggcatga tcgtgaacga caccggccac gagacagacg agaaccgggc caaggtggaa    1080 atcacccca acagccctag agccgaggcc acactgggcg gctttggatc tctgggcctg     1140
gactgcgagc ctagaaccgg cctggatttc agcgacctgt actacctgac catgaacaac    1200
aagcactggc tggtgcacaa agagtggttc cacgacatcc ccctgcctg gcatgccggc    1260 gctgatacag gcacacccca ctggaacaac aaagaggctc tggtggaatt caaggacgcc    1320
cacgccaagc ggcagaccgt ggtggtgctg ggatctcagg aaggcgccgt gcatacagct    1380
ctggctggcg ccctggaagc cgaaatggat ggcgccaaag gcagactgtc cagcggccac    1440
ctgaagtgcc ggctgaagat ggacaagctg cggctgaagg gcgtgtccta cagcctgtgt    1500
accgccgcct tcaccttcac caagatcccc gccgagacac tgcacggcac cgtgactgtg    1560
gaagtgcagt acgccggcac cgacggcccc tgtaaagtgc ctgctcagat ggccgtggat    1620
atgcagaccc tgaccccgt gggcagactg atcaccgcca accctgtgat caccgagagc    1680
accgagaaca gcaagatgat gctggaactg gacccccct cggcgactc ctacatcgtg     1740 atcggcgtgg agagaagaa gatcacccac cactggcaca gaagcggcag caccatcggc    1800
aaggcctttg aggctacagt gcggggagcc aagagaatgg ccgtgctggg agataccgcc    1860 tgggacttg gctctgtggg cggagccctg aactctctgg gcaagggaat ccaccagatc    1920 ttcgagccg cctttaagag cctgttcggc ggcatgagct ggttcagcca gatcctgatc    1980 ggcacctgc tgatgtggct gggcctgaac gccaagaacg gcagcatctc cctgatgtgc    2040
ctggctctgg aggcgtgct gatcttcctg agcacagccg tgtctgccta aatggccata    2100
tgaaaaaaac taacagtaat caaaatgtct gttacagtca agagaatcat tgacaacaca    2160
gtcatagttc caaaacttcc tgcaaatgag gatccagtgg aatacccggc agattacttc    2220
agaaaatcaa aggagattcc tctttacatc aatactacaa aagtttgtc agatctaaga    2280 ggatatgtct accaaggcct caaatccgga atgtatcaa tcatacatgt caacagctac    2340
ttgtatggag cattaaagga catccggggt aagttggata agattggtc aagtttcgga    2400
```

```
ataaacatcg ggaaagcagg ggatacaatc ggaatatttg accttgtatc cttgaaagcc    2460
ctggacggcg tacttccaga tggagtatcg gatgcttcca gaaccagcgc agatgacaaa    2520
tggttgcctt tgtatctact tggcttatac agagtgggca gaacacaaat gcctgaatac    2580
agaaaaagc tcatggatgg gctgacaaat caatgcaaaa tgatcaatga acagtttgaa     2640
cctcttgtgc cagaaggtcg tgacattttt gatgtgtggg gaaatgacag taattacaca    2700
aaaattgtcg ctgcagtgga catgttcttc cacatgttca aaaaacatga atgtgcctcg    2760
ttcagatacg gaactattgt ttccagattc aaagattgtg ctgcattggc aacatttgga    2820
cacctctgca aaataaccgg aatgtctaca gaagatgtaa cgacctggat cttgaaccga    2880
gaagttgcag atgaaatggt ccaaatgatg cttccaggcc aagaaattga caaggccgat    2940
tcatacatgc cttatttgat cgactttgga ttgtcttcta gtctccata ttcttccgtc     3000
aaaaaccctg ccttccactt ctgggggcaa ttgacagctc ttctgctcag atccaccaga    3060
gcaaggaatg cccgacagcc tgatgacatt gagtatacat ctcttactac agcaggtttg    3120
ttgtacgctt atgcagtagg atcctctgcc gacttggcac aacagttttg tgttggagat    3180
aacaaataca ctccagatga tagtaccgga ggattgacga ctaatgcacc gccacaaggc    3240
agagatgtgg tcgaatggct cggatggttt gaagatcaaa acagaaaacc gactcctgat    3300
atgatgcagt atgcgaaaag agcagtcatg tcactgcaag gcctaagaga aagacaatt    3360
ggcaagtatg ctaagtcaga atttgacaaa tgaccctata attctcagat cacctattat    3420
atattatgct acatatgaaa aaactaaca gatatcatgg ataatctcac aaaagttcgt    3480
gagtatctca agtcctattc tcgtctggat caggcggtag gagagataga tgagatcgaa    3540
gcacaacgag ctgaaaagtc caattatgag ttgttccaag aggatggagt ggaagagcat    3600
actaagccct cttattttca ggcagcagat gattctgaca cagaatctga accagaaatt    3660
gaagacaatc aaggtttgta tgcacaggat ccagaagctg agcaagttga aggctttata    3720
caggggcctt tagatgacta tgcagatgag gaagtggatg ttgtatttac ttcggactgg    3780
aaaccacctg agcttgaatc tgacgagcat ggaaagacct tacggttgac atcgccagag    3840
ggtttaagtg gagagcagaa atcccagtgg ctttcgacga ttaaagcagt cgtgcaaagt    3900
gccaaatact ggaatctggc agagtgcaca tttgaagcat cgggagaagg ggtcattatg    3960
aaggagcgcc agataactcc ggatgtatat aaggtcactc cagtgatgaa cacacatccg    4020
tcccaatcag aagcagtatc agatgtttgg tctctctcaa agacatccat gactttccaa    4080
cccaagaaag caagtcttca gcctctcacc atatccttgg atgaattgtt ctcatctaga    4140
ggagagttca tctctgtcgg aggtgacgga cgaatgtctc ataaagaggc catcctgctc    4200
ggcctgagat acaaaagtt gtacaatcag gcgagagtca aatattctct gtagactatg    4260
aaaaaagta acagatatca cgatctaagt gttatcccaa tccattcatc atgagttcct    4320
taaagaagat tctcggtctg aaggggaaag gtaagaaatc taagaaatta gggatcgcac    4380
cacccccta tgaagaggac actagcatgg agtatgctcc gagcgctcca attgacaaat    4440
cctattttgg agttgacgag atggacacct atgatccgaa tcaattaaga tatgagaaat    4500
tcttcttac agtgaaaatg acggttagat ctaatcgtcc gttcagaaca tactcagatg    4560
tggcagccgc tgtatcccat tgggatcaca tgtacatcgg aatggcaggg aaacgtccct    4620
tctacaaaat cttggctttt ttgggttctt ctaatctaaa ggccactcca gcggtattgg    4680
cagatcaagg tcaaccagag tatcacactc actgcgaagg cagggcttat ttgccacata    4740
```

-continued

```
ggatggggaa gaccccctccc atgctcaatg taccagagca cttcagaaga ccattcaata    4800
taggtcttta caagggaacg attgagctca caatgaccat ctacgatgat gagtcactgg    4860
aagcagctcc tatgatctgg gatcatttca attcttccaa attttctgat tcagagaga    4920
aggccttaat gtttggcctg attgtcgaga aaaaggcatc tggagcgtgg gtcctggatt    4980
ctatcagcca cttcaaatga gctagtctaa cttctagctt ctgaacaatc cccggtttac    5040
tcagtctctc ctaattccag cctctcgaac aactaatatc ctgtcttttc tatccctatg    5100
aaaaaaacta acagagatcg atctgtttcc ttgacacgcg taccatgaag tgccttttgt    5160
acttagcttt tttattcatc ggggtgaatt gcaagttcac catagttttt ccacacaacc    5220
gaaaaggaaa ctggaaaaat gttccttcca attaccatta ttgcccgtca agctcagatt    5280
taaattggca taatgactta ataggcacag ccttacaagt caaaatgccc aagagtcaca    5340
aggctattca agcagacggt tggatgtgtc atgcttccaa atgggtcact acttgtgatt    5400
tccgctggta cggaccggag tatataacac attccatccg atccttcact ccatctgtag    5460
aacaatgcaa ggaaagcatt gaacaaacga acaaggaac ttggctgaat ccaggcttcc    5520
ctcctcaaag ttgtggatat gcaactgtga cggatgctga agcagcgatt gtccaggtga    5580
ctcctcacca tgtgcttgtt gatgaataca caggagaatg ggttgattca cagttcatca    5640
acggaaaatg cagcaatgac atatgcccca ctgtccataa ctccacaacc tggcattccg    5700
actataaggt caaagggcta tgtgattcta acctcatttc catggacatc accttcttct    5760
cagaggacgg agagctatca tccctaggaa aggagggcac agggttcaga agtaactact    5820
ttgcttatga aactgagac aaggcctgca aaatgcagta ctgcaagcat tggggagtca    5880
gactcccatc aggtgtctgg ttcgagatgg ctgataagga tctctttgct gcagccagat    5940
tccctgaatg cccagaaggg tcaagtatct ctgctccatc tcagacctca gtggatgtaa    6000
gtctcattca ggacgttgag aggatcttgg attattccct ctgccaagaa acctggagca    6060
aaatcagagc gggtcttccc atctctccag tggatctcag ctatcttgct cctaaaaacc    6120
caggaaccgg tcctgtcttt accataatca atggtaccct aaaatacttt gagaccagat    6180
acatcagagt cgatattgct gctccaatcc tctcaagaat ggtcggaatg atcagtggaa    6240
ctaccacaga aagggaactg tgggatgact gggctccata tgaagacgtg gaaattggac    6300
ccaatggagt tctgaggacc agttcaggat ataagtttcc tttatatatg attggacatg    6360
gtatgttgga ctccgatctt catcttagct caaaggctca ggtgtttgaa catcctcaca    6420
ttcaagacgc tgcttcgcag cttcctgatg atgagacttt atttttggt gatactgggc    6480
tatccaaaaa tccaatcgag tttgtagaag gttggttcag tagttggaag agctctattg    6540
cctcttttttg ctttatcata gggttaatca ttggactatt cttggttctc cgagttggta    6600
tttatctttg cattaaatta aagcacacca agaaaagaca gatttataca gacatagaga    6660
tgaaccgact tggaaagaag cggccgcccct gcacaacaga ttcttcatgt ttggaccaaa    6720
tcaacttgtg ataccatgct caaagaggcc tcaattatat ttgagttttt aattttatg    6780
aaaaaaacta acagcaatca tggaagtcca cgattttgag accgacgagt tcaatgattt    6840
caatgaagat gactatgcca caagagaatt cctgaatccc gatgagcgca tgacgtactt    6900
gaatcatgct gattacaatt tgaattctcc tctaattagt gatgatattg acaatttgat    6960
caggaaattc aattctcttc cgattccctc gatgtgggat agtaagaact gggatggagt    7020
tcttgagatg ttaacatcat gtcaagccaa tcccatctca acatctcaga tgcataaatg    7080
gatgggaagt tggttaatgt ctgataatca tgatgccagt caagggtata gttttttaca    7140
```

```
tgaagtggac aaagaggcag aaataacatt tgacgtggtg gagaccttca tccgcggctg    7200
gggcaacaaa ccaattgaat acatcaaaaa ggaaagatgg actgactcat tcaaaattct    7260
cgcttatttg tgtcaaaagt ttttggactt acacaagttg acattaatct taaatgctgt    7320
ctctgaggtg gaattgctca acttggcgag gactttcaaa ggcaaagtca gaagaagttc    7380
tcatggaacg aacatatgca ggattagggt tcccagcttg gtcctactt ttatttcaga     7440 aggatgggct tacttcaaga aacttgatat tctaatggac cgaaactttc tgttaatggt    7500
caaagatgtg attataggga ggatgcaaac ggtgctatcc atggtatgta gaatagacaa    7560
cctgttctca gagcaagaca tcttctccct tctaaatatc tacagaattg gagataaaat    7620
tgtggagagg cagggaaatt tttcttatga cttgattaaa atggtggaac cgatatgcaa    7680
cttgaagctg atgaaattag caagagaatc aaggccttta gtcccacaat tccctcattt    7740
tgaaaatcat atcaagactt ctgttgatga aggggcaaaa attgaccgag gtataagatt    7800
cctccatgat cagataatga gtgtgaaaac agtggatctc acactggtga tttatggatc    7860
gttcagacat tggggtcatc cttttataga ttattacact ggactagaaa aattacattc    7920
ccaagtaacc atgaagaaag atattgatgt gtcatatgca aaagcacttg caagtgattt    7980
agctcggatt gttctatttc aacagttcaa tgatcataaa aagtggttcg tgaatggaga    8040
cttgctccct catgatcatc cctttaaaag tcatgttaaa gaaaatacat ggcccacagc    8100
tgctcaagtt caagattttg gagataaatg gcatgaactt ccgctgatta atgttttga    8160 aatacccgac ttactagacc catcgataat atactctgac aaaagtcatt caatgaatag    8220
gtcagaggtg ttgaaacatg tccgaatgaa tccgaacact cctatcccta gtaaaaaggt    8280
gttgcagact atgttggaca caaaggctac caattggaaa gaatttctta aagagattga    8340
tgagaagggc ttagatgatg atgatctaat tattggtctt aaaggaaagg agagggaact    8400
gaagttggca ggtagatttt tctccctaat gtcttggaaa ttgcgagaat actttgtaat    8460
taccgaatat ttgataaaga ctcatttcgt ccctatgttt aaaggcctga caatggcgga    8520
cgatctaact gcagtcatta aaaagatgtt agattcctca tccggccaag gattgaagtc    8580
atatgaggca atttgcatag ccaatcacat tgattacgaa aaatgaata accaccaaag     8640 gaagttatca aacggcccag tgttccgagt tatgggccag ttcttaggtt atccatcctt    8700
aatcgagaga actcatgaat tttttgagaa aagtcttata tactacaatg gaagaccaga    8760
cttgatgcgt gttcacaaca acacactgat caattcaacc tcccaacgag tttgttggca    8820
aggacaagag ggtggactgg aaggtctacg gcaaaaagga tggactatcc tcaatctact    8880
ggttattcaa agagaggcta aaatcagaaa cactgctgtc aaagtcttgg cacaaggtga    8940
taatcaagtt atttgcacac agtataaaac gaagaaatcg agaaacgttg tagaattaca    9000
gggtgctctc aatcaaatgg tttctaataa tgagaaaatt atgactgcaa tcaaaatagg    9060
gacagggaag ttaggacttt tgataaatga cgatgagact atgcaatctg cagattactt    9120
gaattatgga aaaataccga ttttccgtgg agtgattaga gggttagaga ccaagagatg    9180
gtcacgagtg acttgtgtca ccaatgacca aataccact tgtgctaata taatgagctc     9240
agtttccaca aatgctctca ccgtagctca ttttgctgag aacccaatca atgccatgat    9300
acagtacaat tattttggga catttgctag actcttgttg atgatgcatg atcctgctct    9360
tcgtcaatca ttgtatgaag ttcaagataa gataccgggc ttgcacagtt ctactttcaa    9420
atacgccatg ttgtatttgg acccttccat tggaggagtg tcgggcatgt ctttgtccag    9480
```

```
gtttttgatt agagccttcc cagatcccgt aacagaaagt ctctcattct ggagattcat    9540
ccatgtacat gctcgaagtg agcatctgaa ggagatgagt gcagtatttg aaacccga     9600
gatagccaag tttcgaataa ctcacataga caagctagta aagatccaa cctctctgaa    9660
catcgctatg ggaatgagtc cagcgaactt gttaaagact gaggttaaaa aatgcttaat   9720
cgaatcaaga caaaccatca ggaaccaggt gattaaggat gcaaccatat atttgtatca   9780
tgaagaggat cggctcagaa gtttcttatg gtcaataaat cctctgttcc ctagatttt    9840
aagtgaattc aaatcaggca cttttttggg agtcgcagac gggctcatca gtctatttca   9900
aaattctcgt actattcgga actcctttaa gaaaaagtat catagggaat tggatgattt   9960
gattgtgagg agtgaggtat cctctttgac acatttaggg aaacttcatt tgagaagggg  10020
atcatgtaaa atgtggacat gttcagctac tcatgctgac acattaagat acaaatcctg  10080
gggccgtaca gttattggga caactgtacc ccatccatta gaaatgttgg gtccacaaca  10140
tcgaaaagag actccttgtg caccatgtaa cacatcaggg ttcaattatg tttctgtgca  10200
ttgtccagac gggatccatg acgtctttag ttcacgggga ccattgcctg cttatctagg  10260
gtctaaaaca tctgaatcta catctatttt gcagccttgg gaaagggaaa gcaaagtccc  10320
actgattaaa agagctacac gtcttagaga tgctatctct tggtttgttg aacccgactc  10380
taaactagca atgactatac tttctaacat ccactcttta acaggcgaag aatggaccaa  10440
aaggcagcat gggttcaaaa gaacagggtc tgcccttcat aggttttcga catctcggat  10500
gagccatggt gggttcgcat ctcagagcac tgcagcattg accaggttga tggcaactac  10560
agacaccatg agggatctgg gagatcagaa tttcgacttt ttattccaag caacgttgct  10620
ctatgctcaa attaccacca ctgttgcaag agacggatgg atcaccagtt gtacagatca  10680
ttatcatatt gcctgtaagt cctgtttgag acccatagaa gagatcaccc tggactcaag  10740
tatggactac acgcccccag atgtatccca tgtgctgaag acatggagga atgggaagg   10800
ttcgtgggga caagagataa aacagatcta cctttagaa gggaattgga agaatttagc   10860
acctgctgag caatcctatc aagtcggcag atgtataggt tttctatatg gagacttggc  10920
gtatagaaaa tctactcatg ccgaggacag ttctctattt cctctatcta tacaaggtcg  10980
tattagaggt cgaggtttct taaaagggtt gctagacgga ttaatgagag caagttgctg  11040
ccaagtaata caccggagaa gtctggctca tttgaagagg ccggccaacg cagtgtacgg  11100
aggtttgatt tacttgattg ataaattgag tgtatcacct ccattccttt ctcttactag  11160
atcaggacct attagagacg aattagaaac gattccccac aagatcccaa cctcctatcc  11220
gacaagcaac cgtgatatgg gggtgattgt cagaaattac ttcaaatacc aatgccgtct  11280
aattgaaaag ggaaaataca gatcacatta ttcacaatta tggttattct cagatgtctt  11340
atccatagac ttcattggac cattctctat ttccaccacc ctcttgcaaa tcctatacaa  11400
gccattttta tctgggaaag ataagaatga gttgagagag ctggcaaatc tttcttcatt  11460
gctaagatca ggagagggt gggaagacat acatgtgaaa ttcttcacca aggacatatt  11520
attgtgtcca gaggaaatca gacatgcttg caagttcggg attgctaagg ataataataa  11580
agacatgagc tatccccctt ggggaaggga atccagaggg acaattacaa caatccctgt  11640
ttattatacg accaccccott acccaaagat gctagagatg cctccaagaa tccaaaatcc  11700
cctgctgtcc ggaatcaggt tgggccaatt accaactggc gctcattata aaattcggag  11760
tatattacat ggaatgggaa tccattacag ggacttcttg agttgtggag acggctccgg  11820
agggatgact gctgcattac tacgagaaaa tgtgcatagc agaggaatat tcaatagtct  11880
```

```
gttagaatta tcagggtcag tcatgcgagg cgcctctcct gagcccccca gtgccctaga    11940
aactttagga ggagataaat cgagatgtgt aaatggtgaa acatgttggg aatatccatc    12000
tgacttatgt gacccaagga cttgggacta tttcctccga ctcaaagcag gcttggggct    12060
tcaaattgat ttaattgtaa tggatatgga agttcgggat tcttctacta gcctgaaaat    12120
tgagacgaat gttagaaatt atgtgcaccg gattttggat gagcaaggag ttttaatcta    12180
caagacttat ggaacatata tttgtgagag cgaaaagaat gcagtaacaa tccttggtcc    12240
catgttcaag acgtcgact tagttcaaac agaatttagt agttctcaaa cgtctgaagt     12300
atatatggta tgtaaaggtt tgaagaaatt aatcgatgaa cccaatcccg attggtcttc    12360
catcaatgaa tcctggaaaa acctgtacgc attccagtca tcagaacagg aatttgccag    12420
agcaaagaag gttagtacat actttacctt gacaggtatt ccctcccaat tcattcctga    12480
tccttttgta aacattgaga ctatgctaca aatattcgga gtacccacgg gtgtgtctca    12540
tgcggctgcc ttaaaatcat ctgatagacc tgcagattta ttgaccatta gccttttta    12600 tatggcgatt atatcgtatt ataacatcaa tcatatcaga gtaggaccga tacctccgaa    12660
ccccccatca gatggaattg cacaaaatgt ggggatcgct ataactggta taagcttttg    12720
gctgagtttg atggagaaag acattccact atatcaacag tgtttagcag ttatccagca    12780
atcattcccg attaggtggg aggctgtttc agtaaaagga ggatacaagc agaagtggag    12840
tactagaggt gatgggctcc caaaagatac ccgaacttca gactccttgg ccccaatcgg    12900
gaactggatc agatctctgg aattggtccg aaaccaagtt cgtctaaatc cattcaatga    12960
gatcttgttc aatcagctat gtcgtacagt ggataatcat ttgaaatggt caaatttgcg    13020
aagaaacaca ggaatgattg aatggatcaa tagacgaatt tcaaaagaag accggtctat    13080
actgatgttg aagagtgacc tacacgagga aaactcttgg agagattaaa aaatcatgag    13140
gagactccaa actttaagta tgaaaaaaac tttgatcctt aagaccctct tgtggttttt    13200 atttttatc tggttttgtg gtcttcgtgg gtcggcatgg catctccacc tcctcgcggt      13260
ccgacctggg catccgaagg aggacgtcgt ccactcggat ggctaaggga gagctcggat    13320
ccggctgcta acaaagcccg aaaggaagct gagttggctg ctgccaccgc tgagcaataa    13380
ctagcataac cccttggggc ctctaaacgg gtcttgaggg gttttttgct gaaaggagga    13440
actatatccg gatcgagatc tctctagagtc gacctgcagg catgcaagct tgtattctat    13500
agtgtcacct aaatcgtatg tgtatgatac ataaggttat gtattaattg tagccgcgtt    13560
ctaacgacaa tatgtacaag cctaattgtg tagcatctgg cttactgaag cagaccctat    13620
catctctctc gtaaactgcc gtcagagtcg gtttggttgg acgaaccttc tgagtttctg    13680
gtaacgccgt cccgcacccg gaaatggtca gcgaaccaat cagcagggtc atcgctagcc    13740
agatcctcta cgccggacgc atcgtggccg gcatcaccgg cgccacaggt gcggttgctg    13800
gcgcctatat cgccgacatc accgatgggg aagatcgggc tcgccacttc gggctcatga    13860
gcgcttgttt cggcgtgggt atggtggcag gccccgtggc cgggggactg ttgggcgcca    13920
tctccttgca ccattccttg cggcggcggt gctcaacggc ctcaacctac tactgggctg    13980
cttcctaatg caggagtcgc ataagggaga gcgtcgaatg gtgcactctc agtacaatct    14040
gctctgatgc cgcatagtta agccagcccc gacacccgcc aacacccgct gacgcgccct    14100
gacgggcttg tctgctcccg gcatccgctt acagacaagc tgtgaccgtc tccgggagct    14160
gcatgtgtca gaggttttca ccgtcatcac cgaaacgcgc gagacgaaag gcctcgtga     14220
```

```
tacgcctatt tttataggtt aatgtcatga taataatggt ttcttagacg tcaggtggca    14280
cttttcgggg aaatgtgcgc ggaacccta  tttgtttatt tttctaaata cattcaaata    14340
tgtatccgct catgagacaa taaccctgat aaatgcttca ataatattga aaaggaaga     14400 gtatgagtat tcaacatttc cgtgtcgccc ttattccctt ttttgcggca ttttgccttc    14460
ctgtttttgc tcacccagaa acgctggtga agtaaaaga  tgctgaagat cagttgggtg    14520
cacgagtggg ttacatcgaa ctggatctca acagcggtaa gatccttgag agttttcgcc    14580
ccgaagaacg tttccaatg  atgagcactt ttaaagttct gctatgtggc gcggtattat    14640
cccgtattga cgccgggcaa gagcaactcg gtcgccgcat acactattct cagaatgact    14700
tggttgagta ctcaccagtc acagaaaagc atcttacgga tggcatgaca gtaagagaat    14760
tatgcagtgc tgccataacc atgagtgata acactgcggc caacttactt ctgacaacga    14820
tcggaggacc gaaggagcta accgcttttt tgcacaacat gggggatcat gtaactcgcc    14880
ttgatcgttg ggaaccggag ctgaatgaag ccataccaaa cgacgagcgt gacaccacga    14940
tgcctgtagc aatggcaaca acgttgcgca aactattaac tggcgaacta cttactctag    15000
cttcccggca acaattaata gactggatgg aggcggataa agttgcagga ccacttctgc    15060
gctcggccct tccggctggc tggtttattg ctgataaatc tggagccggt gagcgtgggt    15120
ctcgcggtat cattgcagca ctggggccag atggtaagcc ctcccgtatc gtagttatct    15180
acacgacggg gagtcaggca actatggatg aacgaaatag acagatcgct gagataggtg    15240
cctcactgat taagcattgg taactgtcag accaagttta ctcatatata ctttagattg    15300
atttaaaact tcatttttaa tttaaaagga tctaggtgaa gatcctttt  gataatctca    15360 tgaccaaaat cccttaacgt gagttttcgt tccactgagc gtcagacccc gtagaaaaga    15420
tcaaaggatc ttcttgagat cctttttttc tgcgcgtaat ctgctgcttg caaacaaaaa    15480
aaccaccgct accagcggtg gttttgtttgc cggatcaaga gctaccaact cttttccga    15540 aggtaactgg cttcagcaga gcgcagatac caaatactgt ccttctagtg tagccgtagt    15600
taggccacca cttcaagaac tctgtagcac cgcctacata cctcgctctg ctaatcctgt    15660
taccagtggc tgctgccagt ggcgataagt cgtgtcttac cgggttggac tcaagacgat    15720
agttaccgga taaggcgcag cggtcgggct gaacggggg  ttcgtgcaca cagcccagct    15780
tggagcgaac gacctacacc gaactgagat acctacagcg tgagctatga gaaagcgcca    15840
cgcttcccga agggagaaag gcggacaggt atccggtaag cggcagggtc ggaacaggag    15900
agcgcacgag ggagcttcca gggggaaacg cctggtatct ttatagtcct gtcgggtttc    15960
gccacctctg acttgagcgt cgatttttgt gatgctcgtc aggggggcgg agcctatgga    16020
aaaacgccag caacgcggcc ttttacggt  tcctggcctt ttgctggcct tttgctcaca    16080
tgttctttcc tgcgttatcc cctgattctg tggataaccg tattaccgcc tttgagtgag    16140
ctgataccgc tcgccgcagc cgaacgaccg agcgcagcga gtcagtgagc gaggaagcgg    16200
aagagcgccc aatacgcaaa ccgcctctcc ccgcgcgttg gccgattcat taatgcaggg    16260
ggatctcgat cccgcgaaat taatacgact cactatagg                          16299
```

<210> SEQ ID NO 8
<211> LENGTH: 16341
<212> TYPE: DNA
<213> ORGANISM: Artificial Sequence
<220> FEATURE:
<223> OTHER INFORMATION: Description of Artificial Sequence: Synthetic polynucleotide

```
<400> SEQUENCE: 8
acgaagacaa acaaaccatt attatcatta aaaggctcag gagaaacttt aacagtaatc      60
agaattcgcc accatgacca gcgtgggcat cgtgggcctg ctgctgacca ccgccatggc     120
cgccgaggtg accagaagag gcagcgccta ctacatgtac ctggaccgga acgatgccgg     180
cgaggccatc agctttccaa ccaccctggg catgaacaag tgctacatcc agatcatgga     240
cctgggccac acctgtgacg ccaccatgag ctacgagtgc cccatgctgg acgagggcgt     300
ggaacccgac gatgtggact gctggtgcaa caccaccagc acctgggtgg tgtacggcac     360
ctgtcaccac aagaagggcg aagccagacg gtccagacgg gccgtgacac tgcctagcca     420
cagcaccaga aagctgcaga cccggtccca gacctggctg gaaagcagag agtacaccaa     480
gcacctgatc cgggtggaaa actggatctt ccggaacccc ggctttgccc tggccgctgc     540
tgctattgct tggctgctgg gcagcagcac ctcccagaaa gtgatctacc tcgtgatgat     600
cctgctgatc gcccctgcct acagcatccg gtgtatcggc gtgtccaacc gggacttcgt     660
ggaaggcatg agcggcggca catgggtgga cgtggtgctg aacatggcg gctgcgtgac      720
agtgatggct caggacaagc ccaccgtgga catcgagctc gtgaccacca ccgtgtccaa     780
tatgccgaa gtgcggagct actgctacga ggccagcatc agcgacatgg caagcgacag      840
cagatgccct acacagggcg aggcctacct ggacaagcag tccgacaccc agtacgtgtg     900
caagcggacc ctggtggata gaggctgggg caatggctgc ggcctgtttg gcaagggcag     960
cctcgtgacc tgcgccaagt tcgcctgcag caagaagatg accggcaaga gcatccagcc    1020
cgagaacctg gaataccgga tcatgctgag cgtgcacggc agccagcact ccggcatgat    1080
cgtgaacgac accggccacg agacagacga gaaccgggcc aaggtggaaa tcacccccaa    1140
cagccctaga gccgaggcca cactgggcgg ctttggatct ctgggcctgg actgcgagcc    1200
tagaaccggc ctggatttca gcgacctgta ctacctgacc atgaacaaca gcactggct     1260
ggtgcacaaa gagtggttcc acgacatccc cctgccctgg catgccggcg ctgatacagg    1320
cacaccccac tggaacaaca agagggctct ggtggaattc aaggacgccc acgccaagcg    1380
gcagaccgtg gtggtgctgg gatctcagga aggcgccgtg catacagctc tggctggcgc    1440
cctggaagcc gaaatggatg cgccaaagg cagactgtcc agcggccacc tgaagtgccg     1500
gctgaagatg gacaagctgc ggctgaaggg cgtgtcctac agcctgtgta ccgccgcctt    1560
caccttcacc aagatccccg ccgagacact gcacggcacc gtgactgtgg aagtgcagta    1620
cgccggcacc gacggccctt gtaaagtgcc tgctcagatg gccgtggata tgcagaccct    1680
gacccccgtg ggcagactga tcaccgccaa ccctgtgatc accgagagca ccgagaacag    1740
caagatgatg ctggaactgg accccccctt cggcgactcc tacatcgtga tcggcgtggg    1800
agagaagaag atcacccacc actggcacag aagcggcagc accatcggca aggcctttga    1860
ggctacagtg cggggagcca agagaatggc cgtgctggga gataccgcct gggactttgg    1920
ctctgtgggc ggagccctga actctctggg caagggaatc caccagatct cggagccgc     1980
ctttaagagc ctgttcggcg gcatgagctg gttcagccag atcctgatcg gcaccctgct    2040
gatgtggctg ggcctgaacg ccaagaacgg cagcatctcc ctgatgtgcc tggctctggg    2100
aggcgtgctg atcttcctga gcacagccgt gtctgcctga tggccatatg aaaaaaacta    2160
acagtaatca aatgtctgt tacagtcaag agaatcattg acaacacagt catagttcca     2220
aaacttcctg caaatgagga tccagtggaa tacccggcag attacttcag aaaatcaaag    2280
gagattcctc tttacatcaa tactacaaaa agtttgtcag atctaagagg atatgtctac    2340
```

```
caaggcctca aatccggaaa tgtatcaatc atacatgtca acagctactt gtatggagca    2400
ttaaaggaca tccggggtaa gttggataaa gattggtcaa gtttcggaat aaacatcggg    2460
aaagcagggg atacaatcgg aatatttgac cttgtatcct tgaaagccct ggacggcgta    2520
cttccagatg gagtatcgga tgcttccaga accagcgcag atgacaaatg gttgcctttg    2580
tatctacttg gcttatacag agtgggcaga acacaaatgc ctgaatacag aaaaaagctc    2640
atggatgggc tgacaaatca atgcaaaatg atcaatgaac agtttgaacc tcttgtgcca    2700
gaaggtcgtg acattttga tgtgtgggga atgacagta attacacaaa aattgtcgct    2760
gcagtggaca tgttcttcca catgttcaaa aaacatgaat gtgcctcgtt cagatacgga    2820
actattgttt ccagattcaa agattgtgct gcattggcaa catttggaca cctctgcaaa    2880
ataaccggaa tgtctacaga agatgtaacg acctggatct tgaaccgaga agttgcagat    2940
gaaatggtcc aaatgatgct tccaggccaa gaaattgaca aggccgattc atacatgcct    3000
tatttgatcg actttggatt gtcttctaag tctccatatt cttccgtcaa aaaccctgcc    3060
ttccacttct gggggcaatt gacagctctt ctgctcagat ccaccagagc aaggaatgcc    3120
cgacagcctg atgacattga gtatacatct cttactacag caggtttgtt gtacgcttat    3180
gcagtaggat cctctgccga cttggcacaa cagttttgtg ttggagataa caaatacact    3240
ccagatgata gtaccggagg attgacgact aatgcaccgc cacaaggcag agatgtggtc    3300
gaatggctcg gatggtttga agatcaaaac agaaaaccga ctcctgatat gatgcagtat    3360
gcgaaaagag cagtcatgtc actgcaaggc ctaagagaga agacaattgg caagtatgct    3420
aagtcagaat ttgacaaatg accctataat tctcagatca cctattatat attatgctac    3480
atatgaaaaa aactaacaga tatcatggat aatctcacaa aagttcgtga gtatctcaag    3540
tcctattctc gtctggatca ggcggtagga gagatagatg agatcgaagc acaacgagct    3600
gaaaagtcca attatgagtt gttccaagag gatggagtgg aagagcatac taagccctct    3660
tattttcagg cagcagatga ttctgacaca gaatctgaac cagaaattga agacaatcaa    3720
ggtttgtatg cacaggatcc agaagctgag caagttgaag gctttataca ggggccttta    3780
gatgactatg cagatgagga agtggatgtt gtatttactt cggactggaa accacctgag    3840
cttgaatctg acgagcatgg aaagacctta cggttgacat cgccagaggg tttaagtgga    3900
gagcagaaat cccagtggct ttcgacgatt aaagcagtcg tgcaaagtgc caaatactgg    3960
aatctggcag agtgcacatt tgaagcatcg ggagaagggg tcattatgaa ggagcgccag    4020
ataactccgg atgtatataa ggtcactcca gtgatgaaca cacatccgtc ccaatcagaa    4080
gcagtatcag atgtttggtc tctctcaaag acatccatga ctttccaacc caagaaagca    4140
agtcttcagc ctctccaccat atccttggat gaattgttct catctagagg agagttcatc    4200
tctgtcggag gtgacggacg aatgtctcat aaagaggcca tcctgctcgg cctgagatac    4260
aaaaagttgt acaatcaggc gagagtcaaa tattctctgt agactatgaa aaaagtaac    4320 agatatcacg atctaagtgt tatcccaatc cattcatcat gagttcctta agaagattc    4380 tcggtctgaa ggggaaaggt aagaaatcta agaaattagg gatcgcacca cccccttatg    4440
aagaggacac tagcatggag tatgctccga gcgctccaat tgcacaaatcc tattttggag    4500 ttgacgagat ggacacctat gatccgaatc aattaagata tgagaaattc ttctttacag    4560
tgaaaatgac ggttagatct aatcgtccgt tcagaacata ctcagatgtg cagccgctg    4620 tatcccattg ggatcacatg tacatcggaa tggcagggaa acgtcccttc tacaaaatct    4680
```

```
tggcttttttt gggttcttct aatctaaagg ccactccagc ggtattggca gatcaaggtc    4740
aaccagagta tcacactcac tgcgaaggca gggcttattt gccacatagg atggggaaga    4800
cccctcccat gctcaatgta ccagagcact tcagaagacc attcaatata ggtctttaca    4860
agggaacgat tgagctcaca atgaccatct acgatgatga gtcactggaa gcagctccta    4920
tgatctggga tcatttcaat tcttccaaat tttctgattt cagagagaag gccttaatgt    4980
ttggcctgat tgtcgagaaa aaggcatctg gagcgtgggt cctggattct atcagccact    5040
tcaaatgagc tagtctaact tctagcttct gaacaatccc cggtttactc agtctctcct    5100
aattccagcc tctcgaacaa ctaatatcct gtcttttcta tccctatgaa aaaaactaac    5160
agagatcgat ctgtttcctt gacactatga agtgcctttt gtacttagcc ttttttattca   5220 ttggggtgaa ttgcaagttc accatagttt ttccacacaa ccaaaaagga aactggaaaa    5280
atgttccttc taattaccat tattgcccgt caagctcaga tttaaattgg cataatgact    5340
taataggcac agccatacaa gtcaaaatgc ccaagagtca caaggctatt caagcagacg    5400
gttggatgtg tcatgcttcc aaatgggtca ctacttgtga tttccgctgg tatggaccga    5460
agtatataac acagtccatc cgatccttca ctccatctgt agaacaatgc aaggaaagca    5520
ttgaacaaac gaaacaagga acttggctga atccaggctt ccctcctcaa agttgtggat    5580
atgcaactgt gacggatgcc gaagcagtga ttgtccaggt gactcctcac catgtgctgg    5640
ttgatgaata cacaggagaa tgggttgatt cacagttcat caacgaaaaa tgcagcaatt    5700
acatatgccc cactgtccat aactctacaa cctggcattc tgactataag gtcaagggc    5760 tatgtgattc taacctcatt tccatggaca tcaccttctt ctcagaggac ggagagctat    5820
catccctggg aaaggagggc acagggttca gaagtaacta ctttgcttat gaaactggag    5880
gcaaggcctg caaaatgcaa tactgcaagc attgggagt cagactccca tcaggtgtct    5940
ggttcgagat ggctgataag gatctctttg ctgcagccag attccctgaa tgcccagaag    6000
ggtcaagtat ctctgctcca tctcagacct cagtggatgt aagtctaatt caggacgttg    6060
agaggatctt ggattattcc ctctgccaag aaacctggag caaaatcaga gcgggtcttc    6120
caatctctcc agtggatctc agctatcttg ctcctaaaaa cccaggaacc ggtcctgctt    6180
tcaccataat caatggtacc ctaaaatact ttgagaccag atacatcaga gtcgatattg    6240
ctgctccaat cctctcaaga atggtcggaa tgatcagtgg aactaccaca gaaagggaac    6300
tgtgggatga ctgggcacca tatgaagacg tggaaattgg acccaatgga gttctgagga    6360
ccagttcagg atataagttt cctttatacca tgattggaca tggtatgttg gactccgatc    6420
ttcatcttag ctcaaaggct caggtgttcg aacatcctca cattcaagac gctgcttcgc    6480
aacttcctga tgatgagagt ttatttttg gtgatactgg gctatccaaa aatccaatcg    6540
agcttgtaga aggttggttc agtagttgga aaagctctat tgcctctttt ttctttatca    6600
tagggttaat cattggacta ttcttggttc tccgagttgg tatccatctt tgcattaaat    6660
taaagcacac caagaaaaga cagatttata cagacataga gatgaaccga cttggaaagt    6720
aactcaaatc ctgcacaaca gattcttcat gtttggacca aatcaacttg tgataccatg    6780
ctcaaagagg cctcaattat atttgagttt ttaattttta tgaaaaaaac taacagcaat    6840
catggaagtc cacgattttg agaccgacga gttcaatgat ttcaatgaag atgactatgc    6900
cacaagagaa ttcctgaatc ccgatgagcg catgacgtac ttgaatcatg ctgattacaa    6960
tttgaattct cctctaatta gtgatgatat tgacaatttg atcaggaaat tcaattctct    7020
tccgattccc tcgatgtggg atagtaagaa ctgggatgga gttcttgaga tgttaacatc    7080
```

```
atgtcaagcc aatcccatct caacatctca gatgcataaa tggatgggaa gttggttaat    7140
gtctgataat catgatgcca gtcaagggta tagttttta catgaagtgg acaaagaggc     7200
agaaataaca tttgacgtgg tggagacctt catccgcggc tggggcaaca aaccaattga    7260
atacatcaaa aaggaaagat ggactgactc attcaaaatt ctcgcttatt tgtgtcaaaa    7320
gtttttggac ttacacaagt tgacattaat cttaaatgct gtctctgagg tggaattgct    7380
caacttggcg aggactttca aaggcaaagt cagaagaagt tctcatggaa cgaacatatg    7440
caggattagg gttcccagct tgggtcctac ttttatttca gaaggatggg cttacttcaa    7500
gaaacttgat attctaatgg accgaaactt tctgttaatg gtcaaagatg tgattatagg    7560
gaggatgcaa acggtgctat ccatggtatg tagaatagac aacctgttct cagagcaaga    7620
catcttctcc cttctaaata tctacagaat tggagataaa attgtggaga ggcagggaaa    7680 ttttcttat gacttgatta aaatggtgga accgatatgc aacttgaagc tgatgaaatt     7740
agcaagagaa tcaaggcctt tagtcccaca attccctcat tttgaaaatc atatcaagac    7800
ttctgttgat gaaggggcaa aaattgaccg aggtataaga ttcctccatg atcagataat    7860
gagtgtgaaa acagtggatc tcacactggt gatttatgga tcgttcagac attggggtca    7920
tccttttata gattattaca ctggactaga aaaattacat tcccaagtaa ccatgaagaa    7980
agatattgat gtgtcatatg caaaagcact tgcaagtgat ttagctcgga ttgttctatt    8040
tcaacagttc aatgatcata aaaagtggtt cgtgaatgga gacttgctcc ctcatgatca    8100 tcccttaaa agtcatgtta aagaaaatac atggcccaca gctgctcaag ttcaagattt     8160
tggagataaa tggcatgaac ttccgctgat taaatgtttt gaaatacccg acttactaga    8220
cccatcgata atatactctg acaaaagtca ttcaatgaat aggtcagagg tgttgaaaca    8280
tgtccgaatg aatccgaaca ctcctatccc tagtaaaaag gtgttgcaga ctatgttgga    8340
cacaaaggct accaattgga aagaatttct taaagagatt gatgagaagg cttagatga    8400 tgatgatcta attattggtc ttaaaggaaa ggagagggaa ctgaagttgg caggtagatt    8460
tttctcccta atgtcttgga aattgcgaga atactttgta attaccgaat atttgataaa    8520
gactcatttc gtccctatgt ttaaaggcct gacaatggcg gacgatctaa ctgcagtcat    8580
taaaaagatg ttagattcct catccggcca aggattgaag tcatatgagg caatttgcat    8640
agccaatcac attgattacg aaaaatgaa taaccaccaa aggaagttat caaacggccc     8700
agtgttccga gttatgggcc agttcttagg ttatccatcc ttaatcgaga gaactcatga    8760
attttttgag aaaagtctta tatactacaa tggaagacca gacttgatgc gtgttcacaa    8820
caacacactg atcaattcaa cctcccaacg agtttgttgg caaggacaag agggtggact    8880
ggaaggtcta cggcaaaaag gatggactat cctcaatcta ctggttattc aaagagaggc    8940
taaaatcaga aacactgctg tcaaagtctt ggcacaaggt gataatcaag ttatttgcac    9000
acagtataaa acgaagaaat cgagaaacgt tgtagaatta cagggtgctc tcaatcaaat    9060
ggtttctaat aatgagaaaa ttatgactgc aatcaaaata gggacaggga agttaggact    9120
tttgataaat gacgatgaga ctatgcaatc tgcagattac ttgaattatg gaaaaatacc    9180
gattttccgt ggagtgatta gagggttaga gaccaagaga tggtcacgag tgacttgtgt    9240
caccaatgac caaataccca cttgtgctaa tataatgagc tcagtttcca caaatgctct    9300
caccgtagct cattttgctg agaacccaat caatgccatg atacagtaca attattttgg    9360
gacatttgct agactcttgt tgatgatgca tgatcctgct cttcgtcaat cattgtatga    9420
```

```
agttcaagat aagataccgg gcttgcacag ttctactttc aaatacgcca tgttgtattt    9480
ggacccttcc attggaggag tgtcgggcat gtctttgtcc aggtttttga ttagagcctt    9540
cccagatccc gtaacagaaa gtctctcatt ctggagattc atccatgtac atgctcgaag    9600
tgagcatctg aaggagatga gtgcagtatt tggaaacccc gagatagcca agtttcgaat    9660
aactcacata gacaagctag tagaagatcc aacctctctg aacatcgcta tgggaatgag    9720
tccagcgaac ttgttaaaga ctgaggttaa aaaatgctta atcgaatcaa gacaaaccat    9780
caggaaccag gtgattaagg atgcaaccat atatttgtat catgaagagg atcggctcag    9840
aagtttctta tggtcaataa atcctctgtt ccctagattt ttaagtgaat tcaaatcagg    9900
cacttttttg ggagtcgcag acgggctcat cagtctattt caaaattctc gtactattcg    9960
gaactccttt aagaaaaagt atcataggga attggatgat ttgattgtga ggagtgaggt   10020
atcctctttg acacatttag ggaaacttca tttgagaagg ggatcatgta aaatgtggac   10080
atgttcagct actcatgctg acacattaag atacaaatcc tggggccgta cagttattgg   10140
gacaactgta ccccatccat tagaaatgtt gggtccacaa catcgaaaag agactccttg   10200
tgcaccatgt aacacatcag ggttcaatta tgtttctgtg cattgtccag acgggatcca   10260
tgacgtcttt agttcacggg gaccattgcc tgcttatcta gggtctaaaa catctgaatc   10320
tacatctatt ttgcagcctt gggaaaggga agcaaagtc ccactgatta aaagagctac   10380
acgtcttaga gatgctatct cttggtttgt tgaacccgac tctaaactag caatgactat   10440
actttctaac atccactctt taacaggcga agaatggacc aaaaggcagc atgggttcaa   10500
aagaacaggg tctgcccttc ataggttttc gacatctcgg atgagccatg gtgggttcgc   10560
atctcagagc actgcagcat tgaccaggtt gatggcaact acagacacca tgagggatct   10620
gggagatcag aatttcgact tttattcca agcaacgttg ctctatgctc aaattaccac   10680
cactgttgca agagacggat ggatcaccag ttgtacagat cattatcata ttgcctgtaa   10740
gtcctgtttg agacccatag aagagatcac cctggactca gtatggact acacgccccc   10800 agatgtatcc catgtgctga agacatggag gaatggggaa ggttcgtggg gacaagagat   10860
aaaacagatc tatcctttag aagggaattg gaagaattta gcacctgctg agcaatccta   10920
tcaagtcggc agatgtatag gttttctata tggagacttg gcgtatagaa aatctactca   10980
tgccgaggac agttctctat ttcctctatc tatacaaggt cgtattagag gtcgaggttt   11040
cttaaaaggg ttgctagacg gattaatgag agcaagttgc tgccaagtaa tacaccggag   11100
aagtctggct catttgaaga ggccggccaa cgcagtgtac ggaggtttga tttacttgat   11160
tgataaattg agtgtatcac ctccattcct ttctcttact agatcaggac ctattagaga   11220
cgaattagaa acgattcccc acaagatccc aacctcctat ccgacaagca accgtgatat   11280 ggggggtgatt gtcagaaatt acttcaaata ccaatgccgt ctaattgaaa agggaaaata   11340
cagatcacat tattcacaat tatggttatt ctcagatgtc ttatccatag acttcattgg   11400
accattctct atttccacca ccctcttgca aatcctatac aagccatttt tatctgggaa   11460
agataagaat gagttgagag agctggcaaa tctttcttca ttgctaagat caggagaggg   11520
gtgggaagac atacatgtga aattcttcac caaggacata ttattgtgtc cagaggaaat   11580
cagacatgct tgcaagttcg ggattgctaa ggataataat aaagacatga gctatccccc   11640
ttggggaagg gaatccagag ggacaattac aacaatccct gtttattata cgaccacccc   11700
ttacccaaag atgctagaga tgcctccaag aatccaaaat cccctgctgt ccggaatcag   11760
gttgggccaa ttaccaactg gcgctcatta taaaattcgg agtatattac atggaatggg   11820
```

```
aatccattac agggacttct tgagttgtgg agacggctcc ggagggatga ctgctgcatt   11880
actacgagaa aatgtgcata gcagaggaat attcaatagt ctgttagaat tatcagggtc   11940
agtcatgcga ggcgcctctc ctgagccccc cagtgccccta gaaactttag gaggagataa   12000
atcgagatgt gtaaatggtg aaacatgttg gaatatcca tctgacttat gtgacccaag   12060
gacttgggac tatttcctcc gactcaaagc aggcttgggg cttcaaattg atttaattgt   12120
aatggatatg gaagttcggg attcttctac tagcctgaaa attgagacga atgttagaaa   12180
ttatgtgcac cggatttttgg atgagcaagg agttttaatc tacaagactt atggaacata   12240
tatttgtgag agcgaaaaga atgcagtaac aatccttggt cccatgttca agacggtcga   12300
cttagttcaa acagaattta gtagttctca aacgtctgaa gtatatatgg tatgtaaagg   12360
tttgaagaaa ttaatcgatg aacccaatcc cgattggtct tccatcaatg aatcctggaa   12420
aaacctgtac gcattccagt catcagaaca ggaatttgcc agagcaaaga aggttagtac   12480
atactttacc ttgacaggta ttccctccca attcattcct gatccttttg taaacattga   12540
gactatgcta caaatattcg gagtacccac gggtgtgtct catgcggctg ccttaaaatc   12600
atctgataga cctgcagatt tattgaccat tagcctttttt tatatggcga ttatatcgta   12660
ttataacatc aatcatatca gagtaggacc gatacctccg aacccccat cagatggaat   12720 tgcacaaaat gtggggatcg ctataactgg tataagcttt tggctgagtt tgatggagaa   12780
agacattcca ctatatcaac agtgtttagc agttatccag caatcattcc cgattaggtg   12840
ggaggctgtt tcagtaaaag gaggatacaa gcagaagtgg agtactagag gtgatgggct   12900
cccaaaagat acccgaactt cagactcctt ggccccaatc gggaactgga tcagatctct   12960
ggaattggtc cgaaaccaag ttcgtctaaa tccattcaat gagatcttgt tcaatcagct   13020
atgtcgtaca gtggataatc atttgaaatg gtcaaatttg cgaagaaaca caggaatgat   13080
tgaatggatc aatagacgaa tttcaaaaga agaccggtct atactgatgt tgaagagtga   13140
cctacacgag gaaaactctt ggagagatta aaaaatcatg aggagactcc aaactttaag   13200
tatgaaaaaa actttgatcc ttaagaccct cttgtggttt ttatttttta tctggttttg   13260
tggtcttcgt gggtcggcat ggcatctcca cctcctcgcg gtccgacctg gcatccgaa   13320 ggaggacgtc gtccactcgg atggctaagg gagagctcgg atccggctgc taacaaagcc   13380
cgaaaggaag ctgagttggc tgctgccacc gctgagcaat aactagcata accccttggg   13440
gcctctaaac gggtcttgag gggttttttg ctgaaaggag gaactatatc cggatcgaga   13500
tcctctagag tcgacctgca ggcatgcaag cttgtattct atagtgtcac ctaaatcgta   13560
tgtgtatgat acataaggtt atgtattaat tgtagccgcg ttctaacgac aatatgtaca   13620
agcctaattg tgtagcatct ggcttactga agcagaccct atcatctctc tcgtaaactg   13680
ccgtcagagt cggtttggtt ggacgaacct tctgagtttc tggtaacgcc gtcccgcacc   13740
cggaaatggt cagcgaacca atcagcaggg tcatcgctag ccagatcctc tacgccggac   13800
gcatcgtggc cggcatcacc ggcgccacag gtgcggttgc tggcgcctat atcgccgaca   13860
tcaccgatgg ggaagatcgg gctcgccact tcgggctcat gagcgcttgt ttcggcgtgg   13920
gtatggtggc aggccccgtg gccgggggac tgttgggcgc catctccttg caccattcct   13980
tgcggcggcg gtgctcaacg gcctcaacct actactgggc tgcttcctaa tgcaggagtc   14040
gcataaggga gagcgtcgaa tggtgcactc tcagtacaat ctgctctgat gccgcatagt   14100
taagccagcc ccgacacccg ccaacacccg ctgacgcgcc ctgacgggct tgtctgctcc   14160
```

```
cggcatccgc ttacagacaa gctgtgaccg tctccgggag ctgcatgtgt cagaggtttt    14220
caccgtcatc accgaaacgc gcgagacgaa agggcctcgt gatacgccta tttttatagg    14280
ttaatgtcat gataataatg gtttcttaga cgtcaggtgg cacttttcgg ggaaatgtgc    14340
gcggaacccc tatttgttta ttttttctaaa tacattcaaa tatgtatccg ctcatgagac    14400
aataaccctg ataaatgctt caataatatt gaaaaaggaa gagtatgagt attcaacatt    14460
tccgtgtcgc ccttattccc ttttttgcgg cattttgcct tcctgttttt gctcacccag    14520
aaacgctggt gaaagtaaaa gatgctgaag atcagttggg tgcacgagtg ggttacatcg    14580
aactggatct caacagcggt aagatccttg agagttttcg ccccgaagaa cgttttccaa    14640
tgatgagcac ttttaaagtt ctgctatgtg gcgcggtatt atcccgtatt gacgccgggc    14700
aagagcaact cggtcgccgc atacactatt ctcagaatga cttggttgag tactcaccag    14760
tcacagaaaa gcatcttacg gatggcatga cagtaagaga attatgcagt gctgccataa    14820
ccatgagtga taacactgcg gccaacttac ttctgacaac gatcggagga ccgaaggagc    14880
taaccgcttt tttgcacaac atgggggatc atgtaactcg ccttgatcgt tgggaaccgg    14940
agctgaatga agccatacca aacgacgagc gtgacaccac gatgcctgta gcaatggcaa    15000
caacgttgcg caaactatta actggcgaac tacttactct agcttcccgg caacaattaa    15060
tagactggat ggaggcggat aaagttgcag gaccacttct gcgctcggcc cttccggctg    15120
gctggtttat tgctgataaa tctggagccg gtgagcgtgg gtctcgcggt atcattgcag    15180
cactggggcc agatggtaag ccctcccgta tcgtagttat ctacacgacg gggagtcagg    15240
caactatgga tgaacgaaat agacagatcg ctgagatagg tgcctcactg attaagcatt    15300
ggtaactgtc agaccaagtt tactcatata ctttagat tgatttaaaa cttcattttt    15360
aatttaaaag gatctaggtg aagatccttt ttgataatct catgaccaaa atcccttaac    15420
gtgagttttc gttccactga gcgtcagacc ccgtagaaaa gatcaaagga tcttcttgag    15480 atccttttttt tctgcgcgta atctgctgct tgcaaacaaa aaaaccaccg ctaccagcgg    15540
tggtttgttt gccggatcaa gagctaccaa ctctttttcc gaaggtaact ggcttcagca    15600
gagcgcagat accaaatact gtccttctag tgtagccgta gttaggccac cacttcaaga    15660
actctgtagc accgcctaca tacctcgctc tgctaatcct gttaccagtg ctgctgcca    15720 gtggcgataa gtcgtgtctt accgggttgg actcaagacg atagttaccg gataaggcgc    15780
agcggtcggg ctgaacgggg ggttcgtgca cacagcccag cttggagcga acgacctaca    15840
ccgaactgag atacctacag cgtgagctat gagaaagcgc cacgcttccc gaagggagaa    15900
aggcggacag gtatccggta agcggcaggg tcggaacagg agagcgcacg agggagcttc    15960 caggggggaaa cgcctggtat ctttatagtc ctgtcgggtt tcgccacctc tgacttgagc    16020
gtcgattttt gtgatgctcg tcaggggggc ggagcctatg gaaaaacgcc agcaacgcgg    16080 ccttttttacg gttcctggcc tttttgctgg ctttttgctca catgttcttt cctgcgttat    16140
cccctgattc tgtggataac cgtattaccg cctttgagtg agctgatacc gctcgccgca    16200
gccgaacgac cgagcgcagc gagtcagtga gcgaggaagc ggaagagcgc ccaatacgca    16260
aaccgcctct ccccgcgcgt tggccgattc attaatgcag ggggatctcg atcccgcgaa    16320
attaatacga ctcactatag g                                              16341
```

<210> SEQ ID NO 9
<211> LENGTH: 504
<212> TYPE: PRT
<213> ORGANISM: Zika virus

<400> SEQUENCE: 9

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Ile Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
```

```
                        405                 410                 415
Gly Ala Lys Arg Met Ala Val Leu Gly Asp Thr Ala Trp Asp Phe Gly
                420                 425                 430

Ser Val Gly Gly Ala Leu Asn Ser Leu Gly Lys Gly Ile His Gln Ile
            435                 440                 445

Phe Gly Ala Ala Phe Lys Ser Leu Phe Gly Gly Met Ser Trp Phe Ser
        450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 10
<211> LENGTH: 164
<212> TYPE: PRT
<213> ORGANISM: Zika virus

<400> SEQUENCE: 10

Arg Arg Gly Ser Ala Tyr Tyr Met Tyr Leu Asp Arg Asn Asp Ala Gly
1               5                   10                  15

Glu Ala Ile Ser Phe Pro Thr Thr Leu Gly Met Asn Lys Cys Tyr Ile
            20                  25                  30

Gln Ile Met Asp Leu Gly His Met Cys Asp Ala Thr Met Ser Tyr Glu
        35                  40                  45

Cys Pro Met Leu Asp Glu Gly Val Glu Pro Asp Asp Val Asp Cys Trp
    50                  55                  60

Cys Asn Thr Thr Ser Thr Trp Val Val Tyr Gly Thr Cys His His Lys
65                  70                  75                  80

Lys Gly Glu Ala Arg Arg Ser Arg Arg Ala Val Thr Leu Pro Ser His
                85                  90                  95

Ser Thr Arg Lys Leu Gln Thr Arg Ser Gln Thr Trp Leu Glu Ser Arg
            100                 105                 110

Glu Tyr Thr Lys His Leu Ile Arg Val Glu Asn Trp Ile Phe Arg Asn
        115                 120                 125

Pro Gly Phe Ala Leu Ala Ala Ala Ala Ile Ala Trp Leu Leu Gly Ser
    130                 135                 140

Ser Thr Ser Gln Lys Val Ile Tyr Leu Val Met Ile Leu Leu Ile Ala
145                 150                 155                 160

Pro Ala Tyr Ser

<210> SEQ ID NO 11
<211> LENGTH: 126
<212> TYPE: PRT
<213> ORGANISM: Zika virus

<400> SEQUENCE: 11

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60
```

```
Leu Ile Asn Arg Trp Gly Ser Val Gly Lys Lys Glu Ala Met Glu Ile
 65                  70                  75                  80

Ile Lys Lys Phe Lys Lys Asp Leu Ala Ala Met Leu Arg Ile Ile Asn
                 85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr
        115                 120                 125

<210> SEQ ID NO 12
<211> LENGTH: 15002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
acgaagacaa acaaaccatt attatcatta aaaggctcag gagaaacttt aacagtaatc       60
agaattctcg agaaagccac catggtgagc aagggcgagg agctgttcac cggggtggtg     120
cccatcctgg tcgagctgga cggcgacgta acgcccaca agttcagcgt gtccggcgag      180
ggcgagggcg atgccaccta cggcaagctg accctgaagt tcatctgcac caccggcaag     240
ctgcccgtgc cctggcccac cctcgtgacc acctgacct acggcgtgca gtgcttcagc      300
cgctaccccg accacatgaa gcagcacgac ttcttcaagt ccgccatgcc cgaaggctac     360
gtccaggagc gcaccatctt cttcaaggac gacggcaact acaagacccg cgccgaggtg     420
aagttcgagg gcgacaccct ggtgaaccgc atcgagctga agggcatcga cttcaaggag     480
gacggcaaca tcctggggca caagctggag tacaactaca acagccacaa cgtctatatc     540
atggccgaca agcagaagaa cggcatcaag gtgaacttca gatccgcca caacatcgag      600 gacggcagcg tgcagctcgc cgaccactac cagcagaaca cccccatcgg cgacggcccc     660
gtgctgctgc ccgacaacca ctacctgagc acccagtccg ccctgagcaa agaccccaac     720
gagaagcgcg atcacatggt cctgctggag ttcgtgaccg ccgccgggat cactctcggc     780
atggacgagc tgtacaagta atggccatat gaaaaaaact aacagtaatc aaaatgtctg     840
ttacagtcaa gagaatcatt gacaacacag tcatagttcc aaaacttcct gcaaatgagg     900
atccagtgga atacccggca gattacttca gaaaatcaaa ggagattcct ctttacatca     960
atactacaaa aagtttgtca gatctaagag gatatgtcta ccaaggcctc aaatccggaa    1020
atgtatcaat catacatgtc aacagctact tgtatggagc attaaaggac atccggggta    1080
agttggataa agattggtca agtttcggaa taaacatcgg gaaagcaggg gatacaatcg    1140
gaatatttga ccttgtatcc ttgaaagccc tggacggcgt acttccagat ggagtatcgg    1200
atgcttccag aaccagcgca gatgacaaat ggttgccttt gtatctactt ggcttataca    1260
gagtgggcag aacacaaatg cctgaataca gaaaaaagct catggatggg ctgacaaatc    1320
aatgcaaaat gatcaatgaa cagtttgaac ctcttgtgcc agaaggtcgt gacattttg     1380 atgtgtgggg aaatgacagt aattacacaa aaattgtcgc tgcagtggac atgttcttcc    1440
acatgttcaa aaaacatgaa tgtgcctcgt tcagatacgg aactattgtt ccagattca     1500 aagattgtgc tgcattggca acatttggac acctctgcaa ataaccgga atgtctacag     1560 aagatgtaac gacctggatc ttgaaccgag aagttgcaga tgaaatggtc caaatgatgc    1620
ttccaggcca agaaattgac aaggccgatt catacatgcc ttatttgatc gactttggat    1680
```

```
tgtcttctaa gtctccatat tcttccgtca aaaccctgc cttccacttc tgggggcaat    1740
tgacagctct tctgctcaga tccaccagag caaggaatgc ccgacagcct gatgacattg    1800
agtatacatc tcttactaca gcaggtttgt tgtacgctta tgcagtagga tcctctgccg    1860
acttggcaca acagttttgt gttggagata acaaatacac tccagatgat agtaccggag    1920
gattgacgac taatgcaccg ccacaaggca gagatgtggt cgaatggctc ggatggtttg    1980
aagatcaaaa cagaaaaccg actcctgata tgatgcagta tgcgaaaaga gcagtcatgt    2040
cactgcaagg cctaagagag aagacaattg gcaagtatgc taagtcagaa tttgacaaat    2100
gaccctataa ttctcagatc acctattata tattatgcta catatgaaaa aaactaacag    2160
atatcatgga taatctcaca aaagttcgtg agtatctcaa gtcctattct cgtctggatc    2220
aggcggtagg agagatagat gagatcgaag cacaacgagc tgaaaagtcc aattatgagt    2280
tgttccaaga ggatggagtg gaagagcata ctaagccctc ttattttcag gcagcagatg    2340
attctgacac agaatctgaa ccagaaattg aagacaatca aggtttgtat gcacaggatc    2400
cagaagctga gcaagttgaa ggctttatac aggggccttt agatgactat gcagatgagg    2460
aagtggatgt tgtatttact tcggactgga accacctga gcttgaatct gacgagcatg    2520
gaaagacctt acggttgaca tcgccagagg gtttaagtgg agagcagaaa tcccagtggc    2580
tttcgacgat taaagcagtc gtgcaaagtg ccaaatactg gaatctggca gagtgcacat    2640
ttgaagcatc gggagaaggg gtcattatga aggagcgcca gataactccg gatgtatata    2700
aggtcactcc agtgatgaac acacatccgt cccaatcaga agcagtatca gatgtttggt    2760
ctctctcaaa gacatccatg actttccaac ccaagaaagc aagtcttcag cctctcacca    2820
tatccttgga tgaattgttc tcatctagag gagagttcat ctctgtcgga ggtgacggac    2880
gaatgtctca taaagaggcc atcctgctcg gcctgagata caaaaagttg tacaatcagg    2940
cgagagtcaa atattctctg tagactatga aaaaagtaa cagatatcac gatctaagtg    3000
ttatcccaat ccattcatca tgagttcctt aaagaagatt ctcggtctga aggggaaagg    3060
taagaaatct aagaaattag ggatcgcacc acccccttat gaagaggaca ctagcatgga    3120
gtatgctccg agcgctccaa ttgacaaatc ctatttggga gttgacgaga tggacaccta    3180
tgatccgaat caattaagat atgagaaatt cttctttaca gtgaaaatga cggttagatc    3240
taatcgtccg ttcagaacat actcagatgt ggcagccgct gtatcccatt gggatcacat    3300
gtacatcgga atggcaggga acgtcccctt ctacaaaatc ttggctttttt tgggttcttc    3360 taatctaaag gccactccag cggtattggc agatcaaggt caaccagagt atcacactca    3420
ctgcgaaggc agggcttatt tgccacatag gatggggaag acccctccca tgctcaatgt    3480
accagagcac ttcagaagac cattcaatat aggtctttac aagggaacga ttgagctcac    3540
aatgaccatc tacgatgatg agtcactgga agcagctcct atgatctggg atcatttcaa    3600
ttcttccaaa ttttctgatt tcagagagaa ggccttaatg tttggcctga ttgtcgagaa    3660
aaaggcatct ggagcgtggg tcctggattc tatcagccac ttcaaatgag ctagtctaac    3720
ttctagcttc tgaacaatcc ccggtttact cagtctctcc taattccagc ctctcgaaca    3780
actaatatcc tgtcttttct atccctatga aaaaactaa cagagatcga tctgtttcct    3840
tgacactatg aagtgccttt tgtacttagc ctttttattc attggggtga attgcaagtt    3900
caccatagtt tttccacaca accaaaaagg aaactggaaa aatgttcctt ctaattacca    3960
ttattgcccg tcaagctcag atttaaattg gcataatgac ttaataggca cagccataca    4020
```

```
agtcaaaatg cccaagagtc acaaggctat tcaagcagac ggttggatgt gtcatgcttc    4080
caaatgggtc actacttgtg atttccgctg gtatggaccg aagtatataa cacagtccat    4140
ccgatccttc actccatctg tagaacaatg caaggaaagc attgaacaaa cgaaacaagg    4200
aacttggctg aatccaggct tccctcctca aagttgtgga tatgcaactg tgacggatgc    4260
cgaagcagtg attgtccagg tgactcctca ccatgtgctg gttgatgaat acacaggaga    4320
atgggttgat tcacagttca tcaacggaaa atgcagcaat tacatatgcc ccactgtcca    4380
taactctaca acctggcatt ctgactataa ggtcaaaggg ctatgtgatt ctaacctcat    4440
ttccatggac atcaccttct tctcagagga cggagagcta tcatccctgg aaaggaggg     4500
cacagggttc agaagtaact actttgctta tgaaactgga ggcaaggcct gcaaaatgca    4560
atactgcaag cattggggag tcagactccc atcaggtgtc tggttcgaga tggctgataa    4620
ggatctcttt gctgcagcca gattccctga atgcccagaa gggtcaagta tctctgctcc    4680
atctcagacc tcagtggatg taagtctaat tcaggacgtt gagaggatct tggattattc    4740
cctctgccaa gaaacctgga gcaaaatcag agcgggtctt ccaatctctc cagtggatct    4800
cagctatctt gctcctaaaa acccaggaac cggtcctgct ttcaccataa tcaatggtac    4860
cctaaaatac tttgagacca gatacatcag agtcgatatt gctgctccaa tcctctcaag    4920
aatggtcgga atgatcagtg gaactaccac agaaagggaa ctgtgggatg actgggcacc    4980
atatgaagac gtggaaattg gacccaatgg agttctgagg accagttcag gatataagtt    5040
tccttttatac atgattggac atggtatgtt ggactccgat cttcatctta gctcaaaggc    5100
tcaggtgttc gaacatcctc acattcaaga cgctgcttcg caacttcctg atgatgagag    5160
tttatttttt ggtgatactg gctatccaa aaatccaatc gagcttgtag aaggttggtt     5220
cagtagttgg aaaagctcta ttgcctcttt tttctttatc atagggttaa tcattggact    5280
attcttggtt ctccgagttg gtatccatct ttgcattaaa ttaaagcaca ccaagaaaag    5340
acagatttat acagacatag agatgaaccg acttggaaag taactcaaat cctgcacaac    5400
agattcttca tgtttggacc aaatcaactt gtgataccat gctcaaagag gcctcaatta    5460
tatttgagtt tttaatttt atgaaaaaaa ctaacagcaa tcatggaagt ccacgatttt     5520
gagaccgacg agttcaatga tttcaatgaa gatgactatg ccacaagaga attcctgaat    5580
cccgatgagc gcatgacgta cttgaatcat gctgattaca atttgaattc tcctctaatt    5640
agtgatgata ttgacaattt gatcaggaaa ttcaattctc ttccgattcc ctcgatgtgg    5700
gatagtaaga actgggatgg agttcttgag atgttaacat catgtcaagc caatcccatc    5760
tcaacatctc agatgcataa atggatggga agttggttaa tgtctgataa tcatgatgcc    5820
agtcaagggt atagtttttt acatgaagtg gacaaagagg cagaaataac atttgacgtg    5880
gtggagacct tcatccgcgg ctggggcaac aaaccaattg aatacatcaa aaaggaaaga    5940
tggactgact cattcaaaat tctcgcttat ttgtgtcaaa agttttggga cttacacaag    6000
ttgacattaa tcttaaatgc tgtctctgag gtggaattgc tcaacttggc gaggactttc    6060
aaaggcaaag tcagaagaag ttctcatgga acgaacatat gcaggattag ggttcccagc    6120
ttgggtccta cttttatttc agaaggatgg gcttacttca agaaacttga tattctaatg    6180
gaccgaaact ttctgttaat ggtcaaagat gtgattatag ggaggatgca aacggtgcta    6240
tccatggtat gtagaataga caacctgttc tcagagcaag acatcttctc ccttctaaat    6300
atctacagaa ttggagataa aattgtggag aggcagggaa attttcctta tgacttgatt    6360
aaaatggtgg aaccgatatg caacttgaag ctgatgaaat tagcaagaga atcaaggcct    6420
```

```
ttagtcccac aattccctca ttttgaaaat catatcaaga cttctgttga tgaagggca      6480 aaaattgacc gaggtataag attcctccat gatcagataa tgagtgtgaa acagtggat      6540 ctcacactgg tgatttatgg atcgttcaga cattggggtc atccttttat agattattac    6600
actggactag aaaaattaca ttcccaagta accatgaaga aagatattga tgtgtcatat    6660
gcaaaagcac ttgcaagtga tttagctcgg attgttctat ttcaacagtt caatgatcat    6720
aaaaagtggt tcgtgaatgg agacttgctc cctcatgatc atccctttaa aagtcatgtt    6780
aaagaaaata catggcccac agctgctcaa gttcaagatt ttggagataa atggcatgaa    6840
cttccgctga ttaaatgttt tgaaataccc gacttactag acccatcgat aatatactct    6900
gacaaaagtc attcaatgaa taggtcagag gtgttgaaac atgtccgaat gaatccgaac    6960
actcctatcc ctagtaaaaa ggtgttgcag actatgttgg acacaaaggc taccaattgg    7020
aaagaatttc ttaaagagat tgatgagaag ggcttagatg atgatgatct aattattggt    7080
cttaaaggaa aggagaggga actgaagttg gcaggtagat ttttctccct aatgtcttgg    7140
aaattgcgag atactttgt aattaccgaa tatttgataa agactcattt cgtccctatg      7200
tttaaaggcc tgacaatggc ggacgatcta actgcagtca ttaaaaagat gttagattcc    7260
tcatccggcc aaggattgaa gtcatatgag gcaatttgca tagccaatca cattgattac    7320 gaaaatgga ataaccacca aaggaagtta tcaaacggcc cagtgttccg agttatgggc      7380
cagttcttag gttatccatc cttaatcgag agaactcatg aatttttga gaaaagtctt      7440 atatactca atggaagacc agacttgatg cgtgttcaca acaacacact gatcaattca      7500
acctcccaac gagtttgttg gcaaggacaa gagggtggac tggaaggtct acggcaaaaa    7560
ggatggacta tcctcaatct actggttatt caaagagagg ctaaaatcag aaacactgct    7620
gtcaaagtct tggcacaagg tgataatcaa gttatttgca cacagtataa aacgaagaaa    7680
tcgagaaacg ttgtagaatt acagggtgct ctcaatcaaa tggtttctaa taatgagaaa    7740
attatgactg caatcaaaat agggacaggg aagttaggac ttttgataaa tgacgatgag    7800
actatgcaat ctgcagatta cttgaattat ggaaaaatac cgattttccg tggagtgatt    7860
agagggttag agaccaagag atggtcacga gtgacttgtg tcaccaatga ccaaataccc    7920
acttgtgcta atataatgag ctcagttttcc acaaatgctc tcaccgtagc tcattttgct    7980
gagaacccaa tcaatgccat gatacagtac aattattttg ggacatttgc tagactcttg    8040
ttgatgatgc atgatcctgc tcttcgtcaa tcattgtatg aagttcaaga taagataccg    8100
ggcttgcaca gttctacttt caaatacgcc atgttgtatt tggacccttc cattggagga    8160
gtgtcgggca tgtctttgtc caggtttttg attagagcct tcccagatcc cgtaacagaa    8220
agtctctcat tctggagatt catccatgta catgctcgaa gtgagcatct gaaggagatg    8280
agtgcagtat ttggaaaccc cgagatagcc aagtttcgaa taactcacat agacaagcta    8340
gtagaagatc caacctctct gaacatcgct atgggaatga gtccagcgaa cttgttaaag    8400
actgaggtta aaaaatgctt aatcgaatca agacaaacca tcaggaacca ggtgattaag    8460
gatgcaacca tatatttgta tcatgaagag gatcggctca gaagtttctt atggtcaata    8520
aatcctctgt tccctagatt tttaagtgaa ttcaaatcag gcacttttt gggagtcgca    8580 gacgggctca tcagtctatt tcaaaattct cgtactattc ggaactcctt taagaaaaag    8640
tatcataggg aattggatga tttgattgtg aggagtgagg tatcctcttt gacacattta    8700
gggaaacttc atttgagaag gggatcatgt aaaatgtgga catgttcagc tactcatgct    8760
```

```
gacacattaa gatacaaatc ctggggccgt acagttattg ggacaactgt accccatcca    8820
ttagaaatgt tgggtccaca acatcgaaaa gagactcctt gtgcaccatg taacacatca    8880
gggttcaatt atgtttctgt gcattgtcca gacgggatcc atgacgtctt tagttcacgg    8940
ggaccattgc ctgcttatct agggtctaaa acatctgaat ctacatctat tttgcagcct    9000
tgggaaaggg aaagcaaagt cccactgatt aaaagagcta cacgtcttag agatgctatc    9060
tcttggtttg ttgaacccga ctctaaacta gcaatgacta tactttctaa catccactct    9120
ttaacaggcg aagaatggac caaaaggcag catgggttca aaagaacagg gtctgccctt    9180
cataggtttt cgacatctcg gatgagccat ggtgggttcg catctcagag cactgcagca    9240
ttgaccaggt tgatggcaac tacagacacc atgagggatc tgggagatca gaatttcgac    9300
tttttattcc aagcaacgtt gctctatgct caaattacca ccactgttgc aagagacgga    9360
tggatcacca gttgtacaga tcattatcat attgcctgta agtcctgttt gagacccata    9420
gaagagatca ccctggactc aagtatggac tacacgcccc cagatgtatc ccatgtgctg    9480
aagacatgga ggaatgggga aggttcgtgg ggacaagaga taaaacagat ctatccttta    9540
gaagggaatt ggaagaattt agcacctgct gagcaatcct atcaagtcgg cagatgtata    9600
ggttttctat atggagactt ggcgtataga aaatctactc atgccgagga cagttctcta    9660
tttcctctat ctatacaagg tcgtattaga ggtcgaggtt tcttaaaagg gttgctagac    9720
ggattaatga gagcaagttg ctgccaagta atacaccgga gaagtctggc tcatttgaag    9780
aggccggcca acgcagtgta cggaggtttg atttacttga ttgataaatt gagtgtatca    9840
cctccattcc tttctcttac tagatcagga cctattagag acgaattaga aacgattccc    9900
cacaagatcc caacctccta tccgacaagc aaccgtgata tgggggtgat tgtcagaaat    9960
tacttcaaat accaatgccg tctaattgaa aagggaaaat acagatcaca ttattcacaa   10020
ttatggttat tctcagatgt cttatccata gacttcattg gaccattctc tatttccacc   10080
accctcttgc aaatcctata caagccattt ttatctggga agataagaa tgagttgaga   10140 gagctggcaa atctttcttc attgctaaga tcaggagagg ggtgggaaga catacatgtg   10200
aaattcttca ccaaggacat attattgtgt ccagaggaaa tcagacatgc ttgcaagttc   10260
gggattgcta aggataataa taaagacatg agctatcccc cttggggaag ggaatccaga   10320
gggacaatta caacaatccc tgtttattat acgaccaccc cttacccaaa gatgctagag   10380
atgcctccaa gaatccaaaa tcccctgctg tccggaatca ggttgggcca attaccaact   10440
ggcgctcatt ataaaattcg gagtatatta catggaatgg gaatccatta cagggacttc   10500
ttgagttgtg gagacggctc cggagggatg actgctgcat tactacgaga aaatgtgcat   10560
agcagaggaa tattcaatag tctgttagaa ttatcagggt cagtcatgcg aggcgcctct   10620
cctgagcccc ccagtgccct agaaacttta ggaggagata aatcgagatg tgtaaatggt   10680
gaaacatgtt gggaatatcc atctgactta tgtgacccaa ggacttggga ctatttcctc    10740
cgactcaaag caggcttggg gcttcaaatt gatttaattg taatggatat ggaagttcgg   10800
gattcttcta ctagcctgaa aattgagacg aatgttagaa attatgtgca ccggattttg   10860
gatgagcaag gagtttttaat ctacaagact tatgaaacat atatttgtga gagcgaaaag   10920
aatgcagtaa caatccttgg tcccatgttc aagacggtcg acttagttca aacagaattt    10980
agtagttctc aaacgtctga agtatatatg tatgtaaag gtttgaagaa attaatcgat   11040
gaacccaatc ccgattggtc ttccatcaat gaatcctgga aaaacctgta cgcattccag   11100
tcatcagaac aggaatttgc cagagcaaag aaggttagta catactttac cttgacaggt   11160
```

```
attccctccc aattcattcc tgatcctttt gtaaacattg agactatgct acaaatattc  11220
ggagtaccca cgggtgtgtc tcatgcggct gccttaaaat catctgatag acctgcagat  11280
ttattgacca ttagccttt ttatatggcg attatatcgt attataacat caatcatatc  11340
agagtaggac cgatacctcc gaaccccca tcagatggaa ttgcacaaaa tgtggggatc  11400
gctataactg gtataagctt ttggctgagt ttgatggaga aagacattcc actatatcaa  11460
cagtgtttag cagttatcca gcaatcattc ccgattaggt gggaggctgt ttcagtaaaa  11520
ggaggataca agcagaagtg gagtactaga ggtgatgggc tcccaaaaga tacccgaact  11580
tcagactcct tggccccaat cgggaactgg atcagatctc tggaattggt ccgaaaccaa  11640
gttcgtctaa atccattcaa tgagatcttg ttcaatcagc tatgtcgtac agtggataat  11700
catttgaaat ggtcaaattt gcgaagaaac acaggaatga ttgaatggat caatagacga  11760
atttcaaaag aagaccggtc tatactgatg ttgaagagtg acctacacga ggaaaactct  11820
tggagagatt aaaaaatcat gaggagactc caaactttaa gtatgaaaaa aactttgatc  11880
cttaagaccc tcttgtggtt tttatttttt atctggtttt gtggtcttcg tgggtcggca  11940
tggcatctcc acctcctcgc ggtccgacct gggcatccga aggaggacgt cgtccactcg  12000
gatggctaag ggagagctcg gatccggctg ctaacaaagc ccgaaaggaa gctgagttgg  12060
ctgctgccac cgctgagcaa taactagcat aacccttgg ggcctctaaa cgggtcttga  12120 ggggttttt gctgaaagga ggaactatat ccggatcgag atcctctaga gtcgacctgc  12180
aggcatgcaa gcttgtattc tatagtgtca cctaaatcgt atgtgtatga tacataaggt  12240
tatgtattaa ttgtagccgc gttctaacga caatatgtac aagcctaatt gtgtagcatc  12300
tggcttactg aagcagaccc tatcatctct ctcgtaaact gccgtcagag tcggtttggt  12360
tggacgaacc ttctgagttt ctggtaacgc cgtcccgcac ccggaaatgg tcagcgaacc  12420
aatcagcagg gtcatcgcta gccagatcct ctacgccgga cgcatcgtgg ccggcatcac  12480
cggcgccaca ggtgcggttg ctggcgccta tatcgccgac atcaccgatg gggaagatcg  12540
ggctcgccac ttcgggctca tgagcgcttg tttcggcgtg ggtatggtgg caggccccgt  12600
ggccggggga ctgttgggcg ccatctcctt gcaccattcc ttgcggcggc ggtgctcaac  12660
ggcctcaacc tactactggg ctgcttccta atgcaggagt cgcataaggg agagcgtcga  12720
atggtgcact ctcagtacaa tctgctctga tgccgcatag ttaagccagc ccgacaccc  12780 gccaacaccc gctgacgcgc cctgacgggc ttgtctgctc ccggcatccg cttacagaca  12840
agctgtgacc gtctccggga gctgcatgtg tcagaggttt tcaccgtcat caccgaaacg  12900
cgcgagacga aagggcctcg tgatacgcct atttttatag gttaatgtca tgataataat  12960
ggtttcttag acgtcaggtg gcacttttcg gggaaatgtg cgcggaaccc ctatttgttt  13020 attttctaa atacattcaa atatgtatcc gctcatgaga caataaccct gataaatgct  13080
tcaataatat tgaaaaagga agagtatgag tattcaacat ttccgtgtcg cccttattcc  13140
cttttttgcg gcattttgcc ttcctgtttt tgctcaccca gaaacgctgg tgaaagtaaa  13200
agatgctgaa gatcagttgg gtgcacgagt gggttacatc gaactggatc tcaacagcgg  13260
taagatcctt gagagttttc gccccgaaga acgttttcca atgatgagca cttttaaagt  13320
tctgctatgt ggcgcggtat tatcccgtat tgacgccggg caagagcaac tcggtcgccg  13380
catacactat tctcagaatg acttggttga gtactcacca gtcacagaaa agcatcttac  13440
ggatggcatg acagtaagag aattatgcag tgctgccata accatgagtg ataacactgc  13500
```

```
ggccaactta cttctgacaa cgatcggagg accgaaggag ctaaccgctt ttttgcacaa   13560
catgggggat catgtaactc gccttgatcg ttgggaaccg gagctgaatg aagccatacc   13620
aaacgacgag cgtgacacca cgatgcctgt agcaatggca acaacgttgc gcaaactatt   13680
aactggcgaa ctacttactc tagcttcccg gcaacaatta atagactgga tggaggcgga   13740
taaagttgca ggaccacttc tgcgctcggc ccttccggct ggctggttta ttgctgataa   13800
atctggagcc ggtgagcgtg gtctcgcgg tatcattgca gcactggggc cagatggtaa    13860
gccctcccgt atcgtagtta tctacacgac ggggagtcag gcaactatgg atgaacgaaa   13920
tagacagatc gctgagatag gtgcctcact gattaagcat tggtaactgt cagaccaagt   13980
ttactcatat atactttaga ttgatttaaa acttcatttt taatttaaaa ggatctaggt   14040
gaagatcctt tttgataatc tcatgaccaa aatcccttaa cgtgagtttt cgttccactg   14100
agcgtcagac cccgtagaaa agatcaaagg atcttcttga gatccttttt ttctgcgcgt   14160
aatctgctgc ttgcaaacaa aaaaaccacc gctaccagcg gtggtttgtt tgccggatca   14220
agagctacca actctttttc cgaaggtaac tggcttcagc agagcgcaga taccaaatac   14280
tgtccttcta gtgtagccgt agttaggcca ccacttcaag aactctgtag caccgcctac   14340
atacctcgct ctgctaatcc tgttaccagt ggctgctgcc agtggcgata gtcgtgtct    14400 taccggttg gactcaagac gatagttacc ggataaggcg cagcggtcgg gctgaacggg     14460
gggttcgtgc acacagccca gcttggagcg aacgacctac accgaactga gatacctaca   14520
gcgtgagcta tgagaaagcg ccacgcttcc cgaagggaga aaggcggaca ggtatccggt   14580
aagcggcagg gtcggaacag gagagcgcac gagggagctt ccaggggaa acgcctggta    14640 tctttatagt cctgtcgggt ttcgccacct ctgacttgag cgtcgatttt tgtgatgctc   14700 gtcaggggg cggagcctat ggaaaaacgc cagcaacgcg gcctttttac ggttcctggc    14760
cttttgctgg ccttttgctc acatgttctt tcctgcgtta tcccctgatt ctgtggataa   14820
ccgtattacc gcctttgagt gagctgatac cgctcgccgc agccgaacga ccgagcgcag   14880
cgagtcagtg agcgaggaag cggaagagcg cccaatacgc aaaccgcctc tccccgcgcg   14940
ttggccgatt cattaatgca ggggatctc gatcccgcga aattaatacg actcactata    15000
gg                                                                  15002
```

ZIKA VIRUS VACCINE

RELATED APPLICATIONS

This application is the U.S. National Stage of International Patent Application No. PCT/US2017/057361, filed Oct. 19, 2017, which claims the benefit of priority to U.S. Provisional Application No. 62/410,165, filed Oct. 19, 2016, the entire contents of each of which are hereby incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 14, 2021, is named HMV-27001 SL.txt and is 132,433 bytes in size.

GOVERNMENT INTEREST

This invention was made with government support under AI109740 awarded by the National Institutes of Health. The government has certain rights in the invention.

BACKGROUND

The ongoing Zika virus outbreak underscores a critical need for the development of candidate vaccines. Vesicular stomatitis virus (VSV), a rhabdovirus, has been successfully used as a vaccine vector, with the recent approval of a recombinant VSV-based Ebola virus vaccine (VSV-EBOV) demonstrating that such VSV based vaccines can be safe and effective. VSV grows robustly in cell culture, is not associated with disease in humans, and can be readily engineered to incorporate foreign antigens. However, to date there are no reports of the successful incorporation of functional flavivirus envelope proteins into VSV particles. Indeed, efforts to incorporate envelope proteins from the flavivirus Dengue into a VSV vector were unsuccessful (Buonocore, et.al. (2002) J. Virol. 76, 6865).

The viral envelope proteins of rhabdoviruses, such as VSV, are structurally very different from the envelope proteins of flaviviruses, such as Zika. Viral envelope proteins mediate attachment to cells and fusion between viral and cellular membranes to initiate the process of infection. Viral fusogens fall into 3 classes. The class I proteins—best exemplified by influenza HA and HIV gp160—are trimeric, activated by cleavage of a precursor to leave an N-terminal fusion peptide and in response to specific triggers undergo conformational changes in which the fusion peptide inserts into a target membrane with subsequent refolding of the protein into the post-fusion trimer. The class II fusion proteins that are present on flaviviruses exist as dimers, have a hydrophobic fusion loop that inserts into the target membrane during conformational rearrangements of the dimer to a trimer. In the case of the class I and class II fusion proteins such conformational rearrangements are irreversible. The class III fusogens are best exemplified by VSV, here the protein exists as a trimer on the surface of the virus that can reversibly adopt pre and post fusion conformations. Fusion is accomplished by the insertion of two small hydrophobic loops into the target membrane. The envelope proteins that have been successfully incorporated into VSV particles are predominantly class I and class III fusogens.

The presentation of the envelope proteins on the surface of flavivirus vs rhabdovirus particles is also markedly different. In immature flavivirus particles, the E protein forms a total of 60 heterodimers with prM, the precursor protein of M on the virion surface. This association prevents E from undergoing conformational changes that lead to fusion of viral and cellular membranes. As the virus matures through the trans-golgi network, prM is cleaved by the host endopeptidase, furin. In the mature flavivirus particle, the envelope proteins are arranged flat on the virion surface as a set of 90 homodimers. Under low pH conditions in the endosome upon entry into cells, the dimers of the E protein rearrange to a trimeric form. By contrast, VSV buds from the cell surface and it is at the plasma membrane where the trimers of VSV G are incorporated into viral particles. Thus both the assembly, and arrangement of the envelope proteins on the mature virions are markedly different.

The geometry of intact virus particles are also completely different. VSV has a bullet shaped geometry and is approximately 180 nm in length and 80 nm in diameter the surface of the virus is decorated by approximately 400 spikes—each corresponding to a trimer of the VSV G protein. By contrast, Zika virus particles are completely coated with 90 homodimers of the E protein and are spherical with a diameter of approximately 40 nm. Consequently, it was not known whether Zika E protein could be successfully incorporated into VSV particles, and whether such incorporated E protein would be functional.

SUMMARY

Provided herein are methods and compositions useful in the treatment and/or prevention of a Zika virus infection. In one aspect, provided herein is a recombinant vesicular stomatitis virus (VSV) comprising in its genome a nucleic acid sequence encoding a Zika virus envelope (E) protein. In some embodiments, the recombinant VSV genome comprises the nucleic acid sequence encoding a Zika virus precursor membrane (prM) protein and/or a Zika virus capsid (C) protein. In some embodiments, the nucleic acid sequence encoding a Zika virus E protein substantially replaces the endogenous VSV viral glycoprotein (G) in the VSV genome.

In some aspects, provided herein is a recombinant VSV comprising a Zika virus envelope (E) protein or fragment thereof. In some embodiments, the recombinant VSV further comprises a Zika virus precursor membrane (prM) protein and/or a Zika virus capsid (C) protein.

In certain aspects, provided herein is a pharmaceutical composition (e.g., a Zika virus vaccine) comprising a recombinant VSV disclosed herein, and a pharmaceutically acceptable carrier. In certain embodiments, the pharmaceutical composition further comprises an adjuvant. In certain embodiments, the recombinant VSV is a live virus.

In certain aspects, provided herein is a method for inducing in a subject an immune response against Zika virus comprising administering to the subject a composition comprising a recombinant VSV disclosed herein. In some aspects, provided herein is a method for protecting a subject from Zika virus, comprising administering to the subject a recombinant VSV disclosed herein. In some aspects, provided herein is a method of treating a Zika virus infection, the method comprising administering a recombinant VSV disclosed herein, a pharmaceutical composition disclosed herein, and/or a vaccine disclosed herein, to a subject (e.g., a subject in need thereof).

In certain aspects, provided herein is a nucleic acid encoding the recombinant VSV disclosed herein. In yet another aspect, provided herein is an expression vector comprising the nucleic acid encoding the recombinant VSV disclosed herein. In certain aspects, provided herein is a method of making virus-like particles (VLP) comprising infecting a cell with an expression vector disclosed herein; culturing the cell under conditions such that the cell produces a Zika virus VLP; and collecting the Zika virus VLP.

BRIEF DESCRIPTION OF THE FIGURES

FIG. 1A and FIG. 1B show exemplary schematic representations of VSV-Zika virus construction and rescue. FIG. 1A shows exemplary schematics of the VSV-Zika virus constructs containing prM-E or C-prM-E. FIG. 1B shows a schematic of an exemplary method of recombinant virus recovery following transfection.

FIG. 2A and FIG. 2B demonstrate infection independent of VSV G. GFP was monitored as an indicator of infection FIG. 3A-FIG. 3C show that VSVΔG-Zika recombinants express Zika E in infected cells. FIG. 3A is a gel showing metabolic labeling of viral proteins. Vero cells were infected with VSV-eGFP or rVSVΔG-Zika-prM-E at an MOI of 3. At 6 hours post infection, cells were starved in methionine-free DMEM for 30 minutes, followed by the addition of $^{35}$S-methionine for 30 minutes. Cells were lysed and analyzed by SDS-PAGE. FIG. 3B is an image of a Western blot of infected cell lysates and culture supernatants probed with a pan flavivirus antibody that reacts with ZIKV-E (4G2) or VSV-M. FIG. 3C shows the immunofluorescence of cells infected with VSV-eGFP or rVSVΔG-Zika-prM-E probed with the 4G2 antibody (red channel).

FIG. 6 shows that Zika E protein is present together with sedimented VSV. SDS-PAGE analysis of recombinant viruses following concentration on sucrose cushions. Lane 1: rVSVΔG-Zika-CprME, Lane 2: r VSV-Zika-CprME, Lane 3: rVSV-EGFP.

Figures 7C, 7D:
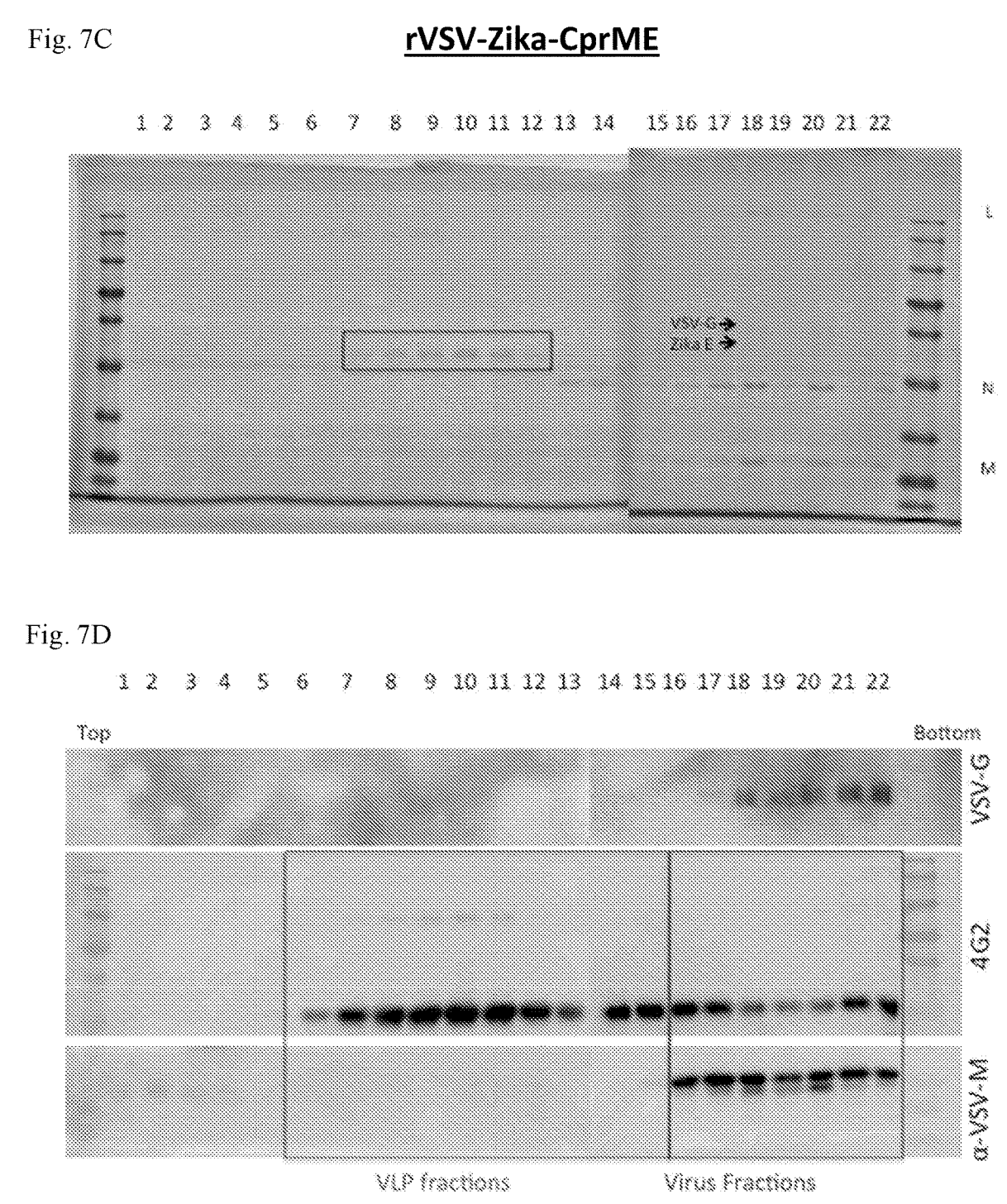

FIG. 7A-FIG. 7D show the production of Zika VLPs and VSV-ZIKA-E coated particles from rVSVΔG-Zika-CprME (FIG. 7A and FIG. 7B) and rVSV-Zika-CprME (FIG. 7C and FIG. 7D). Cells were infected with the indicated recombinant VSV and the cell culture supernatants clarified by centrifugation, virus and VLPs collected by centrifugation through a sucrose cushion, resuspended in NTE and then separated by centrifugation through a linear 15-45% sucrose gradient by ultracentrifugation. Fractions were collected and analyzed by Coomassie stain (FIG. 7A and FIG. 7C) and by blotting to detect the presence of VSV M, G and Zika E proteins (FIG. 7B and FIG. 7D).

FIG. 8A-FIG. 8D show that the production of Zika VLPs and VSV-ZIKA-E coated particles from rVSVΔG-Zika-prME (FIG. 8A and FIG. 8B) and rVSV-Zika-prME (FIG. 8C and FIG. 8D). Cells were infected with the indicated recombinant VSV and the cell culture supernatants clarified by centrifugation, virus and VLPs collected by centrifugation through a sucrose cushion, resuspended in NTE and then separated by centrifugation through a linear 15-45% sucrose gradient by ultracentrifugation. Fractions were collected and analyzed by Coomassie stain (FIG. 8A and FIG. 8C) and by blotting to detect the presence of VSV M protein, and Zika E protein (FIG. 8B and FIG. 8D).

Figures 10A, 10B, 10C, 10D:
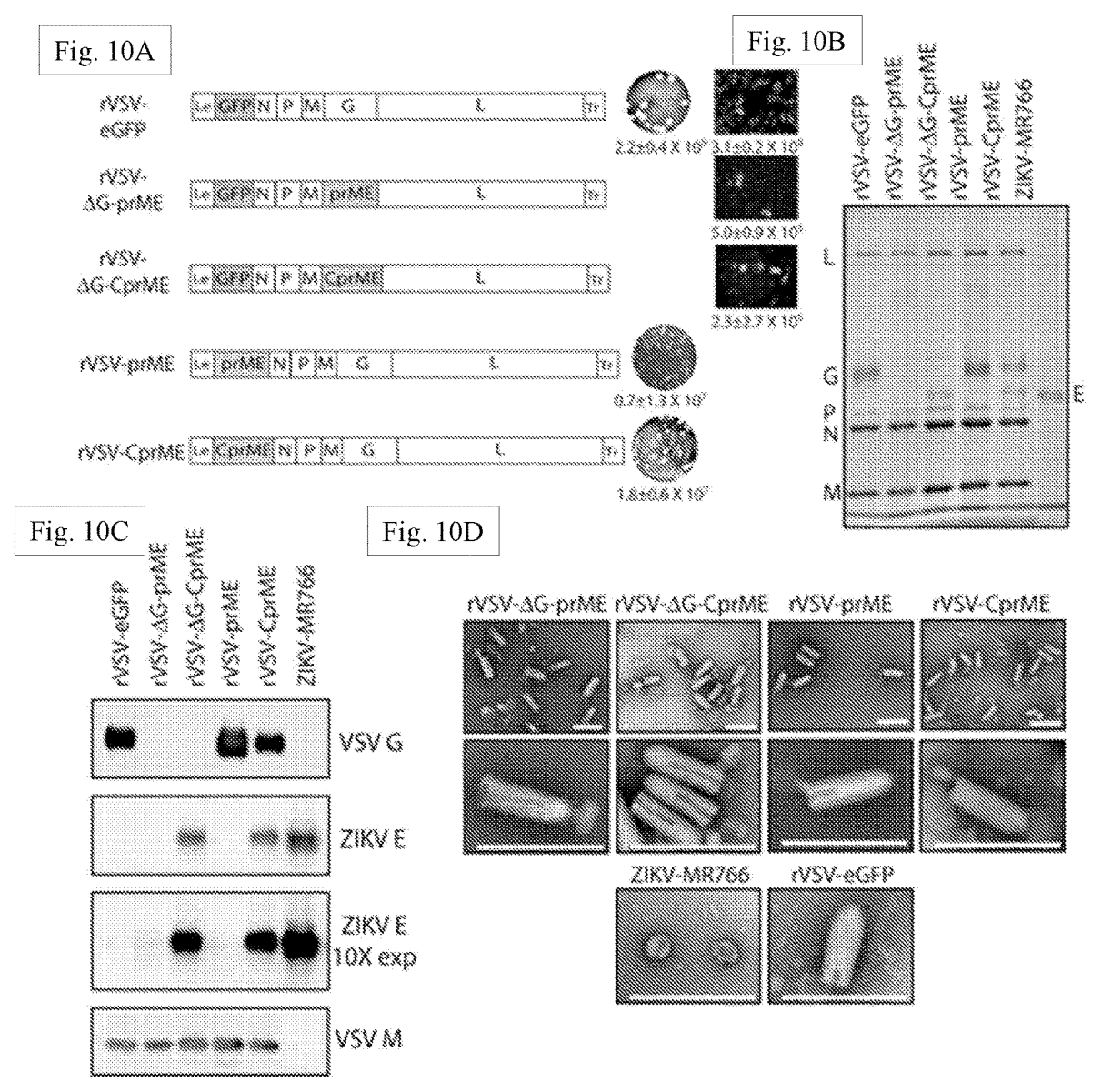

FIG. 10A-FIG. 10D show the composition and infectivity of VSV-ZIKV recombinants. FIG. 10A is a schematic diagram of recombinant VSV-ZIKV genomes. The VSV genes encoding N—nucleocapsid, P—phospho, M—matrix, G—glyco, L—large polymerase and the eGFP—enhanced green fluorescent protein reporter are shown flanked by the viral Le—leader and Tr—trailer regulatory sequences. The ZIKV precursor membrane envelope (prME) together with the signal peptide portion of the capsid protein (C) are shown together with their position of insertion. Viral titers determined by plaque assay on Vero cells for viruses encoding VSV G are expressed as plaque forming units per milliliter (pfu ml$^{-1}$) and representative images shown. For viruses lacking VSV, G titers were determined by flow cytometry detection of the eGFP reporter and are expressed as infectious florescence units per milliliter (ifu ml$^{-1}$) and representative images shown at 40× magnification. FIG. 10B is an image of an SDS-PAGE gel showing protein composition of purified virions. Equivalent protein amounts of VSV-eGFP, the VSV-ZIKV recombinants and wild type ZIKV (strain: MR766) were analyzed by SDS-PAGE and proteins visualized by Coomassie staining. The VSV N, P, M, G and L and the ZIKV E proteins are identified at the side of this representative gel. FIG. 10 is an image of a Western blot showing glycoprotein composition of purified virions. VSV G and ZIKV E were detected by Western blot using antibodies that recognize the cytoplasmic tail of VSV G or flavivirus envelope proteins (4G2) respectively, together with VSV-M as control for virion composition. A 10× exposure of the 4G2 Western blot is also shown to visualize the relatively low levels of E incorporated. FIG. 10D shows exemplary structural properties of purified viral particles. Sucrose gradient purified virions were visualized by negative stain (2% phosphotungstic acid) electron microscopy. Scale bar=200 nm.

Figures 11A, 11B:
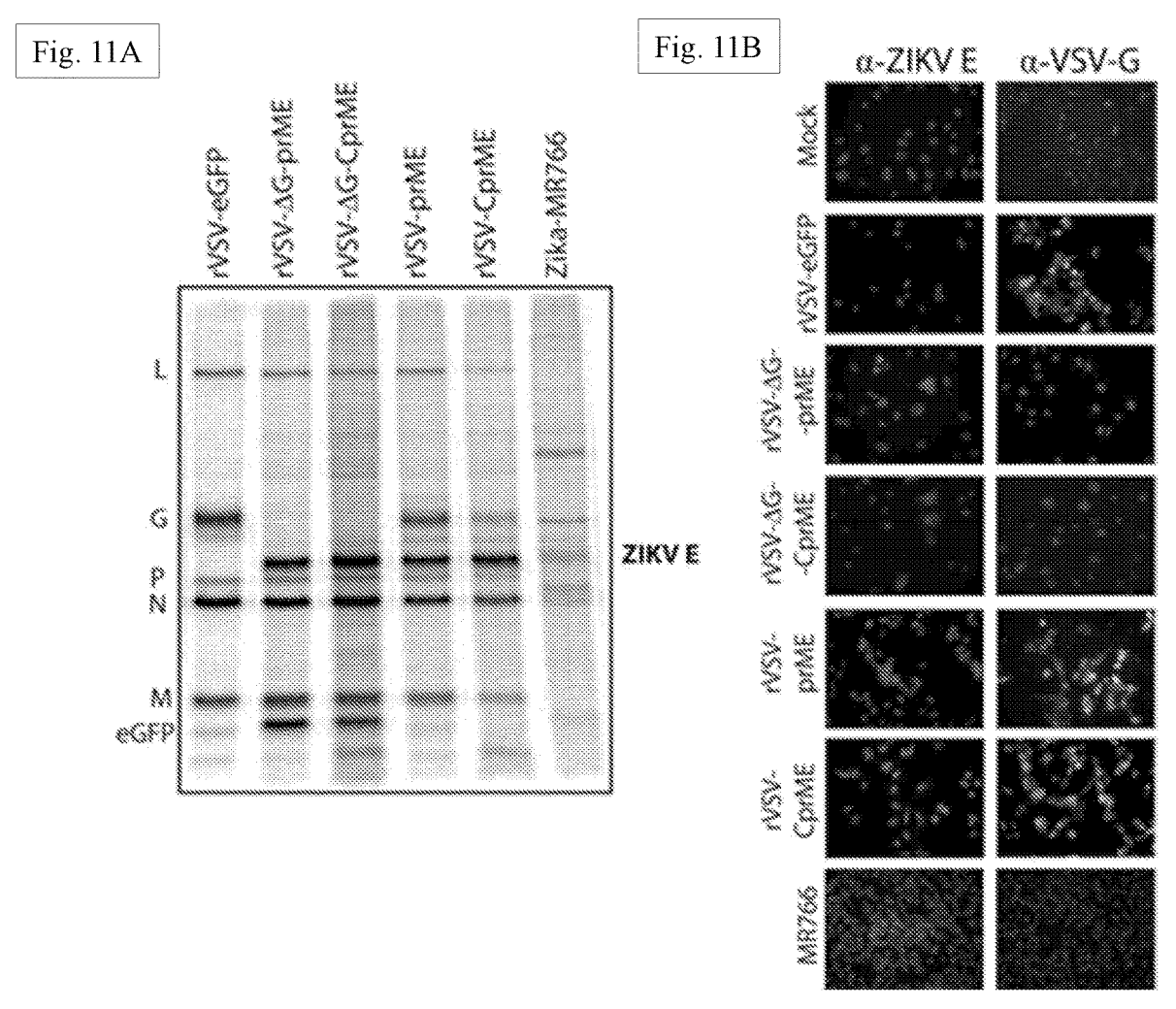

FIG. 11A and FIG. 11B show that VSV-ZIKV vectors express ZIKV E protein in infected cells. FIG. 11A is an image of an SDS-PAGE gel showing total protein synthesis in infected cells. Vero cells were infected (MOI=3) with the indicated VSV recombinant and protein synthesis measured by metabolic incorporation of [$^{35}$5]-methionine from 5-6 h post infection. Protein synthesis in MR766 infected cells (MOI=10) was measured by metabolic labeling for 1 h at 40 h post infection. Total cytoplasmic extracts were prepared, equivalent amounts analyzed by SDS-PAGE and proteins detected by phosphoimage analysis. The VSV proteins, together with the eGFP reporter are identified on the left side of the gel, and ZIKV E on the right. FIG. 11B shows the detection of viral proteins by immunofluorescence microscopy. Vero cells were infected as in FIG. 11A, fixed at 6 h post infection (VSV recombinants) or 48 h post infection (MR766) prior to protein detection using primary antibodies 4G2 for Zika E or IE2 for VSV G. Primary antibodies were detected using Alexa fluor 594 Goat α-mouse secondary antibody and images false colored red for Zika E and green for VSV G. Nuclei (blue) were visualized by NucBlue™.

Figure 12:
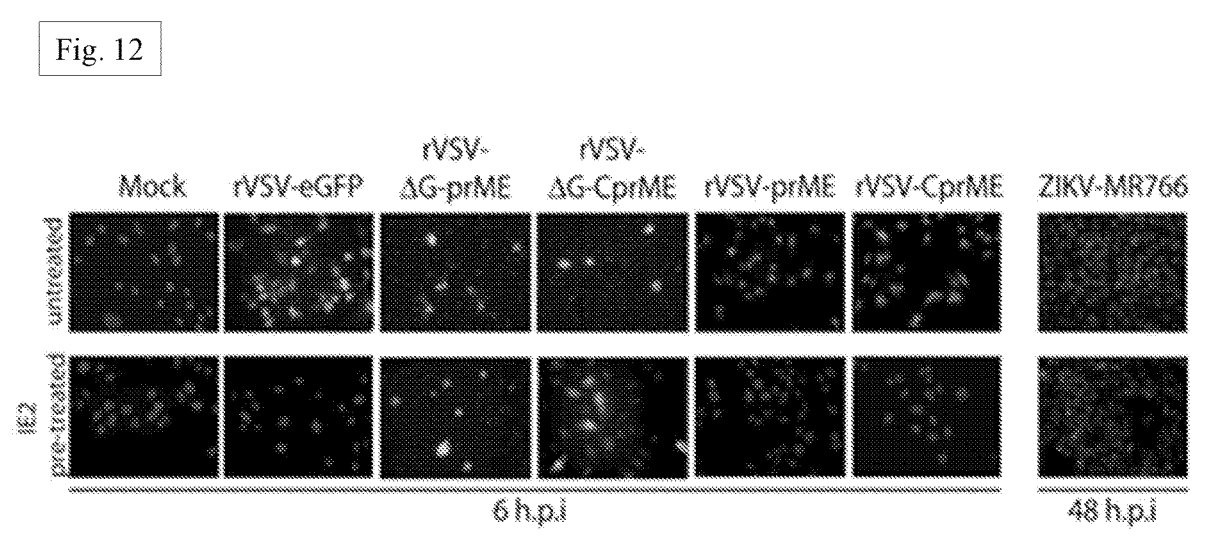

FIG. 12 shows that the Zika envelope is functional on VSV particles.

Immunofluorescence or eGFP epifluorescence of Vero cells infected with the indicated virus. Where indicated, viruses were pre-incubated for 30 minutes at 34° C. with 0.1 mg ml$^{-1}$ of the VSV G neutralizing monoclonal antibody (IE2). Cells were fixed, permeabilized and Zika virus envelope detected using the flavivirus antibody (4G2) and a secondary Alexa fluor 594 Goat α-mouse at 6 h p.i. for VSV recombinants and at 48 h p.i. for ZIKV MR766 strain.

Figure 13A:
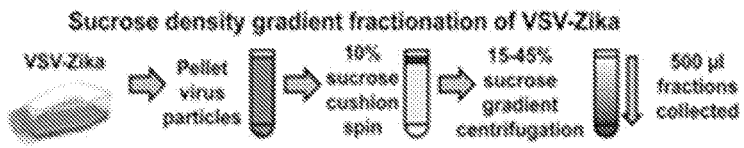
Figure 13B:
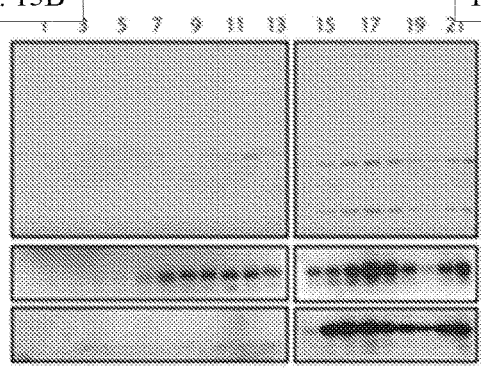
Figure 13C:
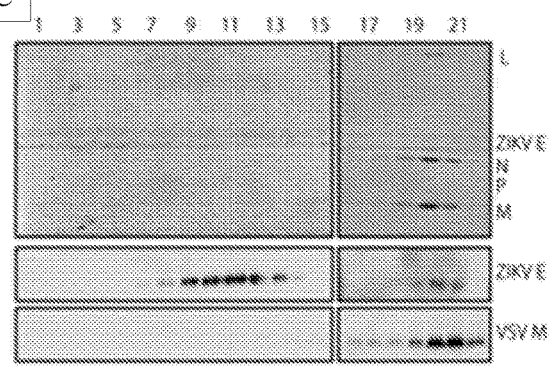
Figure 13D:
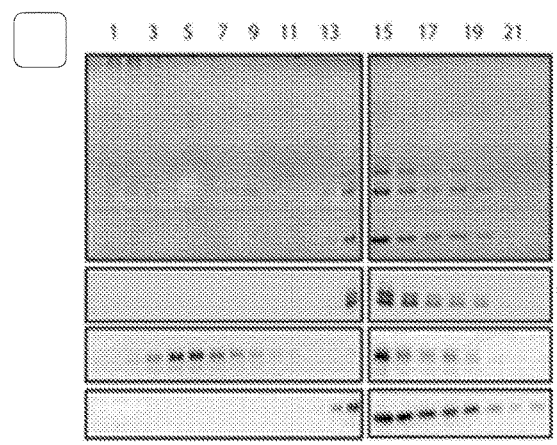
Figure 13E:
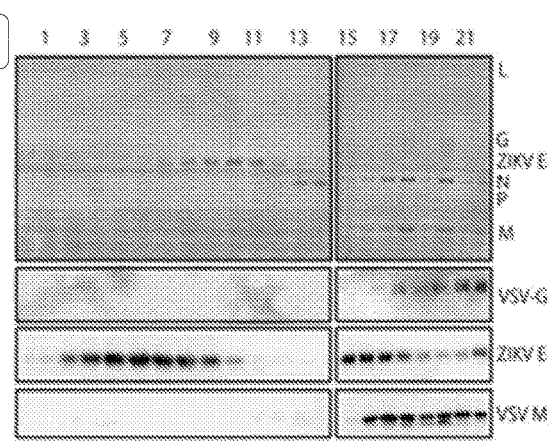

FIG. 13A-FIG. 13E show data regarding the purification of VSV-ZIKV and Zika VLPs. FIG. 13A is a schematic illustrating purification of VSV-Zika and Virus Like Particles (VLPs) from cell culture supernatants. Cell culture supernatants are collected and virions and VLPs recovered by centrifugation followed by sedimentation through a sucrose cushion and subsequent separation on a 15-45% sucrose gradient. Fractions (0.5 ml) were collected from the sucrose gradient and their protein constituents analyzed by SDS-PAGE or Western Blots (FIG. 13B-FIG. 13E). Each of the fractions were resolved on a 10% low bis gel and stained by Coomassie (top panels) or proteins detected using 4G2 antibody (Zika E), VSV-G tail antibody or VSV-M antibody. Fractions are shown on gels going from top (left) to bottom (right). FIG. 13B VSV-AG-prME, FIG. 13C VSV-AG-CprME, FIG. 13D VSV-prME and FIG. 13E VSV-CprME.

Figures 14A, 14B, 14C, 14D, 14E:
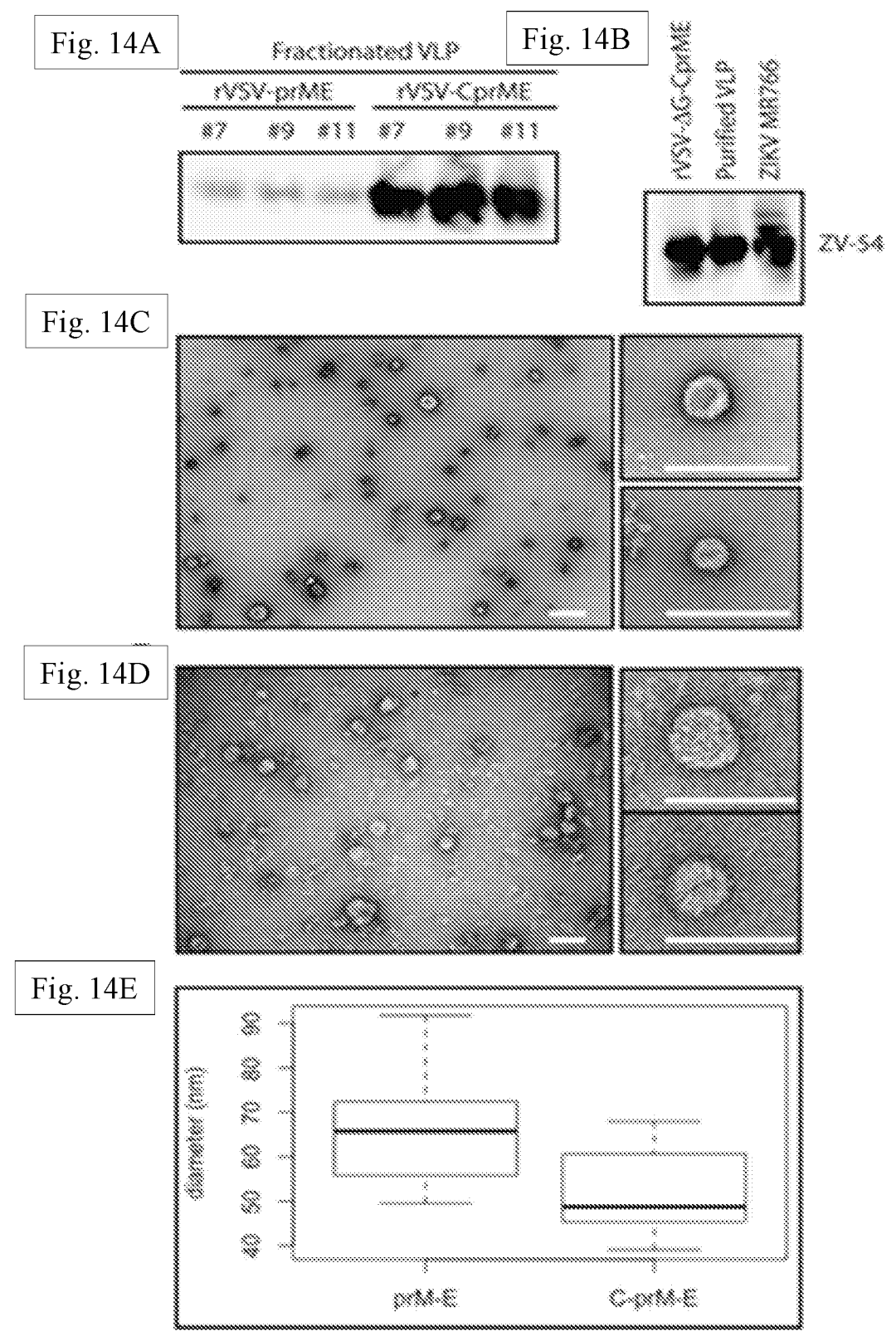

FIG. 14A-FIG. 14E show properties of Zika VLPs produced by VSV-prME and VSV-CprME infections. FIG. 14A shows the image of a Western blot after VLPs were collected from cell culture supernatants by precipitation using polyethylene glycol, resuspended and separated on a 15-45% sucrose gradient and the fractions analyzed by SDS-PAGE and probed by western blot for ZIKV E using the 4G2 antibody. FIG. 14B shows the detection of the E protein in VSV-AG-CprME virions, VLPs from VSV-CprME and purified wt ZIKV MR766 virus using the ZIKV Mab (ZV-54). FIG. 14C and FIG. 14D show negative stain electron micrographs of purified VLPs. stained with 0.5% uranyl formate obtained from the VLP fractions of VSV-prME (FIG. 14C) or VSV-CprME (FIG. 14D) scale bars represent 100 nm. FIG. 14E is a graph showing diameters (nm) of VLPs produced by VSV-prME (prME) and VSV-CprME (CprME).

FIG. 15A-FIG. 15C show that VSV-Zika are immunogenic in BALB/c mice. FIG. 15A is a schematic showing the immunization schedule for BALB/c mice (n=5/group). FIG. 15B is a plot showing results of ELISA assay for E-specific antibody present in animals immunized with the indicated immunogen. FIG. 15C is plot showing Sera from the mice inoculated with the indicated immunogens was used to test the ability to neutralize the MR766 strain of Zika (n=3). Dilutions of serum that protect Vero cells from 100 TCID50 of ZIKV MR766 virus infection are shown.

DETAILED DESCRIPTION

In certain aspects, provided herein are methods and compositions related to the treatment and/or prevention of a Zika virus infection. In some embodiments, disclosed herein are recombinant vesicular stomatis viruses (VSV), proteins produced by these viruses (e.g., variant polypeptides and fragments thereof), nucleic acids encoding the viruses, expression vectors comprising these nucleic acids, methods of making virus like particles from the recombinant VSV or nucleic acids encoding them, and methods for the use of recombinant VSV in various applications, such as methods for treating and/or vaccinating against a number of conditions including, but not limited to, Zika virus infections. While in no way intended to be limiting, exemplary recombinant VSV and methods for making and using any of the foregoing are described below.

Recombinant Vesicular Stomatis Viruses

In certain aspects, provided herein are recombinant vesicular stomatis viruses (VSV). An exemplary nucleic acid sequence for a wild type VSV is as follows (SEQ ID NO: 1):

```
                                                       SEQ ID NO: 1
ACGAAGACAAACAAACCATTATTATCATTAAAAGGCTCAGGAGAAACTTTAACAGTAATCAAA

ATGTCTGTTACAGTCAAGAGAATCATTGACAACACAGTCATAGTTCCAAAACTTCCTGCAAAT

GAGGATCCAGTGGAATACCCGGCAGATTACTTCAGAAAATCAAAGGAGATTCCTCTTTACATC

AATACTACAAAAAGTTTGTCAGATCTAAGAGGATATGTCTACCAAGGCCTCAAATCCGGAAAT

GTATCAATCATACATGTCAACAGCTACTTGTATGGAGCATTAAAGGACATCCGGGGTAAGTTG

GATAAAGATTGGTCAAGTTTCGGAATAAACATCGGGAAAGCAGGGGATACAATCGGAATATTT

GACCTTGTATCCTTGAAAGCCCTGGACGGCGTACTTCCAGATGGAGTATCGGATGCTTCCAGA

ACCAGCGCAGATGACAAATGGTTGCCTTTGTATCTACTTGGCTTATACAGAGTGGGCAGAACA

CAAATGCCTGAATACAGAAAAAAGCTCATGGATGGGCTGACAAATCAATGCAAATGATCAAT

GAACAGTTTGAACCTCTTGTGCCAGAAGGTCGTGACATTTTTGATGTGTGGGGAAATGACAGT

AATTACACAAAAATTGTCGCTGCAGTGGACATGTTCTTCCACATGTTCAAAAAACATGAATGT

GCCTCGTTCAGATACGGAACTATTGTTTCCAGATTCAAAGATTGTGCTGCATTGGCAACATTT

GGACACCTCTGCAAAATAACCGGAATGTCTACAGAAGATGTAACGACCTGGATCTTGAACCGA

GAAGTTGCAGATGAAATGGTCCAAATGATGCTTCCAGGCCAAGAAATTGACAAGGCCGATTCA

TACATGCCTTATTTGATCGACTTTGGATTGTCTTCTAAGTCTCCATATTCTTCCGTCAAAAAC

CCTGCCTTCCACTTCTGGGGGCAATTGACAGCTCTTCTGCTCAGATCCACCAGAGCAAGGAAT

GCCCGACAGCCTGATGACATTGAGTATACATCTCTTACTACAGCAGGTTTGTTGTACGCTTAT
```

-continued

```
GCAGTAGGATCCTCTGCCGACTTGGCACAACAGTTTTGTGTTGGAGATAACAAATACACTCCA

GATGATAGTACCGGAGGATTGACGACTAATGCACCGCCACAAGGCAGAGATGTGGTCGAATGG

CTCGGATGGTTTGAAGATCAAAACAGAAAACCGACTCCTGATATGATGCAGTATGCGAAAAGA

GCAGTCATGTCACTGCAAGGCCTAAGAGAAGACAATTGGCAAGTATGCTAAGTCAGAATTT

GACAAATGACCCTATAATTCTCAGATCACCTATTATATATTATGCTACATATGAAAAAAACTA

ACAGATATCATGGATAATCTCACAAAAGTTCGTGAGTATCTCAAGTCCTATTCTCGTCTGGAT

CAGGCGGTAGGAGAGATAGATGAGATCGAAGCACAACGAGCTGAAAAGTCCAATTATGAGTTG

TTCCAAGAGGATGGAGTGGAAGAGCATACTAAGCCCTCTTATTTTCAGGCAGCAGATGATTCT

GACACAGAATCTGAACCAGAAATTGAAGACAATCAAGGTTTGTATGCACAGGATCCAGAAGCT

GAGCAAGTTGAAGGCTTTATACAGGGGCCTTTAGATGACTATGCAGATGAGGAAGTGGATGTT

GTATTTACTTCGGACTGGAAACCACCTGAGCTTGAATCTGACGAGCATGGAAAGACCTTACGG

TTGACATCGCCAGAGGGTTTAAGTGGAGAGCAGAAATCCCAGTGGCTTTCGACGATTAAAGCA

GTCGTGCAAAGTGCCAAATACTGGAATCTGGCAGAGTGCACATTTGAAGCATCGGGAGAAGGG

GTCATTATGAAGGAGCGCCAGATAACTCCGGATGTATATAAGGTCACTCCAGTGATGAACACA

CATCCGTCCCAATCAGAAGCAGTATCAGATGTTTGGTCTCTCTCAAAGACATCCATGACTTTC

CAACCCAAGAAAGCAAGTCTTCAGCCTCTCACCATATCCTTGGATGAATTGTTCTCATCTAGA

GGAGAGTTCATCTCTGTCGGAGGTGACGGACGAATGTCTCATAAAGAGGCCATCCTGCTCGGC

CTGAGATACAAAAAGTTGTACAATCAGGCGAGAGTCAAATATTCTCTGTAGACTATGAAAAAA

AGTAACAGATATCACGATCTAAGTGTTATCCCAATCCATTCATCATGAGTTCCTTAAAGAAGA

TTCTCGGTCTGAAGGGGAAAGGTAAGAAATCTAAGAAATTAGGGATCGCACCACCCCCTTATG

AAGAGGACACTAGCATGGAGTATGCTCCGAGCGCTCCAATTGACAAATCCTATTTTGGAGTTG

ACGAGATGGACACCTATGATCCGAATCAATTAAGATATGAGAAATTCTTCTTTACAGTGAAAA

TGACGGTTAGATCTAATCGTCCGTTCAGAACATACTCAGATGTGGCAGCCGCTGTATCCCATT

GGGATCACATGTACATCGGAATGGCAGGGAAACGTCCCTTCTACAAAATCTTGGCTTTTTTGG

GTTCTTCTAATCTAAAGGCCACTCCAGCGGTATTGGCAGATCAAGGTCAACCAGAGTATCACA

CTCACTGCGAAGGCAGGGCTTATTTGCCACATAGGATGGGGAAGACCCCTCCCATGCTCAATG

TACCAGAGCACTTCAGAAGACCATTCAATATAGGTCTTTACAAGGGAACGATTGAGCTCACAA

TGACCATCTACGATGATGAGTCACTGGAAGCAGCTCCTATGATCTGGGATCATTTCAATTCTT

CCAAATTTTCTGATTTCAGAGAGAAGGCCTTAATGTTTGGCCTGATTGTCGAGAAAAAGGCAT

CTGGAGCGTGGGTCCTGGATTCTATCAGCCACTTCAAATGAGCTAGTCTAACTTCTAGCTTCT

GAACAATCCCCGGTTTACTCAGTCTCTCCTAATTCCAGCCTCTCGAACAACTAATATCCTGTC

TTTTCTATCCCTATGAAAAAAACTAACAGAGATCGATCTGTTTCCTTGACACTATGAAGTGCC

TTTTGTACTTAGCCTTTTTATTCATTGGGGTGAATTGCAAGTTCACCATAGTTTTTCCACACA

ACCAAAAAGGAAACTGGAAAAATGTTCCTTCTAATTACCATTATTGCCCGTCAAGCTCAGATT

TAAATTGGCATAATGACTTAATAGGCACAGCCATACAAGTCAAAATGCCCAAGAGTCACAAGG

CTATTCAAGCAGACGGTTGGATGTGTCATGCTTCCAAATGGGTCACTACTTGTGATTTCCGCT

GGTATGGACCGAAGTATATAACACAGTCCATCCGATCCTTCACTCCATCTGTAGAACAATGCA

AGGAAAGCATTGAACAAACGAAACAAGGAACTTGGCTGAATCCAGGCTTCCCTCCTCAAAGTT

GTGGATATGCAACTGTGACGGATGCCGAAGCAGTGATTGTCCAGGTGACTCCTCACCATGTGC

TGGTTGATGAATACACAGGAGAATGGGTTGATTCACAGTTCATCAACGGAAAATGCAGCAATT
```

-continued

```
ACATATGCCCCACTGTCCATAACTCTACAACCTGGCATTCTGACTATAAGGTCAAAGGGCTAT
GTGATTCTAACCTCATTTCCATGGACATCACCTTCTTCTCAGAGGACGGAGAGCTATCATCCC
TGGGAAAGGAGGGCACAGGGTTCAGAAGTAACTACTTTGCTTATGAAACTGGAGGCAAGGCCT
GCAAAATGCAATACTGCAAGCATTGGGGAGTCAGACTCCCATCAGGTGTCTGGTTCGAGATGG
CTGATAAGGATCTCTTTGCTGCAGCCAGATTCCCTGAATGCCCAGAAGGGTCAAGTATCTCTG
CTCCATCTCAGACCTCAGTGGATGTAAGTCTAATTCAGGACGTTGAGAGGATCTTGGATTATT
CCCTCTGCCAAGAAACCTGGAGCAAAATCAGAGCGGGTCTTCCAATCTCTCCAGTGGATCTCA
GCTATCTTGCTCCTAAAAACCCAGGAACCGGTCCTGCTTTCACCATAATCAATGGTACCCTAA
AATACTTTGAGACCAGATACATCAGAGTCGATATTGCTGCTCCAATCCTCTCAAGAATGGTCG
GAATGATCAGTGGAACTACCACAGAAAGGGAACTGTGGGATGACTGGGCACCATATGAAGACG
TGGAAATTGGACCCAATGGAGTTCTGAGGACCAGTTCAGGATATAAGTTTCCTTTATACATGA
TTGGACATGGTATGTTGGACTCCGATCTTCATCTTAGCTCAAAGGCTCAGGTGTTCGAACATC
CTCACATTCAAGACGCTGCTTCGCAACTTCCTGATGATGAGAGTTTATTTTTTGGTGATACTG
GGCTATCCAAAAATCCAATCGAGCTTGTAGAAGGTTGGTTCAGTAGTTGGAAAAGCTCTATTG
CCTCTTTTTTCTTTATCATAGGGTTAATCATTGGACTATTCTTGGTTCTCCGAGTTGGTATCC
ATCTTTGCATTAAATTAAAGCACACCAAGAAAAGACAGATTTATACAGACATAGAGATGAACC
GACTTGGAAAGTAACTCAAATCCTGCACAACAGATTCTTCATGTTTGGACCAAATCAACTTGT
GATACCATGCTCAAAGAGGCCTCAATTATATTTGAGTTTTTAATTTTTATGAAAAAAACTAAC
AGCAATCATGGAAGTCCACGATTTTGAGACCGACGAGTTCAATGATTTCAATGAAGATGACTA
TGCCACAAGAGAATTCCTGAATCCCGATGAGCGCATGACGTACTTGAATCATGCTGATTACAA
TTTGAATTCTCCTCTAATTAGTGATGATATTGACAATTTGATCAGGAAATTCAATTCTCTTCC
GATTCCCTCGATGTGGGATAGTAAGAACTGGGATGGAGTTCTTGAGATGTTAACATCATGTCA
AGCCAATCCCATCTCAACATCTCAGATGCATAAATGGATGGGAAGTTGGTTAATGTCTGATAA
TCATGATGCCAGTCAAGGGTATAGTTTTTTACATGAAGTGGACAAAGAGGCAGAAATAACATT
TGACGTGGTGGAGACCTTCATCCGCGGCTGGGGCAACAAACCAATTGAATACATCAAAAAGGA
AAGATGGACTGACTCATTCAAAATTCTCGCTTATTTGTGTCAAAAGTTTTTGGACTTACACAA
GTTGACATTAATCTTAAATGCTGTCTCTGAGGTGGAATTGCTCAACTTGGCGAGGACTTTCAA
AGGCAAAGTCAGAAGAAGTTCTCATGGAACGAACATATGCAGGATTAGGGTTCCCAGCTTGGG
TCCTACTTTTATTTCAGAAGGATGGGCTTACTTCAAGAAACTTGATATTCTAATGGACCGAAA
CTTTCTGTTAATGGTCAAAGATGTGATTATAGGGAGGATGCAAACGGTGCTATCCATGGTATG
TAGAATAGACAACCTGTTCTCAGAGCAAGACATCTTCTCCCTTCTAAATATCTACAGAATTGG
AGATAAAATTGTGGAGAGGCAGGGAAATTTTTCTTATGACTTGATTAAAATGGTGGAACCGAT
ATGCAACTTGAAGCTGATGAAATTAGCAAGAGAATCAAGGCCTTTAGTCCCACAATTCCCTCA
TTTTGAAAATCATATCAAGACTTCTGTTGATGAAGGGGCAAAAATTGACCGAGGTATAAGATT
CCTCCATGATCAGATAATGAGTGTGAAAACAGTGGATCTCACACTGGTGATTTATGGATCGTT
CAGACATTGGGGTCATCCTTTTATAGATTATTACACTGGACTAGAAAAATTACATTCCCAAGT
AACCATGAAGAAAGATATTGATGTGTCATATGCAAAAGCACTTGCAAGTGATTTAGCTCGGAT
TGTTCTATTTCAACAGTTCAATGATCATAAAAAGTGGTTCGTGAATGGAGACTTGCTCCCTCA
TGATCATCCCTTTAAAAGTCATGTTAAAGAAAATACATGGCCCACAGCTGCTCAAGTTCAAGA
TTTTGGAGATAAATGGCATGAACTTCCGCTGATTAAATGTTTTGAAATACCCGACTTACTAGA
CCCATCGATAATATACTCTGACAAAAGTCATTCAATGAATAGGTCAGAGGTGTTGAAACATGT
```

-continued

```
CCGAATGAATCCGAACACTCCTATCCCTAGTAAAAAGGTGTTGCAGACTATGTTGGACACAAA
GGCTACCAATTGGAAAGAATTTCTTAAAGAGATTGATGAGAAGGGCTTAGATGATGATCT
AATTATTGGTCTTAAAGGAAAGGAGAGGGAACTGAAGTTGGCAGGTAGATTTTTCTCCCTAAT
GTCTTGGAAATTGCGAGAATACTTTGTAATTACCGAATATTTGATAAAGACTCATTTCGTCCC
TATGTTTAAAGGCCTGACAATGGCGGACGATCTAACTGCAGTCATTAAAAAGATGTTAGATTC
CTCATCCGGCCAAGGATTGAAGTCATATGAGGCAATTTGCATAGCCAATCACATTGATTACGA
AAAATGGAATAACCACCAAAGGAAGTTATCAAACGGCCCAGTGTTCCGAGTTATGGGCCAGTT
CTTAGGTTATCCATCCTTAATCGAGAGAACTCATGAATTTTTTGAGAAAAGTCTTATATACTA
CAATGGAAGACCAGACTTGATGCGTGTTCACAACAACACACTGATCAATTCAACCTCCCAACG
AGTTTGTTGGCAAGGACAAGAGGGTGGACTGGAAGGTCTACGGCAAAAAGGATGGACTATCCT
CAATCTACTGGTTATTCAAAGAGAGGCTAAAATCAGAAACACTGCTGTCAAAGTCTTGGCACA
AGGTGATAATCAAGTTATTTGCACACAGTATAAAACGAAGAAATCGAGAAACGTTGTAGAATT
ACAGGGTGCTCTCAATCAAATGGTTTCTAATAATGAGAAAATTATGACTGCAATCAAAATAGG
GACAGGGAAGTTAGGACTTTTGATAAATGACGATGAGACTATGCAATCTGCAGATTACTTGAA
TTATGGAAAAATACCGATTTTCCGTGGAGTGATTAGAGGGTTAGAGACCAAGAGATGGTCACG
AGTGACTTGTGTCACCAATGACCAAATACCCACTTGTGCTAATATAATGAGCTCAGTTTCCAC
AAATGCTCTCACCGTAGCTCATTTTGCTGAGAACCCAATCAATGCCATGATACAGTACAATTA
TTTTGGGACATTTGCTAGACTCTTGTTGATGATGCATGATCCTGCTCTTCGTCAATCATTGTA
TGAAGTTCAAGATAAGATACCGGGCTTGCACAGTTCTACTTTCAAATACGCCATGTTGTATTT
GGACCCTTCCATTGGAGGAGTGTCGGGCATGTCTTTGTCCAGGTTTTTGATTAGAGCCTTCCC
AGATCCCGTAACAGAAAGTCTCTCATTCTGGAGATTCATCCATGTACATGCTCGAAGTGAGCA
TCTGAAGGAGATGAGTGCAGTATTTGGAAACCCCGAGATAGCCAAGTTTCGAATAACTCACAT
AGACAAGCTAGTAGAAGATCCAACCTCTCTGAACATCGCTATGGGAATGAGTCCAGCGAACTT
GTTAAAGACTGAGGTTAAAAAATGCTTAATCGAATCAAGACAAACCATCAGGAACCAGGTGAT
TAAGGATGCAACCATATATTTGTATCATGAAGAGGATCGGCTCAGAAGTTTCTTATGGTCAAT
AAATCCTCTGTTCCCTAGATTTTTAAGTGAATTCAAATCAGGCACTTTTTTGGGAGTCGCAGA
CGGGCTCATCAGTCTATTTCAAAATTCTCGTACTATTCGGAACTCCTTTAAGAAAAAGTATCA
TAGGGAATTGGATGATTTGATTGTGAGGAGTGAGGTATCCTCTTTGACACATTTAGGGAAACT
TCATTTGAAGGGGATCATGTAAAATGTGGACATGTTCAGCTACTCATGCTGACACATTAAG
ATACAAATCCTGGGGCCGTACAGTTATTGGGACAACTGTACCCCATCCATTAGAAATGTTGGG
TCCACAACATCGAAAAGAGACTCCTTGTGCACCATGTAACACATCAGGGTTCAATTATGTTTC
TGTGCATTGTCCAGACGGGATCCATGACGTCTTTAGTTCACGGGGACCATTGCCTGCTTATCT
AGGGTCTAAAACATCTGAATCTACATCTATTTTGCAGCCTTGGGAAAGGGAAAGCAAAGTCCC
ACTGATTAAAAGAGCTACACGTCTTAGAGATGCTATCTCTTGGTTTGTTGAACCCGACTCTAA
ACTAGCAATGACTATACTTTCTAACATCCACTCTTTAACAGGCGAAGAATGGACCAAAAGGCA
GCATGGGTTCAAAAGAACAGGGTCTGCCCTTCATAGGTTTTCGACATCTCGGATGAGCCATGG
TGGGTTCGCATCTCAGAGCACTGCAGCATTGACCAGGTTGATGGCAACTACAGACACCATGAG
GGATCTGGGAGATCAGAATTTCGACTTTTTATTCCAAGCAACGTTGCTCTATGCTCAAATTAC
CACCACTGTTGCAAGAGACGGATGGATCACCAGTTGTACAGATCATTATCATATTGCCTGTAA
GTCCTGTTTGAGACCCATAGAAGAGATCACCCTGGACTCAAGTATGGACTACACGCCCCCAGA
```

-continued

```
TGTATCCCATGTGCTGAAGACATGGAGGAATGGGGAAGGTTCGTGGGACAAGAGATAAAACA

GATCTATCCTTTAGAAGGGAATTGGAAGAATTTAGCACCTGCTGAGCAATCCTATCAAGTCGG

CAGATGTATAGGTTTTCTATATGGAGACTTGGCGTATAGAAAATCTACTCATGCCGAGGACAG

TTCTCTATTTCCTCTATCTATACAAGGTCGTATTAGAGGTCGAGGTTTCTTAAAAGGGTTGCT

AGACGGATTAATGAGAGCAAGTTGCTGCCAAGTAATACACCGGAGAAGTCTGGCTCATTTGAA

GAGGCCGGCCAACGCAGTGTACGGAGGTTTGATTTACTTGATTGATAAATTGAGTGTATCACC

TCCATTCCTTTCTCTTACTAGATCAGGACCTATTAGAGACGAATTAGAAACGATTCCCCACAA

GATCCCAACCTCCTATCCGACAAGCAACCGTGATATGGGGGTGATTGTCAGAAATTACTTCAA

ATACCAATGCCGTCTAATTGAAAAGGGAAAATACAGATCACATTATTCACAATTATGGTTATT

CTCAGATGTCTTATCCATAGACTTCATTGGACCATTCTCTATTTCCACCACCCTCTTGCAAAT

CCTATACAAGCCATTTTTATCTGGGAAAGATAAGAATGAGTTGAGAGAGCTGGCAAATCTTTC

TTCATTGCTAAGATCAGGAGAGGGGTGGGAAGACATACATGTGAAATTCTTCACCAAGGACAT

ATTATTGTGTCCAGAGGAAATCAGACATGCTTGCAAGTTCGGGATTGCTAAGGATAATAATAA

AGACATGAGCTATCCCCCTTGGGGAAGGGAATCCAGAGGGACAATTACAACAATCCCTGTTTA

TTATACGACCACCCCTTACCCAAAGATGCTAGAGATGCCTCCAAGAATCCAAAATCCCCTGCT

GTCCGGAATCAGGTTGGGCCAATTACCAACTGGCGCTCATTATAAAATTCGGAGTATATTACA

TGGAATGGGAATCCATTACAGGGACTTCTTGAGTTGTGGAGACGGCTCCGGAGGGATGACTGC

TGCATTACTACGAGAAAATGTGCATAGCAGAGGAATATTCAATAGTCTGTTAGAATTATCAGG

GTCAGTCATGCGAGGCGCCTCTCCTGAGCCCCCAGTGCCCTAGAAACTTTAGGAGGAGATAA

ATCGAGATGTGTAAATGGTGAAACATGTTGGGAATATCCATCTGACTTATGTGACCCAAGGAC

TTGGGACTATTTCCTCCGACTCAAAGCAGGCTTGGGGCTTCAAATTGATTTAATTGTAATGGA

TATGGAAGTTCGGGATTCTTCTACTAGCCTGAAAATTGAGACGAATGTTAGAAATTATGTGCA

CCGGATTTTGGATGAGCAAGGAGTTTTAATCTACAAGACTTATGAACATATATTTGTGAGAG

CGAAAAGAATGCAGTAACAATCCTTGGTCCCATGTTCAAGACGGTCGACTTAGTTCAAACAGA

ATTTAGTAGTTCTCAAACGTCTGAAGTATATATGGTATGTAAAGGTTTGAAGAAATTAATCGA

TGAACCCAATCCCGATTGGTCTTCCATCAATGAATCCTGGAAAAACCTGTACGCATTCCAGTC

ATCAGAACAGGAATTTGCCAGAGCAAAGAAGGTTAGTACATACTTTACCTTGACAGGTATTCC

CTCCCAATTCATTCCTGATCCTTTTGTAAACATTGAGACTATGCTACAAATATTCGGAGTACC

CACGGGTGTGTCTCATGCGGCTGCCTTAAAATCATCTGATAGACCTGCAGATTTATTGACCAT

TAGCCTTTTTTATATGGCGATTATATCGTATTATAACATCAATCATATCAGAGTAGGACCGAT

ACCTCCGAACCCCCCATCAGATGGAATTGCACAAAATGTGGGGATCGCTATAACTGGTATAAG

CTTTTGGCTGAGTTTGATGGAGAAAGACATTCCACTATATCAACAGTGTTTAGCAGTTATCCA

GCAATCATTCCCGATTAGGTGGGAGGCTGTTTCAGTAAAAGGAGGATACAAGCAGAAGTGGAG

TACTAGAGGTGATGGGCTCCCAAAAGATACCCGAACTTCAGACTCCTTGGCCCCAATCGGGAA

CTGGATCAGATCTCTGGAATTGGTCCGAAACCAAGTTCGTCTAAATCCATTCAATGAGATCTT

GTTCAATCAGCTATGTCGTACAGTGGATAATCATTTGAAATGGTCAAATTTGCGAAGAAACAC

AGGAATGATTGAATGGATCAATAGACGAATTTCAAAAGAAGACCGGTCTATACTGATGTTGAA

GAGTGACCTACACGAGGAAAACTCTTGGAGAGATTAAAAAATCATGAGGAGACTCCAAACTTT

AAGTATGAAAAAAACTTTGATCCTTAAGACCCTCTTGTGGTTTTTATTTTTATCTGGTTTTG

TGGTCTTCGTGGGTCGGCATGGCATCTCCACCTCCTCGCGGTCCGACCTGGGCATCCGAAGGA

GGACGTCGTCCACTCGGATGGCTAAGGGAGAGCTCGGATCCGGCTGCTAACAAAGCCCGAAAG
```

-continued

```
GAAGCTGAGTTGGCTGCTGCCACCGCTGAGCAATAACTAGCATAACCCCTTGGGGCCTCTAAA
CGGGTCTTGAGGGGTTTTTGCTGAAAGGAGGAACTATATCCGGATCGAGATCCTCTAGAGTC
GACCTGCAGGCATGCAAGCTTGTATTCTATAGTGTCACCTAAATCGTATGTGTATGATACATA
AGGTTATGTATTAATTGTAGCCGCGTTCTAACGACAATATGTACAAGCCTAATTGTGTAGCAT
CTGGCTTACTGAAGCAGACCCTATCATCTCTCTCGTAAACTGCCGTCAGAGTCGGTTTGGTTG
GACGAACCTTCTGAGTTTCTGGTAACGCCGTcCCGCACCCGGAAATGGTCAGCGAACCAATCA
GCAGGGTCATCGCTAGCCAGATCCTCTACGCCGGACGCATCGTGGCCGGCATCACCGGCGCCA
CAGGTGCGGTTGCTGGCGCCTATATCGCCGACATCACCGATGGGGAAGATCGGGCTCGCCACT
TCGGGCTCATGAGCGCTTGTTTCGGCGTGGGTATGGTGGCAGGCCCCGTGGCCGGGGGACTGT
TGGGCGCCATCTCCTTGCACCATTCCTTGCGGCGGCGGTGCTCAACGGCCTCAACCTACTACT
GGGCTGCTTCCTAATGCAGGAGTCGCATAAGGGAGAGCGTCGAATGGTGCACTCTCAGTACAA
TCTGCTCTGATGCCGCATAGTTAAGCCAGCCCCGACACCCGCCAACACCCGCTGACGCGCCCT
GACGGGCTTGTCTGCTCCCGGCATCCGCTTACAGACAAGCTGTGACCGTCTCCGGGAGCTGCA
TGTGTCAGAGGTTTTCACCGTCATCACCGAAACGCGCGAGACGAAAGGGCCTCGTGATACGCC
TATTTTTATAGGTTAATGTCATGATAATAATGGTTTCTTAGACGTCAGGTGGCACTTTTCGGG
GAAATGTGCGCGGAACCCCTATTTGTTTATTTTTCTAAATACATTCAAATATGTATCCGCTCA
TGAGACAATAACCCTGATAAATGCTTCAATAATATTGAAAAAGGAAGAGTATGAGTATTCAAC
ATTTCCGTGTCGCCCTTATTCCCTTTTTTGCGGCATTTTGCCTTCCTGTTTTTGCTCACCCAG
AAACGCTGGTGAAAGTAAAAGATGCTGAAGATCAGTTGGGTGCACGAGTGGGTTACATCGAAC
TGGATCTCAACAGCGGTAAGATCCTTGAGAGTTTTCGCCCCGAAGAACGTTTTCCAATGATGA
GCACTTTTAAAGTTCTGCTATGTGGCGCGGTATTATCCCGTATTGACGCCGGGCAAGAGCAAC
TCGGTCGCCGCATACACTATTCTCAGAATGACTTGGTTGAGTACTCACCAGTCACAGAAAAGC
ATCTTACGGATGGCATGACAGTAAGAGAATTATGCAGTGCTGCCATAACCATGAGTGATAACA
CTGCGGCCAACTTACTTCTGACAACGATCGGAGGACCGAAGGAGCTAACCGCTTTTTTGCACA
ACATGGGGGATCATGTAACTCGCCTTGATCGTTGGGAACCGGAGCTGAATGAAGCCATACCAA
ACGACGAGCGTGACACCACGATGCCTGTAGCAATGGCAACAACGTTGCGCAAACTATTAACTG
GCGAACTACTTACTCTAGCTTCCCGGCAACAATTAATAGACTGGATGGAGGCGGATAAAGTTG
CAGGACCACTTCTGCGCTCGGCCCTTCCGGCTGGCTGGTTTATTGCTGATAAATCTGGAGCCG
GTGAGCGTGGGTCTCGCGGTATCATTGCAGCACTGGGGCCAGATGGTAAGCCCTCCCGTATCG
TAGTTATCTACACGACGGGGAGTCAGGCAACTATGGATGAACGAAATAGACAGATCGCTGAGA
TAGGTGCCTCACTGATTAAGCATTGGTAACTGTCAGACCAAGTTTACTCATATATACTTTAGA
TTGATTTAAAACTTCATTTTTAATTTAAAAGGATCTAGGTGAAGATCCTTTTTGATAATCTCA
TGACCAAAATCCCTTAACGTGAGTTTTCGTTCCACTGAGCGTCAGACCCCGTAGAAAAGATCA
AAGGATCTTCTTGAGATCCTTTTTTTCTGCGCGTAATCTGCTGCTTGCAAACAAAAAAACCAC
CGCTACCAGCGGTGGTTTGTTTGCCGGATCAAGAGCTACCAACTCTTTTTCCGAAGGTAACTG
GCTTCAGCAGAGCGCAGATACCAAATACTGTCCTTCTAGTGTAGCCGTAGTTAGGCCACCACT
TCAAGAACTCTGTAGCACCGCCTACATACCTCGCTCTGCTAATCCTGTTACCAGTGGCTGCTG
CCAGTGGCGATAAGTCGTGTCTTACCGGGTTGGACTCAAGACGATAGTTACCGGATAAGGCGC
AGCGGTCGGGCTGAACGGGGGGTTCGTGCACACAGCCCAGCTTGGAGCGAACGACCTACACCG
AACTGAGATACCTACAGCGTGAGCTATGAGAAAGCGCCACGCTTCCCGAAGGGAGAAAGGCGG
```

-continued

```
ACAGGTATCCGGTAAGCGGCAGGGTCGGAACAGGAGAGCGCACGAGGGAGCTTCCAGGGGAA

ACGCCTGGTATCTTTATAGTCCTGTCGGGTTTCGCCACCTCTGACTTGAGCGTCGATTTTGT

GATGCTCGTCAGGGGGGCGGAGCCTATGGAAAAACGCCAGCAACGCGGCCTTTTTACGGTTCC

TGGCCTTTTGCTGGCCTTTTGCTCACATGTTCTTTCCTGCGTTATCCCCTGATTCTGTGGATA

ACCGTATTACCGCCTTTGAGTGAGCTGATACCGCTCGCCGCAGCCGAACGACCGAGCGCAGCG

AGTCAGTGAGCGAGGAAGCGGAAGAGCGCCCAATACGCAAACCGCCTCTCCCCGCGCGTTGGC

CGATTCATTAATGCAGGGGGATCTCGATCCCGCGAAATTAATACGACTCACTATAGG
```

In some embodiments, the recombinant viruses further comprise in its genome a nucleic acid sequence encoding an enhanced Green Fluorescent Protein (eGFP) or fragment thereof. An exemplary nucleic acid sequence for wild type VSV with eGFP is as follows (SEQ ID NO: 12):

SEQ ID NO: 12

ACGAAGACAAACAAACCATTATTATCATTAAAAGGCTCAGGAGAAACTTTAACAGTAATCAGA

ATTCTCGAGAAAGCCACCATGGTGAGCAAGGGCGAGGAGCTGTTCACCGGGGTGGTGCCCATC

CTGGTCGAGCTGGACGGCGACGTAAACGGCCACAAGTTCAGCGTGTCCGGCGAGGGCGAGGGC

GATGCCACCTACGGCAAGCTGACCCTGAAGTTCATCTGCACCACCGGCAAGCTGCCCGTGCCC

TGGCCCACCCTCGTGACCACCCTGACCTACGGCGTGCAGTGCTTCAGCCGCTACCCCGACCAC

ATGAAGCAGCACGACTTCTTCAAGTCCGCCATGCCCGAAGGCTACGTCCAGGAGCGCACCATC

TTCTTCAAGGACGACGGCAACTACAAGACCCGCGCCGAGGTGAAGTTCGAGGGCGACACCCTG

GTGAACCGCATCGAGCTGAAGGGCATCGACTTCAAGGAGGACGGCAACATCCTGGGGCACAAG

CTGGAGTACAACTACAACAGCCACAACGTCTATATCATGGCCGACAAGCAGAAGAACGGCATC

AAGGTGAACTTCAAGATCCGCCACAACATCGAGGACGGCAGCGTGCAGCTCGCCGACCACTAC

CAGCAGAACACCCCCATCGGCGACGGCCCCGTGCTGCTGCCCGACAACCACTACCTGAGCACC

CAGTCCGCCCTGAGCAAAGACCCCAACGAGAAGCGCGATCACATGGTCCTGCTGGAGTTCGTG

ACCGCCGCCGGGATCACTCTCGGCATGGACGAGCTGTACAAGTAATGGCCATATGAAAAAAAC

TAACAGTAATCAAAATGTCTGTTACAGTCAAGAGAATCATTGACAACACAGTCATAGTTCCAA

AACTTCCTGCAAATGAGGATCCAGTGGAATACCCGGCAGATTACTTCAGAAAATCAAAGGAGA

TTCCTCTTTACATCAATACTACAAAAAGTTTGTCAGATCTAAGAGGATATGTCTACCAAGGCC

TCAAATCCGGAAATGTATCAATCATACATGTCAACAGCTACTTGTATGGAGCATTAAAGGACA

TCCGGGGTAAGTTGGATAAAGATTGGTCAAGTTTCGGAATAAACATCGGGAAAGCAGGGGATA

CAATCGGAATATTTGACCTTGTATCCTTGAAAGCCCTGGACGGCGTACTTCCAGATGGAGTAT

CGGATGCTTCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTGACAAATCAAT

GCAAAATGATCAATGAACAGTTTGAACCTCTTGTGCCAGAAGGTCGTGACATTTTTGATGTGT

GGGGAAATGACAGTAATTACACAAAAATTGTCGCTGCAGTGGACATGTTCTTCCACATGTTCA

AAAAACATGAATGTGCCTCGTTCAGATACGGAACTATTGTTTCCAGATTCAAAGATTGTGCTG

CATTGGCAACATTTGGACACCTCTGCAAAATAACCGGAATGTCTACAGAAGATGTAACGACCT

GGATCTTGAACCGAGAAGTTGCAGATGAAATGGTCCAAATGATGCTTCCAGGCCAAGAAATTG

ACAAGGCCGATTCATACATGCCTTATTTGATCGACTTTGGATTGTCTTCTAAGTCTCCATATT

CTTCCGTCAAAAACCCTGCCTTCCACTTCTGGGGGCAATTGACAGCTCTTCTGCTCAGATCCA

CCAGAGCAAGGAATGCCCGACAGCCTGATGACATTGAGTATACATCTCTTACTACAGCAGGTT

-continued

```
TGTTGTACGCTTATGCAGTAGGATCCTCTGCCGACTTGGCACAACAGTTTTGTGTTGGAGATA

ACAAATACACTCCAGATGATAGTACCGGAGGATTGACGACTAATGCACCGCCACAAGGCAGAG

ATGTGGTCGAATGGCTCGGATGGTTTGAAGATCAAAACAGAAAACCGACTCCTGATATGATGC

AGTATGCGAAAAGAGCAGTCATGTCACTGCAAGGCCTAAGAGAGAAGACAATTGGCAAGTATG

CTAAGTCAGAATTTGACAAATGACCCTATAATTCTCAGATCACCTATTATATATTATGCTACA

TATGAAAAAAACTAACAGATATCATGGATAATCTCACAAAAGTTCGTGAGTATCTCAAGTCCT

ATTCTCGTCTGGATCAGGCGGTAGGAGAGATAGATGAGATCGAAGCACAACGAGCTGAAAAGT

CCAATTATGAGTTGTTCCAAGAGGATGGAGTGGAAGAGCATACTAAGCCCTCTTATTTTCAGG

CAGCAGATGATTCTGACACAGAATCTGAACCAGAAATTGAAGACAATCAAGGTTTGTATGCAC

AGGATCCAGAAGCTGAGCAAGTTGAAGGCTTTATACAGGGGCCTTTAGATGACTATGCAGATG

AGGAAGTGGATGTTGTATTTACTTCGGACTGGAAACCACCTGAGCTTGAATCTGACGAGCATG

GAAAGACCTTACGGTTGACATCGCCAGAGGGTTTAAGTGGAGAGCAGAAATCCCAGTGGCTTT

CGACGATTAAAGCAGTCGTGCAAAGTGCCAAATACTGGAATCTGGCAGAGTGCACATTTGAAG

CATCGGGAGAAGGGGTCATTATGAAGGAGCGCCAGATAACTCCGGATGTATATAAGGTCACTC

CAGTGATGAACACACATCCGTCCCAATCAGAAGCAGTATCAGATGTTTGGTCTCTCTCAAAGA

CATCCATGACTTTCCAACCCAAGAAAGCAAGTCTTCAGCCTCTCACCATATCCTTGGATGAAT

TGTTCTCATCTAGAGGAGAGTTCATCTCTGTCGGAGGTGACGGACGAATGTCTCATAAAGAGG

CCATCCTGCTCGGCCTGAGATACAAAAAGTTGTACAATCAGGCGAGAGTCAAATATTCTCTGT

AGACTATGAAAAAAAGTAACAGATATCACGATCTAAGTGTTATCCCAATCCATTCATCATGAG

TTCCTTAAAGAAGATTCTCGGTCTGAAGGGGAAAGGTAAGAAATCTAAGAAATTAGGGATCGC

ACCACCCCCTTATGAAGAGGACACTAGCATGGAGTATGCTCCGAGCGCTCCAATTGACAAATC

CTATTTTGGAGTTGACGAGATGGACACCTATGATCCGAATCAATTAAGATATGAGAAATTCTT

CTTTACAGTGAAAATGACGGTTAGATCTAATCGTCCGTTCAGAACATACTCAGATGTGGCAGC

CGCTGTATCCCATTGGGATCACATGTACATCGGAATGGCAGGGAAACGTCCCTTCTACAAAAT

CTTGGCTTTTTTGGGTTCTTCTAATCTAAAGGCCACTCCAGCGGTATTGGCAGATCAAGGTCA

ACCAGAGTATCACACTCACTGCGAAGGCAGGGCTTATTTGCCACATAGGATGGGGAAGACCCC

TCCCATGCTCAATGTACCAGAGCACTTCAGAAGACCATTCAATATAGGTCTTTACAAGGGAAC

GATTGAGCTCACAATGACCATCTACGATGATGAGTCACTGGAAGCAGCTCCTATGATCTGGGA

TCATTTCAATTCTTCCAAATTTTCTGATTTCAGAGAGAAGGCCTTAATGTTTGGCCTGATTGT

CGAGAAAAAGGCATCTGGAGCGTGGGTCCTGGATTCTATCAGCCACTTCAAATGAGCTAGTCT

AACTTCTAGCTTCTGAACAATCCCCGGTTTACTCAGTCTCTCCTAATTCCAGCCTCTCGAACA

ACTAATATCCTGTCTTTTCTATCCCTATGAAAAAAACTAACAGAGATCGATCTGTTTCCTTGA

CACTATGAAGTGCCTTTTGTACTTAGCCTTTTTATTCATTGGGGTGAATTGCAAGTTCACCAT

AGTTTTTCCACACAACCAAAAAGGAAACTGGAAAAATGTTCCTTCTAATTACCATTATTGCCC

GTCAAGCTCAGATTTAAATTGGCATAATGACTTAATAGGCACAGCCATACAAGTCAAAATGCC

CAAGAGTCACAAGGCTATTCAAGCAGACGGTTGGATGTGTCATGCTTCCAAATGGGTCACTAC

TTGTGATTTCCGCTGGTATGGACCGAAGTATATAACACAGTCCATCCGATCCTTCACTCCATC

TGTAGAACAATGCAAGGAAAGCATTGAACAAACGAAACAAGGAACTTGGCTGAATCCAGGCTT

CCCTCCTCAAAGTTGTGGATATGCAACTGTGACGGATGCCGAAGCAGTGATTGTCCAGGTGAC

TCCTCACCATGTGCTGGTTGATGAATACACAGGAGAATGGGTTGATTCACAGTTCATCAACGG
```

```
AAAATGCAGCAATTACATATGCCCCACTGTCCATAACTCTACAACCTGGCATTCTGACTATAA
GGTCAAAGGGCTATGTGATTCTAACCTCATTTCCATGGACATCACCTTCTTCTCAGAGGACGG
AGAGCTATCATCCCTGGGAAAGGAGGGCACAGGGTTCAGAAGTAACTACTTTGCTTATGAAAC
TGGAGGCAAGGCCTGCAAAATGCAATACTGCAAGCATTGGGGAGTCAGACTCCCATCAGGTGT
CTGGTTCGAGATGGCTGATAAGGATCTCTTTGCTGCAGCCAGATTCCCTGAATGCCCAGAAGG
GTCAAGTATCTCTGCTCCATCTCAGACCTCAGTGGATGTAAGTCTAATTCAGGACGTTGAGAG
GATCTTGGATTATTCCCTCTGCCAAGAAACCTGGAGCAAAATCAGAGCGGGTCTTCCAATCTC
TCCAGTGGATCTCAGCTATCTTGCTCCTAAAAACCCAGGAACCGGTCCTGCTTTCACCATAAT
CAATGGTACCCTAAAATACTTTGAGACCAGATACATCAGAGTCGATATTGCTGCTCCAATCCT
CTCAAGAATGGTCGGAATGATCAGTGGAACTACCACAGAAAGGGAACTGTGGGATGACTGGGC
ACCATATGAAGACGTGGAAATTGGACCCAATGGAGTTCTGAGGACCAGTTCAGGATATAAGTT
TCCTTTATACATGATTGGACATGGTATGTTGGACTCCGATCTTCATCTTAGCTCAAAGGCTCA
GGTGTTCGAACATCCTCACATTCAAGACGCTGCTTCGCAACTTCCTGATGATGAGAGTTTATT
TTTTGGTGATACTGGGCTATCCAAAAATCCAATCGAGCTTGTAGAAGGTTGGTTCAGTAGTTG
GAAAAGCTCTATTGCCTCTTTTTTCTTTATCATAGGGTTAATCATTGGACTATTCTTGGTTCT
CCGAGTTGGTATCCATCTTTGCATTAAATTAAAGCACACCAAGAAAAGACAGATTTATACAGA
CATAGAGATGAACCGACTTGGAAAGTAACTCAAATCCTGCACAACAGATTCTTCATGTTTGGA
CCAAATCAACTTGTGATACCATGCTCAAAGAGGCCTCAATTATATTTGAGTTTTTAATTTTTA
TGAAAAAAACTAACAGCAATCATGGAAGTCCACGATTTTGAGACCGACGAGTTCAATGATTTC
AATGAAGATGACTATGCCACAAGAGAATTCCTGAATCCCGATGAGCGCATGACGTACTTGAAT
CATGCTGATTACAATTTGAATTCTCCTCTAATTAGTGATGATATTGACAATTTGATCAGGAAA
TTCAATTCTCTTCCGATTCCCTCGATGTGGGATAGTAAGAACTGGGATGGAGTTCTTGAGATG
TTAACATCATGTCAAGCCAATCCCATCTCAACATCTCAGATGCATAAATGGATGGGAAGTTGG
TTAATGTCTGATAATCATGATGCCAGTCAAGGGTATAGTTTTTTACATGAAGTGGACAAAGAG
GCAGAAATAACATTTGACGTGGTGGAGACCTTCATCCGCGGCTGGGGCAACAAACCAATTGAA
TACATCAAAAAGGAAAGATGGACTGACTCATTCAAAATTCTCGCTTATTTGTGTCAAAAGTTT
TTGGACTTACACAAGTTGACATTAATCTTAAATGCTGTCTCTGAGGTGGAATTGCTCAACTTG
GCGAGGACTTTCAAAGGCAAAGTCAGAAGAAGTTCTCATGGAACGAACATATGCAGGATTAGG
GTTCCCAGCTTGGGTCCTACTTTTATTTCAGAAGGATGGGCTTACTTCAAGAAACTTGATATT
CTAATGGACCGAAACTTTCTGTTAATGGTCAAAGATGTGATTATAGGGAGGATGCAAACGGTG
CTATCCATGGTATGTAGAATAGACAACCTGTTCTCAGAGCAAGACATCTTCTCCCTTCTAAAT
ATCTACAGAATTGGAGATAAAATTGTGGAGAGGCAGGGAAATTTTCTTATGACTTGATTAAA
ATGGTGGAACCGATATGCAACTTGAAGCTGATGAAATTAGCAAGAGAATCAAGGCCTTTAGTC
CCACAATTCCCTCATTTTGAAAATCATATCAAGACTTCTGTTGATGAAGGGGCAAAAATTGAC
CGAGGTATAAGATTCCTCCATGATCAGATAATGAGTGTGAAAACAGTGGATCTCACACTGGTG
ATTTATGGATCGTTCAGACATTGGGGTCATCCTTTTATAGATTATTACACTGGACTAGAAAAA
TTACATTCCCAAGTAACCATGAAGAAAGATATTGATGTGTCATATGCAAAAGCACTTGCAAGT
GATTTAGCTCGGATTGTTCTATTTCAACAGTTCAATGATCATAAAAAGTGGTTCGTGAATGGA
GACTTGCTCCCTCATGATCATCCCTTTAAAAGTCATGTTAAAGAAAATACATGGCCCACAGCT
GCTCAAGTTCAAGATTTTGGAGATAAATGGCATGAACTTCCGCTGATTAAATGTTTTGAAATA
CCCGACTTACTAGACCCATCGATAATATACTCTGACAAAAGTCATTCAATGAATAGGTCAGAG
```

-continued

```
GTGTTGAAACATGTCCGAATGAATCCGAACACTCCTATCCCTAGTAAAAGGTGTTGCAGACT

ATGTTGGACACAAAGGCTACCAATTGGAAAGAATTTCTTAAAGAGATTGATGAGAAGGGCTTA

GATGATGATGATCTAATTATTGGTCTTAAAGGAAAGGAGAGGGAACTGAAGTTGGCAGGTAGA

TTTTTCTCCCTAATGTCTTGGAAATTGCGAGAATACTTTGTAATTACCGAATATTTGATAAAG

ACTCATTTCGTCCCTATGTTTAAAGGCCTGACAATGGCGGACGATCTAACTGCAGTCATTAAA

AAGATGTTAGATTCCTCATCCGGCCAAGGATTGAAGTCATATGAGGCAATTTGCATAGCCAAT

CACATTGATTACGAAAAATGGAATAACCACCAAAGGAAGTTATCAAACGGCCCAGTGTTCCGA

GTTATGGGCCAGTTCTTAGGTTATCCATCCTTAATCGAGAGAACTCATGAATTTTTTGAGAAA

AGTCTTATATACTACAATGGAAGACCAGACTTGATGCGTGTTCACAACAACACACTGATCAAT

TCAACCTCCCAACGAGTTTGTTGGCAAGGACAAGAGGGTGGACTGGAAGGTCTACGGCAAAAA

GGATGGACTATCCTCAATCTACTGGTTATTCAAAGAGAGGCTAAAATCAGAAACACTGCTGTC

AAAGTCTTGGCACAAGGTGATAATCAAGTTATTTGCACACAGTATAAAACGAAGAAATCGAGA

AACGTTGTAGAATTACAGGGTGCTCTCAATCAAATGGTTTCTAATAATGAGAAAATTATGACT

GCAATCAAAATAGGGACAGGGAAGTTAGGACTTTTGATAAATGACGATGAGACTATGCAATCT

GCAGATTACTTGAATTATGGAAAAATACCGATTTTCCGTGGAGTGATTAGAGGGTTAGAGACC

AAGAGATGGTCACGAGTGACTTGTGTCACCAATGACCAAATACCCACTTGTGCTAATATAATG

AGCTCAGTTTCCACAAATGCTCTCACCGTAGCTCATTTTGCTGAGAACCCAATCAATGCCATG

ATACAGTACAATTATTTTGGGACATTTGCTAGACTCTTGTTGATGATGCATGATCCTGCTCTT

CGTCAATCATTGTATGAAGTTCAAGATAAGATACCGGGCTTGCACAGTTCTACTTTCAAATAC

GCCATGTTGTATTTGGACCCTTCCATTGGAGGAGTGTCGGGCATGTCTTTGTCCAGGTTTTTG

ATTAGAGCCTTCCCAGATCCCGTAACAGAAAGTCTCTCATTCTGGAGATTCATCCATGTACAT

GCTCGAAGTGAGCATCTGAAGGAGATGAGTGCAGTATTTGGAAACCCCGAGATAGCCAAGTTT

CGAATAACTCACATAGACAAGCTAGTAGAAGATCCAACCTCTCTGAACATCGCTATGGGAATG

AGTCCAGCGAACTTGTTAAAGACTGAGGTTAAAAAATGCTTAATCGAATCAAGACAAACCATC

AGGAACCAGGTGATTAAGGATGCAACCATATATTTGTATCATGAAGAGGATCGGCTCAGAAGT

TTCTTATGGTCAATAAATCCTCTGTTCCCTAGATTTTTAAGTGAATTCAAATCAGGCACTTTT

TTGGGAGTCGCAGACGGGCTCATCAGTCTATTTCAAAATTCTCGTACTATTCGGAACTCCTTT

AAGAAAAAGTATCATAGGGAATTGGATGATTTGATTGTGAGGAGTGAGGTATCCTCTTTGACA

CATTTAGGGAAACTTCATTTGAGAAGGGGATCATGTAAAATGTGGACATGTTCAGCTACTCAT

GCTGACACATTAAGATACAAATCCTGGGGCCGTACAGTTATTGGGACAACTGTACCCCATCCA

TTAGAAATGTTGGGTCCACAACATCGAAAAGAGACTCCTTGTGCACCATGTAACACATCAGGG

TTCAATTATGTTTCTGTGCATTGTCCAGACGGGATCCATGACGTCTTTAGTTCACGGGGACCA

TTGCCTGCTTATCTAGGGTCTAAAACATCTGAATCTACATCTATTTTGCAGCCTTGGGAAAGG

GAAAGCAAAGTCCCACTGATTAAAAGAGCTACACGTCTTAGAGATGCTATCTCTTGGTTTGTT

GAACCCGACTCTAAACTAGCAATGACTATACTTTCTAACATCCACTCTTTAACAGGCGAAGAA

TGGACCAAAAGGCAGCATGGGTTCAAAAGAACAGGGTCTGCCCTTCATAGGTTTTCGACATCT

CGGATGAGCCATGGTGGGTTCGCATCTCAGAGCACTGCAGCATTGACCAGGTTGATGGCAACT

ACAGACACCATGAGGGATCTGGGAGATCAGAATTTCGACTTTTTATTCCAAGCAACGTTGCTC

TATGCTCAAATTACCACCACTGTTGCAAGAGACGGATGGATCACCAGTTGTACAGATCATTAT

CATATTGCCTGTAAGTCCTGTTTGAGACCCATAGAAGAGATCACCCTGGACTCAAGTATGGAC
```

```
-continued
TACACGCCCCCAGATGTATCCCATGTGCTGAAGACATGGAGGAATGGGGAAGGTTCGTGGGA

CAAGAGATAAAACAGATCTATCCTTTAGAAGGGAATTGGAAGAATTTAGCACCTGCTGAGCAA

TCCTATCAAGTCGGCAGATGTATAGGTTTTCTATATGGAGACTTGGCGTATAGAAAATCTACT

CATGCCGAGGACAGTTCTCTATTTCCTCTATCTATACAAGGTCGTATTAGAGGTCGAGGTTTC

TTAAAAGGGTTGCTAGACGGATTAATGAGAGCAAGTTGCTGCCAAGTAATACACCGGAGAAGT

CTGGCTCATTTGAAGAGGCCGGCCAACGCAGTGTACGGAGGTTTGATTTACTTGATTGATAAA

TTGAGTGTATCACCTCCATTCCTTTCTCTTACTAGATCAGGACCTATTAGAGACGAATTAGAA

ACGATTCCCCACAAGATCCCAACCTCCTATCCGACAAGCAACCGTGATATGGGGGTGATTGTC

AGAAATTACTTCAAATACCAATGCCGTCTAATTGAAAAGGGAAAATACAGATCACATTATTCA

CAATTATGGTTATTCTCAGATGTCTTATCCATAGACTTCATTGGACCATTCTCTATTTCCACC

ACCCTCTTGCAAATCCTATACAAGCCATTTTTATCTGGGAAAGATAAGAATGAGTTGAGAGAG

CTGGCAAATCTTTCTTCATTGCTAAGATCAGGAGAGGGGTGGGAAGACATACATGTGAAATTC

TTCACCAAGGACATATTATTGTGTCCAGAGGAAATCAGACATGCTTGCAAGTTCGGGATTGCT

AAGGATAATAATAAAGACATGAGCTATCCCCCTTGGGGAAGGGAATCCAGAGGGACAATTACA

ACAATCCCTGTTTATTATACGACCACCCCTTACCCAAAGATGCTAGAGATGCCTCCAAGAATC

CAAAATCCCCTGCTGTCCGGAATCAGGTTGGGCCAATTACCAACTGGCGCTCATTATAAAATT

CGGAGTATATTACATGGAATGGGAATCCATTACAGGGACTTCTTGAGTTGTGGAGACGGCTCC

GGAGGGATGACTGCTGCATTACTACGAGAAAATGTGCATAGCAGAGGAATATTCAATAGTCTG

TTAGAATTATCAGGGTCAGTCATGCGAGGCGCCTCTCCTGAGCCCCCCAGTGCCCTAGAAACT

TTAGGAGGAGATAAATCGAGATGTGTAAATGGTGAAACATGTTGGGAATATCCATCTGACTTA

TGTGACCCAAGGACTTGGGACTATTTCCTCCGACTCAAAGCAGGCTTGGGGCTTCAAATTGAT

TTAATTGTAATGGATATGGAAGTTCGGGATTCTTCTACTAGCCTGAAAATTGAGACGAATGTT

AGAAATTATGTGCACCGGATTTTGGATGAGCAAGGAGTTTTAATCTACAAGACTTATGGAACA

TATATTTGTGAGAGCGAAAAGAATGCAGTAACAATCCTTGGTCCCATGTTCAAGACGGTCGAC

TTAGTTCAAACAGAATTTAGTAGTTCTCAAACGTCTGAAGTATATATGGTATGTAAAGGTTTG

AAGAAATTAATCGATGAACCCAATCCCGATTGGTCTTCCATCAATGAATCCTGGAAAAACCTG

TACGCATTCCAGTCATCAGAACAGGAATTTGCCAGAGCAAAGAAGGTTAGTACATACTTTACC

TTGACAGGTATTCCCTCCCAATTCATTCCTGATCCTTTTGTAAACATTGAGACTATGCTACAA

ATATTCGGAGTACCCACGGGTGTGTCTCATGCGGCTGCCTTAAAATCATCTGATAGACCTGCA

GATTTATTGACCATTAGCCTTTTTTATATGGCGATTATATCGTATTATAACATCAATCATATC

AGAGTAGGACCGATACCTCCGAACCCCCCATCAGATGGAATTGCACAAAATGTGGGGATCGCT

ATAACTGGTATAAGCTTTTGGCTGAGTTTGATGGAGAAAGACATTCCACTATATCAACAGTGT

TTAGCAGTTATCCAGCAATCATTCCCGATTAGGTGGGAGGCTGTTTCAGTAAAAGGAGGATAC

AAGCAGAAGTGGAGTACTAGAGGTGATGGGCTCCCAAAAGATACCCGAACTTCAGACTCCTTG

GCCCCAATCGGGAACTGGATCAGATCTCTGGAATTGGTCCGAAACCAAGTTCGTCTAAATCCA

TTCAATGAGATCTTGTTCAATCAGCTATGTCGTACAGTGGATAATCATTTGAAATGGTCAAAT

TTGCGAAGAAACACAGGAATGATTGAATGGATCAATAGACGAATTTCAAAAGAAGACCGGTCT

ATACTGATGTTGAAGAGTGACCTACACGAGGAAAACTCTTGGAGAGATTAAAAAATCATGAGG

AGACTCCAAACTTTAAGTATGAAAAAAACTTTGATCCTTAAGACCCTCTTGTGGTTTTTATTT

TTTATCTGGTTTTGTGGTCTTCGTGGGTCGGCATGGCATCTCCACCTCCTCGCGGTCCGACCT

GGGCATCCGAAGGAGGACGTCGTCCACTCGGATGGCTAAGGGAGAGCTCGGATCCGGCTGCTA
```

-continued

```
ACAAAGCCCGAAAGGAAGCTGAGTTGGCTGCTGCCACCGCTGAGCAATAACTAGCATAACCCC
TTGGGGCCTCTAAACGGGTCTTGAGGGGTTTTTTGCTGAAAGGAGGAACTATATCCGGATCGA
GATCCTCTAGAGTCGACCTGCAGGCATGCAAGCTTGTATTCTATAGTGTCACCTAAATCGTAT
GTGTATGATACATAAGGTTATGTATTAATTGTAGCCGCGTTCTAACGACAATATGTACAAGCC
TAATTGTGTAGCATCTGGCTTACTGAAGCAGACCCTATCATCTCTCGTAAACTGCCGTCAG
AGTCGGTTTGGTTGGACGAACCTTCTGAGTTTCTGGTAACGCCGTcCCGCACCCGGAAATGGT
CAGCGAACCAATCAGCAGGGTCATCGCTAGCCAGATCCTCTACGCCGGACGCATCGTGGCCGG
CATCACCGGCGCCACAGGTGCGGTTGCTGGCGCCTATATCGCCGACATCACCGATGGGGAAGA
TCGGGCTCGCCACTTCGGGCTCATGAGCGCTTGTTTCGGCGTGGGTATGGTGGCAGGCCCCGT
GGCCGGGGACTGTTGGGCGCCATCTCCTTGCACCATTCCTTGCGGCGGCGGTGCTCAACGGC
CTCAACCTACTACTGGGCTGCTTCCTAATGCAGGAGTCGCATAAGGGAGAGCGTCGAATGGTG
CACTCTCAGTACAATCTGCTCTGATGCCGCATAGTTAAGCCAGCCCCGACACCCGCCAACACC
CGCTGACGCGCCCTGACGGGCTTGTCTGCTCCCGGCATCCGCTTACAGACAAGCTGTGACCGT
CTCCGGGAGCTGCATGTGTCAGAGGTTTTCACCGTCATCACCGAAACGCGCGAGACGAAAGGG
CCTCGTGATACGCCTATTTTTATAGGTTAATGTCATGATAATAATGGTTTCTTAGACGTCAGG
TGGCACTTTTCGGGGAAATGTGCGCGGAACCCCTATTTGTTTATTTTTCTAAATACATTCAAA
TATGTATCCGCTCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTGCCTTCCTGT
TTTTGCTCACCCAGAAACGCTGGTGAAAGTAAAAGATGCTGAAGATCAGTTGGGTGCACGAGT
GGGTTACATCGAACTGGATCTCAACAGCGGTAAGATCCTTGAGAGTTTTCGCCCCGAAGAACG
TTTTCCAATGATGAGCACTTTTAAAGTTCTGCTATGTGGCGCGGTATTATCCCGTATTGACGC
CGGGCAAGAGCAACTCGGTCGCCGCATACACTATTCTCAGAATGACTTGGTTGAGTACTCACC
AGTCACAGAAAAGCATCTTACGGATGGCATGACAGTAAGAGAATTATGCAGTGCTGCCATAAC
CATGAGTGATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGAGCTGAA
TGAAGCCATACCAAACGACGAGCGTGACACCACGATGCCTGTAGCAATGGCAACAACGTTGCG
CAAACTATTAACTGGCGAACTACTTACTCTAGCTTCCCGGCAACAATTAATAGACTGGATGGA
GGCGGATAAAGTTGCAGGACCACTTCTGCGCTCGGCCCTTCCGGCTGGCTGGTTTATTGCTGA
TAAATCTGGAGCCGGTGAGCGTGGGTCTCGCGGTATCATTGCAGCACTGGGGCCAGATGGTAA
GCCCTCCCGTATCGTAGTTATCTACACGACGGGGAGTCAGGCAACTATGGATGAACGAAATAG
ACAGATCGCTGAGATAGGTGCCTCACTGATTAAGCATTGGTAACTGTCAGACCAAGTTTACTC
ATATATACTTTAGATTGATTTAAAACTTCATTTTTAATTTAAAAGGATCTAGGTGAAGATCCT
TTTTGATAATCTCATGACCAAAATCCCTTAACGTGAGTTTTCGTTCCACTGAGCGTCAGACCC
CGTAGAAAAGATCAAAGGATCTTCTTGAGATCCTTTTTTTCTGCGCGTAATCTGCTGCTTGCA
AACAAAAAAACCACCGCTACCAGCGGTGGTTTGTTTGCCGGATCAAGAGCTACCAACTCTTTT
TCCGAAGGTAACTGGCTTCAGCAGAGCGCAGATACCAAATACTGTCCTTCTAGTGTAGCCGTA
GTTAGGCCACCACTTCAAGAACTCTGTAGCACCGCCTACATACCTCGCTCTGCTAATCCTGTT
ACCAGTGGCTGCTGCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGCCCAGCTTGGAGCG
AACGACCTACACCGAACTGAGATACCTACAGCGTGAGCTATGAGAAAGCGCCACGCTTCCCGA
```

-continued
```
AGGGAGAAAGGCGGACAGGTATCCGGTAAGCGGCAGGGTCGGAACAGGAGAGCGCACGAGGGA

GCTTCCAGGGGGAAACGCCTGGTATCTTTATAGTCCTGTCGGGTTTCGCCACCTCTGACTTGA

GCGTCGATTTTTGTGATGCTCGTCAGGGGGCGGAGCCTATGGAAAAACGCCAGCAACGCGGC

CTTTTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCGAAC

GACCGAGCGCAGCGAGTCAGTGAGCGAGGAAGCGGAAGAGCGCCCAATACGCAAACCGCCTCT

CCCCGCGCGTTGGCCGATTCATTAATGCAGGGGGATCTCGATCCCGCGAAATTAATACGACTC

ACTATAGG
```

In some embodiments, the recombinant viruses comprise in its genome a nucleic acid sequence encoding a Zika virus envelope protein or fragment thereof. An exemplary nucleic acid sequence for a wild type Zika virus envelope protein is as follows (SEQ ID NO: 2):

SEQ ID NO: 2
```
ATCCGGTGTATCGGCGTGTCCAACCGGGACTTCGTGGAAGGCATGAGCGGCGGCACATGGGTG

GACGTGGTGCTGGAACATGGCGGCTGCGTGACAGTGATGGCTCAGGACAAGCCCACCGTGGAC

ATCGAGCTCGTGACCACCACCGTGTCCAATATGGCCGAAGTGCGGAGCTACTGCTACGAGGCC

AGCATCAGCGACATGGCAAGCGACAGCAGATGCCCTACACAGGGCGAGGCCTACCTGGACAAG

CAGTCCGACACCCAGTACGTGTGCAAGCGGACCCTGGTGGATAGAGGCTGGGGCAATGGCTGC

GGCCTGTTTGGCAAGGGCAGCCTCGTGACCTGCGCCAAGTTCGCCTGCAGCAAGAAGATGACC

GGCAAGAGCATCCAGCCCGAGAACCTGGAATACCGGATCATGCTGAGCGTGCACGGCAGCCAG

CACTCCGGCATGATCGTGAACGACACCGGCCACGAGACAGACGAGAACCGGGCCAAGGTGGAA

ATCACCCCCAACAGCCCTAGAGCCGAGGCCACACTGGGCGGCTTTGGATCTCTGGGCCTGGAC

TGCGAGCCTAGAACCGGCCTGGATTTCAGCGACCTGTACTACCTGACCATGAACAACAAGCAC

TGGCTGGTGCACAAAGAGTGGTTCCACGACATCCCCCTGCCCTGGCATGCCGGCGCTGATACA

GGCACACCCCACTGGAACAACAAAGAGGCTCTGGTGGAATTCAAGGACGCCCACGCCAAGCGG

CAGACCGTGGTGGTGCTGGGATCTCAGGAAGGCGCCGTGCATACAGCTCTGGCTGGCGCCCTG

GAAGCCGAAATGGATGGCGCCAAAGGCAGACTGTCCAGCGGCCACCTGAAGTGCCGGCTGAAG

ATGGACAAGCTGCGGCTGAAGGGCGTGTCCTACAGCCTGTGTACCGCCGCCTTCACCTTCACC

AAGATCCCCGCCGAGACACTGCACGGCACCGTGACTGTGGAAGTGCAGTACGCCGGCACCGAC

GGCCCTTGTAAAGTGCCTGCTCAGATGGCCGTGGATATGCAGACCCTGACCCCCGTGGGCAGA

CTGATCACCGCCAACCCTGTGATCACCGAGAGCACCGAGAACAGCAAGATGATGCTGGAACTG

GACCCCCCCTTCGGCGACTCCTACATCGTGATCGGCGTGGGAGAGAAGAAGATCACCCACCAC

TGGCACAGAAGCGGCAGCACCATCGGCAAGGCCTTTGAGGCTACAGTGCGGGGAGCCAAGAGA

ATGGCCGTGCTGGGAGATACCGCCTGGGACTTTGGCTCTGTGGGCGGAGCCCTGAACTCTCTG

GGCAAGGGAATCCACCAGATCTTCGGAGCCGCCTTTAAGAGCCTGTTCGGCGGCATGAGCTGG

TTCAGCCAGATCCTGATCGGCACCCTGCTGATGTGGCTGGGCCTGAACGCCAAGAACGGCAGC

ATCTCCCTGATGTGCCTGGCTCTGGGAGGCGTGCTGATCTTCCTGAGCACAGCCGTGTCTGCC
```

In some embodiments, the recombinant viruses further comprise in its genome a nucleic acid sequence encoding a Zika virus precursor membrane (prM) protein or fragment thereof. An exemplary nucleic acid sequence for a prM protein is as follows (SEQ ID NO: 3):

SEQ ID NO: 3
AGAAGAGGCAGCGCCTACTACATGTACCTGGACCGGAACGATGCCGGCGAGGCCATCAGCTTT

CCAACCACCCTGGGCATGAACAAGTGCTACATCCAGATCATGGACCTGGGCCACACCTGTGAC

GCCACCATGAGCTACGAGTGCCCCATGCTGGACGAGGGCGTGGAACCCGACGATGTGGACTGC

TGGTGCAACACCACCAGCACCTGGGTGGTGTACGGCACCTGTCACCACAAGAAGGGCGAAGCC

AGACGGTCCAGACGGGCCGTGACACTGCCTAGCCACAGCACCAGAAAGCTGCAGACCCGGTCC

CAGACCTGGCTGGAAAGCAGAGAGTACACCAAGCACCTGATCCGGGTGGAAAACTGGATCTTC

CGGAACCCCGGCTTTGCCCTGGCCGCTGCTGCTATTGCTTGGCTGCTGGGCAGCAGCACCTCC

CAGAAAGTGATCTACCTCGTGATGATCCTGCTGATCGCCCCTGCCTACAGC

In some embodiments, the recombinant viruses further comprise in its genome a nucleic acid sequence encoding Zika virus capsid (C) protein or fragment thereof. An exemplary nucleic acid sequence for a portion of the C protein (codon optimized) is as follows (SEQ ID NO: 4):

SEQ ID NO: 4
ACCAGCGTGGGCATCGTGGGCCTGCTGCTGACCACCGCCATGGCCGCCGA

GGTGACC

In some embodiments, the recombinant VSV comprises a nucleic acid sequence that is at least 80 (e.g., at least 81, 82, 83, 84, 85, 86, 87, 88, 89, 90, 91, 92, 93, 94, 95, 96, 97, 98, or 99) % identical to: (i) the nucleic acid of SEQ ID NO:2; (ii) the nucleic acid of SEQ ID NO:3; or (iii) the nucleic acid of SEQ ID NO:4. In some embodiments, the recombinant VSV comprises a nucleic acid sequence that is identical to: (i) the nucleic acid of SEQ ID NO:2; (ii) the nucleic acid of SEQ ID NO:3; or (iii) the nucleic acid of SEQ ID NO:4.

In some embodiments, the nucleic acid sequence encoding a Zika virus E protein substantially replaces the endogenous VSV viral glycoprotein (G) in the VSV genome. Exemplary sequences where the Zika coding sequences were cloned into the VSV genome, replacing the endogenous VSV viral glycoprotein (G), include the sequences of rVSVΔGZika-prME (SEQ ID NO:5) and rVSVΔGZika-CprME (SEQ ID NO:6).

SEQ ID NO: 5
ACGAAGACAAACAAACCATTATTATCATTAAAAGGCTCAGGAGAAACTTTAACAGTAATCAGA

ATTCTCGAGAAAGCCACCATGGTGAGCAAGGGCGAGGAGCTGTTCACCGGGGTGGTGCCCATC

CTGGTCGAGCTGGACGGCGACGTAAACGGCCACAAGTTCAGCGTGTCCGGCGAGGGCGAGGGC

GATGCCACCTACGGCAAGCTGACCCTGAAGTTCATCTGCACCACCGGCAAGCTGCCCGTGCCC

TGGCCCACCCTCGTGACCACCCTGACCTACGGCGTGCAGTGCTTCAGCCGCTACCCCGACCAC

ATGAAGCAGCACGACTTCTTCAAGTCCGCCATGCCCGAAGGCTACGTCCAGGAGCGCACCATC

TTCTTCAAGGACGACGGCAACTACAAGACCCGCGCCGAGGTGAAGTTCGAGGGCGACACCCTG

GTGAACCGCATCGAGCTGAAGGGCATCGACTTCAAGGAGGACGGCAACATCCTGGGGCACAAG

CTGGAGTACAACTACAACAGCCACAACGTCTATATCATGGCCGACAAGCAGAAGAACGGCATC

AAGGTGAACTTCAAGATCCGCCACAACATCGAGGACGGCAGCGTGCAGCTCGCCGACCACTAC

CAGCAGAACACCCCCATCGGCGACGGCCCCGTGCTGCTGCCCGACAACCACTACCTGAGCACC

CAGTCCGCCCTGAGCAAAGACCCCAACGAGAAGCGCGATCACATGGTCCTGCTGGAGTTCGTG

ACCGCCGCCGGGATCACTCTCGGCATGGACGAGCTGTACAAGTAATGGCCATATGAAAAAAAC

TAACAGTAATCAAAATGTCTGTTACAGTCAAGAGAATCATTGACAACACAGTCATAGTTCCAA

AACTTCCTGCAAATGAGGATCCAGTGGAATACCCGGCAGATTACTTCAGAAAATCAAAGGAGA

TTCCTCTTTACATCAATACTACAAAAAGTTTGTCAGATCTAAGAGGATATGTCTACCAAGGCC

TCAAATCCGGAAATGTATCAATCATACATGTCAACAGCTACTTGTATGGAGCATTAAAGGACA

TCCGGGGTAAGTTGGATAAAGATTGGTCAAGTTTCGGAATAAACATCGGGAAAGCAGGGGATA

CAATCGGAATATTTGACCTTGTATCCTTGAAAGCCCTGGACGGCGTACTTCCAGATGGAGTAT

CGGATGCTTCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTGACAAATCAAT

-continued

```
GCAAAATGATCAATGAACAGTTTGAACCTCTTGTGCCAGAAGGTCGTGACATTTTTGATGTGT

GGGGAAATGACAGTAATTACACAAAAATTGTCGCTGCAGTGGACATGTTCTTCCACATGTTCA

AAAAACATGAATGTGCCTCGTTCAGATACGGAACTATTGTTTCCAGATTCAAAGATTGTGCTG

CATTGGCAACATTTGGACACCTCTGCAAAATAACCGGAATGTCTACAGAAGATGTAACGACCT

GGATCTTGAACCGAGAAGTTGCAGATGAAATGGTCCAAATGATGCTTCCAGGCCAAGAAATTG

ACAAGGCCGATTCATACATGCCTTATTTGATCGACTTTGGATTGTCTTCTAAGTCTCCATATT

CTTCCGTCAAAAACCCTGCCTTCCACTTCTGGGGGCAATTGACAGCTCTTCTGCTCAGATCCA

CCAGAGCAAGGAATGCCCGACAGCCTGATGACATTGAGTATACATCTCTTACTACAGCAGGTT

TGTTGTACGCTTATGCAGTAGGATCCTCTGCCGACTTGGCACAACAGTTTTGTGTTGGAGATA

ACAAATACACTCCAGATGATAGTACCGGAGGATTGACGACTAATGCACCGCCACAAGGCAGAG

ATGTGGTCGAATGGCTCGGATGGTTTGAAGATCAAAACAGAAAACCGACTCCTGATATGATGC

AGTATGCGAAAAGAGCAGTCATGTCACTGCAAGGCCTAAGAGAAGACAATTGGCAAGTATG

CTAAGTCAGAATTTGACAAATGACCCTATAATTCTCAGATCACCTATTATATATTATGCTACA

TATGAAAAAAACTAACAGATATCATGGATAATCTCACAAAAGTTCGTGAGTATCTCAAGTCCT

ATTCTCGTCTGGATCAGGCGGTAGGAGAGATAGATGAGATCGAAGCACAACGAGCTGAAAGT

CCAATTATGAGTTGTTCCAAGAGGATGGAGTGGAAGAGCATACTAAGCCCTCTTATTTTCAGG

CAGCAGATGATTCTGACACAGAATCTGAACCAGAAATTGAAGACAATCAAGGTTTGTATGCAC

AGGATCCAGAAGCTGAGCAAGTTGAAGGCTTTATACAGGGGCCTTTAGATGACTATGCAGATG

AGGAAGTGGATGTTGTATTTACTTCGGACTGGAAACCACCTGAGCTTGAATCTGACGAGCATG

GAAAGACCTTACGGTTGACATCGCCAGAGGGTTTAAGTGGAGAGCAGAAATCCCAGTGGCTTT

CGACGATTAAAGCAGTCGTGCAAAGTGCCAAATACTGGAATCTGGCAGAGTGCACATTTGAAG

CATCGGGAGAAGGGGTCATTATGAAGGAGCGCCAGATAACTCCGGATGTATATAAGGTCACTC

CAGTGATGAACACACATCCGTCCCAATCAGAAGCAGTATCAGATGTTTGGTCTCTCTCAAAGA

CATCCATGACTTTCCAACCCAAGAAAGCAAGTCTTCAGCCTCTCACCATATCCTTGGATGAAT

TGTTCTCATCTAGAGGAGAGTTCATCTCTGTCGGAGGTGACGGACGAATGTCTCATAAAGAGG

CCATCCTGCTCGGCCTGAGATACAAAAAGTTGTACAATCAGGCGAGAGTCAAATATTCTCTGT

AGACTATGAAAAAAAGTAACAGATATCACGATCTAAGTGTTATCCCAATCCATTCATCATGAG

TTCCTTAAAGAAGATTCTCGGTCTGAAGGGGAAAGGTAAGAAATCTAAGAAATTAGGGATCGC

ACCACCCCCTTATGAAGAGGACACTAGCATGGAGTATGCTCCGAGCGCTCCAATTGACAAATC

CTATTTTGGAGTTGACGAGATGGACACCTATGATCCGAATCAATTAAGATATGAGAAATTCTT

CTTTACAGTGAAAATGACGGTTAGATCTAATCGTCCGTTCAGAACATACTCAGATGTGGCAGC

CGCTGTATCCCATTGGGATCACATGTACATCGGAATGGCAGGGAAACGTCCCTTCTACAAAAT

CTTGGCTTTTTTGGGTTCTTCTAATCTAAAGGCCACTCCAGCGGTATTGGCAGATCAAGGTCA

ACCAGAGTATCACACTCACTGCGAAGGCAGGGCTTATTTGCCACATAGGATGGGGAAGACCCC

TCCCATGCTCAATGTACCAGAGCACTTCAGAAGACCATTCAATATAGGTCTTTACAAGGGAAC

GATTGAGCTCACAATGACCATCTACGATGATGAGTCACTGGAAGCAGCTCCTATGATCTGGGA

TCATTTCAATTCTTCCAAATTTTCTGATTTCAGAGAGAAGGCCTTAATGTTTGGCCTGATTGT

CGAGAAAAAGGCATCTGGAGCGTGGGTCCTGGATTCTATCAGCCACTTCAAATGAGCTAGTCT

AACTTCTAGCTTCTGAACAATCCCCGGTTTACTCAGTCTCTCCTAATTCCAGCCTCTCGAACA

ACTAATATCCTGTCTTTTCTATCCCTATGAAAAAAACTAACAGAGATCGATCTGTTTCCTTGA

CACGCGTACCATGAGAAGAGGCAGCGCCTACTACATGTACCTGGACCGGAACGATGCCGGCGA
```

-continued

```
GGCCATCAGCTTTCCAACCACCCTGGGCATGAACAAGTGCTACATCCAGATCATGGACCTGGG

CCACACCTGTGACGCCACCATGAGCTACGAGTGCCCCATGCTGGACGAGGGCGTGGAACCCGA

CGATGTGGACTGCTGGTGCAACACCACCAGCACCTGGGTGGTGTACGGCACCTGTCACCACAA

GAAGGGCGAAGCCAGACGGTCCAGACGGGCCGTGACACTGCCTAGCCACAGCACCAGAAAGCT

GCAGACCCGGTCCCAGACCTGGCTGGAAAGCAGAGAGTACACCAAGCACCTGATCCGGGTGGA

AAACTGGATCTTCCGGAACCCCGGCTTTGCCCTGGCCGCTGCTGCTATTGCTTGGCTGCTGGG

CAGCAGCACCTCCCAGAAAGTGATCTACCTCGTGATGATCCTGCTGATCGCCCCTGCCTACAG

CATCCGGTGTATCGGCGTGTCCAACCGGGACTTCGTGGAAGGCATGAGCGGCGGCACATGGGT

GGACGTGGTGCTGGAACATGGCGGCTGCGTGACAGTGATGGCTCAGGACAAGCCCACCGTGGA

CATCGAGCTCGTGACCACCACCGTGTCCAATATGGCCGAAGTGCGGAGCTACTGCTACGAGGC

CAGCATCAGCGACATGGCCAGCGACAGCAGATGCCCTACACAGGGCGAGGCCTACCTGGACAA

GCAGTCCGACACCCAGTACGTGTGCAAGCGGACCCTGGTGGATAGAGGCTGGGGCAATGGCTG

CGGCCTGTTTGGCAAGGGCAGCCTCGTGACCTGCGCCAAGTTCGCCTGCAGCAAGAAGATGAC

CGGCAAGAGCATCCAGCCCGAGAACCTGGAATACCGGATCATGCTGAGCGTGCACGGCAGCCA

GCACTCCGGCATGATCGTGAACGACACCGGCCACGAGACAGACGAGAACCGGGCCAAGGTGGA

AATCACCCCCAACAGCCCTAGAGCCGAGGCCACACTGGGCGGCTTTGGATCTCTGGGCCTGGA

CTGCGAGCCTAGAACCGGCCTGGATTTCAGCGACCTGTACTACCTGACCATGAACAACAAGCA

CTGGCTGGTGCACAAAGAGTGGTTCCACGACATCCCCCTGCCCTGGCATGCCGGCGCTGATAC

AGGCACACCCCACTGGAACAACAAAGAGGCTCTGGTGGAATTCAAGGACGCCCACGCCAAGCG

GCAGACCGTGGTGGTGCTGGGATCTCAGGAAGGCGCCGTGCATACAGCTCTGGCTGGCGCCCT

GGAAGCCGAAATGGATGGCGCCAAAGGCAGACTGTCCAGCGGCCACCTGAAGTGCCGGCTGAA

GATGGACAAGCTGCGGCTGAAGGGCGTGTCCTACAGCCTGTGTACCGCCGCCTTCACCTTCAC

CAAGATCCCCGCCGAGACACTGCACGGCACCGTGACTGTGGAAGTGCAGTACGCCGGCACCGA

CGGCCCTTGTAAAGTGCCTGCTCAGATGGCCGTGGATATGCAGACCCTGACCCCCGTGGGCAG

ACTGATCACCGCCAACCCTGTGATCACCGAGAGCACCGAGAACAGCAAGATGATGCTGGAACT

GGACCCCCCCTTCGGCGACTCCTACATCGTGATCGGCGTGGGAGAGAAGAAGATCACCCACCA

CTGGCACAGAAGCGGCAGCACCATCGGCAAGGCCTTTGAGGCTACAGTGCGGGGAGCCAAGAG

AATGGCCGTGCTGGGAGATACCGCCTGGGACTTTGGCTCTGTGGGCGGAGCCCTGAACTCTCT

GGGCAAGGGAATCCACCAGATCTTCGGAGCCGCCTTTAAGAGCCTGTTCGGCGGCATGAGCTG

GTTCAGCCAGATCCTGATCGGCACCCTGCTGATGTGGCTGGGCCTGAACGCCAAGAACGGCAG

CATCTCCCTGATGTGCCTGGCTCTGGGAGGCGTGCTGATCTTCCTGAGCACAGCCGTGTCTGC

CTAAGCGGCCGCCCTGCACAACAGATTCTTCATGTTTGGACCAAATCAACTTGTGATACCATG

CTCAAAGAGGCCTCAATTATATTTGAGTTTTTAATTTTTATGAAAAAAACTAACAGCAATCAT

GGAAGTCCACGATTTTGAGACCGACGAGTTCAATGATTTCAATGAAGATGACTATGCCACAAG

AGAATTCCTGAATCCCGATGAGCGCATGACGTACTTGAATCATGCTGATTACAATTTGAATTC

TCCTCTAATTAGTGATGATATTGACAATTTGATCAGGAAATTCAATTCTCTTCCGATTCCCTC

GATGTGGGATAGTAAGAACTGGGATGGAGTTCTTGAGATGTTAACATCATGTCAAGCCAATCC

CATCTCAACATCTCAGATGCATAAATGGATGGGAAGTTGGTTAATGTCTGATAATCATGATGC

CAGTCAAGGGTATAGTTTTTTACATGAAGTGGACAAAGAGGCAGAAATAACATTTGACGTGGT

GGAGACCTTCATCCGCGGCTGGGGCAACAAACCAATTGAATACATCAAAAAGGAAAGATGGAC
```

-continued

```
TGACTCATTCAAAATTCTCGCTTATTTGTGTCAAAAGTTTTTGGACTTACACAAGTTGACATT
AATCTTAAATGCTGTCTCTGAGGTGGAATTGCTCAACTTGGCGAGGACTTTCAAAGGCAAAGT
CAGAAGAAGTTCTCATGGAACGAACATATGCAGGATTAGGGTTCCCAGCTTGGGTCCTACTTT
TATTTCAGAAGGATGGGCTTACTTCAAGAAACTTGATATTCTAATGGACCGAAACTTTCTGTT
AATGGTCAAAGATGTGATTATAGGGAGGATGCAAACGGTGCTATCCATGGTATGTAGAATAGA
CAACCTGTTCTCAGAGCAAGACATCTTCTCCCTTCTAAATATCTACAGAATTGGAGATAAAAT
TGTGGAGAGGCAGGGAAATTTTTCTTATGACTTGATTAAAATGGTGGAACCGATATGCAACTT
GAAGCTGATGAAATTAGCAAGAGAATCAAGGCCTTTAGTCCCACAATTCCCTCATTTTGAAAA
TCATATCAAGACTTCTGTTGATGAAGGGGCAAAAATTGACCGAGGTATAAGATTCCTCCATGA
TCAGATAATGAGTGTGAAAACAGTGGATCTCACACTGGTGATTTATGGATCGTTCAGACATTG
GGGTCATCCTTTTATAGATTATTACACTGGACTAGAAAAATTACATTCCCAAGTAACCATGAA
GAAAGATATTGATGTGTCATATGCAAAAGCACTTGCAAGTGATTTAGCTCGGATTGTTCTATT
TCAACAGTTCAATGATCATAAAAAGTGGTTCGTGAATGGAGACTTGCTCCCTCATGATCATCC
CTTTAAAAGTCATGTTAAAGAAAATACATGGCCCACAGCTGCTCAAGTTCAAGATTTTGGAGA
TAAATGGCATGAACTTCCGCTGATTAAATGTTTTGAAATACCCGACTTACTAGACCCATCGAT
AATATACTCTGACAAAAGTCATTCAATGAATAGGTCAGAGGTGTTGAAACATGTCCGAATGAA
TCCGAACACTCCTATCCCTAGTAAAAAGGTGTTGCAGACTATGTTGGACACAAAGGCTACCAA
TTGGAAAGAATTTCTTAAAGAGATTGATGAGAAGGGCTTAGATGATGATGATCTAATTATTGG
TCTTAAAGGAAAGGAGAGGGAACTGAAGTTGGCAGGTAGATTTTTCTCCCTAATGTCTTGGAA
ATTGCGAGAATACTTTGTAATTACCGAATATTTGATAAAGACTCATTTCGTCCCTATGTTTAA
AGGCCTGACAATGGCGGACGATCTAACTGCAGTCATTAAAAAGATGTTAGATTCCTCATCCGG
CCAAGGATTGAAGTCATATGAGGCAATTTGCATAGCCAATCACATTGATTACGAAAAATGGAA
TAACCACCAAAGGAAGTTATCAAACGGCCCAGTGTTCCGAGTTATGGGCCAGTTCTTAGGTTA
TCCATCCTTAATCGAGAGAACTCATGAATTTTTTGAGAAAAGTCTTATATACTACAATGGAAG
ACCAGACTTGATGCGTGTTCACAACAACACACTGATCAATTCAACCTCCCAACGAGTTTGTTG
GCAAGGACAAGAGGGTGGACTGGAAGGTCTACGGCAAAAAGGATGGACTATCCTCAATCTACT
GGTTATTCAAAGAGAGGCTAAAATCAGAAACACTGCTGTCAAAGTCTTGGCACAAGGTGATAA
TCAAGTTATTTGCACACAGTATAAAACGAAGAAATCGAGAAACGTTGTAGAATTACAGGGTGC
TCTCAATCAAATGGTTTCTAATAATGAGAAAATTATGACTGCAATCAAAATAGGGACAGGGAA
GTTAGGACTTTTGATAAATGACGATGAGACTATGCAATCTGCAGATTACTTGAATTATGGAAA
AATACCGATTTTCCGTGGAGTGATTAGAGGGTTAGAGACCAAGAGATGGTCACGAGTGACTTG
TGTCACCAATGACCAAATACCCACTTGTGCTAATATAATGAGCTCAGTTTCCACAAATGCTCT
CACCGTAGCTCATTTTGCTGAGAACCCAATCAATGCCATGATACAGTACAATTATTTTGGGAC
ATTTGCTAGACTCTTGTTGATGATGCATGATCCTGCTCTTCGTCAATCATTGTATGAAGTTCA
AGATAAGATACCGGGCTTGCACAGTTCTACTTTCAAATACGCCATGTTGTATTTGGACCCTTC
CATTGGAGGAGTGTCGGGCATGTCTTTGTCCAGGTTTTTGATTAGAGCCTTCCCAGATCCCGT
AACAGAAAGTCTCTCATTCTGGAGATTCATCCATGTACATGCTGAAGTGAGCATCTGAAGGA
GATGAGTGCAGTATTTGGAAACCCCGAGATAGCCAAGTTTCGAATAACTCACATAGACAAGCT
AGTAGAAGATCCAACCTCTCTGAACATCGCTATGGGAATGAGTCCAGCGAACTTGTTAAAGAC
TGAGGTTAAAAAATGCTTAATCGAATCAAGACAAACCATCAGGAACCAGGTGATTAAGGATGC
AACCATATATTTGTATCATGAAGAGGATCGGCTCAGAAGTTTCTTATGGTCAATAAATCCTCT
```

```
GTTCCCTAGATTTTTAAGTGAATTCAAATCAGGCACTTTTTTGGGAGTCGCAGACGGGCTCAT

CAGTCTATTTCAAAATTCTCGTACTATTCGGAACTCCTTTAAGAAAAAGTATCATAGGGAATT

GGATGATTTGATTGTGAGGAGTGAGGTATCCTCTTTGACACATTTAGGGAAACTTCATTTGAG

AAGGGGATCATGTAAAATGTGGACATGTTCAGCTACTCATGCTGACACATTAAGATACAAATC

CTGGGGCCGTACAGTTATTGGGACAACTGTACCCCATCCATTAGAAATGTTGGGTCCACAACA

TCGAAAAGAGACTCCTTGTGCACCATGTAACACATCAGGGTTCAATTATGTTTCTGTGCATTG

TCCAGACGGGATCCATGACGTCTTTAGTTCACGGGACCATTGCCTGCTTATCTAGGGTCTAA

AACATCTGAATCTACATCTATTTTGCAGCCTTGGGAAAGGGAAAGCAAAGTCCCACTGATTAA

AAGAGCTACACGTCTTAGAGATGCTATCTCTTGGTTTGTTGAACCCGACTCTAAACTAGCAAT

GACTATACTTTCTAACATCCACTCTTTAACAGGCGAAGAATGGACCAAAAGGCAGCATGGGTT

CAAAAGAACAGGGTCTGCCCTTCATAGGTTTTCGACATCTCGGATGAGCCATGGTGGGTTCGC

ATCTCAGAGCACTGCAGCATTGACCAGGTTGATGGCAACTACAGACACCATGAGGGATCTGGG

AGATCAGAATTTCGACTTTTTATTCCAAGCAACGTTGCTCTATGCTCAAATTACCACCACTGT

TGCAAGAGACGGATGGATCACCAGTTGTACAGATCATTATCATATTGCCTGTAAGTCCTGTTT

GAGACCCATAGAAGAGATCACCCTGGACTCAAGTATGGACTACACGCCCCAGATGTATCCCA

TGTGCTGAAGACATGGAGGAATGGGGAAGGTTCGTGGGACAAGAGATAAAACAGATCTATCC

TTTAGAAGGGAATTGGAAGAATTTAGCACCTGCTGAGCAATCCTATCAAGTCGGCAGATGTAT

AGGTTTTCTATATGGAGACTTGGCGTATAGAAAATCTACTCATGCCGAGGACAGTTCTCTATT

TCCTCTATCTATACAAGGTCGTATTAGAGGTCGAGGTTTCTTAAAAGGGTTGCTAGACGGATT

AATGAGAGCAAGTTGCTGCCAAGTAATACACCGGAGAAGTCTGGCTCATTTGAAGAGGCCGGC

CAACGCAGTGTACGGAGGTTTGATTTACTTGATTGATAAATTGAGTGTATCACCTCCATTCCT

TTCTCTTACTAGATCAGGACCTATTAGAGACGAATTAGAAACGATTCCCCACAAGATCCCAAC

CTCCTATCCGACAAGCAACCGTGATATGGGGGTGATTGTCAGAAATTACTTCAAATACCAATG

CCGTCTAATTGAAAAGGGAAAATACAGATCACATTATTCACAATTATGGTTATTCTCAGATGT

CTTATCCATAGACTTCATTGGACCATTCTCTATTTCCACCACCCTCTTGCAAATCCTATACAA

GCCATTTTTATCTGGGAAAGATAAGAATGAGTTGAGAGAGCTGGCAAATCTTTCTTCATTGCT

AAGATCAGGAGAGGGGTGGGAAGACATACATGTGAAATTCTTCACCAAGGACATATTATTGTG

TCCAGAGGAAATCAGACATGCTTGCAAGTTCGGGATTGCTAAGGATAATAATAAAGACATGAG

CTATCCCCCTTGGGGAAGGGAATCCAGAGGGACAATTACAACAATCCCTGTTTATTATACGAC

CACCCCTTACCCAAAGATGCTAGAGATGCCTCCAAGAATCCAAAATCCCCTGCTGTCCGGAAT

CAGGTTGGGCCAATTACCAACTGGCGCTCATTATAAAATTCGGAGTATATTACATGGAATGGG

AATCCATTACAGGGACTTCTTGAGTTGTGGAGACGGCTCCGGAGGGATGACTGCTGCATTACT

ACGAGAAAATGTGCATAGCAGAGGAATATTCAATAGTCTGTTAGAATTATCAGGGTCAGTCAT

GCGAGGCGCCTCTCCTGAGCCCCCCAGTGCCCTAGAAACTTTAGGAGGAGATAAATCGAGATG

TGTAAATGGTGAAACATGTTGGGAATATCCATCTGACTTATGTGACCCAAGGACTTGGGACTA

TTTCCTCCGACTCAAAGCAGGCTTGGGGCTTCAAATTGATTTAATTGTAATGGATATGGAAGT

TCGGGATTCTTCTACTAGCCTGAAAATTGAGACGAATGTTAGAAATTATGTGCACCGGATTTT

GGATGAGCAAGGAGTTTTAATCTACAAGACTTATGGAACATATATTTGTGAGAGCGAAAAGAA

TGCAGTAACAATCCTTGGTCCCATGTTCAAGACGGTCGACTTAGTTCAAACAGAATTTAGTAG

TTCTCAAACGTCTGAAGTATATATGGTATGTAAAGGTTTGAAGAAATTAATCGATGAACCCAA
```

-continued

```
TCCCGATTGGTCTTCCATCAATGAATCCTGGAAAAACCTGTACGCATTCCAGTCATCAGAACA

GGAATTTGCCAGAGCAAAGAAGGTTAGTACATACTTTACCTTGACAGGTATTCCCTCCCAATT

CATTCCTGATCCTTTTGTAAACATTGAGACTATGCTACAAATATTCGGAGTACCCACGGGTGT

GTCTCATGCGGCTGCCTTAAAATCATCTGATAGACCTGCAGATTTATTGACCATTAGCCTTTT

TTATATGGCGATTATATCGTATTATAACATCAATCATATCAGAGTAGGACCGATACCTCCGAA

CCCCCCATCAGATGGAATTGCACAAAATGTGGGGATCGCTATAACTGGTATAAGCTTTTGGCT

GAGTTTGATGGAGAAAGACATTCCACTATATCAACAGTGTTTAGCAGTTATCCAGCAATCATT

CCCGATTAGGTGGGAGGCTGTTTCAGTAAAAGGAGGATACAAGCAGAAGTGGAGTACTAGAGG

TGATGGGCTCCCAAAAGATACCCGAACTTCAGACTCCTTGGCCCCAATCGGGAACTGGATCAG

ATCTCTGGAATTGGTCCGAAACCAAGTTCGTCTAAATCCATTCAATGAGATCTTGTTCAATCA

GCTATGTCGTACAGTGGATAATCATTTGAAATGGTCAAATTTGCGAAGAAACACAGGAATGAT

TGAATGGATCAATAGACGAATTTCAAAAGAAGACCGGTCTATACTGATGTTGAAGAGTGACCT

ACACGAGGAAAACTCTTGGAGAGATTAAAAAATCATGAGGAGACTCCAAACTTTAAGTATGAA

AAAAACTTTGATCCTTAAGACCCTCTTGTGGTTTTTATTTTTTATCTGGTTTTGTGGTCTTCG

TGGGTCGGCATGGCATCTCCACCTCCTCGCGGTCCGACCTGGGCATCCGAAGGAGGACGTCGT

CCACTCGGATGGCTAAGGGAGAGCTCGGATCCGGCTGCTAACAAAGCCCGAAAGGAAGCTGAG

TTGGCTGCTGCCACCGCTGAGCAATAACTAGCATAACCCCTTGGGGCCTCTAAACGGGTCTTG

AGGGGTTTTTTGCTGAAAGGAGGAACTATATCCGGATCGAGATCCTCTAGAGTCGACCTGCAG

GCATGCAAGCTTGTATTCTATAGTGTCACCTAAATCGTATGTGTATGATACATAAGGTTATGT

ATTAATTGTAGCCGCGTTCTAACGACAATATGTACAAGCCTAATTGTGTAGCATCTGGCTTAC

TGAAGCAGACCCTATCATCTCTCGTAAACTGCCGTCAGAGTCGGTTTGGTTGGACGAACCT

TCTGAGTTTCTGGTAACGCCGTcCCGCACCCGGAAATGGTCAGCGAACCAATCAGCAGGGTCA

TCGCTAGCCAGATCCTCTACGCCGGACGCATCGTGGCCGGCATCACCGGCGCCACAGGTGCGG

TTGCTGGCGCCTATATCGCCGACATCACCGATGGGGAAGATCGGGCTCGCCACTTCGGGCTCA

TGAGCGCTTGTTTCGGCGTGGGTATGGTGGCAGGCCCCGTGGCCGGGGGACTGTTGGGCGCCA

TCTCCTTGCACCATTCCTTGCGGCGGCGGTGCTCAACGGCCTCAACCTACTACTGGGCTGCTT

CCTAATGCAGGAGTCGCATAAGGGAGAGCGTCGAATGGTGCACTCTCAGTACAATCTGCTCTG

ATGCCGCATAGTTAAGCCAGCCCCGACACCCGCCAACACCCGCTGACGCGCCCTGACGGGCTT

GTCTGCTCCCGGCATCCGCTTACAGACAAGCTGTGACCGTCTCCGGGAGCTGCATGTGTCAGA

GGTTTTCACCGTCATCACCGAAACGCGCGAGACGAAAGGGCCTCGTGATACGCCTATTTTAT

AGGTTAATGTCATGATAATAATGGTTTCTTAGACGTCAGGTGGCACTTTTCGGGGAAATGTGC

GCGGAACCCCTATTTGTTTATTTTTCTAAATACATTCAAATATGTATCCGCTCATGAGACAAT

AACCCTGATAAATGCTTCAATAATATTGAAAAAGGAAGAGTATGAGTATTCAACATTTCCGTG

TCGCCCTTATTCCCTTTTTTGCGGCATTTTGCCTTCCTGTTTTTGCTCACCCAGAAACGCTGG

TGAAAGTAAAAGATGCTGAAGATCAGTTGGGTGCACGAGTGGGTTACATCGAACTGGATCTCA

ACAGCGGTAAGATCCTTGAGAGTTTTCGCCCCGAAGAACGTTTTCCAATGATGAGCACTTTTA

AAGTTCTGCTATGTGGCGCGGTATTATCCCGTATTGACGCCGGGCAAGAGCAACTCGGTCGCC

GCATACACTATTCTCAGAATGACTTGGTTGAGTACTCACCAGTCACAGAAAAGCATCTTACGG

ATGGCATGACAGTAAGAGAATTATGCAGTGCTGCCATAACCATGAGTGATAACACTGCGGCCA

ACTTACTTCTGACAACGATCGGAGGACCGAAGGAGCTAACCGCTTTTTTGCACAACATGGGGG

ATCATGTAACTCGCCTTGATCGTTGGGAACCGGAGCTGAATGAAGCCATACCAAACGACGAGC
```

-continued

```
GTGACACCACGATGCCTGTAGCAATGGCAACAACGTTGCGCAAACTATTAACTGGCGAACTAC
TTACTCTAGCTTCCCGGCAACAATTAATAGACTGGATGGAGGCGGATAAAGTTGCAGGACCAC
TTCTGCGCTCGGCCCTTCCGGCTGGCTGGTTTATTGCTGATAAATCTGGAGCCGGTGAGCGTG
GGTCTCGCGGTATCATTGCAGCACTGGGGCCAGATGGTAAGCCCTCCCGTATCGTAGTTATCT
ACACGACGGGGAGTCAGGCAACTATGGATGAACGAAATAGACAGATCGCTGAGATAGGTGCCT
CACTGATTAAGCATTGGTAACTGTCAGACCAAGTTTACTCATATATACTTTAGATTGATTTAA
AACTTCATTTTTAATTTAAAAGGATCTAGGTGAAGATCCTTTTTGATAATCTCATGACCAAAA
TCCCTTAACGTGAGTTTTCGTTCCACTGAGCGTCAGACCCCGTAGAAAAGATCAAAGGATCTT
CTTGAGATCCTTTTTTTCTGCGCGTAATCTGCTGCTTGCAAACAAAAAAACCACCGCTACCAG
CGGTGGTTTGTTTGCCGGATCAAGAGCTACCAACTCTTTTTCCGAAGGTAACTGGCTTCAGCA
GAGCGCAGATACCAAATACTGTCCTTCTAGTGTAGCCGTAGTTAGGCCACCACTTCAAGAACT
CTGTAGCACCGCCTACATACCTCGCTCTGCTAATCCTGTTACCAGTGGCTGCTGCCAGTGGCG
ATAAGTCGTGTCTTACCGGGTTGGACTCAAGACGATAGTTACCGGATAAGGCGCAGCGGTCGG
GCTGAACGGGGGGTTCGTGCACACAGCCCAGCTTGGAGCGAACGACCTACACCGAACTGAGAT
ACCTACAGCGTGAGCTATGAGAAAGCGCCACGCTTCCCGAAGGGAGAAAGGCGGACAGGTATC
CGGTAAGCGGCAGGGTCGGAACAGGAGAGCGCACGAGGGAGCTTCCAGGGGGAAACGCCTGGT
ATCTTTATAGTCCTGTCGGGTTTCGCCACCTCTGACTTGAGCGTCGATTTTTGTGATGCTCGT
CAGGGGGGCGGAGCCTATGGAAAAACGCCAGCAACGCGGCCTTTTTACGGTTCCTGGCCTTTT
GCTGGCCTTTTGCTCACATGTTCTTTCCTGCGTTATCCCCTGATTCTGTGGATAACCGTATTA
CCGCCTTTGAGTGAGCTGATACCGCTCGCCGCAGCCGAACGACCGAGCGCAGCGAGTCAGTGA
GCGAGGAAGCGGAAGAGCGCCCAATACGCAAACCGCCTCTCCCCGCGCGTTGGCCGATTCATT
AATGCAGGGGATCTCGATCCCGCGAAATTAATACGACTCACTATAGG
                                                          SEQ ID NO: 6
ACGAAGACAAACAAACCATTATTATCATTAAAAGGCTCAGGAGAAACTTTAACAGTAATCAGA
ATTCTCGAGAAAGCCACCATGGTGAGCAAGGGCGAGGAGCTGTTCACCGGGGTGGTGCCCATC
CTGGTCGAGCTGGACGGCGACGTAAACGGCCACAAGTTCAGCGTGTCCGGCGAGGGCGAGGGC
GATGCCACCTACGGCAAGCTGACCCTGAAGTTCATCTGCACCACCGGCAAGCTGCCCGTGCCC
TGGCCCACCCTCGTGACCACCCTGACCTACGGCGTGCAGTGCTTCAGCCGCTACCCCGACCAC
ATGAAGCAGCACGACTTCTTCAAGTCCGCCATGCCCGAAGGCTACGTCCAGGAGCGCACCATC
TTCTTCAAGGACGACGGCAACTACAAGACCCGCGCCGAGGTGAAGTTCGAGGGCGACACCCTG
GTGAACCGCATCGAGCTGAAGGGCATCGACTTCAAGGAGGACGGCAACATCCTGGGGCACAAG
CTGGAGTACAACTACAACAGCCACAACGTCTATATCATGGCCGACAAGCAGAAGAACGGCATC
AAGGTGAACTTCAAGATCCGCCACAACATCGAGGACGGCAGCGTGCAGCTCGCCGACCACTAC
CAGCAGAACACCCCCATCGGCGACGGCCCCGTGCTGCTGCCCGACAACCACTACCTGAGCACC
CAGTCCGCCCTGAGCAAAGACCCCAACGAGAAGCGCGATCACATGGTCCTGCTGGAGTTCGTG
ACCGCCGCCGGGATCACTCTCGGCATGGACGAGCTGTACAAGTAATGGCCATATGAAAAAAAC
TAACAGTAATCAAAATGTCTGTTACAGTCAAGAGAATCATTGACAACACAGTCATAGTTCCAA
AACTTCCTGCAAATGAGGATCCAGTGGAATACCCGGCAGATTACTTCAGAAAATCAAAGGAGA
TTCCTCTTTACATCAATACTACAAAAAGTTTGTCAGATCAAGAGGATATGTCTACCAAGGCC
TCAAATCCGGAAATGTATCAATCATACATGTCAACAGCTACTTGTATGGAGCATTAAAGGACA
TCCGGGGTAAGTTGGATAAAGATTGGTCAAGTTTCGGAATAAACATCGGGAAAGCAGGGGATA
```

-continued

```
CAATCGGAATATTTGACCTTGTATCCTTGAAAGCCCTGGACGGCGTACTTCCAGATGGAGTAT
CGGATGCTTCCAGAACCAGCGCAGATGACAAATGGTTGCCTTTGTATCTACTTGGCTTATACA
GAGTGGGCAGAACACAAATGCCTGAATACAGAAAAAAGCTCATGGATGGGCTGACAAATCAAT
GCAAAATGATCAATGAACAGTTTGAACCTCTTGTGCCAGAAGGTCGTGACATTTTTGATGTGT
GGGGAAATGACAGTAATTACACAAAAATTGTCGCTGCAGTGGACATGTTCTTCCACATGTTCA
AAAAACATGAATGTGCCTCGTTCAGATACGGAACTATTGTTTCCAGATTCAAAGATTGTGCTG
CATTGGCAACATTTGGACACCTCTGCAAAATAACCGGAATGTCTACAGAAGATGTAACGACCT
GGATCTTGAACCGAGAAGTTGCAGATGAAATGGTCCAAATGATGCTTCCAGGCCAAGAAATTG
ACAAGGCCGATTCATACATGCCTTATTTGATCGACTTTGGATTGTCTTCTAAGTCTCCATATT
CTTCCGTCAAAAACCCTGCCTTCCACTTCTGGGGGCAATTGACAGCTCTTCTGCTCAGATCCA
CCAGAGCAAGGAATGCCCGACAGCCTGATGACATTGAGTATACATCTCTTACTACAGCAGGTT
TGTTGTACGCTTATGCAGTAGGATCCTCTGCCGACTTGGCACAACAGTTTTGTGTTGGAGATA
ACAAATACACTCCAGATGATAGTACCGGAGGATTGACGACTAATGCACCGCCACAAGGCAGAG
ATGTGGTCGAATGGCTCGGATGGTTTGAAGATCAAAACAGAAAACCGACTCCTGATATGATGC
AGTATGCGAAAAGAGCAGTCATGTCACTGCAAGGCCTAAGAGAGAAGACAATTGGCAAGTATG
CTAAGTCAGAATTTGACAAATGACCCTATAATTCTCAGATCACCTATTATATATTATGCTACA
TATGAAAAAAACTAACAGATATCATGGATAATCTCACAAAAGTTCGTGAGTATCTCAAGTCCT
ATTCTCGTCTGGATCAGGCGGTAGGAGAGATAGATGAGATCGAAGCACAACGAGCTGAAAAGT
CCAATTATGAGTTGTTCCAAGAGGATGGAGTGGAAGAGCATACTAAGCCCTCTTATTTTCAGG
CAGCAGATGATTCTGACACAGAATCTGAACCAGAAATTGAAGACAATCAAGGTTTGTATGCAC
AGGATCCAGAAGCTGAGCAAGTTGAAGGCTTTATACAGGGGCCTTTAGATGACTATGCAGATG
AGGAAGTGGATGTTGTATTTACTTCGGACTGGAAACCACCTGAGCTTGAATCTGACGAGCATG
GAAAGACCTTACGGTTGACATCGCCAGAGGGTTTAAGTGGAGAGCAGAAATCCCAGTGGCTTT
CGACGATTAAAGCAGTCGTGCAAAGTGCCAAATACTGGAATCTGGCAGAGTGCACATTTGAAG
CATCGGGAGAAGGGGTCATTATGAAGGAGCGCCAGATAACTCCGGATGTATATAAGGTCACTC
CAGTGATGAACACACATCCGTCCCAATCAGAAGCAGTATCAGATGTTTGGTCTCTCTCAAAGA
CATCCATGACTTTCCAACCCAAGAAAGCAAGTCTTCAGCCTCTCACCATATCCTTGGATGAAT
TGTTCTCATCTAGAGGAGAGTTCATCTCTGTCGGAGGTGACGGACGAATGTCTCATAAAGAGG
CCATCCTGCTCGGCCTGAGATACAAAAAGTTGTACAATCAGGCGAGAGTCAAATATTCTCTGT
AGACTATGAAAAAAAGTAACAGATATCACGATCTAAGTGTTATCCCAATCCATTCATCATGAG
TTCCTTAAAGAAGATTCTCGGTCTGAAGGGGAAAGGTAAGAAATCTAAGAAATTAGGGATCGC
ACCACCCCCTTATGAAGAGGACACTAGCATGGAGTATGCTCCGAGCGCTCCAATTGACAAATC
CTATTTTGGAGTTGACGAGATGGACACCTATGATCCGAATCAATTAAGATATGAGAAATTCTT
CTTTACAGTGAAAATGACGGTTAGATCTAATCGTCCGTTCAGAACATACTCAGATGTGGCAGC
CGCTGTATCCCATTGGGATCACATGTACATCGGAATGGCAGGGAAACGTCCCTTCTACAAAAT
CTTGGCTTTTTTGGGTTCTTCTAATCTAAAGGCCACTCCAGCGGTATTGGCAGATCAAGGTCA
ACCAGAGTATCACACTCACTGCGAAGGCAGGGCTTATTTGCCACATAGGATGGGAAGACCCC
TCCCATGCTCAATGTACCAGAGCACTTCAGAAGACCATTCAATATAGGTCTTTACAAGGGAAC
GATTGAGCTCACAATGACCATCTACGATGATGAGTCACTGGAAGCAGCTCCTATGATCTGGGA
TCATTTCAATTCTTCCAAATTTTCTGATTTCAGAGAGAAGGCCTTAATGTTTGGCCTGATTGT
```

-continued

```
CGAGAAAAAGGCATCTGGAGCGTGGGTCCTGGATTCTATCAGCCACTTCAAATGAGCTAGTCT
AACTTCTAGCTTCTGAACAATCCCCGGTTTACTCAGTCTCTCCTAATTCCAGCCTCTCGAACA
ACTAATATCCTGTCTTTTCTATCCCTATGAAAAAAACTAACAGAGATCGATCTGTTTCCTTGA
CACGCGTGCCACCATGACCAGCGTGGGCATCGTGGGCCTGCTGCTGACCACCGCCATGGCCGC
CGAGGTGACCAGAAGAGGCAGCGCCTACTACATGTACCTGGACCGGAACGATGCCGGCGAGGC
CATCAGCTTTCCAACCACCCTGGGCATGAACAAGTGCTACATCCAGATCATGGACCTGGGCCA
CACCTGTGACGCCACCATGAGCTACGAGTGCCCCATGCTGGACGAGGGCGTGGAACCCGACGA
TGTGGACTGCTGGTGCAACACCACCAGCACCTGGGTGGTGTACGGCACCTGTCACCACAAGAA
GGGCGAAGCCAGACGGTCCAGACGGGCCGTGACACTGCCTAGCCACAGCACCAGAAAGCTGCA
GACCCGGTCCCAGACCTGGCTGGAAAGCAGAGAGTACACCAAGCACCTGATCCGGGTGGAAAA
CTGGATCTTCCGGAACCCCGGCTTTGCCCTGGCCGCTGCTGCTATTGCTTGGCTGCTGGGCAG
CAGCACCTCCCAGAAAGTGATCTACCTCGTGATGATCCTGCTGATCGCCCCTGCCTACAGCAT
CCGGTGTATCGGCGTGTCCAACCGGGACTTCGTGGAAGGCATGAGCGGCGGCACATGGGTGGA
CGTGGTGCTGGAACATGGCGGCTGCGTGACAGTGATGGCTCAGGACAAGCCCACCGTGGACAT
CGAGCTCGTGACCACCACCGTGTCCAATATGGCCGAAGTGCGGAGCTACTGCTACGAGGCCAG
CATCAGCGACATGGCCAGCGACAGCAGATGCCCTACACAGGGCGAGGCCTACCTGGACAAGCA
GTCCGACACCCAGTACGTGTGCAAGCGGACCCTGGTGGATAGAGGCTGGGGCAATGGCTGCGG
CCTGTTTGGCAAGGGCAGCCTCGTGACCTGCGCCAAGTTCGCCTGCAGCAAGAAGATGACCGG
CAAGAGCATCCAGCCCGAGAACCTGGAATACCGGATCATGCTGAGCGTGCACGGCAGCCAGCA
CTCCGGCATGATCGTGAACGACACCGGCCACGAGACAGACGAGAACCGGGCCAAGGTGGAAAT
CACCCCCAACAGCCCTAGAGCCGAGGCCACACTGGGCGGCTTTGGATCTCTGGGCCTGGACTG
CGAGCCTAGAACCGGCCTGGATTTCAGCGACCTGTACTACCTGACCATGAACAACAAGCACTG
GCTGGTGCACAAAGAGTGGTTCCACGACATCCCCCTGCCCTGGCATGCCGGCGCTGATACAGG
CACACCCCACTGGAACAACAAAGAGGCTCTGGTGGAATTCAAGGACGCCCACGCCAAGCGGCA
GACCGTGGTGGTGCTGGGATCTCAGGAAGGCGCCGTGCATACAGCTCTGGCTGGCGCCCTGGA
AGCCGAAATGGATGGCGCCAAAGGCAGACTGTCCAGCGGCCACCTGAAGTGCCGGCTGAAGAT
GGACAAGCTGCGGCTGAAGGGCGTGTCCTACAGCCTGTGTACCGCCGCCTTCACCTTCACCAA
GATCCCCGCCGAGACACTGCACGGCACCGTGACTGTGGAAGTGCAGTACGCCGGCACCGACGG
CCCTTGTAAAGTGCCTGCTCAGATGGCCGTGGATATGCAGACCCTGACCCCCGTGGGCAGACT
GATCACCGCCAACCCTGTGATCACCGAGAGCACCGAGAACAGCAAGATGATGCTGGAACTGGA
CCCCCCCTTCGGCGACTCCTACATCGTGATCGGCGTGGGAGAGAAGAAGATCACCCACCACTG
GCACAGAAGCGGCAGCACCATCGGCAAGGCCTTTGAGGCTACAGTGCGGGGAGCCAAGAGAAT
GGCCGTGCTGGGAGATACCGCCTGGGACTTTGGCTCTGTGGGCGGAGCCCTGAACTCTCTGGG
CAAGGGAATCCACCAGATCTTCGGAGCCGCCTTTAAGAGCCTGTTCGGCGGCATGAGCTGGTT
CAGCCAGATCCTGATCGGCACCCTGCTGATGTGGCTGGGCCTGAACGCCAAGAACGGCAGCAT
CTCCCTGATGTGCCTGGCTCTGGGAGGCGTGCTGATCTTCCTGAGCACAGCCGTGTCTGCCtg
agcggccgcCCTGCACAACAGATTCTTCATGTTTGGACCAAATCAACTTGTGATACCATGCTC
AAAGAGGCCTCAATTATATTTGAGTTTTTAATTTTTATGAAAAAAACTAACAGCAATCATGGA
AGTCCACGATTTTGAGACCGACGAGTTCAATGATTTCAATGAAGATGACTATGCCACAAGAGA
ATTCCTGAATCCCGATGAGCGCATGACGTACTTGAATCATGCTGATTACAATTTGAATTCTCC
TCTAATTAGTGATGATATTGACAATTTGATCAGGAAATTCAATTCTCTTCCGATTCCCTCGAT
```

```
GTGGGATAGTAAGAACTGGGATGGAGTTCTTGAGATGTTAACATCATGTCAAGCCAATCCCAT

CTCAACATCTCAGATGCATAAATGGATGGGAAGTTGGTTAATGTCTGATAATCATGATGCCAG

TCAAGGGTATAGTTTTTTACATGAAGTGGACAAAGAGGCAGAAATAACATTTGACGTGGTGGA

GACCTTCATCCGCGGCTGGGGCAACAAACCAATTGAATACATCAAAAAGGAAAGATGGACTGA

CTCATTCAAAATTCTCGCTTATTTGTGTCAAAAGTTTTTGGACTTACACAAGTTGACATTAAT

CTTAAATGCTGTCTCTGAGGTGGAATTGCTCAACTTGGCGAGGACTTTCAAAGGCAAAGTCAG

AAGAAGTTCTCATGGAACGAACATATGCAGGATTAGGGTTCCCAGCTTGGGTCCTACTTTTAT

TTCAGAAGGATGGGCTTACTTCAAGAAACTTGATATTCTAATGGACCGAAACTTTCTGTTAAT

GGTCAAAGATGTGATTATAGGGAGGATGCAAACGGTGCTATCCATGGTATGTAGAATAGACAA

CCTGTTCTCAGAGCAAGACATCTTCTCCCTTCTAAATATCTACAGAATTGGAGATAAAATTGT

GGAGAGGCAGGGAAATTTTCTTATGACTTGATTAAAATGGTGGAACCGATATGCAACTTGAA

GCTGATGAAATTAGCAAGAGAATCAAGGCCTTTAGTCCCACAATTCCCTCATTTTGAAAATCA

TATCAAGACTTCTGTTGATGAAGGGGCAAAAATTGACCGAGGTATAAGATTCCTCCATGATCA

GATAATGAGTGTGAAAACAGTGGATCTCACACTGGTGATTTATGGATCGTTCAGACATTGGGG

TCATCCTTTTATAGATTATTACACTGGACTAGAAAAATTACATTCCCAAGTAACCATGAAGAA

AGATATTGATGTGTCATATGCAAAAGCACTTGCAAGTGATTTAGCTCGGATTGTTCTATTTCA

ACAGTTCAATGATCATAAAAAGTGGTTCGTGAATGGAGACTTGCTCCCTCATGATCATCCCTT

TAAAAGTCATGTTAAAGAAAATACATGGCCCACAGCTGCTCAAGTTCAAGATTTTGGAGATAA

ATGGCATGAACTTCCGCTGATTAAATGTTTTGAAATACCCGACTTACTAGACCCATCGATAAT

ATACTCTGACAAAAGTCATTCAATGAATAGGTCAGAGGTGTTGAAACATGTCCGAATGAATCC

GAACACTCCTATCCCTAGTAAAAAGGTGTTGCAGACTATGTTGGACACAAAGGCTACCAATTG

GAAAGAATTTCTTAAAGAGATTGATGAGAAGGGCTTAGATGATGATGATCTAATTATTGGTCT

TAAAGGAAAGGAGAGGGAACTGAAGTTGGCAGGTAGATTTTTCTCCCTAATGTCTTGGAAATT

GCGAGAATACTTTGTAATTACCGAATATTTGATAAAGACTCATTTCGTCCCTATGTTTAAAGG

CCTGACAATGGCGGACGATCTAACTGCAGTCATTAAAAAGATGTTAGATTCCTCATCCGGCCA

AGGATTGAAGTCATATGAGGCAATTTGCATAGCCAATCACATTGATTACGAAAAATGGAATAA

CCACCAAAGGAAGTTATCAAACGGCCCAGTGTTCCGAGTTATGGGCCAGTTCTTAGGTTATCC

ATCCTTAATCGAGAGAACTCATGAATTTTTTGAGAAAAGTCTTATATACTACAATGGAAGACC

AGACTTGATGCGTGTTCACAACAACACACTGATCAATTCAACCTCCCAACGAGTTTGTTGGCA

AGGACAAGAGGGTGGACTGGAAGGTCTACGGCAAAAAGGATGGACTATCCTCAATCTACTGGT

TATTCAAAGAGAGGCTAAAATCAGAAACACTGCTGTCAAAGTCTTGGCACAAGGTGATAATCA

AGTTATTTGCACACAGTATAAAACGAAGAAATCGAGAAACGTTGTAGAATTACAGGGTGCTCT

CAATCAAATGGTTTCTAATAATGAGAAAATTATGACTGCAATCAAAATAGGGACAGGGAAGTT

AGGACTTTTGATAAATGACGATGAGACTATGCAATCTGCAGATTACTTGAATTATGGAAAAAT

ACCGATTTTCCGTGGAGTGATTAGAGGGTTAGAGACCAAGAGATGGTCACGAGTGACTTGTGT

CACCAATGACCAAATACCCACTTGTGCTAATATAATGAGCTCAGTTTCCACAAATGCTCTCAC

CGTAGCTCATTTTGCTGAGAACCCAATCAATGCCATGATACAGTACAATTATTTTGGGACATT

TGCTAGACTCTTGTTGATGATGCATGATCCTGCTCTTCGTCAATCATTGTATGAAGTTCAAGA

TAAGATACCGGGCTTGCACAGTTCTACTTTCAAATACGCCATGTTGTATTTGGACCCTTCCAT

TGGAGGAGTGTCGGGCATGTCTTTGTCCAGGTTTTTGATTAGAGCCTTCCCAGATCCCGTAAC
```

```
AGAAAGTCTCTCATTCTGGAGATTCATCCATGTACATGCTCGAAGTGAGCATCTGAAGGAGAT

GAGTGCAGTATTTGGAAACCCCGAGATAGCCAAGTTTCGAATAACTCACATAGACAAGCTAGT

AGAAGATCCAACCTCTCTGAACATCGCTATGGGAATGAGTCCAGCGAACTTGTTAAAGACTGA

GGTTAAAAAATGCTTAATCGAATCAAGACAAACCATCAGGAACCAGGTGATTAAGGATGCAAC

CATATATTTGTATCATGAAGAGGATCGGCTCAGAAGTTTCTTATGGTCAATAAATCCTCTGTT

CCCTAGATTTTTAAGTGAATTCAAATCAGGCACTTTTTTGGGAGTCGCAGACGGGCTCATCAG

TCTATTTCAAAATTCTCGTACTATTCGGAACTCCTTTAAGAAAAAGTATCATAGGGAATTGGA

TGATTTGATTGTGAGGAGTGAGGTATCCTCTTTGACACATTTAGGGAAACTTCATTTGAGAAG

GGGATCATGTAAAATGTGGACATGTTCAGCTACTCATGCTGACACATTAAGATACAAATCCTG

GGGCCGTACAGTTATTGGGACAACTGTACCCCATCCATTAGAAATGTTGGGTCCACAACATCG

AAAAGAGACTCCTTGTGCACCATGTAACACATCAGGGTTCAATTATGTTTCTGTGCATTGTCC

AGACGGGATCCATGACGTCTTTAGTTCACGGGGACCATTGCCTGCTTATCTAGGGTCTAAAAC

ATCTGAATCTACATCTATTTTGCAGCCTTGGGAAAGGGAAAGCAAAGTCCCACTGATTAAAAG

AGCTACACGTCTTAGAGATGCTATCTCTTGGTTTGTTGAACCCGACTCTAAACTAGCAATGAC

TATACTTTCTAACATCCACTCTTTAACAGGCGAAGAATGGACCAAAAGGCAGCATGGGTTCAA

AAGAACAGGGTCTGCCCTTCATAGGTTTTCGACATCTCGGATGAGCCATGGTGGGTTCGCATC

TCAGAGCACTGCAGCATTGACCAGGTTGATGGCAACTACAGACACCATGAGGGATCTGGGAGA

TCAGAATTTCGACTTTTTATTCCAAGCAACGTTGCTCTATGCTCAAATTACCACCACTGTTGC

AAGAGACGGATGGATCACCAGTTGTACAGATCATTATCATATTGCCTGTAAGTCCTGTTTGAG

ACCCATAGAAGAGATCACCCTGGACTCAAGTATGGACTACACGCCCCCAGATGTATCCCATGT

GCTGAAGACATGGAGGAATGGGGAAGGTTCGTGGGACAAGAGATAAAACAGATCTATCCTTT

AGAAGGGAATTGGAAGAATTTAGCACCTGCTGAGCAATCCTATCAAGTCGGCAGATGTATAGG

TTTTCTATATGGAGACTTGGCGTATAGAAAATCTACTCATGCCGAGGACAGTTCTCTATTTCC

TCTATCTATACAAGGTCGTATTAGAGGTCGAGGTTTCTTAAAAGGGTTGCTAGACGGATTAAT

GAGAGCAAGTTGCTGCCAAGTAATACACCGGAGAAGTCTGGCTCATTTGAAGAGGCCGGCCAA

CGCAGTGTACGGAGGTTTGATTTACTTGATTGATAAATTGAGTGTATCACCTCCATTCCTTTC

TCTTACTAGATCAGGACCTATTAGAGACGAATTAGAAACGATTCCCCACAAGATCCCAACCTC

CTATCCGACAAGCAACCGTGATATGGGGGTGATTGTCAGAAATTACTTCAAATACCAATGCCG

TCTAATTGAAAAGGGAAAATACAGATCACATTATTCACAATTATGGTTATTCTCAGATGTCTT

ATCCATAGACTTCATTGGACCATTCTCTATTTCCACCACCCTCTTGCAAATCCTATACAAGCC

ATTTTTATCTGGGAAAGATAAGAATGAGTTGAGAGAGCTGGCAAATCTTTCTTCATTGCTAAG

ATCAGGAGAGGGGTGGGAAGACATACATGTGAAATTCTTCACCAAGGACATATTATTGTGTCC

AGAGGAAATCAGACATGCTTGCAAGTTCGGGATTGCTAAGGATAATAATAAAGACATGAGCTA

TCCCCCTTGGGGAAGGGAATCCAGAGGGACAATTACAACAATCCCTGTTTATTATACGACCAC

CCCTTACCCAAAGATGCTAGAGATGCCTCCAAGAATCCAAAATCCCCTGCTGTCCGGAATCAG

GTTGGGCCAATTACCAACTGGCGCTCATTATAAAATTCGGAGTATATTACATGGAATGGGAAT

CCATTACAGGGACTTCTTGAGTTGTGGAGACGGCTCCGGAGGGATGACTGCTGCATTACTACG

AGAAAATGTGCATAGCAGAGGAATATTCAATAGTCTGTTAGAATTATCAGGGTCAGTCATGCG

AGGCGCCTCTCCTGAGCCCCCCAGTGCCCTAGAAACTTTAGGAGGAGATAAATCGAGATGTGT

AAATGGTGAAACATGTTGGGAATATCCATCTGACTTATGTGACCCAAGGACTTGGGACTATTT

CCTCCGACTCAAAGCAGGCTTGGGGCTTCAAATTGATTTAATTGTAATGGATATGGAAGTTCG
```

-continued

```
GGATTCTTCTACTAGCCTGAAAATTGAGACGAATGTTAGAAATTATGTGCACCGGATTTTGGA

TGAGCAAGGAGTTTTAATCTACAAGACTTATGGAACATATATTTGTGAGAGCGAAAAGAATGC

AGTAACAATCCTTGGTCCCATGTTCAAGACGGTCGACTTAGTTCAAACAGAATTTAGTAGTTC

TCAAACGTCTGAAGTATATATGGTATGTAAAGGTTTGAAGAAATTAATCGATGAACCCAATCC

CGATTGGTCTTCCATCAATGAATCCTGGAAAAACCTGTACGCATTCCAGTCATCAGAACAGGA

ATTTGCCAGAGCAAAGAAGGTTAGTACATACTTTACCTTGACAGGTATTCCCTCCCAATTCAT

TCCTGATCCTTTTGTAAACATTGAGACTATGCTACAAATATTCGGAGTACCCACGGGTGTGTC

TCATGCGGCTGCCTTAAAATCATCTGATAGACCTGCAGATTTATTGACCATTAGCCTTTTTTA

TATGGCGATTATATCGTATTATAACATCAATCATATCAGAGTAGGACCGATACCTCCGAACCC

CCCATCAGATGGAATTGCACAAAATGTGGGGATCGCTATAACTGGTATAAGCTTTTGGCTGAG

TTTGATGGAGAAAGACATTCCACTATATCAACAGTGTTTAGCAGTTATCCAGCAATCATTCCC

GATTAGGTGGGAGGCTGTTTCAGTAAAAGGAGGATACAAGCAGAAGTGGAGTACTAGAGGTGA

TGGGCTCCCAAAAGATACCCGAACTTCAGACTCCTTGGCCCCAATCGGGAACTGGATCAGATC

TCTGGAATTGGTCCGAAACCAAGTTCGTCTAAATCCATTCAATGAGATCTTGTTCAATCAGCT

ATGTCGTACAGTGGATAATCATTTGAAATGGTCAAATTTGCGAAGAAACACAGGAATGATTGA

ATGGATCAATAGACGAATTTCAAAAGAAGACCGGTCTATACTGATGTTGAAGAGTGACCTACA

CGAGGAAAACTCTTGGAGAGATTAAAAAATCATGAGGAGACTCCAAACTTTAAGTATGAAAAA

AACTTTGATCCTTAAGACCCTCTTGTGGTTTTTATTTTTATCTGGTTTTGTGGTCTTCGTGG

GTCGGCATGGCATCTCCACCTCCTCGCGGTCCGACCTGGGCATCCGAAGGAGGACGTCGTCCA

CTCGGATGGCTAAGGGAGAGCTCGGATCCGGCTGCTAACAAAGCCCGAAAGGAAGCTGAGTTG

GCTGCTGCCACCGCTGAGCAATAACTAGCATAACCCCTTGGGGCCTCTAAACGGGTCTTGAGG

GGTTTTTTGCTGAAAGGAGGAACTATATCCGGATCGAGATCCTCTAGAGTCGACCTGCAGGCA

TGCAAGCTTGTATTCTATAGTGTCACCTAAATCGTATGTGTATGATACATAAGGTTATGTATT

AATTGTAGCCGCGTTCTAACGACAATATGTACAAGCCTAATTGTGTAGCATCTGGCTTACTGA

AGCAGACCCTATCATCTCTCTCGTAAACTGCCGTCAGAGTCGGTTTGGTTGGACGAACCTTCT

GAGTTTCTGGTAACGCCGTcCCGCACCCGGAAATGGTCAGCGAACCAATCAGCAGGGTCATCG

CTAGCCAGATCCTCTACGCCGGACGCATCGTGGCCGGCATCACCGGCGCCACAGGTGCGGTTG

CTGGCGCCTATATCGCCGACATCACCGATGGGGAAGATCGGGCTCGCCACTTCGGGCTCATGA

GCGCTTGTTTCGGCGTGGGTATGGTGGCAGGCCCCGTGGCCGGGGGACTGTTGGGCGCCATCT

CCTTGCACCATTCCTTGCGGCGGCGGTGCTCAACGGCCTCAACCTACTACTGGGCTGCTTCCT

AATGCAGGAGTCGCATAAGGGAGAGCGTCGAATGGTGCACTCTCAGTACAATCTGCTCTGATG

CCGCATAGTTAAGCCAGCCCCGACACCCGCCAACACCCGCTGACGCGCCCTGACGGGCTTGTC

TGCTCCCGGCATCCGCTTACAGACAAGCTGTGACCGTCTCCGGGAGCTGCATGTGTCAGAGGT

TTTCACCGTCATCACCGAAACGCGCGAGACGAAAGGGCCTCGTGATACGCCTATTTTTATAGG

TTAATGTCATGATAATAATGGTTTCTTAGACGTCAGGTGGCACTTTTCGGGGAAATGTGCGCG

GAACCCCTATTTGTTTATTTTTCTAAATACATTCAAATATGTATCCGCTCATGAGACAATAAC

CCTGATAAATGCTTCAATAATATTGAAAAAGGAAGAGTATGAGTATTCAACATTTCCGTGTCG

CCCTTATTCCCTTTTTTGCGGCATTTTGCCTTCCTGTTTTTGCTCACCCAGAAACGCTGGTGA

AAGTAAAAGATGCTGAAGATCAGTTGGGTGCACGAGTGGGTTACATCGAACTGGATCTCAACA

GCGGTAAGATCCTTGAGAGTTTTCGCCCCGAAGAACGTTTTCCAATGATGAGCACTTTTAAAG
```

```
                        -continued
TTCTGCTATGTGGCGCGGTATTATCCCGTATTGACGCCGGGCAAGAGCAACTCGGTCGCCGCA

TACACTATTCTCAGAATGACTTGGTTGAGTACTCACCAGTCACAGAAAAGCATCTTACGGATG

GCATGACAGTAAGAGAATTATGCAGTGCTGCCATAACCATGAGTGATAACACTGCGGCCAACT

TACTTCTGACAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACGACGAGCGTG

ACACCACGATGCCTGTAGCAATGGCAACAACGTTGCGCAAACTATTAACTGGCGAACTACTTA

CTCTAGCTTCCCGGCAACAATTAATAGACTGGATGGAGGCGGATAAAGTTGCAGGACCACTTC

TGCGCTCGGCCCTTCCGGCTGGCTGGTTTATTGCTGATAAATCTGGAGCCGGTGAGCGTGGGT

CTCGCGGTATCATTGCAGCACTGGGGCCAGATGGTAAGCCCTCCCGTATCGTAGTTATCTACA

CGACGGGGAGTCAGGCAACTATGGATGAACGAAATAGACAGATCGCTGAGATAGGTGCCTCAC

TGATTAAGCATTGGTAACTGTCAGACCAAGTTTACTCATATATACTTTAGATTGATTTAAAAC

TTCATTTTTAATTTAAAAGGATCTAGGTGAAGATCCTTTTTGATAATCTCATGACCAAAATCC

CTTAACGTGAGTTTTCGTTCCACTGAGCGTCAGACCCCGTAGAAAAGATCAAAGGATCTTCTT

GAGATCCTTTTTTTCTGCGCGTAATCTGCTGCTTGCAAACAAAAAAACCACCGCTACCAGCGG

TGGTTTGTTTGCCGGATCAAGAGCTACCAACTCTTTTTCCGAAGGTAACTGGCTTCAGCAGAG

CGCAGATACCAAATACTGTCCTTCTAGTGTAGCCGTAGTTAGGCCACCACTTCAAGAACTCTG

TAGCACCGCCTACATACCTCGCTCTGCTAATCCTGTTACCAGTGGCTGCTGCCAGTGGCGATA

AGTCGTGTCTTACCGGGTTGGACTCAAGACGATAGTTACCGGATAAGGCGCAGCGGTCGGGCT

GAACGGGGGGTTCGTGCACACAGCCCAGCTTGGAGCGAACGACCTACACCGAACTGAGATACC

TACAGCGTGAGCTATGAGAAAGCGCCACGCTTCCCGAAGGGAGAAAGGCGGACAGGTATCCGG

TAAGCGGCAGGGTCGGAACAGGAGAGCGCACGAGGGAGCTTCCAGGGGGAAACGCCTGGTATC

TTTATAGTCCTGTCGGGTTTCGCCACCTCTGACTTGAGCGTCGATTTTTGTGATGCTCGTCAG

GGGGGCGGAGCCTATGGAAAAACGCCAGCAACGCGGCCTTTTTACGGTTCCTGGCCTTTTGCT

GGCCTTTTGCTCACATGTTCTTTCCTGCGTTATCCCCTGATTCTGTGGATAACCGTATTACCG

CCTTTGAGTGAGCTGATACCGCTCGCCGCAGCCGAACGACCGAGCGCAGCGAGTCAGTGAGCG

AGGAAGCGGAAGAGCGCCCAATACGCAAACCGCCTCTCCCCGCGCGTTGGCCGATTCATTAAT

GCAGGGGATCTCGATCCCGCGAAATTAATACGACTCACTATAGG
```

In some embodiments, the nucleic acid sequence encoding a Zika virus prM protein is adjacent in the VSV genome to the nucleic acid sequence encoding a Zika virus E protein. In some embodiments, the nucleic acid sequence encoding a Zika virus prM protein is adjacent in the VSV genome to the nucleic acid sequence encoding a Zika virus C protein. Exemplary sequences include rVSV-Zika-prME (SEQ ID NO:7) and rVSV-Zika-CprME (SEQ ID NO:8)

```
SEQ ID NO: 7   ACGAAGACAAACAAACCATTATTATCATTAAAAGGCTCAGGAGAAACTTTAACAGTAATCAGA
               ATTCTCGAGAAAGCCACCATGAGAAGAGGCAGCGCCTACTACATGTACCTGGACCGGAACGAT
               GCCGGCGAGGCCATCAGCTTTCCAACCACCCTGGGCATGAACAAGTGCTACATCCAGATCATG
               GACCTGGGCCACACCTGTGACGCCACCATGAGCTACGAGTGCCCCATGCTGGACGAGGGCGTG
               GAACCCGACGATGTGGACTGCTGGTGCAACACCACCAGCACCTGGGTGGTGTACGGCACCTGT
               CACCACAAGAAGGGCGAAGCCAGACGGTCCAGACGGGCCGTGACACTGCCTAGCCACAGCACC
               AGAAAGCTGCAGACCCGGTCCCAGACCTGGCTGGAAAGCAGAGAGTACACCAAGCACCTGATC
               CGGGTGGAAAACTGGATCTTCCGGAACCCCGGCTTTGCCCTGGCCGCTGCTGCTATTGCTTGG
               CTGCTGGGCAGCAGCACCTCCCAGAAAGTGATCTACCTCGTGATGATCCTGCTGATCGCCCCT
               GCCTACAGCATCCGGTGTATCGGCGTGTCCAACCGGGACTTCGTGGAAGGCATGAGCGGCGGC
               ACATGGGTGGACGTGGTGCTGGAACATGGCGGCTGCGTGACAGTGATGGCTCAGGACAAGCCC
               ACCGTGGACATCGAGCTCGTGACCACCACCGTGTCCAATATGGCCGAAGTGCGGAGCTACTGC
               TACGAGGCCAGCATCAGCGACATGGCCAGCGACAGCAGATGCCCTACACAGGGCGAGGCCTAC
               CTGGACAAGCAGTCCGACACCCAGTACGTGTGCAAGCGGACCCTGGTGGATAGAGGCTGGGGC
               AATGGCTGCGGCCTGTTTGGCAAGGGCAGCCTCGTGACCTGCGCCAAGTTCGCCTGCAGCAAG
               AAGATGACCGGCAAGAGCATCCAGCCCGAGAACCTGGAATACCGGATCATGCTGAGCGTGCAC
               GGCAGCCAGCACTCCGGCATGATCGTGAACGACACCGGCCACGAGACAGACGAGAACCGGGCC
               AAGGTGGAAATCACCCCCAACAGCCCTAGAGCCGAGGCCACACTGGGCGGCTTTGGATCTCTG
               GGCCTGGACTGCGAGCCTAGAACCGGCCTGGATTTCAGCGACCTGTACTACCTGACCATGAAC
```

```
AACAAGCACTGGCTGGTGCACAAAGAGTGGTTCCACGACATCCCCCTGCCCTGGCATGCCGGC
GCTGATACAGGCACACCCCACTGGAACAACAAAGAGGCTCTGGTGGAATTCAAGGACGCCCAC
GCCAAGCGGCAGACCGTGGTGGTGCTGGGATCTCAGGAAGGCGCCGTGCATACAGCTCTGGCT
GGCGCCCTGGAAGCCGAAATGGATGGCGCCAAAGGCAGACTGTCCAGCGGCCACCTGAAGTGC
CGGCTGAAGATGGACAAGCTGCGGCTGAAGGGCGTGTCCTACAGCCTGTGTACCGCCGCCTTC
ACCTTCACCAAGATCCCCGCCGAGACACTGCACGGCACCGTGACTGTGGAAGTGCAGTACGCC
GGCACCGACGGCCCTTGTAAAGTGCCTGCTCAGATGGCCGTGGATATGCAGACCCTGACCCCC
GTGGGCAGACTGATCACCGCCAACCCTGTGATCACCGAGAGCACCGAGAACAGCAAGATGATG
CTGGAACTGGACCCCCCCTTCGGCGACTCCTACATCGTGATCGGCGTGGGAGAGAAGAAGATC
ACCCACCACTGGCACAGAAGCGGCAGCACCATCGGCAAGGCCTTTGAGGCTACAGTGCGGGGA
GCCAAGAGAATGGCCGTGCTGGGAGATACCGCCTGGGACTTTGGCTCTGTGGGCGGAGCCCTG
AACTCTCTGGGCAAGGGAATCCACCAGATCTTCGGAGCCGCCTTTAAGAGCCTGTTCGGCGGC
ATGAGCTGGTTCAGCCAGATCCTGATCGGCACCCTGCTGATGTGGCTGGGCCTGAACGCCAAG
AACGGCAGCATCTCCCTGATGTGCCTGGCTCTGGGAGGCGTGCTGATCTTCCTGAGCACAGCC
GTGTCTGCCTAAATGGCCATATGAAAAAAACTAACAGTAATCAAAATGTCTGTTACAGTCAAG
AGAATCATTGACAACACAGTCATAGTTCCAAAACTTCCTGCAAATGAGGATCCAGTGGAATAC
CCGGCAGATTACTTCAGAAAATCAAAGGAGATTCCTCTTTACATCAATACTACAAAAAGTTTG
TCAGATCTAAGAGGATATGTCTACCAAGGCCTCAAATCCGGAAATGTATCAATCATACATGTC
AACAGCTACTTGTATGGAGCATTAAAGGACATCCGGGGTAAGTTGGATAAAGATTGGTCAAGT
TTCGGAATAAACATCGGGAAAGCAGGGGATACAATCGGAATATTTGACCTTGTATCCTTGAAA
GCCCTGGACGGCGTACTTCCAGATGGAGTATCGGATGCTTCCAGAACCAGCGCAGATGACAAA
TGGTTGCCTTTGTATCTACTTGGCTTATACAGAGTGGGCAGAACACAAATGCCTGAATACAGA
AAAAAGCTCATGGATGGGCTGACAAATCAATGCAAAATGATCAATGAACAGTTTGAACCTCTT
GTGCCAGAAGGTCGTGACATTTTTGATGTGTGGGGAAATGACAGTAATTACACAAAAATTGTC
GCTGCAGTGGACATGTTCTTCCACATGTTCAAAAAACATGAATGTGCCTCGTTCAGATACGGA
ACTATTGTTTCCAGATTCAAAGATTGTGCTGCATTGGCAACATTTGGACACCTCTGCAAAATA
ACCGGAATGTCTACAGAAGATGTAACGACCTGGATCTTGAACCGAGAAGTTGCAGATGAAATG
GTCCAATGATGCTTCCAGGCCAAGAAATTGACAAGGCCGATTCATACATGCCTTATTTGATC
GACTTTGGATTGTCTTCTAAGTCTCCATATTCTTCCGTCAAAAACCCTGCCTTCCACTTCTGG
GGGCAATTGACAGCTCTTCTGCTCAGATCCACCAGAGCAAGGAATGCCCGACAGCCTGATGAC
ATTGAGTATACATCTCTTACTACAGCAGGTTTGTTGTACGCTTATGCAGTAGGATCCTCTGCC
GACTTGGCACAACAGTTTTGTGTTGGAGATAACAAATACACTCCAGATGATAGTACCGGAGGA
TTGACGACTAATGCACCGCCACAAGGCAGAGATGTGGTCGAATGGCTCGGATGGTTTGAAGAT
CAAAACAGAAAACCGACTCCTGATATGATGCAGTATGCGAAAAGAGCAGTCATGTCACTGCAA
GGCCTAAGAGAAGACAATTGGCAAGTATGCTAAGTCAGAATTTGACAAATGACCCTATAAT
TCTCAGATCACCTATTATATATTATGCTACATATGAAAAAAACTAACAGATATCATGGATAAT
CTCACAAAAGTTCGTGAGTATCTCAAGTCCTATTCTCGTCTGGATCAGGCGGTAGGAGAGATA
GATGAGATCGAAGCACAACGAGCTGAAAAGTCCAATTATGAGTTGTTCCAAGAGGATGGAGTG
GAAGAGCATACTAAGCCCTCTTATTTTCAGGCAGCAGATGATTCTGACACAGAATCTGAACCA
GAAATTGAAGACAATCAAGGTTTGTATGCACAGGATCCAGAAGCTGAGCAAGTTGAAGGCTTT
ATACAGGGGCCTTTAGATGACTATGCAGATGAGGAAGTGGATGTTGTATTTACTTCGGACTGG
AAACCACCTGAGCTTGAATCTGACGAGCATGGAAAGACCTTACGGTTGACATCGCCAGAGGGT
TTAAGTGGAGAGCAGAAATCCCAGTGGCTTTCGACGATTAAAGCAGTCGTGCAAAGTGCCAAA
TACTGGAATCTGGCAGAGTGCACATTTGAAGCATCGGGAGAAGGGGTCATTATGAAGGAGCGC
CAGATAACTCCGGATGTATATAAGGTCACTCCAGTGATGAACACACATCCGTCCCAATCAGAA
GCAGTATCAGATGTTTGGTCTCTCTCAAAGACATCCATGACTTTCCAACCCAAGAAAGCAAGT
CTTCAGCCTCTCACCATATCCTTGGATGAATTGTTCTCATCTAGAGGGAGAGTTCATCTCTGTC
GGAGGTGACGGACGAATGTCTCATAAAGAGGCCATCCTGCTCGGCCTGAGATACAAAAAGTTG
TACAATCAGGCGAGAGTCAAATATTCTCTGTAGACTATGAAAAAAAGTAACAGATATCACGAT
CTAAGTGTTATCCCAATCCATTCATCATGAGTTCCTTAAAGAAGATTCTCGGTCTGAAGGGGA
AAGGTAAGAAATCTAAGAAATTAGGGATCGCACCACCCCCTTATGAAGAGGACACTAGCATGG
AGTATGCTCCGAGCGCTCCAATTGACAAATCCTATTTTGGAGTTGACGAGATGGACACCTATG
ATCCGAATCAATTAAGATATGAGAAATTCTTCTTTACAGTGAAATGACGGTTAGATCTAATC
GTCCGTTCAGAACATACTCAGATGTGGCAGCCGCTGTATCCCATTGGGATCACATGTACATCG
GAATGGCAGGGAAACGTCCCTTCTACAAAATCTTGGCTTTTTTGGGTTCTTCTAATCTAAAGG
CCACTCCAGCGGTATTGGCAGATCAAGGTCAACCAGAGTATCACACTCACTGCGAAGGCAGGG
CTTATTTGCCACATAGGATGGGGAAGACCCCTCCCATGCTCAATGTACCAGAGCACTTCAGAA
GACCATTCAATATAGGTCTTTACAAGGGAACGATTGAGCTCACAATGACCATCTACGATGATG
AGTCACTGGAAGCAGCTCCTATGATCTGGGATCATTTCAATTCTTCCAAATTTTCTGATTTCA
GAGAGAAGGCCTTAATGTTTGGCCTGATTGTCGAGAAAAAGGCATCTGGAGCGTGGGTCCTGG
ATTCTATCAGCCACTTCAAATGAGCTAGTCTAACTTCAGCTTCTGAACAATCCCCGGTTTAC
TCAGTCTCTCCTAATTCCAGCCTCTCGAACAACTAATATCCTGTCTTTTCTATCCCTATGAAA
AAAACTAACAGAGATCGATCTGTTTCCTTGACACGCGTACCATGAAGTGCCTTTTGTACTTAG
CTTTTTTATTCATCGGGGTGAATTGCAAGTTCACCATAGTTTTTCCACACAACCGAAAAGGAA
ACTGGAAAAATGTTCCTTCCAATTACCATTATTGCCCGTCAAGCTCAGATTTAAATTGGCATA
ATGACTTAATAGGCACAGCCTTACAAGTCAAAATGCCCAAGAGTCACAAGGCTATTCAAGCAG
ACGGTTGGATGTGTCATGCTTCCAAATGGGTCACTACTTGTGATTTCCGCTGGTACGGACCGG
AGTATATAACACATTCCATCCGATCCTTCACTCCATCTGTAGAACAATGCAAGGAAAGCATTG
AACAAACGAAACAAGGAACTTGGCTGAATCCAGGCTTCCCTCCTCAAAGTTGTGGATATGCAA
CTGTGACGGATGCTGAAGCAGCGATTGTCCAGGTGACTCCTCACCATGTGCTTGTTGATGAAT
ACACAGGAGAATGGGTTGATTCACAGTTCATCAACGGAAAATGCAGCAATGACATATGCCCCA
CTGTCCATAACTCCACAACCTGGCATTCCGACTATAAGGTCAAAGGGCTATGTGATTCTAACC
TCATTTCCATGGACATCACCTTCTTCTCAGAGGACGGAGAGCTATCATCCCTAGGAAAGGAGG
GCACAGGGTTCAGAAGTAACTACTTTGCTTATGAAACTGGAGACAAGGCCTGCAAAATGCAGT
ACTGCAAGCATTGGGGAGTCAGACTCCCATCAGGTGTCTGGTTCGAGATGGCTGATAAGGATC
TCTTTGCTGCAGCCAGATTCCCTGAATGCCCAGAAGGGTCAAGTATCTCTGCTCCATCTCAGA
CCTCAGTGGATGTAAGTCTCATTCAGGACGTTGAGAGGATCTTGGATTATTCCCTCTGCCAAG
AAACCTGGAGCAAAATCAGAGCGGGTCTTCCCATCTCTCCAGTGGATCTCAGCTATCTTGCTC
CTAAAAACCCAGGAACCGGTCCTGTCTTTACCATAATCAATGGTACCCTAAAATACTTTGAGA
```

```
CCAGATACATCAGAGTCGATATTGCTGCTCCAATCCTCTCAAGAATGGTCGGAATGATCAGTG
GAACTACCACAGAAAGGGAACTGTGGGATGACTGGGCTCCATATGAAGACGTGGAAATTGGAC
CCAATGGAGTTCTGAGGACCAGTTCAGGATATAAGTTTCCTTTATATATGATTGGACATGGTA
TGTTGGACTCCGATCTTCATCTTAGCTCAAAGGCTCAGGTGTTTGAACATCCTCACATTCAAG
ACGCTGCTTCGCAGCTTCCTGATGATGAGACTTTATTTTTTGGTGATACTGGGCTATCCAAAA
ATCCAATCGAGTTTGTAGAAGGTTGGTTCAGTAGTTGGAAGAGCTCTATTGCCTCTTTTTGCT
TTATCATAGGGTTAATCATTGGACTATTCTTGGTTCTCCGAGTTGGTATTTATCTTTGCATTA
AATTAAAGCACACCAAGAAAAGACAGATTTATACAGACATAGAGATGAACCGACTTGGAAAGA
AGCGGCCGCCCTGCACAACAGATTCTTCATGTTTGGACCAAATCAACTTGTGATACCATGCTC
AAAGAGGCCTCAATTATATTTGAGTTTTTAATTTTTATGAAAAAAACTAACAGCAATCATGGA
AGTCCACGATTTTGAGACCGACGAGTTCAATGATTTCAATGAAGATGACTATGCCACAAGAGA
ATTCCTGAATCCCGATGAGCGCATGACGTACTTGAATCATGCTGATTACAATTTGAATTCTCC
TCTAATTAGTGATGATATTGACAATTTGATCAGGAAATTCAATTCTCTTCCGATTCCCTCGAT
GTGGGATAGTAAGAACTGGGATGGAGTTCTTGAGATGTTAACATCATGTCAAGCCAATCCCAT
CTCAACATCTCAGATGCATAAATGGATGGGAAGTTGGTTAATGTCTGATAATCATGATGCCAG
TCAAGGGTATAGTTTTTTACATGAAGTGGACAAAGAGGCAGAAATAACATTTGACGTGGTGGA
GACCTTCATCCGCGGCTGGGGCAACAAACCAATTGAATACATCAAAAAGGAAAGATGGACTGA
CTCATTCAAAATTCTCGCTTATTTGTGTCAAAAGTTTTTGGACTTACACAAGTTGACATTAAT
CTTAAATGCTGTCTCTGAGGTGGAATTGCTCAACTTGGCGAGGACTTTCAAAGGCAAAGTCAG
AAGAAGTTCTCATGGAACGAACATATGCAGGATTAGGGTTCCCAGCTTGGGTCCTACTTTTAT
TTCAGAAGGATGGGCTTACTTCAAGAAACTTGATATTCTAATGGACCGAAACTTTCTGTTAAT
GGTCAAAGATGTGATTATAGGGAGGATGCAAACGGTGCTATCCATGGTATGTAGAATAGACAA
CCTGTTCTCAGAGCAAGACATCTTCTCCCTTCTAAATATCTACAGAATTGGAGATAAAATTGT
GGGAGAGGCAGGGAAATTTTTCTTATGACTTGATTAAAATGGTGGAACCGATATGCAACTTGAA
GCTGATGAAATTAGCAAGAGAATCAAGGCCTTTAGTCCCACAATTCCCTCATTTGAAAATCA
TATCAAGACTTCTGTTGATGAAGGGGCAAAAATTGACCGAGGTATAAGATTCCTCCATGATCA
GATAATGAGTGTGAAAACAGTGGATCTCACACTGGTGATTTATGGATCGTTCAGACATTGGGG
TCATCCTTTATAGATTATTACACTGGACTAGAAAAATTACATTCCCAAGTAACCATGAAGAA
AGATATTGATGTGTCATATGCAAAAGCACTTGCAAGTGATTTAGCTCGGATTGTTCTATTTCA
ACAGTTCAATGATCATAAAAAGTGGTTCGTGAATGGAGACTTGCTCCCTCATGATCATCCCTT
TAAAAGTCATGTTAAAGAAAATACATGGCCCACAGCTGCTCAAGTTCAAGATTTTGGAGATAA
ATGGCATGAACTTCCGCTGATTAAATGTTTTGAAATACCCGACTTACTAGACCCATCGATAAT
ATACTCTGACAAAAGTCATTCAATGAATAGGTCAGAGGTGTTGAAACATGTCCGAATGAATCC
GAACACTCCTATCCCTAGTAAAAAGGTGTTGCAGACTATGTTGGACACAAAGGCTACCAATTG
GAAAGAATTTCTTAAAGAGATTGATGAGAAGGGCTTAGATGATGATGATCTAATTATTGGTCT
TAAAGGAAAGGAGAGGGAACTGAAGTTGGCAGGTAGATTTTTCTCCCTAATGTCTTGGAAATT
GCGAGAATACTTTGTAATTACCGAATATTTGATAAAGACTCATTTCGTCCCTATGTTTAAAGG
CCTGACAATGGCGGACGATCTAACTGCAGTCATTAAAAAGATGTTAGATTCCTCATCCGGCCA
AGGATTGAAGTCATATGAGGCAATTTGCATAGCCAATCACATTGATTACGAAAAATGGAATAA
CCACCAAAGGAAGTTATCAAACGGCCCAGTGTTCCGAGTTATGGGCCAGTTCTTAGGTTATCC
ATCCTTAATCGAGAGAACTCATGAATTTTTTGAGAAAAGTCTTATATACTACAATGGAAGACC
AGACTTGATGCGTGTTCACAACAACACACTGATCAATTCAACCTCCCAACGAGTTTGTTGGCA
AGGACAAGAGGGTGGACTGGAAGGTCTACGGCAAAAAGGATGGACTATCCTCAATCTACTGGT
TATTCAAAGAGAGGCTAAAATCAGAAACACTGCTGTCAAAGTCTTGGCACAAGGTGATAATCA
AGTTATTTGCACACAGTATAAAACGAAGAAATCGAGAAACGTTGTAGAATTACAGGGTGCTCT
CAATCAAATGGTTTCTAATAATGAGAAAATTATGACTGCAATCAAAATAGGGACAGGGAAGTT
AGGACTTTTGATAAATGACGATGAGACTATGCAATCTGCAGATTACTTGAATTATGGAAAAAT
ACCGATTTTCCGTGGAGTGATTAGAGGGTTAGAGACCAAGAGATGGTCACGAGTGACTTGTGT
CACCAATGACCAAATACCCACTTGTGCTAATATAATGAGCTCAGTTTCCACAAATGCTCTCAC
CGTAGCTCATTTTGCTGAGAACCCAATCAATGCCATGATACAGTACAATTATTTTGGGACATT
TGCTAGACTCTTGTTGATGATGCATGATCCTGCTCTTCGTCAATCATTGTATGAAGTTCAAGA
TAAGATACCGGGCTTGCACAGTTCTACTTTCAAATACGCCATGTTGTATTTGGACCCTTCCAT
TGGAGGAGTGTCGGGCATGTCTTTGTCCAGGTTTTTGATTAGAGCCTTCCCAGATCCCGTAAC
AGAAAGTCTCTCATTCTGGAGATTCATCCATGTACATGCTCGAAGTGAGCATCTGAAGGAGAT
GAGTGCAGTATTTGGAAACCCCGAGATAGCCAAGTTTCGAATAACTCACATAGACAAGCTAGT
AGAAGATCCAACCTCTCTGAACATCGCTATGGGAATGAGTCCAGCGAACTTGTTAAAGACTGA
GGTTAAAAAATGCTTAATCGAATCAAGACAAACCATCAGGAACCAGGTGATTAAGGATGCAAC
CATATATTTGTATCATGAAGAGGATCGGCTCAGAAGTTTCTTATGGTCAATAAATCCTCTGTT
CCCTAGATTTTTAAGTGAATTCAAATCAGGCACTTTTTTGGGAGTCGCAGACGGGCTCATCAG
TCTATTTCAAAATTCTCGTACTATTCGGAACTCCTTTAAGAAAAAGTATCATAGGGAATTGGA
TGATTTGATTGTGAGGAGTGAGGTATCCTCTTTGACACATTTAGGGAAACTTCATTTGAGAAG
GGGATCATGTAAAATGTGGACATGTTCAGCTACTCATGCTGACACATTAAGATACAAATCCTG
GGGCCGTACAGTTATTGGGACAACTGTACCCCATCCATTAGAAATGTTGGGTCCACAACATCG
AAAAGAGACTCCTTGTGCACCATGTAACACATCAGGGTTCAATTATGTTTCTGTGCATTGTCC
AGACGGGATCCATGACGTCTTTAGTTCACGGGACCATTGCCTGCTTATCTAGGGTCTAAAAC
ATCTGAATCTACATCTATTTTGCAGCCTTGGGAAAGGGAAAGCAAAGTCCCACTGATTAAAAG
AGCTACACGTCTTAGAGATGCTATCTCTTGGTTTGTTGAACCCGACTCTAAACTAGCAATGAC
TATACTTTCTAACATCCACTCTTTAACAGGCGAAGAATGACCAAAAGGCAGCATGGGTTCAA
AAGAACAGGGTCTGCCCTTCATAGGTTTTCGACATCTCGGATGAGCCATGGTGGGTTCGCATC
TCAGAGCACTGCAGCATTGACCAGGTTGATGGCAACTACAGACACCATGAGGGATCTGGGAGA
TCAGAATTTCGACTTTTTATTCCAAGCAACGTTGCTCTATGCTCAAATTACCACCACTGTTGC
AAGAGACGGATGGATCACCAGTTGTACAGATCATTATCATATTGCCTGTAAGTCCTGTTTGAG
ACCCATAGAAGAGATCACCCTGGACTCAAGTATGGACTACCCCCCAGATGTATCCCATGT
GCTGAAGACATGGAGGAATGGGGAAGGTTCGTGGGGACAAGAGATAAAACAGATCTATCCTTT
AGAAGGGAATTGGAAGAATTTAGCACCTGCTGAGCAATCCTATCAAGTCGGCAGATGTATAGG
TTTTCTATATGGAGACTTGGCGTATAGAAAATCTACTCATGCCGAGGACAGTTCTCTATTTCC
TCTATCTATACAAGGTCGTATTAGAGGTCGAGGTTTCTTAAAAGGGTTGCTAGACGGATTAAT
GAGAGCAAGTTGCTGCCAAGTAATACACCGGAGAAGTCTGGCTCATTTGAAGAGGCCGGCCAA
CGCAGTGTACGGAGGTTTGATTTACTTGATTGATAAATTGAGTGTATCACCTCCATTCCTTTC
```

```
TCTTACTAGATCAGGACCTATTAGAGACGAATTAGAAACGATTCCCCACAAGATCCCAACCTC
CTATCCGACAAGCAACCGTGATATGGGGGTGATTGTCAGAAATTACTTCAAATACCAATGCCG
TCTAATTGAAAAGGGAAAATACAGATCACATTATTCACAATTATGGTTATTCTCAGATGTCTT
ATCCATAGACTTCATTGGACCATTCTCTATTTCCACCACCCTCTTGCAAATCCTATACAAGCC
ATTTTTATCTGGGAAAGATAAGAATGAGTTGAGAGAGCTGGCAAATCTTTCTTCATTGCTAAG
ATCAGGAGAGGGGTGGGAAGACATACATGTGAAATTCTTCACCAAGGACATATTATTGTGTCC
AGAGGAAATCAGACATGCTTGCAAGTTCGGGATTGCTAAGGATAATAATAAAGACATGAGCTA
TCCCCCTTGGGGAAGGGAATCCAGAGGGACAATTACAACAATCCCTGTTTATTATACGACCAC
CCCTTACCCAAAGATGCTAGAGATGCCTCCAAGAATCCAAAATCCCCTGCTGTCCGGAATCAG
GTTGGGCCAATTACCAACTGGCGCTCATTATAAAATTCGGAGTATATTACATGGAATGGGAAT
CCATTACAGGGACTTCTTGAGTTGTGGAGACGGCTCCGGAGGGATGACTGCTGCATTACTACG
AGAAAATGTGCATAGCAGAGGAATATTCAATAGTCTGTTAGAATTATCAGGGTCAGTCATGCG
AGGCGCCTCTCCTGAGCCCCCAGTGCCCTAGAAACTTTAGGAGGAGATAAATCGAGATGTGT
AAATGGTGAAACATGTTGGGAATATCCATCTGACTTATGTGACCCAAGGACTTGGGACTATTT
CCTCCGACTCAAAGCAGGCTTGGGGCTTCAAATTGATTTAATTGTAATGGATATGGAAGTTCG
GGATTCTTCTACTAGCCTGAAAATTGAGACGAATGTTAGAAATTATGTGCACCGGATTTTGGA
TGAGCAAGGAGTTTTAATCTACAAGACTTATGGAACATATATTTGTGAGAGCGAAAAGAATGC
AGTAACAATCCTTGGTCCCATGTTCAAGACGGTCGACTTAGTTCAAACAGAATTTAGTAGTTC
TCAAACGTCTGAAGTATATATGGTATGTAAAGGTTTGAAGAAATTAATCGATGAACCCAATCC
CGATTGGTCTTCCATCAATGAATCCTGGAAAAACCTGTACGCATTCCAGTCATCAGAACAGGA
ATTTGCCAGAGCAAAGAAGGTTAGTACATACTTTACCTTGACAGGTATTCCCTCCCAATTCAT
TCCTGATCCTTTTGTAAACATTGAGACTATGCTACAAATATTCGGAGTACCCACGGGTGTGTC
TCATGCGGCTGCCTTAAAATCATCTGATAGACCTGCAGATTTATTGACCATTAGCCTTTTTTA
TATGGCGATTATATCGTATTATAACATCAATCATATCAGAGTAGGACCGATACCTCCGAACCC
CCCATCAGATGGAATTGCACAAAATGTGGGGATCGCTATAACTGGTATAAGCTTTTGGCTGAG
TTTGATGGAGAAAGACATTCCACTATATCAACAGTGTTTAGCAGTTATCCAGCAATCATTCCC
GATTAGGTGGGAGGCTGTTTCAGTAAAAGGAGGATACAAGCAGAAGTGGAGTACTAGAGGTGA
TGGGCTCCCAAAAGATACCCGAACTTCAGACTCCTTGGCCCCAATCGGGAACTGGATCAGATC
TCTGGAATTGGTCCGAAACCAAGTTCGTCTAAATCCATTCAATGAGATCTTGTTCAATCAGCT
ATGTCGTACAGTGGATAATCATTTGAAATGGTCAAATTTGCGAAGAAACACAGGAATGATTGA
ATGGATCAATAGACGAATTTCAAAAGAAGACCGGTCTATACTGATGTTGAAGAGTGACCTACA
CGAGGAAAACTCTTGGAGAGATTAAAAAATCATGAGGAGACTCCAAACTTTAAGTATGAAAAA
AACTTTGATCCTTAAGACCCTCTTGTGGTTTTTATTTTTTATCTGGTTTTGTGGTCTTCGTGG
GTCGGCATGGCATCTCCACCTCCTCGCGGTCCGACCTGGGCATCCGAAGGAGGACGTCGTCCA
CTCGGATGGCTAAGGGAGAGCTCGGATCCGGCTGCTAACAAAGCCCGAAAGGAAGCTGAGTTG
GCTGCTGCCACCGCTGAGCAATAACTAGCATAACCCCTTGGGGCCTCTAAACGGGTCTTGAGG
GGTTTTTTGCTGAAAGGAGGAACTATATCCGGATCGAGATCCTCTAGAGTCGACCTGCAGGCA
TGCAAGCTTGTATTCTATAGTGTCACCTAAATCGTATGTGTATGATACATAAGGTTATGTATT
AATTGTAGCCGCGTTCTAACGACAATATGTACAAGCCTAATTGTGTAGCATCTGGCTTACTGA
AGCAGACCCTATCATCTCTCGTAAACTGCCGTCAGAGTCGGTTTGGTTGGACGAACCTTCT
GAGTTTCTGGTAACGCCGTcCCGCCACCCGGAAATGGTCAGCGAACCAATCAGCAGGGTCATCG
CTAGCCAGATCCTCTACGCCGGACGCATCGTGGCCGGCATCACCGGCGCCACAGGTGCGGTTG
CTGGCGCCTATATCGCCGACATCACCGATGGGGAAGATCGGGCTCGCCACTTCGGGCTCATGA
GCGCTTGTTTCGGCGTGGGTATGGTGGCAGGCCCCGTGGCCGGGGGACTGTTGGGCGCCATCT
CCTTGCACCATTCCTTGCGGCGGCGGTGCTCAACGGCCTCAACCTACTACTGGGCTGCTTCCT
AATGCAGGAGTCGCATAAGGGAGAGCGTCGAATGGTGCACTCTCAGTACAATCTGCTCTGATG
CCGCATAGTTAAGCCAGCCCCGACACCCGCCAACACCCGCTGACGCGCCCTGACGGGCTTGTC
TGCTCCCGGCATCCGCTTACAGACAAGCTGTGACCGTCTCCGGGAGCTGCATGTGTCAGAGGT
TTTCACCGTCATCACCGAAACGCGCGAGACGAAAGGGCCTCGTGATACGCCTATTTTTATAGG
TTAATGTCATGATAATAATGGTTTCTTAGACGTCAGGTGGCACTTTTCGGGGAAATGTGCGCG
GAACCCCTATTTGTTTATTTTTCTAAATACATTCAAATATGTATCCGCTCATGAGACAATAAC
CCTGATAAATGCTTCAATAATATTGAAAAAGGAAGAGTATGAGTATTCAACATTTCCGTGTCG
CCCTTATTCCCTTTTTTGCGGCATTTTGCCTTCCTGTTTTTGCTCACCCAGAAACGCTGGTGA
AAGTAAAAGATGCTGAAGATCAGTTGGGTGCACGAGTGGGTTACATCGAACTGGATCTCAACA
GCGGTAAGATCCTTGAGAGTTTTCGCCCCGAAGAACGTTTTCCAATGATGAGCACTTTTAAAG
TTCTGCTATGTGGCGCGGTATTATCCCGTATTGACGCCGGGCAAGAGCAACTCGGTCGCCGCA
TACACTATTCTCAGAATGACTTGGTTGAGTACTCACCAGTCACAGAAAAGCATCTTACGGATG
GCATGACAGTAAGAGAATTATGCAGTGCTGCCATAACCATGAGTGATAACACTGCGGCCAACT
TACTTCTGACAACGATCGGAGGACCGAAGGAGCTAACCGCTTTTTTGCACAACATGGGGGATC
ATGTAACTCGCCTTGATCGTTGGGAACCGGAGCTGAATGAAGCCATACCAAACGACGAGCGTG
ACACCACGATGCCTGTAGCAATGGCAACAACGTTGCGCAAACTATTAACTGGCGAACTACTTA
CTCTAGCTTCCCGGCAACAATTAATAGACTGGATGGAGGCGGATAAAGTTGCAGGACCACTTC
TGCGCTCGGCCCTTCCGGCTGGCTGGTTTATTGCTGATAAATCTGGAGCCGGTGAGCGTGGGT
CTCGCGGTATCATTGCAGCACTGGGGCCAGATGGTAAGCCCTCCCGTATCGTAGTTATCTACA
CGACGGGAGTCAGGCAACTATGGATGAACGAAATAGACAGATCGCTGAGATAGGTGCCTCAC
TGATTAAGCATTGGTAACTGTCAGACCAAGTTTACTCATATATACTTTAGATTGATTTAAAAC
TTCATTTTTAATTTAAAAGGATCTAGGTGAAGATCCTTTTTGATAATCTCATGACCAAAATCC
CTTAACGTGAGTTTTCGTTCCACTGAGCGTCAGACCCCGTAGAAAAGATCAAAGGATCTTCTT
GAGATCCTTTTTTTCTGCGCGTAATCTGCTGCTTGCAAACAAAAAAACCACCGCTACCAGCGG
TGGTTTGTTTGCCGGATCAAGAGCTACCAACTCTTTTTCCGAAGGTAACTGGCTTCAGCAGAG
CGCAGATACCAAATACTGTCCTTCTAGTGTAGCCGTAGTTAGGCCACCACTTCAAGAACTCTG
TAGCACCGCCTACATACCTCGCTCTGCTAATCCTGTTACCAGTGGCTGCTGCCAGTGGCGATA
AGTCGTGTCTTACCGGGTTGGACTCAAGACGATAGTTACCGGATAAGGCGCAGCGGTCGGGCT
GAACGGGGGGTTCGTGCACACAGCCCAGCTTGGAGCGAACGACCTACACCGAACTGAGATACC
TACAGCGTGAGCTATGAGAAAGCGCCACGCTTCCCGAAGGGAGAAAGGCGGACAGGTATCCGG
TAAGCGGCAGGGTCGGAACAGGAGAGCGCACGAGGGAGCTTCCAGGGGGAAACGCCTGGTATC
TTTATAGTCCTGTCGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTCCTGGCCTTTTGCT
GGCCTTTTGCTCACATGTTCTTTCCTGCGTTATCCCCTGATTCTGTGGATAACCGTATTACCG
```

|  |  |
|---|---|
|  | CCTTTGAGTGAGCTGATACCGCTCGCCGCAGCCGAACGACCGAGCGCAGCGAGTCAGTGAGCG<br>AGGAAGCGGAAGAGCGCCCAATACGCAAACCGCCTCTCCCCGCGCGTTGGCCGATTCATTAAT<br>GCAGGGGGATCTCGATCCCGCGAAATTAATACGACTCACTATAGG |
| SEQ ID NO: 8 | ACGAAGACAAACAAACCATTATTATCATTAAAAGGCTCAGGAGAAACTTTAACAGTAATCAGA<br>ATTCGCCACCATGACCAGCGTGGGCATCGTGGGCCTGCTGCTGACCACCGCCATGGCCGCCGA<br>GGTGACCAGAAGAGGCAGCGCCTACTACATGTACCTGGACCGGAACGATGCCGGCGAGGCCAT<br>CAGCTTTCCAACCACCCTGGGCATGAACAAGTGCTACATCCAGATCATGGACCTGGGCCACAC<br>CTGTGACGCCACCATGAGCTACGAGTGCCCCATGCTGGACGAGGGCGTGGAACCCGACGATGT<br>GGACTGCTGGTGCAACACCACCAGCACCTGGGTGGTGTACGGCACCTGTCACCACAAGAAGGG<br>CGAAGCCAGACGGTCCAGACGGGCCGTGACACTGCCTAGCCACAGCACCAGAAAGCTGCAGAC<br>CCGGTCCCAGACCTGGCTGGAAAGCAGAGAGTACACCAAGCACCTGATCCGGGTGGAAAACTG<br>GATCTTCCGGAACCCCGGCTTTGCCCTGGCCGCTGCTGCTATTGCTTGGCTGCTGGGCAGCAG<br>CACCTCCCAGAAAGTGATCTACCTCGTGATGATCCTGCTGATCGCCCCTGCCTACAGCATCCG<br>GTGTATCGGCGTGTCCAACCGGGACTTCGTGGAAGGCATGAGCGGCGGCACATGGGTGGACGT<br>GGTGCTGGAACATGGCGGCTGCGTGACAGTGATGGCTCAGGACAAGCCCACCGTGGACATCGA<br>GCTCGTGACCACCACCGTGTCCAATATGGCCGAAGTGCGGAGCTACTGCTACGAGGCCAGCAT<br>CAGCGACATGGCAAGCGACAGCAGATGCCCTACACAGGGCGAGGCCTACCTGGACAAGCAGTC<br>CGACACCCAGTACGTGTGCAAGCGGACCCTGGTGGATAGAGGCTGGGGCAATGGCTGCGGCCT<br>GTTTGGCAAGGGCAGCCTCGTGACCTGCGCCAAGTTCGCCTGCAGCAAGAAGATGACCGGCAA<br>GAGCATCCAGCCCGAGAACCTGGAATACCGGATCATGCTGAGCGTGCACGGCAGCCAGCACTC<br>CGGCATGATCGTGAACGACACCGGCCACGAGACAGACGAGAACCGGGCCAAGGTGGAAATCAC<br>CCCCAACAGCCCTAGAGCCGAGGCCACACTGGGCGGCTTTGGATCTCTGGGCCTGGACTGCGA<br>GCCTAGAACCGGCCTGGATTTCAGCGACCTGTACTACCTGACCATGAACAACAAGCACTGGCT<br>GGTGCACAAAGAGTGGTTCCACGACATCCCCCTGCCCTGGCATGCCGGCGCTGATACAGGCAC<br>ACCCCACTGGAACAACAAAGAGGCTCTGGTGGAATTCAAGGACGCCCACGCCAAGCGGCAGAC<br>CGTGGTGGTGCTGGGATCTCAGGAAGGCGCCGTGCATACAGCTCTGGCTGGCGCCCTGGAAGC<br>CGAAATGGATGGCGCCAAAGGCAGACTGTCCAGCGGCCACCTGAAGTGCCGGCTGAAGATGGA<br>CAAGCTGCGGCTGAAGGGCGTGTCCTACAGCCTGTGTACCGCCGCCTTCACCTTCACCAAGAT<br>CCCCGCCGAGACACTGCACGGCACCGTGACTGTGGAAGTGCAGTACGCCGGCACCGACGGCCC<br>TTGTAAAGTGCCTGCTCAGATGGCCGTGGATATGCAGACCCTGACCCCCGTGGGCAGACTGAT<br>CACCGCCAACCCTGTGATCACCGAGAGCACCGAGAACAGCAAGATGATGCTGGAACTGGACCC<br>CCCCTTCGGCGACTCCTACATCGTGATCGGCGTGGGAGAGAAGAAGATCACCCACCACTGGCA<br>CAGAAGCGGCAGCACCATCGGCAAGGCCTTTGAGGCTACAGTGCGGGGAGCCAAGAGAATGGC<br>CGTGCTGGGAGATACCGCCTGGGACTTTGGCTCTGTGGGCGGAGCCCTGAACTCTCTGGGCAA<br>GGGAATCCACCAGATCTTCGGAGCCGCCTTTAAGAGCCTGTTCGGCGGCATGAGCTGGTTCAG<br>CCAGATCCTGATCGGCACCCTGCTGATGTGGCTGGGCCTGAACGCCAAGAACGGCAGCATCTC<br>CCTGATGTGCCTGGCTCTGGGAGGCGTGCTGATCTTCCTGAGCACAGCCGTGTCTGCCTGATG<br>GCCATATGAAAAAAACTAACAGTAATCAAAATGTCTGTTACAGTCAAGAGAATCATTGACAAC<br>ACAGTCATAGTTCCAAAACTTCCTGCAAATGAGGATCCAGTGGAATACCCGGCAGATTACTTC<br>AGAAAATCAAAGGAGATTCCTCTTTACATCAATACTACAAAAAGTTTGTCAGATCTAAGAGGA<br>TATGTCTACCAAGGCCTCAAATCCGGAAATGTATCAATCATACATGTCAACAGCTACTTGTAT<br>GGAGCATTAAAGGACATCCGGGGTAAGTTGGATAAAGATTGGTCAAGTTTCGGAATAAACATC<br>GGGAAAGCAGGGGATACAATCGGAATATTTGACCTTGTATCCTTGAAAGCCCTGGACGGCGTA<br>CTTCCAGATGGAGTATCGGATGCTTCCAGAACCAGCGCAGATGACAAATGGTTGCCTTTGTAT<br>CTACTTGGCTTATACAGAGTGGGCAGAACACAAATGCCTGAATACAGAAAAAAGCTCATGGAT<br>GGGCTGACAAATCAATGCAAAATGATCAATGAACAGTTTGAACCTCTTGTGCCAGAAGGTCGT<br>GACATTTTTGATGTGTGGGGAAATGACAGTAATTACACAAAAATTGTCGCTGCAGTGGACATG<br>TTCTTCCACATGTTCAAAAAACATGAATGTGCCTCGTTCAGATACGGAACTATTGTTTCCAGA<br>TTCAAAGATTGTGCTGCATTGGCAACATTTGGACACCTCTGCAAAATAACCGGAATGTCTACA<br>GAAGATGTAACGACCTGGATCTTGAACCGAGAAGTTGCAGATGAAATGGTCCAAATGATGCTT<br>CCAGGCCAAGAAATTGACAAGGCCGATTCATACATGCCTTATTTGATCGACTTTGGATTGTCT<br>TCTAAGTCTCCATATTCTTCCGTCAAAAACCCTGCCTTCCACTTCTGGGGGCAATTGACAGCT<br>CTTCTGCTCAGATCCACCAGAGCAAGGAATGCCCGACAGCCTGATGACATTGAGTATACATCT<br>CTTACTACAGCAGGTTTGTTGTACGCTTATGCAGTAGGATCCTCTGCCGACTTGGCACAACAG<br>TTTTGTGTTGGAGATAACAAATACACTCCAGATGATAGTACCGGAGGATTGACGACTAATGCA<br>CCGCCACAAGGCAGAGATGTGGTCGAATGGCTCGGATGGTTTGAAGATCAAAACAGAAACCG<br>ACTCCTGATATGATGCAGTATGCGAAAAGAGCAGTCATGTCACTGCAAGGCCTAAGAGAGAAG<br>ACAATTGGCAAGTATGCTAAGTCAGAATTTGACAAATGACCCTATAATTCTCAGATCACCTAT<br>TATATATTATGCTACATATGAAAAAAACTAACAGATATCATGGATAATCTCACAAAAGTTCGT<br>GAGTATCTCAAGTCCTATTCTCGTCTGGATCAGGCGGTAGGAGAGATAGATGAGATCGAAGCA<br>CAACGAGCTGAAAAGTCCAATTATGAGTTGTTCCAAGAGGATGGAGTGGAAGAGCATACTAAG<br>CCCTCTTATTTTCAGGCAGCAGATGATTCTGACACAGAATCTGAACCAGAAATTGAAGACAAT<br>CAAGGTTTGTATGCACAGGATCCAGAAGCTGAGCAAGTTGAAGGCTTTATACAGGGGCCTTTA<br>GATGACTATGCAGATGAGGAAGTGGATGTTGTATTTACTTCGGACTGGAAACCACCTGAGCTT<br>GAATCTGACGAGCATGGAAAGACCTTACGGTTGACATCGCCAGAGGGTTTAAGTGGAGAGCAG<br>AAATCCCAGTGGCTTTCGACGATTAAAGCAGTCGTGCAAAGTGCCAAATACTGGAATCTGGCA<br>GAGTGCACATTTGAAGCATCGGGAGAAGGGGTCATTATGAAGGAGCGCCAGATAACTCCGGAT<br>GTATATAAGGTCACTCCAGTGATGAACACACATCCGTCCCAATCAGAAGCAGTATCAGATGTT<br>TGGTCTCTCTCAAAGACATCCATGACTTTCCAACCCAAGAAAGCAAGTCTTCAGCCTCTCACC<br>ATATCCTTGGATGAATTGTTCTCATCTAGAGGAGAGTTCATCTCTGTCGGAGGTGACGGACGA<br>ATGTCTCATAAAGAGGCCATCCTGCTCGGCCTGAGATACAAAAAGTTGTACAATCAGGCGAGA<br>GTCAAATATTCTCTGTAGACTATGAAAAAAAGTAACAGATATCACGATCTAAGTGTTATCCCA<br>ATCCATTCATCATGAGTTCCTTAAAGAAGATTCTCGGTCTGAAGGGGAAAGGTAAGAAATCTA<br>AGAAATTAGGGATCGCACCACCCCCCTTATGAAGAGGACACTAGCATGGAGTATGCTCCGAGCG<br>CTCCAATTGACAAATCCTATTTTGGAGTTGACGAGATGGACACCTATGATCCGAATCAATTAA<br>GATATGAGAAATTCTTCTTTACAGTGAAAATGACGGTTAGATCTAATCGTCCGTTCAGAACAT<br>ACTCAGATGTGGCAGCCGCTGTATCCCATTGGGATCACATGTACATCGGAATGGCAGGGAAAC<br>GTCCCTTCTACAAAATCTTGGCTTTTTTGGGGTTCTTCTAATCTAAAGGCCACTCCAGCGGTAT |

-continued

```
TGGCAGATCAAGGTCAACCAGAGTATCACACTCACTGCGAAGGCAGGGCTTATTTGCCACATA
GGATGGGGAAGACCCCTCCCATGCTCAATGTACCAGAGCACTTCAGAAGACCATTCAATATAG
GTCTTTACAAGGGAACGATTGAGCTCACAATGACCATCTACGATGATGAGTCACTGGAAGCAG
CTCCTATGATCTGGGATCATTTCAATTCTTCCAAATTTTCTGATTTCAGAGAGAAGGCCTTAA
TGTTTGGCCTGATTGTCGAGAAAAAGGCATCTGGAGCGTGGGTCCTGGATTCTATCAGCCACT
TCAAATGAGCTAGTCTAACTTCTAGCTTCTGAACAATCCCCGGTTTACTCAGTCTCTCCTAAT
TCCAGCCTCTCGAACAACTAATATCCTGTCTTTTCTATCCCTATGAAAAAAACTAACAGAGAT
CGATCTGTTTCCTTGACACTATGAAGTGCCTTTTGTACTTAGCCTTTTTATTCATTGGGGTGA
ATTGCAAGTTCACCATAGTTTTTCCACACAACCAAAAAGGAAACTGGAAAAATGTTCCTTCTA
ATTACCATTATTGCCCGTCAAGCTCAGATTTAAATTGGCATAATGACTTAATAGGCACAGCCA
TACAAGTCAAAATGCCCAAGAGTCACAAGGCTATTCAAGCAGACGGTTGGATGTGTCATGCTT
CCAAATGGGTCACTACTTGTGATTTCCGCTGGTATGGACCGAAGTATATAACACAGTCCATCC
GATCCTTCACTCCATCTGTAGAACAATGCAAGGAAAGCATTGAACAAACGAAACAAGGAACTT
GGCTGAATCCAGGCTTCCCTCCTCAAAGTTGTGGATATGCAACTGTGACGGATGCCGAAGCAG
TGATTGTCCAGGTGACTCCTCACCATGTGCTGGTTGATGAATACACAGGAGAATGGGTTGATT
CACAGTTCATCAACGGAAAATGCAGCAATTACATATGCCCCACTGTCCATAACTCTACAACCT
GGCATTCTGACTATAAGGTCAAAGGGCTATGTGATTCTAACCTCATTTCCATGGACATCACCT
TCTTCTCAGAGGACGGAGAGCTATCATCCCTGGGAAAGGAGGGCACAGGGTTCAGAAGTAACT
ACTTTGCTTATGAAACTGGAGGCAAGGCCTGCAAAATGCAATACTGCAAGCATTGGGGAGTCA
GACTCCCATCAGGTGTCTGGTTCGAGATGGCTGATAAGGATCTCTTTGCTGCAGCCAGATTCC
CTGAATGCCCAGAAGGGTCAAGTATCTCTGCTCCATCTCAGACCTCAGTGGATGTAAGTCTAA
TTCAGGACGTTGAGAGGATCTTGGATTATTCCCTGCCAAGAAACCTGGAGCAAAATCAGAG
CGGGTCTTCCAATCTCTCCAGTGGATCTCAGCTATCTTGCTCCTAAAAACCCAGGAACCGGTC
CTGCTTTCACCATAATCAATGGTACCCTAAAATACTTTGAGACCAGATACATCAGAGTCGATA
TTGCTGCTCCAATCCTCTCAAGAATGGTCGGAATGATCAGTGGAACTACCACAGAAAGGGAAC
TGTGGGATGACTGGGCACCATATGAAGACGTGGAAATTGGACCCAATGGAGTTCTGAGGACCA
GTTCAGGATATAAGTTTCCTTTATACATGATTGGACATGGTATGTTGGACTCCGATCTTCATC
TTAGCTCAAAGGCTCAGGTGTTCGAACATCCTCACATTCAAGACGCTGCTTCGCAACTTCCTG
ATGATGAGAGTTTATTTTTTGGTGATACTGGGCTATCCAAAAATCCAATCGAGCTTGTAGAAG
GTTGGTTCAGTAGTTGGAAAAGCTCTATTGCCTCTTTTTTCTTTATCATAGGGTTAATCATTG
GACTATTCTTGGTTCTCCGAGTTGGTATCCATCTTTGCATTAAATTAAAGCACACCAAGAAAA
GACAGATTTATACAGACATAGAGATGAACCGACTTGGAAAGTAACTCAAATCCTGCACAACAG
ATTCTTCATGTTTGGACCAAATCAACTTGTGATACCATGCTCAAAGAGGCCTCAATTATATTT
GAGTTTTTAATTTTTATGAAAAAAACTAACAGCAATCATGGAAGTCCACGATTTTGAGACCGAA
CGAGTTCAATGATTTCAATGAAGATGACTATGCCACAAGAGAATTCCTGAATCCCGATGAGCG
CATGACGTACTTGAATCATGCTGATTACAATTTGAATTCTCCTCTAATTAGTGATGATATTGA
CAATTTGATCAGGAAATTCAATTCTCTTCCGATTCCCTCGATGTGGGATAGTAAGAACTGGGA
TGGAGTTCTTGAGATGTTAACATCATGTCAAGCCAATCCCATCTCAACATCTCAGATGCATAA
ATGGATGGGAAGTTGGTTAATGTCTGATAATCATGATGCCAGTCAAGGGTATAGTTTTTTACA
TGAAGTGGACAAAGAGGCAGAAATAACATTTGACGTGGTGGAGACCTTCATCCGCGGCTGGGG
CAACAAACCAATTGAATACATCAAAAAGGAAAGATGGACTGACTCATTCAAAATTCTCGCTTA
TTTGTGTCAAAAGTTTTTGGACTTACACAAGTTGACATTAATCTTAAATGCTGTCTCTGAGGT
GGAATTGCTCAACTTGGCGAGGACTTTCAAAGGCAAAGTCAGAAGAAGTTCTCATGGAACGAA
CATATGCAGGATTAGGGTTCCCAGCTTGGGTCCTACTTTTATTTCAGAAGGATGGGCTTACTT
CAAGAAACTTGATATTCTAATGGACCGAAACTTTCTGTTAATGGTCAAAGATGTGATTATAGG
GAGGATGCAAACGGTGCTATCCATGGTATGTAGAATAGACAACCTGTTCTCAGAGCAAGACAT
CTTCTCCCTTCTAAATATCTACAGAATTGGAGATAAAATTGTGGAGAGGCAGGGAAATTTTTC
TTATGACTTGATTAAAATGGTGGAACCGATATGCAACTTGAAGCTGATGAAATTAGCAAGAGA
ATCAAGGCCTTTAGTCCCACAATTCCCTCATTTTGAAATCATATCAAGACTTCTGTTGATGA
AGGGGCAAAAATTGACCGAGGTATAAGATTCCTCCATGATCAGATAATGAGTGTGAAAACAGT
GGATCTCACACTGGTGATTTATGGATCGTTCAGACATTGGGGTCATCCTTTTATAGATTATTA
CACTGGACTAGAAAATTACATTCCCAAGTAACCATGAAGAAAGATATTGATGTGTCATATGC
AAAAGCACTTGCAAGTGATTTAGCTCGGATTGTTCTATTTCAACAGTTCAATGATCATAAAAA
GTGGTTCGTGAATGGAGACTTGCTCCCTCATGATCATCCCTTTAAAAGTCATGTTAAAGAAAA
TACATGGCCCACAGCTGCTCAAGTTCAAGATTTTGGAGATAAATGGCATGAACTTCCGCTGAT
TAAATGTTTTGAAATACCCGACTTACTAGACCCATCGATAATATACTCTGACAAAAGTCATTC
AATGAATAGGTCAGAGGTGTTGAAACATGTCCGAATGAATCCGAACACTCCTATCCCTAGTAA
AAAGGTGTTGCAGACTATGTTGGACACAAAGGCTACCAATTGGAAAGAATTTCTTAAAGAGAT
TGATGAGAAGGGCTTAGATGATGATGATCTAATTATTGGTCTTAAAGGAAAGGAGAAGGACCT
GAAGTTGGCAGGTAGATTTTTCTCCCTAATGTCTTGGAAATTGCGAGAATACTTTGTAATTAC
CGAATATTTGATAAAGACTCATTTCGTCCCTATGTTAAAGGCCTGACAATGGCGGACGATCT
AACTGCAGTCATTAAAAAGATGTTAGATTCCTCATCCGGCCAAGGATTGAAGTCATATGAGGC
AATTTGCATAGCCAATCACATTGATTACGAAAAATGCCACCAAAGGAAGTTATCAA
CGGCCCAGTGTTCCGAGTTATGGGCCAGTTCTTAGGTTATCCATCCTTAATCGAGAGAACTCA
TGAATTTTTTGAGAAAAGTCTTATATACTACAATGGAAGACCAGACTTGATGCGTGTTCACAA
CAACACACTGATCAATTCAACCTCCCAACGAGTTTGTTGGCAAGGACAAGAGGGTGGACTGGA
AGGTCTACGGCAAAAAGGATGGACTATCCTCAATCTACTGGTTATTCAAAGAGAGGCTAAAAT
CAGAAACACTGCTGTCAAAGTCTTGGCACAAGGTGATAATCAAGTTATTTGCACACAGTATAA
AACGAAGAAATCGAGAACGTTGTAGAATTACAGGGTGCTCTCAATCAAATGGTTTCTAATAA
TGAGAAAATTATGACTGCAATCAAAATAGGGACAGGGAAGTTAGGACTTTTGATAAATGACGA
TGAGACTATGCAATCTGCAGATTACTTGAATTATGGAAAAATACCGATTTTCCGTGGAGTGAT
TAGAGGGTTAGAGACCAAGAGATGGTCACGAGTGACTTGTGTCACCAATGACCAAATACCCAC
TTGTGCTAATATAATGAGCTCAGTTTCCACAAATGCTCTCACCGTAGCTCATTTTGCTGAGAA
CCCAATCAATGCCATGATACAGTACAATTATTTTGGGACATTTGCTAGACTCTTGTTGATGAT
GCATGATCCTGCTCTTCGTCAATCATTGTATGAAGTTCAAGATAAGATACCGGGCTTGCACAG
TTCTACTTTCAAATACGCCATGTTGTATTTGGACCCTTCCATTGGAGGAGTGTCGGGCATGTC
TTTGTCCAGGTTTTTGATTAGAGCCTTCCCAGATCCCGTAACAGAAAGTCTCTCATTCTGGAG
ATTCATCCATGTACATGCTCGAAGTGAGCATCTGAAGGAGATGAGTGCAGTATTTGGAAACCC
CGAGATAGCCAAGTTTCGAATAACTCACATAGACAAGCTAGTAGAAGATCCAACCTCTCTGAA
```

```
CATCGCTATGGGAATGAGTCCAGCGAACTTGTTAAAGACTGAGGTTAAAAAATGCTTAATCGA
ATCAAGACAAACCATCAGGAACCAGGTGATTAAGGATGCAACCATATATTTGTATCATGAAGA
GGATCGGCTCAGAAGTTTCTTATGGTCAATAAATCCTCTGTTCCCTAGATTTTTAAGTGAATT
CAAATCAGGCACTTTTTGGGAGTCGCAGACGGGCTCATCAGTCTATTTCAAAATTCTCGTAC
TATTCGGAACTCCTTTAAGAAAAAGTATCATAGGGAATTGATGATTTGATTGTGAGGAGTGA
GGTATCCTCTTTGACACATTTAGGGAAACTTCATTTGAGAAGGGGATCATGTAAAATGTGGAC
ATGTTCAGCTACTCATGCTGACACATTAAGATACAAATCCTGGGGCCGTACAGTTATTGGGAC
AACTGTACCCCATCCATTAGAAATGTTGGGTCCAACATCGAAAAGAGACTCCTTGTGCACC
ATGTAACACATCAGGGTTCAATTATGTTTCTGTGCATTGTCCAGACGGGATCCATGACGTCTT
TAGTTCACGGGGACCATTGCCTGCTTATCTAGGGTCTAAAACATCTGAATCTACATCTATTTT
GCAGCCTTGGGAAAGGGAAAGCAAAGTCCCACTGATTAAAAGAGCTACACGTCTTAGAGATGC
TATCTCTTGGTTTGTTGAACCCGACTCTAAACTAGCAATGACTATACTTTCTAACATCCACTC
TTTAACAGGCGAAGAATGGACCAAAAGGCAGCATGGGTTCAAAAGAACAGGGTCTGCCCTTCA
TAGGTTTTCGACATCTCGGATGAGCCATGGTGGGTTCGCATCTCAGAGCACTGCAGCATTGAC
CAGGTTGATGGCAACTACAGACACCATGAGGGATCTGGGAGATCAGAATTTCGACTTTTTATT
CCAAGCAACGTTGCTCTATGCTCAAATTACCACCACTGTTGCAAGAGACGGATGGATCACCAG
TTGTACAGATCATTATCATATTGCCTGTAAGTCCTGTTTGAGACCCATAGAAGAGATCACCCT
GGACTCAAGTATGGACTACACGCCCCCAGATGTATCCCATGTGCTGAAGACATGGAGGAATGG
GGAAGGTTCGTGGGACAAGAGATAAAACAGATCTATCCTTTAGAAGGGAATTGGAAGAATTT
AGCACCTGCTGAGCAATCCTATCAAGTCGGCAGATGTATAGGTTTTCTATATGGAGACTTGGC
GTATAGAAAATCTACTCATGCCGAGGACAGTTCTCTATTTCCTCTATCTATACAAGGTCGTAT
TAGAGGTCGAGGTTTCTTAAAAGGGTTGCTAGACGGATTAATGAGAGCAAGTTGCTGCCAAGT
AATACACCGGAGAAGTCTGGCTCATTTGAAGAGGCCGGCCAACGCAGTGTACGGAGGTTTGAT
TTACTTGATTGATAAATTGAGTGTATCACCTCCATTCCTTTCTCTTACTAGATCAGGACCTAT
TAGAGACGAATTAGAAACGATTCCCCACAAGATCCCAACCTCCTATCCGACAAGCAACCGTGA
TATGGGGGTGATTGTCAGAAATTACTTCAAATACCAATGCCGTCTAATTGAAAAGGGAAAATA
CAGATCACATTATTCACAATTATGGTTATTCTCAGATGTCTTATCCATAGACTTCATTGGACC
ATTCTCTATTTCCACCACCCTCTTGCAAATCCTATACAAGCCATTTTTATCTGGGAAAGATAA
GAATGAGTTGAGAGAGCTGGCAAATCTTTCTTCATTGCTAAGATCAGGAGAGGGGTGGGAAGA
CATACATGTGAAATTCTTCACCAAGGACATATTATTGTGTCCAGAGGAAATCAGACATGCTTG
CAAGTTCGGGATTGCTAAGGATAATAATAAAGACATGAGCTATCCCCCTTGGGGAAGGGAATC
CAGAGGGACAATTACAACAATCCCTGTTTATTATACGACCACCCCTTACCCAAAGATGCTAGA
GATGCCTCCAAGAATCCAAAATCCCCTGCTGTCCGGAATCAGGTTGGGCCAATTACCAACTGG
CGCTCATTATAAAATTCGGAGTATATTACATGGAATGGGAATCCATTACAGGGACTTCTTGAG
TTGTGGGAGACGGCTCCGGAGGGATGACTGCTGCATTACTACGAGAAAATGTGCATAGCAGAGG
AATATTCAATAGTCTGTTAGAATTATCAGGGTCAGTCATGCGAGGCGCCTCTCCTGAGCCCCC
CAGTGCCCTAGAAACTTTAGGAGGAGATAAATCGAGATGTGTAAATGGTGAAACATGTTGGGA
ATATCCATCTGACTTATGTGACCCAAGGACTTGGGACTATTTCCTCCGACTCAAAGCAGGCTT
GGGGCTTCAAATTGATTTAATTGTAATGGATATGGAAGTTCGGGATTCTTCTACTAGCCTGAA
AATTGAGACGAATGTTAGAAATTATGTGCACCGGATTTTGGATGAGCAAGGAGTTTTAATCTA
CAAGACTTATGGAACATATATTTGTGAGAGCGAAAAGAATGCAGTAACAATCCTTGGTCCCAT
GTTCAAGACGGTCGACTTAGTTCAAACAGAATTTAGTAGTTCTCAAACGTCTGAAGTATATAT
GGTATGTAAAGGTTTGAAGAAATTAATCGATGAACCCAATCCCGATTGGTCTTCCATCAATGA
ATCCTGGAAAAACCTGTACGCATTCCAGTCATCAGAACAGGAATTTGCCAGAGCAAAGAAGGT
TAGTACATACTTTACCTTGACAGGTATTCCCTCCCAATTCATTCCTGATCCTTTTGTAAACAT
TGAGACTATGCTACAAATATTCGGAGTACCCACGGGTGTGTCTCATGCGGCTGCCTTAAAATC
ATCTGATAGACCTGCAGATTTATTGACCATTAGCCTTTTTTATATGGCGATTATATCGTATTA
TAACATCAATCATATCAGAGTAGGACCGATACCTCCGAACCCCCCATCAGATGGAATTGCACA
AAATGTGGGGATCGCTATAACTGGTATAAGCTTTTGGCTGAGTTTGATGGAGAAAGACATTCC
ACTATATCAACAGTGTTTAGCAGTTATCCAGCAATCATTCCCGATTAGGTGGGAGGCTGTTTC
AGTAAAAGGAGGATACAAGCAGAAGTGGAGTACTAGAGGTGATGGGCTCCCAAAAGATACCCG
AACTTCAGACTCCTTGGCCCCAATCGGGAACTGGATCAGATCTCTGGAATTGGTCCGAAACCA
AGTTCGTCTAAATCCATTCAATGAGATCTTGTTCAATCAGCTATGTCGTACAGTGGATAATCA
TTTGAAATGGTCAAATTTGCGAAGAAACACAGGAATGATTGAATGGATCAATAGACGAATTTC
AAAAGAAGACCGGTCTATACTGATGTTGAAGAGTGACCTACACGAGGAAAACTCTTGGAGAGA
TTAAAAAATCATGAGGAGACTCCAAACTTTAAGTATGAAAAAACTTTGATCCTTAAGACCCT
CTTGTGGTTTTATTTTTTATCTGGTTTTGTGGTCTTCGTGGGTCGGCATGGCATCTCCACCT
CCTCGCGGTCCGACCTGGGCATCCGAAGGAGGACGTCGTCCACTCGGATGGCTAAGGGAGAGC
TCGGATCCGGCTGCTAACAAAGCCCGAAAGGAAGCTGAGTTGGCTGCTGCCACCGCTGAGCAA
TAACTAGCATAACCCCTTGGGGCCTCTAAACGGGTCTTGAGGGGTTTTTGCTGAAAGGAGGA
ACTATATCCGGATCGAGATCCTCTAGAGTCGACCTGCAGGCATGCAAGCTTGTATTCTATAGT
GTCACCTAAATCGTATGTGTATGATACATAAGGTTATGTATTAATTGTAGCCGCGTTCTAACG
ACAATATGTACAAGCCTAATTGTGTAGCATCTGGCTTACTGAAGCAGACCCTATCATCTCTCT
CGTAAACTGCCGTCAGAGTCGGTTTGGTTGGACGAACCTTCTGAGTTTCTGGTAACGCCGTcC
CGCACCCGGAAATGGTCAGCGAACCAATCAGCAGGGTCATCGCTAGCCAGATCCTCTACGCCG
GACGCATCGTGGCCGGCATCACCGGCGCCACAGGTGCGGTTGCTGGCGCCTATATCGCCGACA
TCACCGATGGGGAAGATCGGGCTCGCCACTTCGGGCTCATGAGCGCTTGTTTCGGCGTGGGTA
TGGTGGCAGGCCCCGTGGCCGGGGGACTGTTGGGCGCCATCTCCTTGCATGCACCATTCCTTGCGGC
GGCGGTGCTCAACGGCCTCAACCTACTACTGGGCTGCTTCCTAATGCAGGAGTCGCATAAGGG
AGAGCGTCGAATGGTGCACTCTCAGTACAATCTGCTCTGATGCCGCATAGTTAAGCCAGCCCC
GACACCCGCCAACACCCGCTGACGCGCCCTGACGGGCTTGTCTGCTCCCGGCATCCGCTTACA
GACAAGCTGTGACCGTCTCCGGGAGCTGCATGTGTCAGAGGTTTTCACCGTCATCACCGAAAC
GCGCGAGACGAAAGGGCCTCGTGATACGCCTATTTTTATAGGTTAATGTCATGATAATAATGG
TTTCTTAGACGTCAGGTGGCACTTTTCGGGGAAATGTGCGCGGAACCCCTATTTGTTTATTTT
TCTAAATACATTCAAATATGTATCCGCTCATGAGACAATAACCCTGATAAATGCTTCAATAAT
ATTGAAAAAGGAAGAGTATGAGTATTCAACATTTCCGTGTCGCCCTTATTCCCTTTTTTGCGG
CATTTTGCCTTCCTGTTTTTGCTCACCCAGAAACGCTGGTGAAAGTAAAAGATGCTGAAGATC
```

```
AGTTGGGTGCACGAGTGGGTTACATCGAACTGGATCTCAACAGCGGTAAGATCCTTGAGAGTT
TTCGCCCCGAAGAACGTTTTCCAATGATGAGCACTTTTAAAGTTCTGCTATGTGGCGCGGTAT
TATCCCGTATTGACGCCGGGCAAGAGCAACTCGGTCGCCGCATACACTATTCTCAGAATGACT
TGGTTGAGTACTCACCAGTCACAGAAAAGCATCTTACGGATGGCATGACAGTAAGAGAATTAT
GCAGTGCTGCCATAACCATGAGTGATAACACTGCGGCCAACTTACTTCTGACAACGATCGGAG
GACCGAAGGAGCTAACCGCTTTTTTGCACAACATGGGGGATCATGTAACTCGCCTTGATCGTT
GGGAACCGGAGCTGAATGAAGCCATACCAAACGACGAGCGTGACACCACGATGCCTGTAGCAA
TGGCAACAACGTTGCGCAAACTATTAACTGGCGAACTACTTACTCTAGCTTCCCGGCAACAAT
TAATAGACTGGATGGAGGCGGATAAAGTTGCAGGACCACTTCTGCGCTCGGCCCTTCCGGCTG
GCTGGTTTATTGCTGATAAATCTGGAGCCGGTGAGCGTGGGTCTCGCGGTATCATTGCAGCAC
TGGGGCCAGATGGTAAGCCCTCCCGTATCGTAGTTATCTACACGACGGGGAGTCAGGCAACTA
TGGATGAACGAAATAGACAGATCGCTGAGATAGGTGCCTCACTGATTAAGCATTGGTAACTGT
CAGACCAAGTTTACTCATATATACTTTAGATTGATTTAAAACTTCATTTTTAATTTAAAAGGA
TCTAGGTGAAGATCCTTTTTGATAATCTCATGACCAAAATCCCTTAACGTGAGTTTTCGTTCC
ACTGAGCGTCAGACCCCGTAGAAAAGATCAAAGGATCTTCTTGAGATCCTTTTTTTCTGCGCG
TAATCTGCTGCTTGCAAACAAAAAAACCACCGCTACCAGCGGTGGTTTGTTTGCCGGATCAAG
AGCTACCAACTCTTTTTCCGAAGGTAACTGGCTTCAGCAGAGCGCAGATACCAAATACTGTCC
TTCTAGTGTAGCCGTAGTTAGGCCACCACTTCAAGAACTCTGTAGCACCGCCTACATACCTCG
CTCTGCTAATCCTGTTACCAGTGGCTGCTGCCAGTGGCGATAAGTCGTGTCTTACCGGGTTGG
ACTCAAGACGATAGTTACCGGATAAGGCGCAGCGGTCGGGCTGAACGGGGGGTTCGTGCACAC
AGCCCAGCTTGGAGCGAACGACCTACACCGAACTGAGATACCTACAGCGTGAGCTATGAGAAA
GCGCCACGCTTCCCGAAGGGAGAAAGGCGGACAGGTATCCGTAAGCGGCAGGGTCGGAACAG
GAGAGCGCACGAGGGAGCTTCCAGGGGGAAACGCCTGGTATCTTTATAGTCCTGTCGGGTTTC
GCCACCTCTGACTTGAGCGTCGATTTTTGTGATGCTCGTCAGGGGGGCGGAGCCTATGGAAAA
ACGCCAGCAACGCGGCCTTTTTACGGTTCCTGGCCTTTTGCTGGCCTTTTGCTCACATGTTCT
TTCCTGCGTTATCCCCTGATTCTGTGGATAACCGTATTACCGCCTTTGAGTGAGCTGATACCG
CTCGCCGCAGCCGAACGACCGAGCGCAGCGAGTCAGTGAGCGAGGAAGCGGAAGAGCGCCCAA
TACGCAAACCGCCTCTCCCCGCGCGTTGGCCGATTCATTAATGCAGGGGGATCTCGATCCCGC
GAAATTAATACGACTCACTATAGG
```

In some embodiments, the recombinant VSV comprises a nucleic acid sequence that is at least 80 (e.g., at least 81, 82, 83, 84, 85, 86, 87, 88, 89, 90, 91, 92, 93, 94, 95, 96, 97, 98, or 99) % identical to: (i) the nucleic acid of SEQ ID NO:5; (ii) the nucleic acid of SEQ ID NO:6; (iii) the nucleic acid of SEQ ID NO:7; or (iv) the nucleic acid of SEQ ID NO:8. In some embodiments, the recombinant VSV comprises a nucleic acid sequence that is identical to: (i) the nucleic acid of SEQ ID NO:5; (ii) the nucleic acid of SEQ ID NO:6; (iii) the nucleic acid of SEQ ID NO:7; or (iv) the nucleic acid of SEQ ID NO:8.

Nucleic acid molecules provided herein can be obtained using standard molecular biology techniques. For example, nucleic acid molecules described herein can be cloned using standard PCR techniques or chemically synthesized.

In certain embodiments, provided herein are vectors that contain the isolated nucleic acid molecules described herein. As used herein, the term "vector," refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby be replicated along with the host genome. Moreover, certain vectors are capable of directing the expression of genes. Such vectors are referred to herein as "recombinant expression vectors" (or simply, "expression vectors").

In another aspect, disclosed herein are recombinant VSV comprising a Zika virus envelope (E) protein or fragment thereof. An exemplary amino acid sequence for a wild type Zika virus envelope protein is as follows (SEQ ID NO: 9):

| SEQ ID NO: 9 | IRCIGVSNRDFVEGMSGGTWVDVVLEHGGCVT VMAQDKPTVDIELVTTTVSNMAEIRSYCYEAS ISDMASDSRCPTQGEAYLDKQSDTQYVCKRTL VDRGWGNGCGLFGKGSLVTCAKFACSKKMTGK SIQPENLEYRIMLSVHGSQHSGMIVNDTGHET DENRAKVEITPNSPRAEATLGGFGSLGLDCEP RTGLDFSDLYYLTMNNKHWLVHKEWFHDIPLP WHAGADTGTPHWNNKEALVEFKDAHAKRQTVV VLGSQEGAVHTALAGALEAEMDGAKGRLSSGH LKCRLKMDKLRLKGVSYSLCTAAFTFTKIPAE TLHGTVTVEVQYAGTDGPCKVPAQMAVDMQTL TPVGRLITANPVITESTENSKMMLELDPPFGD SYIVIGVGEKKITHHWHRSGSTIGKAFEATVR GAKRMAVLGDTAWDFGSVGGALNSLGKGIHQI FGAAFKSLEGGMSWESQILIGTLLMWLGLNTK NGSISLMCLALGGVLIFLSTAVSA |
|---|---|

In some embodiments, the recombinant viruses further comprise a Zika virus precursor membrane (prM) protein or fragment thereof. An exemplary amino acid sequence for a wild type Zika virus prM protein is as follows (SEQ ID NO: 10):

| SEQ ID NO: 10 | RRGSAYYMYLDRNDAGEAISFPTTLGMNKCYI QIMDLGHMCDATMSYECPMLDEGVEPDDVDCW CNTTSTWVVYGTCHHKKGEARRSRRAVTLPSH STRKLQTRSQTWLESREYTKHLIRVENWIFRN PGFALAAAAIAWLLGSSTSQKVIYLVMILLIA PAYS |
|---|---|

In some embodiments, the recombinant viruses further comprise a Zika virus capsid (C) protein or fragment thereof. An exemplary amino acid sequence for a wild type Zika virus capsid protein is as follows (SEQ ID NO: 11):

| SEQ ID NO: 11 | MKNPKKKSGGFRIVNMLKRGVARVSPFGGLKR LPAGLLLGHGPIRMVLAILAFLRFTAIKPSLG LINRWGSVGKKEAMEIIKKFKKDLAAMLRIIN ARKEKKRRGADTSVGIVGLLLTTAMAAEVT |
|---|---|

In some embodiments, a protein described herein, or a fragment thereof, has an amino acid sequence that is at least 80 (e.g., at least 81, 82, 83, 84, 85, 86, 87, 88, 89, 90, 91, 92, 93, 94, 95, 96, 97, 98, or 99) % identical to: (i) the amino acid of SEQ ID NO:9; (ii) the amino acid of SEQ ID NO:10; or (iii) the amino acid of SEQ ID NO:11. In some embodiments, a protein described herein, or a fragment thereof, has an amino acid sequence that is identical to: (i) the amino acid of SEQ ID NO:9; (ii) the amino acid of SEQ ID NO:10; or (iii) the amino acid of SEQ ID NO:11.

Percent amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software, such as BLAST software or ClustalW2. Appropriate parameters for measuring alignment, including any algorithms needed to achieve maximal alignment over the full-length of the sequences being compared can be determined by known methods.

Suitable cell lines for propagating a recombinant VSV or producing virus like particles include mammalian cells, such as BSRT7cells, Vero cells, AGMK cells, BHK-21 cells, COS-I or COS-7 cells, MDCK cells, CV-I cells, LLC-MK2 cells, primary cell lines such as fetal Rhesus lung (FRhL-2) cells, BSC-I cells, and MRC-5 cells, or human diploid fibroblasts, as well as avian cells, chicken or duck embryo derived cell lines, e.g., AGE1 cells, and primary, chicken embryo fibroblasts, and insect cell lines, such as C6/36 or Sf9 or Sf21. To propagate virus in cell culture, a recombinant vesicular stomatitis virus is used to infect the host cell (for example, selected from among the suitable cell types listed above). After virus adsorption, the cultures are fed with medium capable of supporting growth of the cells. The host cells are maintained in culture until the desired virus titer is achieved.

To recover virus, the virus is harvested by common methods known in the art including slow-speed centrifugation, or by filtration through a filter of pore size of 0.45 µm. Methods for concentrating recovered virus or VLPs are within the scope of a person with ordinary skill in the art and include, for example, ultrafiltration (e.g., with a membrane of no greater than 300 kDa pore size), or precipitation with polyethylene glycol (PEG) 8000. Methods for purifying viruses are known to a person with ordinary skill in the art and include continuous or multi-step sucrose gradients, purification by column chromatography using size exclusion, ion exchange, adsorption, or affinity columns, or purification by partitioning in polymer two-phase or multi-phase systems, and any combination thereof. Methods for assaying for virus positive fractions include plaque assay, hemagglutination (HA) assay, and/or antigen assays such as immunoassays.

Pharmaceutical Compositions and Vaccines

In certain aspects, provided herein are pharmaceutical compositions and/or vaccines comprising a recombinant VSV described herein.

In some embodiments, the pharmaceutical compositions and/or vaccines described herein include a recombinant VSV comprising a Zika virus envelope (E) protein together with one or more excipients and/or adjuvants. In some embodiments, the recombinant VSV further comprises a Zika virus precursor membrane (prM) protein and/or a Zika virus capsid (C) protein or fragment thereof.

In some embodiments, the pharmaceutical composition and/or vaccine described herein comprises a recombinant VSV viral genome and/or a gene encoding a Zika virus envelope (E) protein. In some embodiments, the pharmaceutical composition and/or vaccine described herein comprises a gene encoding a Zika virus precursor membrane (prM) protein and/or a Zika virus capsid (C) protein or fragment thereof. The pharmaceutical composition and/or vaccine can contain genetic material expressing a Zika virus envelope (E), a Zika virus precursor membrane (prM) protein and/or a Zika virus capsid (C) protein or fragment thereof. In such a case, the a Zika virus envelope (E), a Zika virus precursor membrane (prM) protein and/or a Zika virus capsid (C) protein can be expressed in cells of a susceptible species immunized with the vaccine containing a recombinant VSV. The cells infected with these viruses release Zika virus like particles. The viruses, and the virus like particles can be isolated, purified and used as source of antigen for vaccine purposes. Immunity against wild type Zika virus can thereby be conferred in a species and/or tissue normally susceptible to a Zika virus infection.

In some embodiments, the pharmaceutical composition and/or vaccine may further comprise an adjuvant that can augment the immune response by increasing delivery of antigen, stimulating cytokine production, and/or stimulating antigen presenting cells. In some embodiments, the adjuvant can be administered concurrently with the pharmaceutical composition and/or vaccine composition disclosed herein, e.g., in the same composition or in separate compositions. For example, an adjuvant can be administered prior or subsequent to the pharmaceutical composition and/or vaccine composition disclosed herein. Such adjuvants include, but are not limited to: aluminum salts, non-toxic bacterial fragments, cholera toxin (and detoxified fractions thereof), chitosan, homologous heat-labile of E. coli (and detoxified fractions thereof), lactide/glycolide homo and copolymers (PLA/GA), polyanhydride e.g. trimellitylimido-L-tyrosine, DEAE-dextran, saponins complexed to membrane protein antigens (immune stimulating complexes—ISCOMS), bacterial products such as lipopolysaccharide (LPS) and muramyl dipeptide, (MDP), liposomes, cochelates, proteinoids, cytokines (interleukins, interferons), genetically engineered live microbial vectors, non-infectious pertussis mutant toxin, neurimidase/galactose oxidase, and attenuated bacterial and viral toxins derived from mutant strains.

In some embodiments, the recombinant VSV is able to induce an immune response in a subject against the Zika virus.

In certain embodiments, the pharmaceutical composition, vaccine and/or adjuvant can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Therapeutic Methods

In certain aspects, provided herein is a method for inducing an immune response against Zika virus in a subject comprising administering to the subject a composition (e.g., a vaccine composition) disclosed herein. In some embodiments, provided herein is a method for protecting a subject from Zika virus, comprising administering to the subject a composition disclosed herein. In some embodiments, provided herein is a method of treating a subject for a Zika virus infection comprising administering to the subject a composition disclosed herein.

A "subject," as used herein, can be any mammal. For example, a subject can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant). In some embodiments, the subject is female (e.g., a human female). For example, a subject can be a human female of child-bearing age or a human female who is pregnant.

In certain embodiments, the subject is exposed to Zika virus due to the subject's exposure to a mosquito comprising the Zika virus. The subject may be exposed to a Aedes mosquitoes, particularly A. aegypti. Such a subject may be at risk of developing a Zika virus infection and disease states related to or caused by such an infection. In certain embodiments, the subject was exposed to Zika virus or a mosquito, within the last 6 month, within the last month, within the last two weeks, within the last week, within the last 72 hours, within the last 48 hours, within the last 24 hours, within the last 12 hours, within the last 6 hours, within the last 4 hours, within the last 2 hours, or within the last hour.

In certain embodiments, the subject does not have, but is at risk of developing a Zika virus infection. A subject "at risk" may or may not have detectable disease, and may or may not have displayed detectable disease prior to the treatment methods described herein. "At risk" denotes that an individual who is determined to be more likely to develop a symptom based on conventional risk assessment methods or has one or more risk factors that correlate with development of a particular condition. An individual having one or more of these risk factors has a higher probability of developing a condition than an individual without these risk factors. Examples (i.e., categories) of risk groups are well known in the art and discussed herein, such as those subjects who are traveling to a region of the world where Zika virus is prevalent. For example, in some embodiments the region is in the United States, Anguilla, Antigua, Argentina, Aruba, Barbados, Barbuda, Belize, Bolivia, Bonaire, Brazil, Cayman Islands, Colombia, Commonwealth of Puerto Rico, Costa Rica, Cuba, Curacao, Dominica, Dominican Republic, Ecuador, El Salvador, French Guiana, Grenada, Guadeloupe, Guatemala, Guyana, Haiti, Honduras, Jamaica, Martinique, Mexico, Nicaragua, Panama, Paraguay, Peru, Saba, Saint Barthelemy, Saint Lucia, Saint Martin, Saint Vincent and the Grenadines, Sint Eustatius, Sint Maarten, Suriname, Trinidad and Tobago, Turks and Caicos, U.S. Virgin Islands, American Samoa, Fiji, Kosrae, Federated States of Micronesia, Marshall Islands, New Caledonia, Papua New Guinea, Samoa, Tonga, Venezuela, and Cape Verde.

EXAMPLES

The invention now being generally described will be more readily understood by reference to the following examples which are included merely for purposes of illustration of certain aspects and embodiments of the present invention, and are not intended to limit the invention in any way.

Example 1

Construction and Recovery of Recombinant VSV Expressing ZIKV Envelope

As a first step to develop recombinant VSV expressing Zika virus envelope protein, or producing Zika virus VLPs, a fragment of the Zika virus spanning the prM (membrane), and E (envelope) proteins was chemically synthesized which generated four different recombinant VSV. Two variants of Zika fragment were selected that differ in their N-terminus. In one case, the sequence that spans prM-E (prM-E) was included. In the second variant, the N-terminus of prM was extended into the capsid sequence of Zika because this region is predicted to be a transmembrane region that may help with the proper processing and folding of prM, (CprM-E). Those two different Zika fragments, prM-E and C-prM-E were each cloned into two different VSV vectors. In one VSV vector, the Zika coding sequences were cloned into the VSV genome, replacing the endogenous VSV viral glycoprotein (G), to yield rVSVΔGZika-prME and rVSVΔGZika-CprME (see schematic in FIG. 1A). The second vector was designed to maximally express the Zika virus antigens and therefore the Zika sequences were cloned into wild type VSV in front of the N gene of the virus to yield rVSV-Zika-prME and rVSV-Zika-CprME.

Example 2

Rescue of Recombinant Virus with Zika Envelope Replacing VSV Envelope rVSVΔG-Zika-CprME and rVSVΔG-Zika-prME rVSVΔG-Zika-CprME and rVSVΔG-Zika-prME infectious viruses were recovered by transfection of BSRT7 cells with each of the corresponding constructs together with the necessary VSV expression plasmids N, P, L and G. (as a tool to monitor infection of cells in culture eGFP was included in the VSV genome.) FIG. 1A illustrates the arrangement of coding sequences for the constructs and the method for transfection and recovery of virus.

Following subsequent amplification of each virus in BSRT7 cells by complementation with VSV G expressed in trans, rVSVΔG-Zika-prME and rVSVΔG-Zika-C-prME yielded $1.2 \times 10^8$ and $1 \times 10^7$ infectious units per ml respectively as determined by eGFP expression (FIG. 2A-FIG. 2D). By contrast, when virus was propagated in cells that lack VSV G expressed by transfection of plasmid, infectivity of both rVSVΔG-Zika-prME and rVSVΔG-Zika-CprME was reduced approximately 2 logs. It is important to note, however, that infection of the recombinant viruses propagated in the absence of VSV G indicating that infection is mediated by the Zika envelope protein and demonstrating that it is functionally incorporated into infectious particles.

The complete sequence of the recovered viruses was determined by RT-PCR and shown to contain no additional mutations.

Example 3

Expression of Zika E in Cells Infected with VSVΔG Variants

Next, the VSV recombinants were confirmed to express the Zika envelope protein. To this end, cells were infected with VSV or the rVSVΔG-Zika variants and were monitored for expression of Zika proteins by metabolic incorporation of $^{35}$S-methionine (FIG. 3A). Recombinant virus expresses a unique protein not seen in VSV infected cells of the molecular weight expected for Zika envelope, together with the expected VSV proteins N, P, L and M.

When analyzed by Western blot using the anti- Dengue envelope monoclonal antibody 4G2 that cross reacts with Zika envelope (FIG. 3B), ZIKV envelope could be detected in extracts from infected cells (FIG. 3B, lanes 4 and 5). Note that the recombinant virus containing sequences of the Zika capsid protein (rVSVΔG-ZikaCprME) produce more envelope protein than the recombinant lacking C (rVSVΔG-ZikaprME). Zika envelope was also present in the cell culture supernatants of infected cells (FIG. 3B, lane 3) and infectious virus stocks (FIG. 3B, lane 6) suggesting that the ZIKV envelope incorporated into VSV particles or that Zika virus like particles were produced from the infected cells. As a control for the western blot, purified Zika virus, MR766 strain (lane 2) was included which confirms that the antibody recognizes E and confirming its mobility. As shown in FIG. 3C, monoclonal antibody 4G2 also uniquely labels cells infected with recombinant virus, but not wild type VSV.

Example 4

Zika Envelope is Incorporated into VSVΔG Particles

Figure 2A:
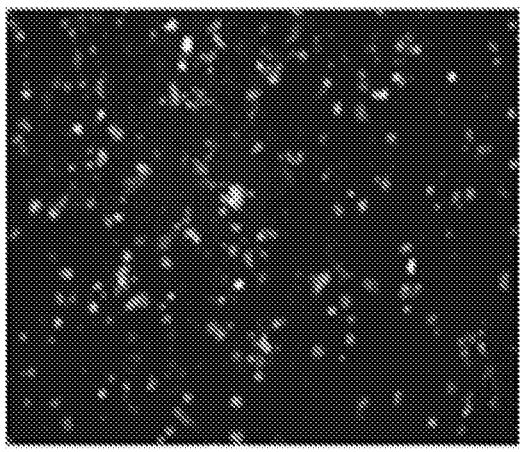
FIG. 2A-FIG. 2D show infection of Vero cells with rVSVΔG-Zika-CprME.
Figure 2C:
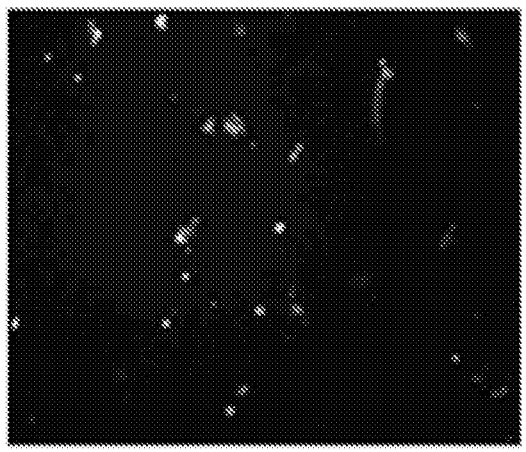
Figure 2B:
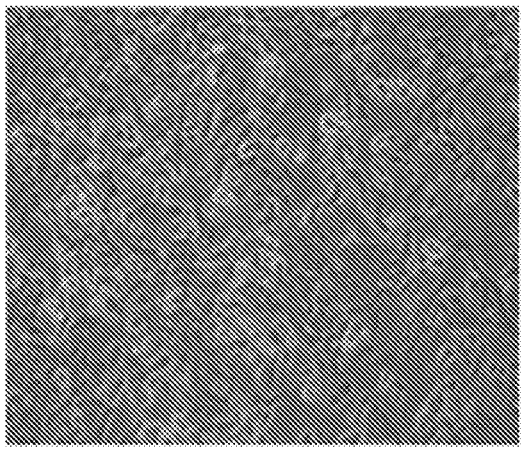
Figure 2D:
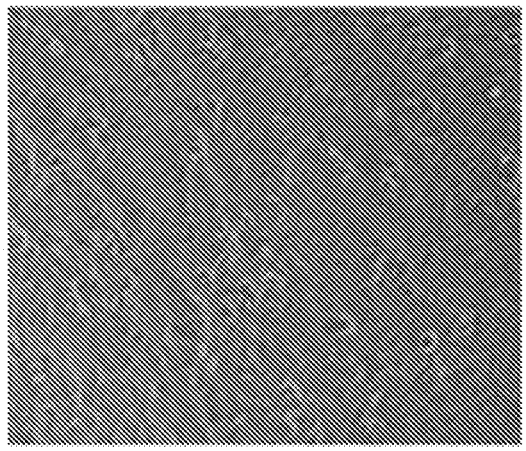
Figure 4:
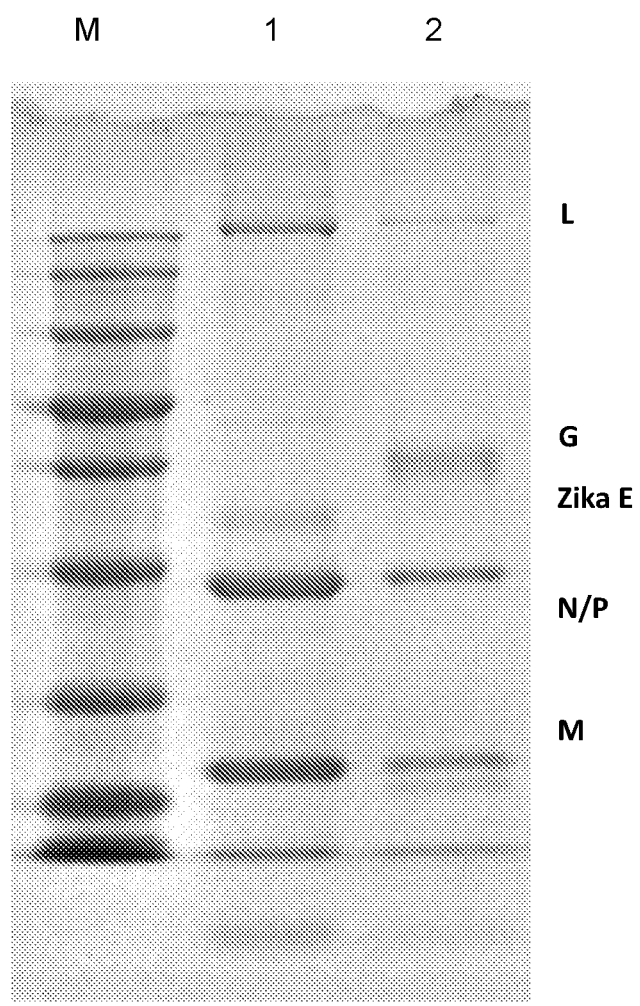
FIG. 4 show that Zika E protein is incorporated into VSV particles. A Coomassie stained SDS-PAGE of purified virus, following sedimentation through sucrose is shown. M: molecular weight markers. Lane 1: rVSVΔG-Zika-C-prM-E. Lane 2: rVSV. The Zika E band is identified.

To determine whether the recombinant VSVΔG-Zika incorporate Zika E into virions, cell culture supernatants were collected and purified by centrifugation. The sedimented particles were analyzed for their protein composition by SDS-PAGE and compared them to rVSV-eGFP. This result (FIG. 4) demonstrates that rVSVΔG-ZikaCprME incorporates Zika E into the virions further substantiating that the infectivity of these particles is mediated by E.

Example 5

Figure 5:
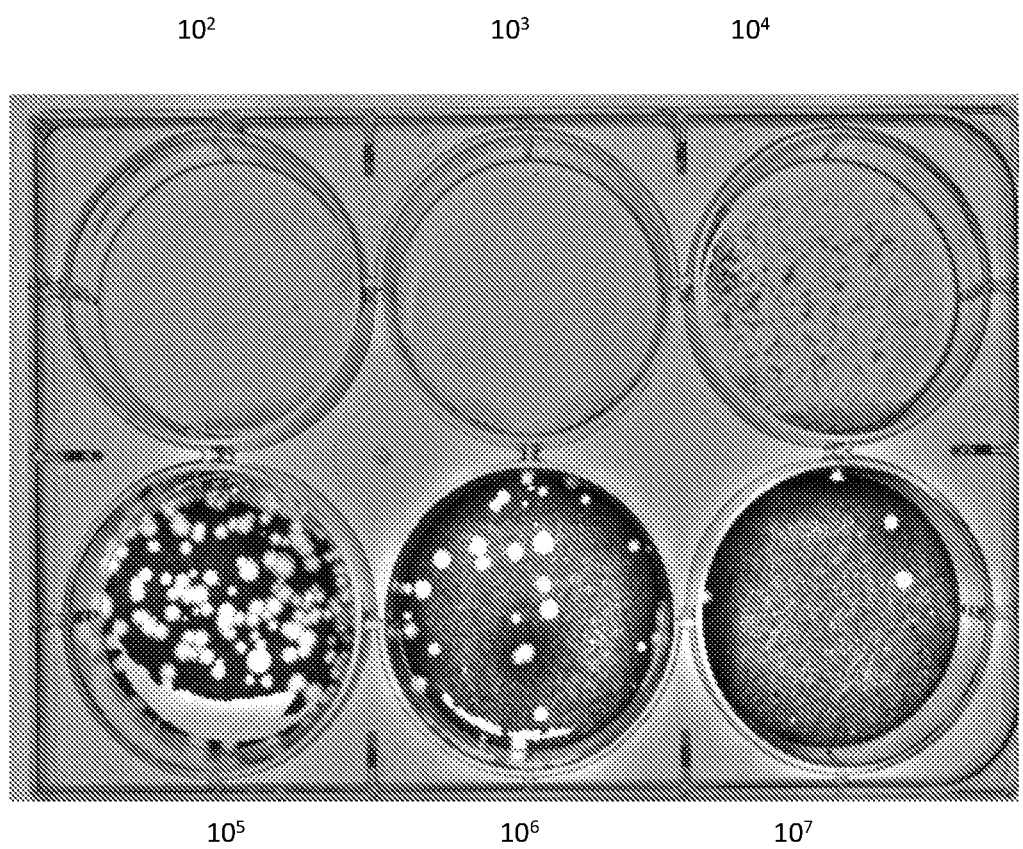
FIG. 5 shows a plaque assay of rVSV-Zika-CprME on Vero cells. The numbers represent the dilutions of a typical virus stock which demonstrates the high titer of the stocks routinely attained.

Recovery and Growth of Recombinant VSV Containing Both VSV G and Zika E rVSV-Zika-prME and rVSV-Zika-CprME rVSV-Zika-prME and rVSV-Zika-CprME were assembled and virus recovered by the schematic of FIG. 1A. Note from the sequence that the Zika encoding sequences were cloned into wild type VSV in front of the N gene, and the wild type VSV G remains in the genome, so that these viruses have the genetic structure 3'-Le-ZIKA-N-P-M-G-L-Tr-5'. Note also that these viruses did not contain GFP as a tool to monitor infection. Infectious virus were recovered from both constructs and a representative plaque assay is shown (FIG. 5) demonstrating routine titers of $1.5 \times 10^8$ pfu/ml.

Example 6

VSV-Zika Particles Incorporate Zika E

Figure 6:
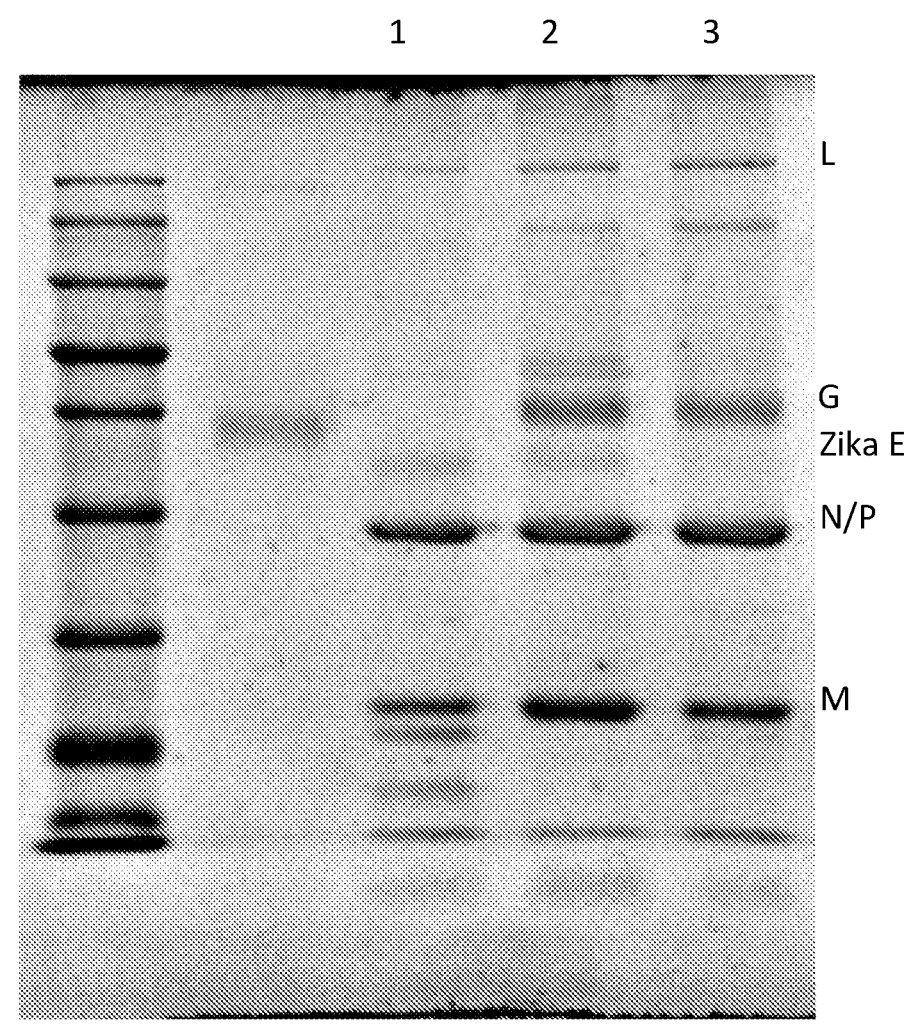

To determine whether the VSV-Zika particles incorporate Zika E, infectious virus were purified through a sucrose cushion and analyzed those particles by SDS-PAGE (FIG. 6). Both VSV-G and Zika E envelope proteins are present in the purified material—despite the presence of the cognate VSV-G protein. This result suggests that either E was incorporated into the VSV particles or Zika like VLPs were generated.

Example 7

All VSV-Zika Recombinants Incorporate E and Produce Zika VLPs to Different Extents To determine whether the different viruses produce Zika VLPs and incorporate Zika E into the VSV particles, the products of infection were analyzed by sucrose gradient centrifugation. Briefly, Vero cells were infected with the indicated virus (FIG. 7A-7D and FIG. 8A-8D) and the cell culture fluids collected at 48 h post infection. The cell culture fluids were clarified by low speed centrifugation to eliminate cellular debris and the resultant supernatant subjected to further centrifugation through a sucrose cushion to collect the viral particles and VLPs. The pellet fraction was resuspended in NTE and laid over a preformed linear 15-45% sucrose gradient. Following centrifugation to separate the different particles based on their density, fractions were collected using a gradient fractionator and analyzed for the presence of protein by SDS-PAGE and detection with Coomassie stain and by Western blot with the indicated antibodies (FIG. 7A-7D and FIG. 8A-8D). Each of the recombinant viruses generate both VLPs and VSV particles that contained Zika virus E. In addition, the recombinants rVSV-Zika-prME and rVSV-Zika-CprME showed the presence of VSV G in the VSV fractions (FIG. 7A-7D and FIG. 8A-8D) reflecting the presence of G in the viral genome and its expression during infection. Note the absence of VSV G in the corresponding fractions of rVSVΔG-Zika-prME and rVSVΔG-Zika-CprME (FIG. 7A-7D and FIG. 8A-8D). By comparing the levels of E incorporated into various VSV fractions, it appears that Zika E is most efficiently incorporated by rVSVΔG-Zika-prME. Although all the viruses produce Zika VLPs we note that the rVSV-Zika-CprME appears to be most efficient (compare FIG. 7A-7D and FIG. 8A-8D).

Figure 9A:
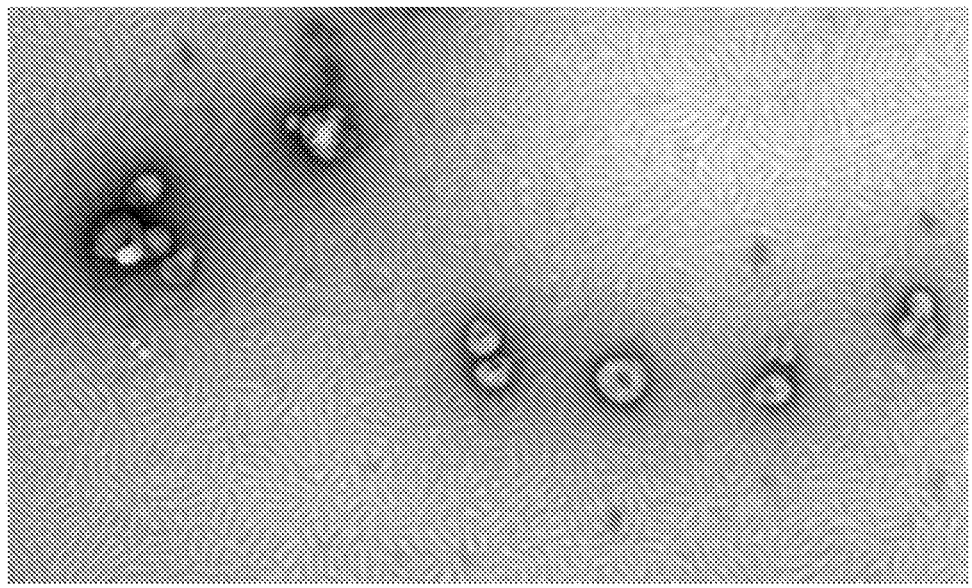
FIG. 9A and FIG. 9B show the electron micrographs of VLPs and VSV-Zika particles. Gradient fractions containing Zika VLPs (FIG. 9A) and VSV particles (FIG. 9B) were analyzed by negative-stain electron microscopy. Size bars are 100 nm and 500 nm respectively.
Figure 9B:
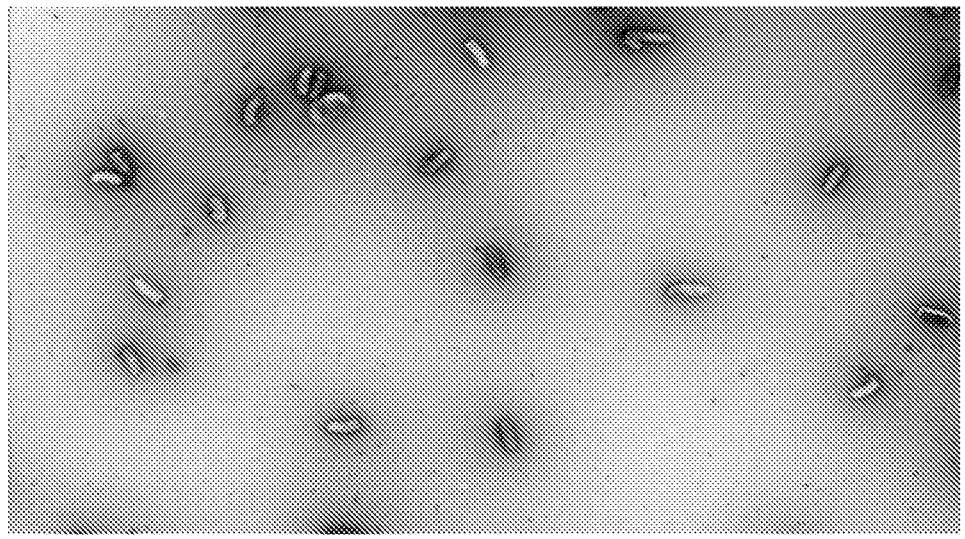

To confirm that the fractions correspond to VLPs and VSV particles, the fractions were analyzed by negative-stain electron microscopy. As shown (FIG. 9A and FIG. 9B) the VLP fraction have the spherical appearance of flavivirus VLPs and their dimensions (40 nm diameter) are also consistent with this. The VSV-recombinants retain their bullet shape and are approximately 200 nm by 80 nm. Collectively, these data (EM and gradient fractions) confirm that the recombinants generate Zika VLPs and VSV with Zika envelope. These data also demonstrate that the viruses that express VSV G from their genome also yield particles that incorporate VSV G.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

All publications, patents, patent applications and sequence accession numbers mentioned herein are hereby incorporated by reference in their entirety as if each individual publication, patent or patent application was specifically and individually indicated to be incorporated by reference. In case of conflict, the present application, including any definitions herein, will control.

What is claimed is:

1. A recombinant vesicular stomatitis virus (VSV) comprising in its genome a nucleic acid sequence encoding a Zika virus envelope (E) protein or fragment thereof, wherein the nucleic acid encoding the Zika virus E protein has a sequence that is at least 90% identical to SEQ ID NO:2.

2. A recombinant vesicular stomatitis virus (VSV) comprising in its genome a nucleic acid sequence encoding a Zika virus envelope (E) protein or fragment thereof, further comprising in its genome a nucleic acid sequence encoding a Zika virus precursor membrane (prM) protein or fragment thereof, wherein the nucleic acid encoding Zika virus prM has a sequence that is at least 90% identical to SEQ ID NO: 3.

3. A recombinant vesicular stomatitis virus (VSV) comprising in its genome a nucleic acid sequence encoding a Zika virus envelope (E) protein or fragment thereof, further comprising in its genome a nucleic acid sequence encoding a Zika virus precursor membrane (prM) protein or fragment thereof and a nucleic acid sequence encoding Zika virus capsid (C) protein or fragment thereof, wherein the nucleic acid encoding Zika virus capsid (C) protein has a sequence that is at least 90% identical to SEQ ID NO:4.

4. A recombinant vesicular stomatitis virus (VSV) comprising in its genome a nucleic acid sequence encoding a Zika virus envelope (E) protein or fragment thereof, wherein the genome of the recombinant VSV has a nucleic acid sequence that is at least 90% identical to SEQ ID NO:5.

5. A recombinant vesicular stomatitis virus (VSV) comprising in its genome a nucleic acid sequence encoding a Zika virus envelope (E) protein or fragment thereof, wherein the genome of the recombinant VSV has a nucleic acid sequence that is at least 90% identical to SEQ ID NO:6.

6. A recombinant vesicular stomatitis virus (VSV) comprising in its genome a nucleic acid sequence encoding a Zika virus envelope (E) protein or fragment thereof, wherein the genome of the recombinant VSV has a nucleic acid sequence that is at least 90% identical to SEQ ID NO:7.

* * * * *